US008895026B2

(12) United States Patent
Meyers et al.

(10) Patent No.: US 8,895,026 B2
(45) Date of Patent: Nov. 25, 2014

(54) ATTENUATED PESTIVIRUS

(75) Inventors: Gregor Meyers, Walddorfhaeslach (DE); Birke Andrea Tews, Lille (FR); Eva-Maria Schuermann, Tuebingen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 872 days.

(21) Appl. No.: 13/000,962

(22) PCT Filed: Jun. 24, 2009

(86) PCT No.: PCT/EP2009/057911
§ 371 (c)(1),
(2), (4) Date: Jan. 21, 2011

(87) PCT Pub. No.: WO2009/156448
PCT Pub. Date: Dec. 30, 2009

(65) Prior Publication Data
US 2011/0117126 A1 May 19, 2011

(30) Foreign Application Priority Data
Jun. 25, 2008 (EP) .................... 08159009

(51) Int. Cl.
*A61K 39/12* (2006.01)
*C12N 7/04* (2006.01)
*C07K 14/005* (2006.01)
*A61K 39/00* (2006.01)

(52) U.S. Cl.
CPC ......... *C12K 7/00* (2013.01); *C12N 2770/24362* (2013.01); *C12N 2770/24322* (2013.01); *A61K 39/12* (2013.01); *A61K 2039/5254* (2013.01); *C07K 2319/50* (2013.01); *C07K 14/005* (2013.01)
USPC ...................... 424/205.1; 435/236

(58) Field of Classification Search
None
See application file for complete search history.

(56) References Cited

U.S. PATENT DOCUMENTS

| | | | |
|---|---|---|---|
| 4,719,177 A | 1/1988 | Baltimore et al. | |
| 5,206,163 A | 4/1993 | Renard et al. | |
| 6,001,613 A | 12/1999 | Donis et al. | |
| 6,168,942 B1 | 1/2001 | Cao et al. | |
| 6,610,305 B1 | 8/2003 | Elbers et al. | |
| 7,135,561 B2 | 11/2006 | Elbers et al. | |
| 7,179,473 B2 | 2/2007 | Meyers | |
| 7,572,455 B2* | 8/2009 | Meyers et al. | 424/218.1 |
| 7,858,099 B2 | 12/2010 | Meyers | |
| 2003/0044426 A1 | 3/2003 | Meyers | |
| 2003/0147914 A1 | 8/2003 | Keich et al. | |
| 2003/0165520 A1 | 9/2003 | Cao et al. | |
| 2004/0038198 A1 | 2/2004 | Elbers et al. | |
| 2004/0081666 A1 | 4/2004 | Dominowski | |
| 2004/0146854 A1 | 7/2004 | Cao et al. | |
| 2004/0185056 A1 | 9/2004 | Jones | |
| 2004/0208901 A1 | 10/2004 | Ellsworth et al. | |
| 2005/0002966 A1 | 1/2005 | Meyers | |
| 2005/0053621 A1 | 3/2005 | Welch et al. | |
| 2005/0287171 A1* | 12/2005 | Meyers et al. | 424/204.1 |
| 2006/0024320 A1 | 2/2006 | Meyers | |
| 2007/0015203 A1 | 1/2007 | Elbers et al. | |
| 2009/0004216 A1 | 1/2009 | Meyers | |
| 2009/0068223 A1 | 3/2009 | Meyers et al. | |
| 2009/0226488 A1 | 9/2009 | Meyers et al. | |
| 2010/0178301 A1 | 7/2010 | Rinehart et al. | |
| 2011/0117126 A1* | 5/2011 | Meyers et al. | 424/205.1 |

FOREIGN PATENT DOCUMENTS

| | | | |
|---|---|---|---|
| CA | 2363493 | A1 | 5/2002 |
| EP | 0794257 | A1 | 9/1997 |
| EP | 0982402 | A1 | 3/2000 |
| EP | 1013757 | A2 | 6/2000 |
| WO | 9964604 | A2 | 12/1999 |
| WO | 0139801 | A2 | 6/2001 |
| WO | 03023041 | A2 | 3/2003 |
| WO | 2005111201 | A1 | 11/2005 |
| WO | 2007117303 | A2 | 10/2007 |
| WO | 2009156448 | A1 | 12/2009 |

OTHER PUBLICATIONS

Langedijk et al. (Journal of Virology. 2002; 76 (20): 10383-10392).*
Hulst et al. ("[35] Erns protein of pestiviruses." Methods in enzymology 342 (2001): 431-440).*
Meyers et al., "Molecular Characterization of Pestiviruses". Advances in Virus Resarch, vol. 47, 1996, pp. 53-118.
Meyers et al., "Molecular Cloning and Nucleotide Sequence of the Genome of Hog Cholera Virus". Virology, vol. 171, 1989, pp. 555-567.
Meyers et al., "Mutations Abrogating the RNase Activity in Glycoprotein Erns of the *Pestivirus* Clasical Swine Fever Virus Lead to Virus Attenuation". Journal of Virology, vol. 73, No. 12, Dec. 1999, pp. 10224-10235.
Meyers et al., "Recovery of Cytopathogenic and Noncytopathogenic Bovine Viral Diarrhea Viruses from cDNA Constructs". Journal of Virology, vol. 70, No. 12, Dec. 1996, pp. 8606-8613.
Moennig et al., "The Pestiviruses". Advances in Virus Research, vol. 41, 1992, pp. 53-98.
Moormann et al., "Infectious RNA Transcribed from an Engineered Full-Length cDNA Template of the Genome of a *Pestivirus*". Journal of Virology, vol. 70, No. 2, Feb. 1996, pp. 763-770.
Moser et al., "A Recombinant Classical Swine Fever Virus Stably Expresses a Marker Gene". Journal of Virology, vol. 72, No. 6, Jun. 1998, pp. 5318-5322.

(Continued)

*Primary Examiner* — Shanon A Foley
(74) *Attorney, Agent, or Firm* — Michael P. Morris; Wendy M. Gombert

(57) ABSTRACT

The present invention relates to recombinant attenuated pestiviruses, in particular to recombinant attenuated CSFV, BVDV, or BDV, wherein said recombinant attenuated pestivirus does not produce a dimeric $E^{rns}$ glycoprotein. The present invention also relates to immunogenic compositions comprising such a pestivirus as well to a method of attenuating a pestivirus comprising the step of modifying the $E^{rns}$ glycoprotein by a deletion, insertion or substitution wherein such modification results in a non dimeric $E^{rns}$ glycoprotein.

25 Claims, 5 Drawing Sheets

(56) References Cited

OTHER PUBLICATIONS

Murphy et al., "Flaviviridae". Veterinary Virology, Third Edition, Academic Press, San Diego, CA, 1999, pp. 564-566.
Odeon et al., "Experimental infection of calves with bovine viral diarrhea virus genotype II (NY-93)". Journal of Veterinary Diagnostic Investigation, vol. 11, 1999, pp. 221-228.
Paoletti et al., "Highly attenuated poxvirus vectors: NYVAC, ALVAC and TROVAC". Developments in Biological Standardization, vol. 84, 1995, pp. 159-163.
Paton et al., "Epitope Mapping of the gp53 Envelope Protein of Bovine Viral Diarrhea Virus". Virology, vol. 190, 1992, pp. 763-772.
Pellerin et al., "Identification of a New Group of Bovine Viral Diarrhea Virus Strains Associated with Severe Outbreaks and High Mortalities". Virology, vol. 203, 1994, pp. 260-268.
Racaniello et al., "Cloned Poliovirus Complementary DNA Is Infectious in Mammalian Cells". Science, vol. 214, Nov. 1981, pp. 916-919.
Ramig, R.F., "Principles of Animal Virus Genetics". in Fundamental Virology, Second Edition, Raven Press, New York, New York 1991, pp. 96-122.
Rice et al., "Transcription of infectious yellow fever RNA from full-length cDNA templates produced by in vitro ligation". The New Biologist, vol. 1, No. 3, Dec. 1989, pp. 285-296.
Rice, Charles M., "Flaviviridae: The Viruses and Their Replication" in Fields Virology (3rd Edition), Lippincott-Raven Publishers, Philadelphia, PA, 1996, pp. 931-959.
Ridpath et al., "The Genomic Sequence of a Virulent Bovine Viral Diarrhea Virus (BVDV) from the Type 2 Genotype: Detection of a Large Genomic Insertion in a Noncytopathic BVDV". Virology, vol. 212, No. 1, Sep. 1995, pp. 39-46.
Ruggli et al., "Nucleotide Sequence of Classical Swine Fever Virus Strain Alfort/187 and Transription of Infectious RNA from Stably Cloned Full-Length cDNA".Journal of Virology, vol. 70, No. 6, Jun. 1996, pp. 3478-3487.
Rümenapf et al., "N-Terminal Protease of Pestiviruses: Identification of Putative Catalytic Residues by Site-Directed Mutagenesis" Journal of Virology, vol. 72, No. 3, Mar. 1998, pp. 2544-2547.
Rümenapf et al., "Processing of the Envelope Glycoproteins of Pestiviruses". Journal of Virology, vol. 67, No. 6, Jun. 1993, pp. 3288-3294.
Schaefer et al., "Revolutions in Rapid Amplification of cDNA Ends: New Strategies for Polymerase Chain Reaction Cloning of Full-Length cDNA Ends". Analytical Biochemistry, vol. 277, 1995, pp. 255-273.
Schneider et al., "Identifitication of a Structural Glycoprotein of an RNA Virus as a Ribonuclease". Science, vol. 261, Aug. 1993, pp. 1169-1171.
Sequence Alignment Provided of SEQ ID No. 1 with GenEmbl database accession No. BVU18059, submitted Dec. 7, 1995.
Stark et al., "Processing of *Pestivirus* Polyprotein: Cleavage Site between Autoprotease and Nucleocapsid Protein of Classical Swine Fever Virus". Journal of Virology, vol. 67, No. 12, Dec. 1993, pp. 7088-7095.
Stedman's Medical Dictionary. 27th Edition, Internet edition. Definition of "Vaccine". http://www.pdrel.com/pdr/static.htm?path=pdrel/stedmans/v/s43000.htm., Accessed on Aug. 14, 2002.
Stoffregen et al., "Morphologic lesions in type 2 BVDV infections experimentally induced by strain BVDV2-1373 recovered from a field case". Veterinary Microbiology, vol. 77, 2000, pp. 157-162.
Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.
Thiel et al., "Hog Cholera Virus: Molecular Composition ofo Virions from a *Pestivirus*". Journal of Virology, vol. 65, No. 9, Sep. 1991, pp. 4705-4712.
Thiel et al., "Pestiviruses" in Fields Virology (3rd Edition), Lippincott-Raven Publishers, Philadelphia, PA, 1996, pp. 1059-1073.
Tijssen et al., "Immunodominant E2 (gp53) Sequences of Highly Virulent Bovine Viral Diarrhea Group II Viruses Indicate a Close resemblance to a Subgroup of Border Disease Viruses". Virology, vol. 217, 1996, pp. 356-361.
Topliff et al., "Virulence Markers in the 5' Untranslated Region of Genotype 2 Bovine Viral Diarrhea Virus Isolates". Virology, vol. 250, 1998, pp. 164-172.
Tratschin et al., "Classical Swine Fever Virus Leader Proteinase NPRO Is Not Required for Viral Replication in Cell Culture". Journal of Virology, vol. 72, No. 9, Sep. 1998, pp. 7681-7684.
Van Der Poel et al., "Experimental Reproduction of Respiratory Disease in Calves with Non-Cell-Culture-Passaged Bovine Respiratory Syncytial Virus". The Veterinary Quarterly, vol. 18, No. 3, Sep. 1996, pp. 81-86.
Van Gennip et al., "Experimental non-transmissible marker vaccines for classical swine fever (CSF) by trans-complementation of Erns or E2 of CSFV". Vaccine, vol. 20, Nos. 11-12, Feb. 2002, pp. 1544-1556.
Van Gennip, et al., "Recovery of infectious classical swine fever virus (CSFV) from full-length genomic cDNA clones by a swine kidney cell line expressing bacteriophage T7 RNA polymerase". Journal of Virological Methods, vol. 78, 1999, pp. 117-128.
Van Oirschot et al., "Vaccination of cattle against bovine viral diarrhoea". Veterinary Microbiology, vol. 64, 1999, pp. 169-183.
Van Rijn et al., "Epitope mapping of envelope glycoprotein E1 of hog cholera virus strain Brescia". Journal of General Virology, vol. 74, 1993, pp. 2053-2060.
Vassilev et al., "Authentic and Chimeric Full-Length Genomic cDNA Clones of Bovine Viral Diarrhea Virus That Yield Infectious Transcripts". Journal of Virology, vol. 71, No. 1, Jan. 1997, pp. 471-478.
Walker et al., "Deoxyribonucleic Acid Relatedness Among "*Haemophilus somnus,*" "*Haemophilus agni,*" "*Histophilus ovis,*" "*Actinobacillus seminis,*" and *Haemophilus influenzae*". Jan. 1985, International Journal of Systematic Bacteriology, vol. 35, No. 1, pp. 46-49.
Weiland et al., "A Second Envelope Glycoprotein Mediates Neutralization of a Pestivirus, Hog Cholera Virus". Journal of Virology, vol. 66, No. 6, Jun. 1992, pp. 3677-3682.
Weiland et al., "Development of monoclonal neutralizing antibodies against bovine viral diarrhea virus after pretreatment of mice with normal bovine cells and cyclophosphamide". Journal of Virological Methods, vol. 24, 1989, pp. 237-244.
Weiland et al., "*Pestivirus* Glycoprotein Which Induces Neutralizing Antibodies Forms Part of a Disulfide-Linked Heterodimer". Journal of Virology, vol. 64, No. 8, Aug. 1990, pp. 3563-3569.
Windisch et al., "RNase of Classical Swine Fever Virus: Biochemical Characterization and Inhibition by Virus-Neutralizing Monoclonal Antibodies". Journal of Virology, vol. 70, No. 1, Jan. 1996, pp. 352-358.
Yu et al., "Genetic engineering of a *Lymantria dispar* nuclear polyhedrosis virus for expression of foreign genes". Journal of General Virology, vol. 73, 1992, pp. 1509-1514.
van Gennip, et al., "Dimerisation of glycoprotein Erns of classical swine fever virus is not essential for viral replication and infection". 2005, Archives of Virology, vol. 150, pp. 2271-2286.
International Search Report PCT/EP2009/057911 mailed on Jul. 9, 2009.
Avalos-Ramirez, et al., "Evidence for the Presence of Two Novel *Pestivirus* Species". Virology, vol. 286, 2001, pp. 456-465.
Baker et al., "Bovine viral diarrhea virus: A review". Journal of the American Veterinary Medical Association, vol. 190, No. 11, Jun. 1987, pp. 1449-1458.
Becher et al., "Further Characterization of Border Disease Virus Isolates: Evidence for the Presence of More than Three Species within the Genus *Pestivirus*". Virology, vol. 209, 1995, pp. 200-206.
Becher et al., "Phylogenetic analysis of pestiviruses from domestic and wild ruminants". Journal of General Virology, vol. 78, 1997, pp. 1357-1366.
Beer et al., "A new inactivated BVDV genotype I and II vaccine: An immunisation and challenge study with BVDV genotype I". Veterinary Microbiology, vol. 77, 2000, pp. 195-208.

(56) References Cited

OTHER PUBLICATIONS

Behrens et al., "Characterization of an Autonomous Subgenomic *Pestivirus* RNA Replicon". Journal of Virology, vol. 72, No. 3, Mar. 1998, pp. 2364-2372.

Bolin et al., "Assessment of protection from systemic infection or disease afforded by low to intermediate titers of passively acquired neutralizing antibody against bovine viral diarrhea virus in calves". American Journal of Veterinary Research, vol. 56, 1995, pp. 755-759.

Bolin, S. R., "Control of Bovine Viral Diarrhea Infection by Use of Vaccination". Veterinary Clinics of North America: Food Animal Practice, vol. 11, No. 3, Nov. 1995, pp. 615-625.

Bowie et al., "Deciphering the Message in Protein Sequences: Tolerance to Amino Acid Substitutions". Science, vol. 247, 1990, pp. 1306-1310.

Boyer et al., "Infectious Transcripts and cDNA Clones of RNA Viruses". Virology, vol. 198, 1994, pp. 415-426.

Brock et al., "Nucleotide sequencing of 5' and 3' termini of bovine viral diarrhea virus by RNA ligation and PCR". Journal of Virological Methods, vol. 38, 1992, pp. 39-46.

Carman et al., "Sever acute bovine viral diarrhea in Ontario, 1993-1995". Journal of Veterinary Diagnostic Investigation, vol. 10, 1998, pp. 27-35.

Chambers et al., "Mutagenesis of the Yellow Fever Virus NS2B Protein: Effects on Proteolytic Processing, NS2B-NS3 Complex Formation, and Viral Replication". Journal of Virology, vol. 67, No. 11, Nov. 1993, pp. 6797-6807.

Chon et al., "Genetic Analysis of the Internal Ribosome Entry Segment of Bovine Viral Diarrhea Virus". Virology, vol. 251, 1998, pp. 370-382.

Chong et al., "Modulation of Protein Splicing of the *Saccharomyces cerevisiae* Vacuolar Membrane ATPase Intein*". Apr. 1998, The Journal of Biological Chemistry, vol. 272, No. 17, pp. 10567-10577.

Collett et al., "Molecular Cloning and Nucleotide Sequence of the *Pestivirus* Bovine Viral Diarrhea Virus". Virology, vol. 165, 1988, pp. 191-199.

Collett et al., "Proteins Encoded by Bovine Viral Diarrhea Virus: The Genomic Organization of a *Pestivirus*". Virology, vol. 165, 1988, pp. 200-208.

Constans et al., "Recent developments in RT-PCR technology move reverse transcription in the right direction". The Scientist-Reverse Psychology, vol. 14[17]: Sep. 29, 2000, pp. 1-4.

Cortese et al., "Clinical and immunologic responses of vaccinated and unvaccinated calves to infection with a virulent type-II isolate of bovine viral diarrhea virus". Journal of the American Veterinary Medical Association, vol. 213, No. 9, Nov. 1998, pp. 1312-1319.

Cortese et al., "Specificity and Duration of Neutralizing Antibodies Induced in Healthy Cattle After Administration of a Modified-Live Virus Vaccine Against Bovine Viral Diarrhea". American Journal of Veterinary Research, vol. 59, 1998, pp. 848-850.

Database EMBL Online! retrieved from EMBL Database accession No. AF145967 XP002251610. (As cited in ISR for PCT/EP2002/09925), Jun. 1999.

De Smit et al., "Duration of the protection of an E2 subunit marker vaccine against classical swine fever after a single vaccination". Veterinary Microbiology, vol. 78, 2001, pp. 307-317.

Donis et al., "Neutralizing Monoclonal Antibodies to Bovine Viral Diarrhoea Virus Bind to the 56k to 58k Glycoprotein". Journal of General Virology, vol. 69, 1988, pp. 77-86.

European Search Report for EP02003408 dated Dec. 15, 2003.

Fekadu et al., "Immunogenicity, efficacy and safety of an oral rabies vaccine (SAG-2) in dogs". Vaccine, vol. 14, No. 6, 1996, pp. 465-468.

Fuerst et al., "Eukaryotic transient-expression system based on recombinant vaccinia virus that synthesizes bacteriophage T7 RNA polymerase". Nov. 1986, Proceedings of the National Academy of Sciences, vol. 83, pp. 8122-8126.

Fulton et al., "Bovine viral diarrhea virus types 1 and 2 antibody response in calves receiving modified live virus or inactivated vaccines". Vaccine, vol. 19, 2001, pp. 264-274.

Grebennikova et al., "Genetic Characteristics of Hog Cholera Virus Vaccine Strains: Comparative Analysis of Primary Sequences of Surface Glycoprotein Ems, E1 and E2 Genes". Mol. Gen. Mikrobiol. Virusol., vol. 2, Jan. 1999, pp. 34-40. (See Abstract at p. 40).

Greenspan et al., "Defining epitopes: It's not as easy as it seems". Nature Biotechnology, vol. 17, Oct. 1999, pp. 936-937.

Gu et al., "The RNA Helicase and Nucleotide Triphosphatase Activities of the Bovine Viral Diarrhea Virus NS3 Protein Are Essential for Viral Replication". Journal of Virology, vol. 74, No. 4, Feb. 2000, pp. 1794-1800.

Heinz, et al., "Family Flaviviridae". 2000, Virus Taxonomy: Classification and Nomenclature of Viruses, Academic Press, Sand Diego, pp. 859-878.

Houe et al., "Application of antibody titers against bovine viral diarrhea virus (BVDV) as a measure to detect herds with cattle persistently infected with BVDV". Journal of Veterinary Diagnostic Investigation, vol. 7, 1995, pp. 327-332.

Huang, et al., "An in vitro ligation and transfection system for inserting DNA sequences into the latency-associated transcripts (LATs) gene of herpes simplex virus type 1". Gene Therapy, vol. 1, 1994, pp. 300-306.

Hulst et al., "Glycoprotein E2 of Classical Swine Fever Virus: Expression in Insect Cells and Identification as a Ribonuclease". Virology, vol. 200, 1994, pp. 558-565.

Hulst et al., "Inactivation of the RNase Activity of Glycoprotein Ems of Classical Swine Fever Virus Results in a Cytopathogenic Virus". Journal of Virology, vol. 72, No. 1, Jan. 1998, pp. 151-157.

International Search Report and Written Opinion for PCT/EP2009/057911 mailed on Sep. 7, 2009.

Kit et al., "Sensitive glycoprotein gIII blocking ELISA to distinguish between pseudorabies (Aujeszky's disease)—infected and vaccinated pigs". Veterinary Microbiology, vol. 28, 1991, pp. 141-155.

Kovacs et al., "The live attenuated bovine viral diarrhea virus components of a multi-valent vaccine confer protection against fetal infection". 2003, Veterinary Microbiology, vol. 96, pp. 117-131.

Kunkel et al., "Rapid and Efficient Site-Specific Mutagenesis without Phenotypic Selection". 1987, Methods of Enzymology, vol. 154, pp. 367-392.

Kupfermann et al., "Bovine Viral Diarrhea Virus: Characterization of a Cytopathogenic Defective Interfering Particle with Two Internal Deletions". Journal of Virology, vol. 70, No. 11, Nov. 1996, pp. 8175-8181.

Kümmerer et al., "Correlation between Point Mutations in NS2 and the Viability and Cytopathogenicity of Bovine Viral Diarrhea Virus Strain Oregon Analysed with and Infectious cDNA Clone". Journal of Virology, vol. 74, No. 1, Jan. 2000, pp. 390-400.

Lai et al., "Infectious RNA transcribed from stably cloned full-length cDNA of dengue type 4 virus". Proceedings of the National Academy of Sciences of the United States of America, vol. 8, Jun. 1991, pp. 5139-5143.

Lindenbach et al., "Flaviviridae: The Viruses and Their Replication". 2001, Fields Virology, Fourth Edition, Lippincott Williams & Wilkins, Philadelphia, pp. 991-1041.

Mayer et al., "Attenuation of classical swine fever virus by deletion of the viral Npro gene". Vaccine, vol. 22, Nos. 3-4, Jan. 2004, pp. 317-328.

Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys". Journal of Virology, vol. 70, No. 6, Jun. 1996, pp. 3930-3937.

Mendez et al., "Infectious Bovine Viral Diarrhea Virus (Strain NADL) RNA from Stable cDNA Clones: a Cellular Insert Determines NS3 production and Viral Cytopathogenicity". Journal of Virology, vol. 72, No. 6, Jun. 1998, pp. 4737-4745.

Meyer et al., "Recovery of Virulent and RNase-Negative Attenuated Type 2 Bovine Viral Diarrhea Viruses from Infectious cDNA Clones". Journal of Virology, vol. 76, No. 16, Aug. 2002, pp. 8494-8503.

Meyers et al. "Rabbit Hemorrhagic Disease Virus: Genome Organization and Polyprotein Processing of a Calicivirus Studied after Transient Expression of cDNA Constructs". 2000, Virology, vol. 276, pp. 349-363.

(56) References Cited

OTHER PUBLICATIONS

Meyers et al., "Bovine Viral Diarrhea Virus: Prevention of Persistent Fetal Infection by a Combination of Two Mutations Affecting Erns RNase and Npro Protease". Journal of Virology, vol. 81, No. 7, Apr. 2007, pp. 3327-3338.

Meyers et al., "Classical Swine Fever Virus: Recovery of Infectious Viruses from cDNA Constructs and Generation of Recombinant Cytopathogenic Defective Interfering Particles". Journal of Virology, vol. 70, No. 3, Mar. 1996, pp. 1588-1595.
Platt et al., "Comparison of humoral and cellular immune response to a pentavalent modified live virus vaccine in three age groups of calves with maternal antibodies, before and after BVDV type 2 challenge". Vaccine, vol. 27, 2009, pp. 4508-4519.
Neill et al., "Recombination with a cellular mRNA encoding a novel DnaJ protein results in biotype conversion in genotype 2 bovine viral diarrhea viruses". Virus Research, vol. 79, 2001, pp. 59-69.
McClurkin et al., "Comparison of Low- and High-Passage Bovine Turbinate Cells for Assay and Bovine Viral Diarrhea Virus". Archly Mr die gesamte Virusforschung, vol. 45, 1974, pp. 285-289.

* cited by examiner

US 8,895,026 B2

ATTENUATED PESTIVIRUS

This application is the national phase entry under 35 U.S.C. §371 of International Application No. PCT/EP2009/057911, filed Jun. 24, 2009, that claims priority to European Patent Application No. 08159009.3, which was filed Jun. 25, 2008. These applications are hereby incorporated by reference in their entireties.

SEQUENCE LISTING

The present application includes a sequence listing in accordance with 37 C.F.R. 1.821-1.825. The sequence listing accompanying this application is hereby incorporated by reference in its entirety.

BACKGROUND OF THE INVENTION

1. Technical Field

The present invention relates to the field of animal health and in particular to attenuated pestiviruses such as classical swine fever virus (CSFV), bovine viral diarrhea virus (BVDV) or border disease virus (BDV).

2. Background Information

Pestiviruses are causative agents of economically important diseases of animals in many countries worldwide. Presently known virus isolates have been grouped into four different species which together form one genus within the family Flaviviridae.

I/II Bovine viral diarrhea virus (BVDV) type 1 (BVDV-1) and type 2 (BVDV-2) cause bovine viral diarrhea (BVD) and mucosal disease (MD) in cattle (Baker, 1987; Moennig and Plagemann, 1992; Thiel et al., 1996). The division of BVDV into 2 species is based on significant differences at the level of genomic sequences (summarized in Heinz et al., 2000) which are also obvious from limited cross neutralizing antibody reactions (Ridpath et al. 1994).

III Classical swine fever virus (CSFV), formerly named hog cholera virus, is responsible for classical swine fever (CSF) or hog cholera (HC) (Moennig and Plagemann, 1992; Thiel et al., 1996).

IV Border disease virus (BDV) is typically found in sheep and causes border disease (BD). After intrauterine infection of lambs with BDV persistently infected lambs can be born that are weak and show different abnormalities among which the 'hairy shaker' syndrome is best known (Moennig and Plagemann, 1992; Thiel et al., 1996).

Pestiviruses are small enveloped viruses with a single stranded RNA genome of positive polarity lacking both 5' cap and 3' poly(A) sequences. The viral genome codes for a polyprotein of about 4000 amino acids giving rise to final cleavage products by co- and posttranslational processing involving cellular and viral proteases. The viral proteins are arranged in the polyprotein in the order $NH_2$-$NP^{pro}$-C-$E^{rns}$-E1-E2-p7-NS2-NS3-NS4A-NS4B-NS5A-NS5B-COOH (Lindenbach and Rice, 2001). Protein C (=core- or capsid-protein) and the glycoproteins $E^{rns}$, E1 and E2 represent structural components of the pestivirus virion as demonstrated for CSFV (Thiel et al., 1991). This also holds true for BVDV. E2 and to a lesser extent $E^{rns}$ were found to be targets for antibody neutralization (Donis et al., 1988; Paton et al., 1992; van Rijn et al., 1993; Weiland et al., 1990, 1992). $E^{rns}$ lacks a typical membrane anchor and is secreted in considerable amounts from the infected cells; this protein has been reported to exhibit RNase activity (Hulst et al., 1994; Schneider et al., 1993; Windisch et al., 1996). The function of this enzymatic activity for the viral life cycle is presently unknown. The enzymatic activity depends on the presence of two stretches of amino acids conserved between the pestivirus $E^{rns}$ and different known RNases of plant and fungal origin. Both of these conserved sequences contain a histidine residue (Schneider et al., 1993). Inactivation of the RNase activity residing within the $E^{rns}$ results in an attenuated apathogenic pestivirus which is capable to be used as a modified live vaccine (WO 99/64604).

The pestivirus glycoprotein $E^{rns}$ is expressed on the surface of virions and in infected cells as a disulfide-linked homodimer. The most C-terminal cysteine residue forms the intermolecular disulfide bond between two $E^{rns}$ monomers, resulting in the $E^{rns}$ homodimer (Schneider et al., 1993). Recently it has been reported for CSFV that a substitution of the most C-terminal cysteine against serine results in a viable CSFV, which, however, lacks the ability to form any $E^{rns}$ homodimers (van Gennip et al., 2005).

$N^{pro}$ represents the first protein encoded by the long open reading frame in the pestivirus RNA. $N^{pro}$ represents a nonstructural protein that has protease activity and cleaves itself of the nascent polyprotein (Stark et al., 1993; Wiskerchen et al., 1991) presumably already during translation. $N^{pro}$ is a cysteine protease (Rümenapf et al., 1998) that is not essential for virus replication (Tratschin et al., 1998). Recently, it was shown that $N^{pro}$ somehow interferes with the cellular antiviral defense so that it can be hypothesized to modulate the immune system within an infected host (Rüggli et al., 2003). Mayer and coworkers presented indications for an attenuation of CSFV in consequence of a deletion of the $N^{pro}$ gene (Mayer et al., 2004).

Present BVDV vaccines for the prevention and treatment of BVDV infections still have drawbacks (Oirschot et al. 1999). Vaccines against the classical BVDV-1 provide only partial protection from BVDV-2 infection, and vaccinated dams may produce calves that are persistently infected with virulent BVDV-2 (Bolin et al., 1991, Ridpath et al., 1994). This problem is probably due to the great antigenic diversity between type 1 and type 2 strains which is most pronounced in the glycoprotein E2, the major antigen for virus neutralization (Tijssen et al., 1996). Most monoclonal antibodies against type 1 strains fail to bind to type 2 viruses (Ridpath et al., 1994).

Vaccines comprising attenuated or killed viruses or viral proteins expressed in heterologous expression systems have been generated for CSFV and BVDV and are presently used. Conventional BVDV life vaccines are typically generated by cell culture passages resulting in viruses with attenuated virulence in the target species. The structural basis of the attenuation of BVDV used as life vaccines is not known. Therefore it is not possible to assess the molecular stability of the attenuation process. These vaccines, although attenuated, are most often associated with safety problems regarding use in breeding animals. The vaccine viruses may cross the placenta of pregnant animals, e.g. cows and lead to clinical manifestations in the fetus and/or the induction of persistently infected calves. The international patent application WO2005/111201 provides a new generation of a modified live pestivirus vaccine, which comprises a multiple modified pestivirus, having at least one mutation in the coding sequence for glycoprotein $E^{rns}$ and at least another mutation in the coding sequence for $N^{pro}$, wherein said mutation in the coding sequence for glycoprotein $E^{rns}$ leads to inactivation of RNase activity residing in $E^{rns}$ and/or said mutation in the coding sequence for $N^{pro}$ leads to inactivation of said $N^{pro}$.

However, in view of the importance of an effective and safe as well as detectable prophylaxis and treatment of pestiviral infections, there is a strong need for attenuated pestiviruses, such as BVDV, with a high potential for induction of immunity as well as a defined basis of attenuation which can also be distinguished from pathogenic pestiviruses, such as BVDV, as well as compositions and vaccines comprising said attenuated pestiviruses, such as BVDV.

Therefore, the technical problem underlying the present invention is to provide new attenuated pestiviruses, preferably an attenuated BVDV for use as live attenuated vaccines. Such improved attenuated pestivirus, preferably BVDV, should especially (i) not cross the placenta themselves and (ii) induce an immunity that prevents viral transmission across the placenta and thereby prevents pregnancy problems like abortion of the fetus or birth of persistently calves from infected host animals in the case of BVDV infection.

Figure 1:
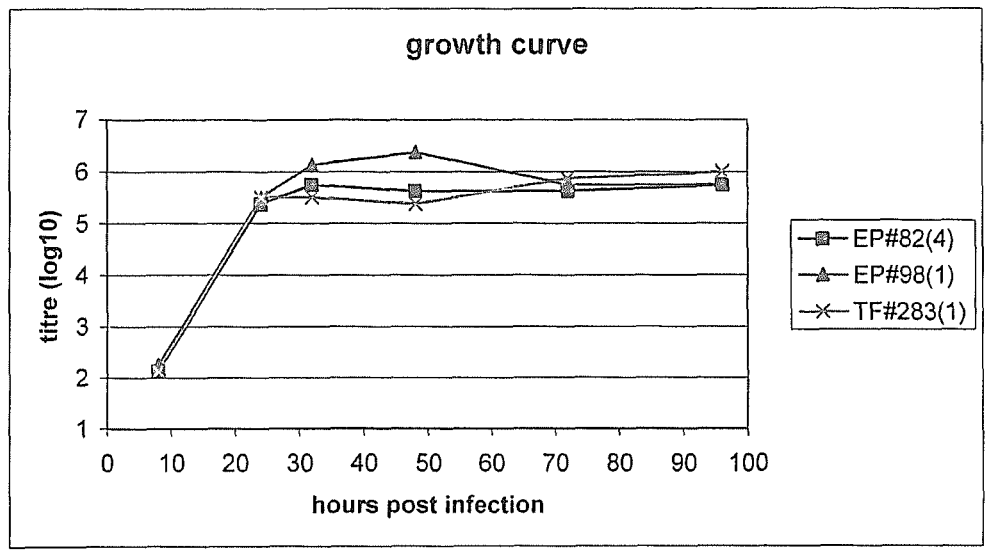
FIG. 1: Growth curves of viruses EP #82(4), EP #98(1) and TF #283(1).
Figure 2:
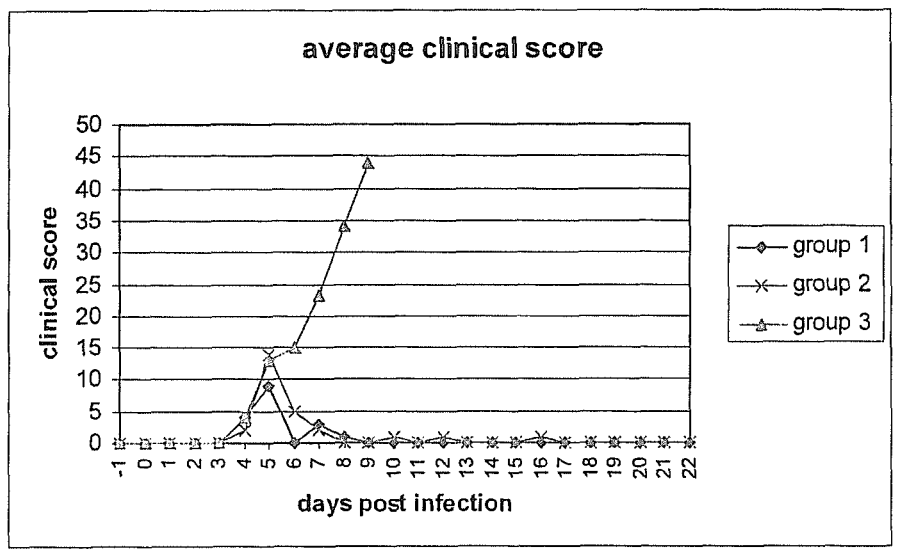
FIG. 2: average clinical score for group 1/2/3
Figure 3:
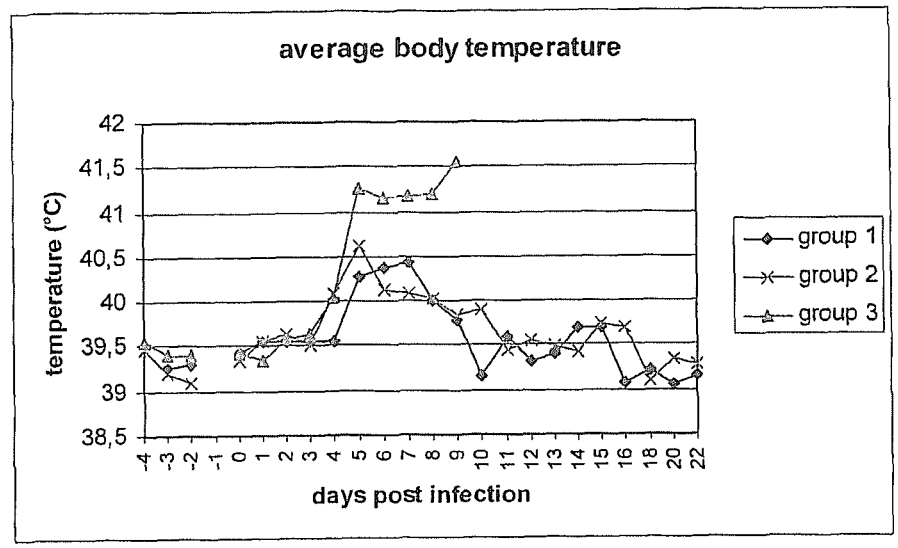
FIG. 3: average body temperature of group 1/2/3
Figure 4:
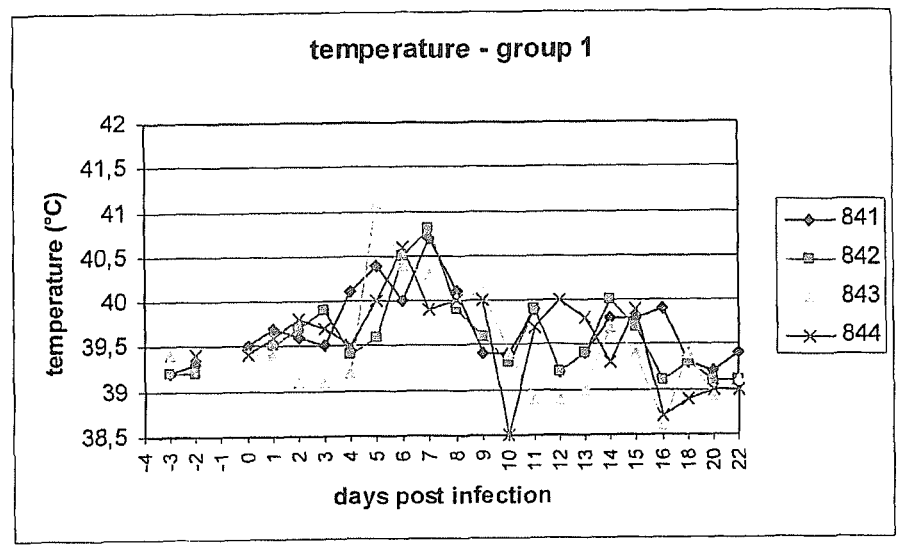
FIG. 4: body temperature of group 1 infected with TF #283 (1)
Figure 5:
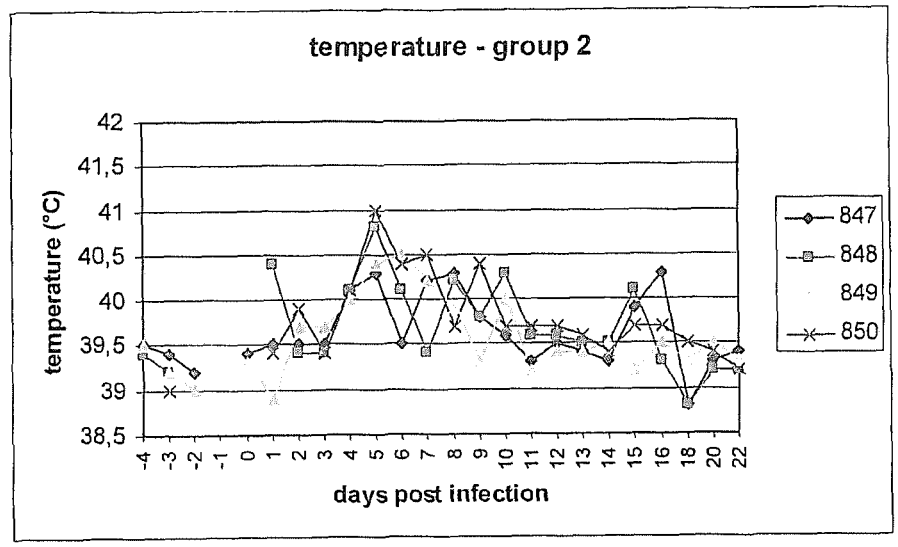
FIG. 5: body temperature of group 2 infected with EP #82 (4)
Figure 6:
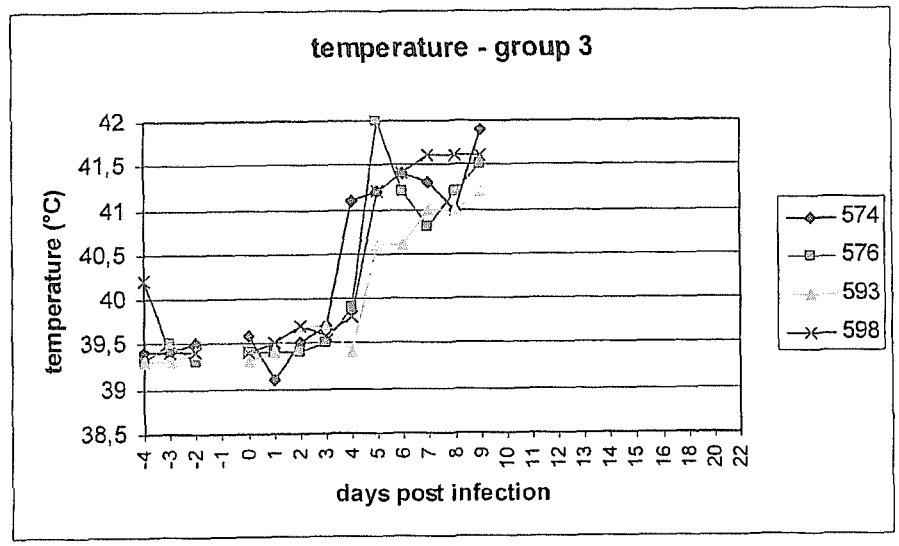
FIG. 6: body temperature of group 3 infected with TF #1347/TF #230/3
Figure 7:
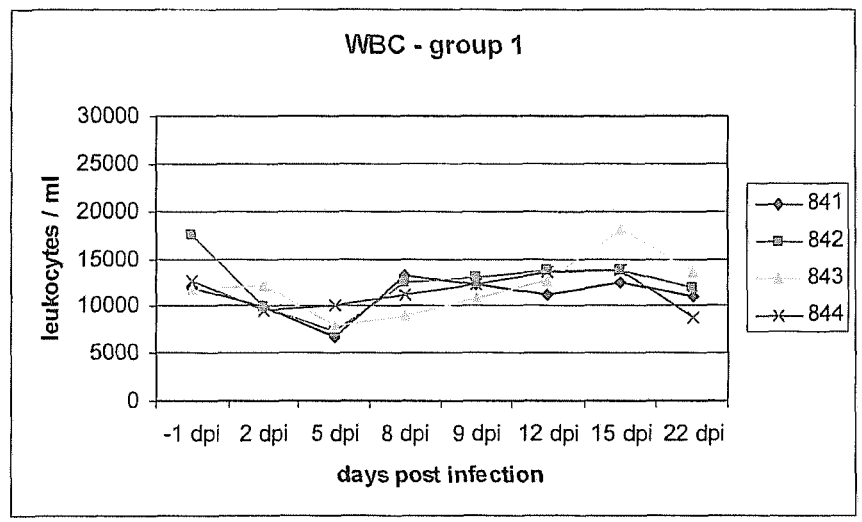
FIG. 7: WBC counts of group 1
Figure 8:
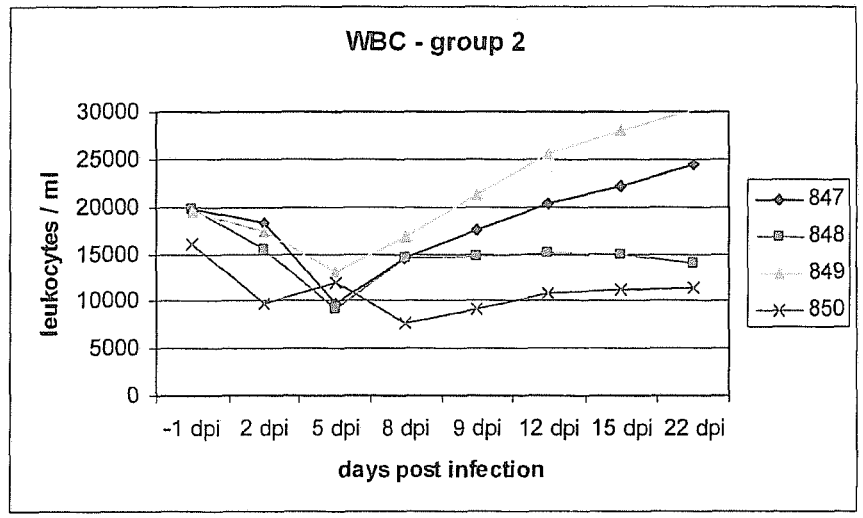
FIG. 8: WBC counts of group 2
Figure 9:
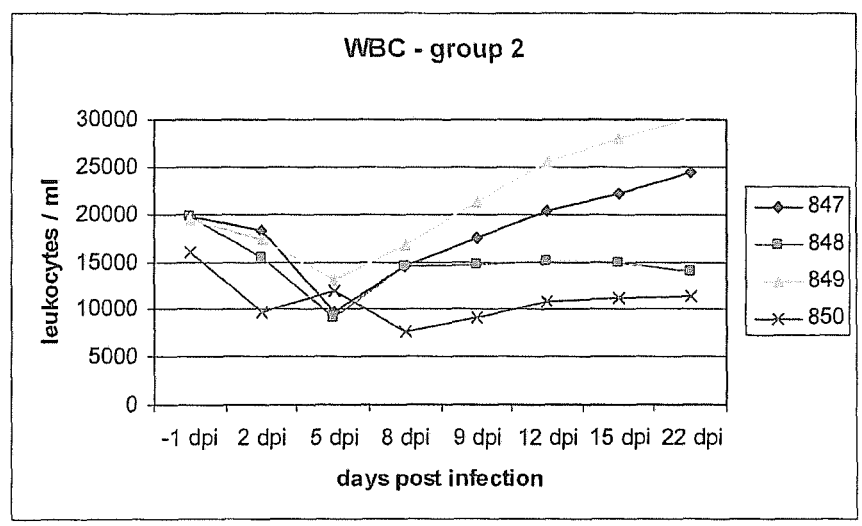
FIG. 9: WBC counts of group 3

All subsequent Sequences are depicting the deleted regions with dashes (_d), which are also numbered, whereas the sequences in the sequence listing attached hereto are continuously numbered without the deleted regions or amino acid codons.

SEQ ID NO:1 (CSFV_wt) amino acid sequence of CSFV wildtype

SEQ ID NO:2 (CSFV_d) amino acid sequence of CSFV comprising a deletion of cystein at amino acid position 438 as compared to SEQ ID NO:1

SEQ ID NO:3 (CSFV_S) amino acid sequence of CSFV comprising a cystein/serine substitution at amino acid position 438 as compared to SEQ ID NO:1

SEQ ID NO:4 (BVDV_Ke9_wt) amino acid sequence of BVDV type 1 wildtype

SEQ ID NO:5 (BVDV_Ke9_d) amino acid sequence of BVDV type 1 comprising a deletion of cystein at amino acid position 441 as compared to SEQ ID NO:4

SEQ ID NO:6 (BVDV_Ke9_S) amino acid sequence of BVDV type 1 comprising a cystein/serine substitution at amino acid position 441 as compared to SEQ ID NO:4

SEQ ID NO:7 (BVDV_NY_wt) amino acid sequence of BVDV type 2 wildtype

SEQ ID NO:8 (BVDV_NY_d) amino acid sequence of BVDV type 2 comprising a deletion of cystein at amino acid position 441 as compared to SEQ ID NO:7

SEQ ID NO:9 (BVDV_NY_S) amino acid sequence of BVDV type 2 comprising a cystein/serine substitution at amino acid position 441 as compared to SEQ ID NO:7

SEQ ID NO:10 (BDV_x818_wt) amino acid sequence of BDV wildtype

SEQ ID NO:11 (BDV_x818_d) amino acid sequence of BDV comprising a deletion of cystein at amino acid position 439 as compared to SEQ ID NO:10

SEQ ID NO:12 (BDV_x818_S) amino acid sequence of BDV comprising a cystein/serine substitution at amino acid position 439 as compared to SEQ ID NO:10

BRIEF SUMMARY OF THE INVENTION

It has surprisingly been found that a modification in the coding region of the $E^{rns}$ glycoprotein of a pestivirus, which results in the lack of homodimer formation of the $E^{rns}$ glycoprotein, leads to an attenuated pestivirus. Such attenuated pestiviruses can be used as modified live vaccine for the prophylaxis and/or treatment of pestivirus infections. Hence, one aspect of the present patent application relates to a recombinant attenuated pestivirus, wherein said recombinant attenuated pestivirus does not produce a dimeric $E^{rns}$ glycoprotein. Preferably, that pestivirus is selected from the group consisting of CSFV, BVDV and BDV, including any subtype of any of these pestiviruses.

It is known from the international patent application WO2005/111201 that pestiviruses attenuated by a modification within the $E^{rns}$ glycoprotein as well as in the $N^{pro}$ protein show a higher safety level in terms of the prevention of fetal infections by the vaccine virus. Therefore, according to a further aspect, the present invention also relates to attenuated pestiviruses, wherein said attenuated pestiviruses do not produce a dimeric $E^{rns}$ glycoprotein and having at least a mutation in the $N^{pro}$ protein, wherein said mutation in the $N^{pro}$ protein leads to inactivation of said $N^{pro}$ protein. Preferably, that pestivirus is selected from the group consisting of CSFV, BVDV and BDV, including any subtype of any of these pestiviruses.

Any of the attenuated pestiviruses mentioned above are suitable vaccine candidates for developing a modified live vaccine for the prophylaxis and/or treatment of pestivirus infections. Thus, according to a further aspect, the present invention relates to an immunogenic composition comprising an attenuated pestivirus, wherein said attenuated pestivirus does not produce a dimeric $E^{rns}$ glycoprotein. Preferably, that pestivirus has at least a further mutation in the $NP^{pro}$ protein, wherein said mutation in the $NP^{pro}$ protein leads to inactivation of said $NP^{pro}$ protein. Preferred pestiviruses are selected from the group consisting of CSFV, BVDV and BDV, including any subtype of any of these pestiviruses.

According to a further aspect, the present invention also relates to a method for attenuating a pestivirus, comprising modifications in the $E^{rns}$ glycoprotein of said pestivirus in such that said attenuated pestivirus does not produce a dimeric $E^{rns}$ glycoprotein. Preferably, that pestivirus is selected from the group consisting of CSFV, BVDV and BDV, including any subtype of any of these pestiviruses.

DETAILED DESCRIPTION OF THE INVENTION

Definitions of Terms Used in the Description

Before the embodiments of the present invention it must be noted that as used herein and in the appended claims, the singular forms "a", "an", and "the" include plural reference unless the context clearly dictates otherwise. Thus, for example, reference to "a BVDV" includes a plurality of such BVDV, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The term "pestivirus" as used herein refers to all members of the genus Pestivirus, including BVDV, CSFV and BDV, within the family Flaviviridae.

The term "CSFV" as used herein refers to all viruses belonging to species of classical swine fever virus (CSFV) in the genus Pestivirus within the family Flaviviridae.

The term "BVDV" as used herein refers to all viruses belonging to species bovine viral diarrhea virus (BVDV) type 1 (BVDV-1) and BVDV type 2 (BVDV-2) in the genus Pestivirus within the family Flaviviridae (Heinz et al., 2000). The more classical BVDV type 1 strains and the more recently recognized BVDV type 2 strains display some limited but distinctive differences in nucleotide and amino acid sequences.

The term "$N^{pro}$" as understood herein relates to the first protein encoded by the viral open reading frame and cleaves itself from the rest of the synthesized polyprotein (Stark, et al., J. Virol. 67:7088-7093 (1993); Wiskerchen, et al., Virol. 65:4508-4514 (1991)). Said term, depending on the context, may also relate to the remaining "$N^{pro}$" amino acids after mutation of the encoding nucleotide sequence or to the coding nucleotide sequence for said protein itself. "Protease activity residing in $N^{pro}$" relates to the polypeptide cleavage activity of said "$N^{pro}$".

"$E^{rns}$" as used herein relates to the glycoprotein $E^{rns}$ which represents a structural component of the pestivirus virion (Thiel et al., 1991). $E^{rns}$ lacks a typical membrane anchor and is secreted in considerable amounts from the infected cells; this protein has been reported to exhibit RNase activity (Hulst et al., 1994; Schneider et al., 1993; Windisch et al., 1996). It should be noted that the term glycoprotein E0 is often used synonymously to glycoprotein $E^{rns}$ in publications. Said term, depending on the context, may also relate to the mutated "$E^{rns}$" protein after mutation of the encoding nucleotide sequence or to the coding nucleotide sequence for said protein itself. "RNase activity residing in glycoprotein $E^{rns}$" relates to the RNA cleavage activity of said glycoprotein, i.e. the ability of the glycoprotein $E^{rns}$ to hydrolyze RNA. The term "inactivation of the RNase activity residing in said glycoprotein" refers to the inability or reduced capability of a modified glycoprotein $E^{rns}$ to hydrolyze RNA as compared to the unmodified wild type of said glycoprotein $E^{rns}$.

Attenuation: "An attenuated pestivirus or BVDV particle" as used herein means that there is a statistically significant difference between the virulence of attenuated pestivirus or BVDV particles of the present invention, wherein said attenuated viral particles being attenuated by a method described herein, and wild-type pestivirus or BVDV isolates from which said attenuated pestivirus or BVDV particles have been derived, for the predominant clinical parameters, in case of BVDV for diarrhea, pyrexia and lethality in animals infected with the same dose, preferably $6 \times 10^6$ $TCID_{50}$. Thus, said attenuated BVDV particles do not cause diarrhea, pyrexia and lethality and thus may be used in a vaccine.

Inactivation of $E^{rns}$ as used herein means RNase activity not significantly above the level measured for noninfected control cells in an RNase assay as described in Meyers et al., 1999. "Not significantly above the level measured for noninfected control cells in an RNase assay as described in Meyers et al., 1999, means for example, that the RNase activity is less than 150% compared to the noninfected control cells.

Inactivation of $N^{pro}$ as used herein means the prevention or considerable reduction of the probable immunemodulating activity of $N^{pro}$ by mutation. In a preferred embodiment this mutation prevents or considerably reduces the interference of $N^{pro}$ with the induction of an interferon response by the infected cells as described by Rüggli et al., (2003). In this case, the inactivation of $N^{pro}$ would allow the cell to mount a normal interferon response.

The "dimeric $E^{rns}$ glycoproteins" means a homodimer of two monomers of $E^{rns}$ glycoproteins. It should be noted that the two monomers of the $E^{rns}$ glycoprotein which build the homodimer may comprise a certain level of sequence diversity within their amino acid sequence. In this context, "a certain level of sequence diversity" shall mean that the monomers forming the homodimer show at least 80%, preferably 90%, more preferably 95%, even more preferably 98% sequence homology in respect to the amino acid sequence of the $E^{rns}$ gene region.

The term "non-dimeric $E^{rns}$ glycoprotein" shall mean, but is not limited to an $E^{rns}$ glycoprotein that is not capable to form a detectable amount of homodimer with a second $E^{rns}$ glycoprotein. Preferably, the term "non-dimeric $E^{rns}$ glycoprotein" shall mean, but is not limited to an $E^{rns}$ glycoprotein that is not capable to any homodimer with a second $E^{rns}$ glycoprotein "Processing signal" as used herein relates to a substance that ensures the generation of a functional N-terminal of the C protein of the pestivirus, preferably of BVDV, in particular a substance selected from the group of ubiquitin, LC3, SUMO-1, NEDD8, GATE-16 and GABA(A)RAP. Also proteases selected from the group of Intein, picornavirus 3C, caridovirus 2A, and p15 of rabbit hemorrhagic disease virus are understood as "processing signals" as used herein. Similarly, 2A proteins of aphtoviruses or related sequences that promote the expression of two separate proteins by translational discontinuity are included in the term "Processing signal". Any other similar processing signal known to the skilled person that ensures the generation of a functional N-terminal of the C protein shall also be comprised in the term "processing signal".

"Protein C" or "C protein" or "C-protein" as used herein relates to a structural component of the pestivirus virion (Thiel et al., 1991). "Protein C" is the capsid or core protein of pestiviruses. Said term, depending on the context, may also relate to the "Protein C" with one or several amino acids exchanges resulting from mutation of the encoding nucleotide sequence.

A "fragment" according to the invention is any subunit of a polynucleotide molecule according to the invention, i.e. any subset. For DNA, said fragment is characterized in that it is shorter than the DNA covering the full length viral genome.

A "functional variant" of the nucleotide molecule according to the invention is a nucleotide molecule which possesses a biological activity (either functional or structural) that is substantially similar to the nucleotide molecule according to the invention. The term "functional variant" also includes "a fragment", "a functional variant", "variant based on the degenerative nucleic acid code" or "chemical derivative". Such a "functional variant" e.g. may carry one or several nucleotide exchanges, deletions or insertions. Said functional variant at least partially retains its biological activity, e.g. function as an infectious clone or a vaccine strain, or even exhibits improved biological activity. "Possess a biological activity that is substantially similar" means with respect to the pestiviruses provided herewith, for example, that said pestivirus is attenuated in a manner described herein and result in a non-pathogenic virus suitable for the production of live attenuated virus, which loss ability to pass the placenta but mediates an immune response after vaccination.

A "variant based on the degenerative nature of the genetic code" is a variant resulting from the fact that a certain amino acid may be encoded by several different nucleotide triplets. Said variant at least partially retains its biological activity, or even exhibits improved biological activity.

A molecule is "substantially similar" to another molecule if both molecules have substantially similar nucleotide sequences or biological activity. Thus, provided that two molecules possess a similar activity, they are considered variants as that term is used herein if the nucleotide sequence is not identical, and two molecules which have a similar nucleotide sequence are considered variants as that term is used herein even if their biological activity is not identical.

A mutation as used herein relates to modifications in the nucleic acid molecules encoding the proteins/amino acids according to the invention. Said mutations relate to, but are not limited to, substitutions (replacement of one or several nucleotides/base pairs), deletions (removal of one or several nucleotides/base pairs), and/or insertions (addition of one or several nucleotides/base pairs). As used herein, mutation may be a single mutation or several mutations, therefore, often the term "mutation(s)" is used and relates to both a single mutation and several mutations. Said mutations include, but are not limited to point mutations (single nucleotide mutations) or larger mutations wherein e.g. parts of the encoding nucleic acid molecules are deleted, substituted and/or additional coding nucleic acid is inserted. Said mutations may result in a modified expressed polypeptide due to the change in the coding sequence. Such modified polypeptides are desired, as set out in the disclosure of the invention as set out below.

The term "vaccine" as used herein refers to a pharmaceutical composition comprising at least one immunologically active component that induces an immunological response in an animal and possibly but not necessarily one or more additional components that enhance the immunological activity of said active component. A vaccine may additionally comprise further components typical to pharmaceutical compositions. The immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of said organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian other species plus optionally subsequent isolation and purification procedures, or by induction of said synthetic processes in the animal needing a vaccine by direct incorporation of genetic material using suitable pharmaceutical compositions (polynucleotide vaccination). A vaccine may comprise one or simultaneously more than one of the elements described above. The term "vaccine" as understood herein is a vaccine for veterinary use comprising antigenic substances and is administered for the purpose of inducing a specific and active immunity against a disease provoked by a pestivirus infection, preferably by a BVDV infection. The attenuated pestivirus, in particular the attenuated BVDV as described herein, confer active immunity that may be transferred passively via maternal antibodies against the immunogens it contains and sometimes also against antigenically related organisms. A vaccine of the invention refers to a vaccine as defined above, wherein one immunologically active component is a BVDV or of pestiviral origin or derived from a nucleotide sequence that is more than 70% homologous to any known pestivirus sequence (sense or antisense).

The term "live vaccine" refers to a vaccine comprising a living, in particular, a living viral active component.

Additional components to enhance the immune response are constituents commonly referred to as "adjuvants", like e.g. aluminiumhydroxide, mineral or other oils or ancillary molecules added to the vaccine or generated by the body after the respective induction by such additional components, like but not restricted to interferons, interleukins or growth factors.

A "pharmaceutical composition" essentially consists of one or more ingredients capable of modifying physiological e.g. immunological functions of the organism it is administered to, or of organisms living in or on the organism. The term includes, but is not restricted to, antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties. One non-limiting example of such a pharmaceutical composition, solely given for demonstration purposes, could be prepared as follows: Cell culture supernatant of an infected cell culture is mixed with a stabilizer (e.g. spermidine and/or BSA (bovine serum albumin)) and the mixture is subsequently lyophilized dehydrated by other methods. Prior to vaccination, said mixture is then rehydrated in aqueous (e.g. saline, PBS (phosphate buffered saline)) or non-aqueous solutions (e.g. oil emulsion, aluminum-based adjuvant).

DISCLOSURE OF THE INVENTION

The solution to the above technical problem is achieved by the description and the embodiments characterized in the claims.

As mentioned above, at least for the CSFV it has been shown that the last C-terminal cystein of the $E^{rns}$ glycoprotein is involved in the homodimer formation of two monomers of $E^{rns}$ glycoprotein. A substitution of this last C-terminal cystein against serine (cystein/serine substitution) results in a pestivirus that is not longer capable to form homodimers of the $E^{rns}$ glycoprotein (van Gennip et al., 2005). Now it has been surprisingly found that a pestivirus lacking the ability to form homodimers of the $E^{rns}$ glycoprotein is also apathogenic for its host. Consequently, pestiviruses lacking the ability to form homodimers of the $E^{rns}$ glycoprotein are well attenuated and suitable candidates for a modified live vaccine for the prophylaxis and/or treatment of animals against a pestivirus infection (see example section for more details). Hence, one aspect of the present patent application relates to an attenuated pestivirus, wherein said attenuated pestivirus does not produce a dimeric $E^{rns}$ glycoprotein. Preferably, that pestivirus is selected from the group consisting of CSFV, BVDV and BDV, including any subtype of any of these pestiviruses.

According to the further aspect, the pestivirus lacking the ability to form homodimers of the $E^{rns}$ glycoprotein can be established by recombinant bioengineering techniques. For instances, a deletion or substitution at least of the cystein at amino acid position 438 of the CSFV pestivirus (according to SEQ ID NO:1 as shown in an exemplarily manner) results in such a recombinant attenuated CSFV pestivirus lacking the ability to form $E^{rns}$ homodimers, because such $E^{rns}$ glycoprotein is not longer able to form intermolecular disulfide bonds between to $E^{rns}$ monomers. With regard to the BVDV pestivirus (type 1 and/or 2), a deletion or substitution of at least the cystein at amino acid position 441 of the BVDV pestivirus (according to SEQ ID NO:4 (BVDV-1) or SEQ ID NO:7 (BVDV type 2) as shown in an exemplarily manner) results in such a recombinant attenuated BVDV pestivirus lacking the ability to form $E^{rns}$ homodimers. In respect to BDV, a deletion or substitution of at least the cystein at amino acid position 439 of the BDV pestivirus (according to SEQ ID NO:10 as shown in an exemplarily manner) results in such a recombinant attenuated BDV pestivirus lacking the ability to form $E^{rns}$ homodimers. Preferred substitutions are cystein/serine substitutions. However, any other substitutions of the last C-terminal cystein within the $E^{rns}$ glycoprotein (e.g. Cys438 of CSFV, Cys441 of BVDV type 1 or 2, Cys439 of BDV) are also within the meaning of the present invention.

The key element of the present invention is to provide a pestivirus that is not longer able to form homodimers of the $E^{rns}$ glycoprotein. Homodimer formation can be prevented by a deletion or substitution of at least the last C-terminal cystein within the $E^{rns}$ glycoprotein as described above, because any such pestiviruses are not longer capable to form intermolecular disulfide bonds between two $E^{rns}$ glycoprotein monomers. Beside the deletion or substitution of the last C-terminal cystein of the $E^{rns}$ glycoprotein, homodimerisation between two monomers of the $E^{rns}$ glycoprotein can also be inhibited by a modification of the amino acid environment of the last C-terminal cystein of the $E^{rns}$ glycoprotein, if this modification leads, for instance, to a change of the charge and/or conformation of the direct environment of the last C-terminal cystein in a manner that the intermolecular disulfide bonds can not be formed any more. For instance, an insertion, deletion or substitution of prolin close to that last C-terminal cystein may change the conformation of the $E^{rns}$ glycoprotein in such that the last C-terminal cystein of the $E^{rns}$ glycoprotein is not longer exposed in a manner that it can form intermolecular disulfide bonds with a second $E^{rns}$ glycoprotein. Moreover, modifications of the cystein environment with result in a strong positive or negative polarity of such environment (e.g by insertion of or substitution by positive charged amino acids such as argnin, lysine and/or histidine; by insertion of or substitution by negative charged amino acids such as aspratate or glutamate) could also inhibit the formation of intermolecular disulfide bonds between two $E^{rns}$ glycoproteins. Thus, the present invention does not only relate to recombinant attenuated pestiviruses, wherein the last C-terminal cystein of such $E^{rns}$ glycoprotein is deleted or substituted by a non-cystein residue, it also relates to any modified attenuated pestivirus, wherein the formation of homodimers of the $E^{rns}$ glycoprotein of said pestivirus is (in general) inhibited by a deletion, insertion or modification. Preferably, such modification is introduced closely to the last C-terminal cystein of the $E^{rns}$ glycoprotein, preferably such modification affects the amino acids between the amino acid positions 410 to 470, preferably 420 to 460. A skilled person in the art is able to modify the coding sequence of a pestivirus in such that the pestivirus may not longer form any $E^{rns}$ glycoprotein dimers by routine work. The publication of van Gennip et al., (2005) teaches a person skilled in the art how he can estimate dimerization of the $E^{rns}$ glycoprotein.

Thus, one aspect of the present invention relates to a recombinant attenuated pestivirus, wherein said attenuated pestivirus does not produce a dimeric $E^{rns}$ glycoprotein.

According to further aspect, the carboxy-terminus of the $E^{rns}$ glycoprotein of said attenuated pestivirus is modified by a deletion, insertion or substitution.

According to further aspect, at least the last C-terminal Cystein-residue of the $E^{rns}$ glyoprotein of said attenuated pestivirus is deleted or substituted by non-Cys amino acid residue.

According to further aspect, at least the most last Cystein-residue in the $E^{rns}$ glycoprotein of said attenuated pestivirus is deleted.

According to further aspect, said attenuated pestivirus selected from the group consisting of CSFV, BVDV type 1 and/or 2, and BDV.

According to further aspect, said attenuated pestivirus is a CSF pestivirus.

According to a further aspect, at least the Cystein-residue at amino acid position 438 according to SEQ ID NO: 1 of the $E^{rns}$ glyoprotein of said attenuated CSFV is deleted or substituted by a non Cystein-residue.

According to further aspect, said attenunated pestivirus is a BVD type 1 and/or 2 pestivirus.

According to a further aspect, at least the Cystein-residue at amino acid position 441 according to SEQ ID NO: 4 (BVDV type 1) or SEQ ID NO:7 (BVDV type 2) of the $E^{rns}$ glyoprotein of said attenuated BVDV is deleted or substituted by a non Cystein-residue.

According to further aspect, said attenunated pestivirus is a BDV pestivirus.

According to a further aspect, at least the Cystein-residue at amino acid position 439 according to SEQ ID NO: 10 of the $E^{rns}$ glyoprotein of said attenuated BDV is deleted or substituted by a non Cystein-residue.

In WO 99/64604 it is described that the inactivation of the RNAse activity residing within the $E^{rns}$ also results in an attenuated apathogenic pestivirus, which is capable to be used as a modified live vaccine. According to a further aspect of the present invention, both modifications can be combined which would result in an attenuated pestivirus, wherein the RNAse activity residing within the $E^{rns}$ is inactivated by a deletion, insertion or substitution and which is not capable to form any $E^{rns}$ dimers. Suitable modifications of the glycoprotein $E^{rns}$ which result in RNase negative $E^{rns}$ glycoproteins are for example, the single substitutions/deletions: S298G, H300K, H300L, H300R, H300del, W303G, P304del, E305A, C308G, R343G, E345del, W346G, K348A, H349K, H349L, H349del, H349Q, H349SV (mutation H349S and insertion of V), K348R, W351P, W351G, W351L, W351K, W351H; the double substitutions/deletions: H300L/H349L, K348del/H349del, H349del/G350del, E345del/H349del, W303G/E305A, H300K/H349K, H300K/H349L and the triple deletions: L299del/H300del/G300del, K348del/H349del/G350del. Numbering is according to the published amino acid sequence of BVDV CP7 for all the mutants listed above (the given numbers minus 3 would correspond to the equivalent residues of the CSFV Alfort/Tübingen amino acid sequence). All the above-listed mutants were at least tested as respective CSFV or BVDV mutants. Suitable mutants of the pestiviral glycoprotein $E^{rns}$ are provided, for example, by WO 99/64604, which is incorporated herein at its whole.

The putative active site of the RNase is represented by the conserved $E^{rns}$ sequences SLHGIWPEKICTG (SEQ ID NO:13) and/or LQRHEWNKHGWCNWFHIEPW (SEQ ID NO: 14) (sequence of the BVDV-2 New York '93 protein given here in an exemplary manner; minor changes can possibly be found in other pestivirus sequences but the identity of the motif will always be obvious for an expert in the field. As an example, the corresponding amino acid sequences of BVDV-1 CP7 would be SLHGIWPEKICTG (SEQ ID NO:13) and/or LQRHEWNKHGWCNWYNIEPW (SEQ ID NO:15) and that of CSFV Alfort/Tubingen SLHGIWPE-KICKG (SEQ ID NO:16)/or LQRHEWNKHGWCNW-YNIDPW (SEQ ID NO:17). Thus, preferably, the invention further relates to a BVDV according to the invention, wherein said RNase negative mutation(s) in the coding sequence for glycoprotein $E^{rns}$ are located in the nucleotide sequence coding for the conserved $E^{rns}$ sequence SLHGIWPEKICTG (SEQ ID NO:13) and/or LQRHEWNKHGWCNWFHIEPW (SEQ ID NO:14). These sequences are representing the putative active site of the RNase. The sequences SLHGIWPEKIC (SEQ ID NO:18) and RHEWNKHGWCNW (SEQ ID NO:19) of the putative $E^{rns}$ active site are even more conserved across pestiviruses.

It is known from the international patent application WO2005/111201 that pestiviruses attenuated by a modification within the $E^{rns}$ glycoprotein as well as in the $N^{pro}$ protein show a higher safety level in terms of the prevention of fetal infections. Therefore, according to a further aspect, the present invention also relates to attenuated pestiviruses, wherein said attenuated pestiviruses do not produce a dimeric $E^{RNS}$ glycoprotein and having at least a mutation in the $N^{pro}$ protein, wherein said mutation in the $N^{pro}$ protein leads to inactivation of said $N^{pro}$ protein. Preferably, that pestivirus is selected from the group consisting of CSFV, BVDV and BDV, including any subtype of any of these pestiviruses.

Inactivation of the $N^{pro}$ is achieved in pestiviruses, in particular BVDV of the specified formula described more in detail below, wherein between 0 and all amino acids of $N^{pro}$ are present; ubiquitin or LC3 or another sequence serving as processing signal (e.g. SUMO-1, NEDD8, GATE-16, GABA (A)RAP, or proteases like e.g. Intein, picornavirus 3C, caridovirus 2A, or p15 of rabbit hemorrhagic disease virus, or sequences like aphtovirus 2A that lead to discontinuous translation) is present or absent. In case a processing signal is present, the coding sequence of the processing signal is inserted at or close to the C-terminal end of the (remaining part of the) $N^{pro}$-protein. Only in the case that a processing signal is present, any number of amino acids coding for $N^{pro}$ (=$N^{pro}$ amino acids) may be present. In case no processing signal sequence is inserted, a maximum of 12 amino acids, preferably aminoterminal amino acids, of $N^{pro}$ may be present, the remaining amino acids have to be deleted. Furthermore, other than the $E^{rns}$ mutations as disclosed above (at least one of which has to be present in the pestivirus, in particular in BVDV according to the invention), the remaining sequences of the pestivirus, in particular BVDV may remain unchanged, i.e. are not mutated, or may also have mutations close to the N-terminal end of the C-protein. A number of more specific embodiments as disclosed below exemplify this.

Thus, the invention relates to a pestivirus, in particular to BVDV according to the invention, wherein said mutation(s) in the coding sequence for $N^{pro}$ lead to an encoded polyprotein as characterized by the following formula:

$$[N^{pro}]_x\text{-}[PS]_y\text{-}[C\text{-term}]$$

and wherein:
- $[N^{pro}]$ relates to the $N^{pro}$ portion of said polyprotein, wherein "x" represents the number of amino acids of the $N^{pro}$ present in the polyprotein;
- $[PS]$ relates to a processing signal selected from: ubiquitin, LC3, SUMO-1, NEDD8, GATE-16 or GABA(A)RAP or proteases like e.g. Intein, picornavirus 3C, caridovirus 2A, or p15 of rabbit hemorrhagic disease virus or any processing signal known to the skilled person that ensures the generation of a functional N-terminal of the C-protein. "Y" may be =0, which means that no processing signal is present (=PS is absent), or "Y" may be =1, which means that a processing signal is present (=PS present).
- [C-term] relates to the complete pestivirus, in particular the complete BVDV polyprotein except for $N^{pro}$, but including the capsid (C)-protein and any other protein present in the pestivirus polyprotein, in particular in the BVDV polyprotein including the carboxyterminal NS5B. Preferably, the glycoprotein $E^{rns}$ in said [C-term] is mutated, in such that the RNase activity residing in the glycoprotein $E^{rns}$ is inactivated. The term "any other protein present in the pestivirus polyprotein/BVDV polyprotein" relates to $E^{rns}$, E1, E2, p7, NS2, NS3, NS4A, NS4B and NS5A, wherein glycoprotein $E^{rns}$ is mutated, preferably as disclosed herein (see above), in such that the RNase activity residing in the glycoprotein $E^{rns}$ is inactivated. Preferably, the pestivirus, in particular the BVDV according to the invention has a C-protein which is not mutated except for the amino acid at position 2 which is changed from D to N. Therefore, [C-term*] is the same as [C-term] but with a mutation at position 2 of the C-protein (N instead of D);
- if "y" is =0 (means no [PS] present) then "x" is 0 to 12, (means no $N^{pro}$ specific amino acid or 1 to 12 amino acids of $N^{pro}$, preferably of the N-terminus of $N^{pro}$, are present);
- if "y" is =1 (means [PS] is present) then "x" is 0 to 168; (means no $N^{pro}$ specific amino acid or 1 to all 168 amino acids of $N^{pro}$, preferably of the N-terminus of $N^{pro}$, are present).

Also more preferably, the invention relates to a pestivirus, in particular to BVDV according to the invention, wherein said mutation(s) in the coding sequence for $N^{pro}$ lead to an encoded polyprotein as characterized by the following formula:

$$[N^{pro}]_1\text{-}[PS]_0\text{-}[C\text{-term}]$$

and wherein the definitions are as defined above.

A specific example thereof is disclosed below, wherein the N-terminal methionine is followed by the C-protein and any other protein present in the polyprotein including the carboxyterminal NS5B. Hence, most preferably, the invention relates to a pestivirus, in particular BVDV according to the invention, wherein said mutation(s) in the coding sequence for $N^{pro}$ lead to an encoded polyprotein as characterized by the following formula:

$$M[C\text{-term}].$$

and wherein the definitions are as defined above.

Also more preferably, the invention relates to a pestivirus, in particular to BVDV according to the invention, wherein said mutation(s) in the coding sequence for $N^{pro}$ lead to an encoded polyprotein as characterized by the following formula:

$$[N^{pro}]_3\text{-}[PS]_0\text{-}[C\text{-term}]$$

and wherein the definitions are as defined above.

A specific example of BVDV is disclosed below, wherein the N-terminal methionine is followed by the $N^{pro}$ sequence EL and the C-protein and any other protein present in the polyprotein including the carboxyterminal NS5B. Hence, most preferably, the invention relates to a BVDV according to the invention, wherein said mutation(s) in the coding sequence for $N^{pro}$ lead to an encoded polyprotein as characterized by the following formula:

MEL-[C-term]

and wherein the definitions are as defined above.

Also more preferably, the invention relates to a pestivirus, in particular to BVDV according to the invention, wherein said mutation(s) in the coding sequence for $N^{pro}$ lead to an encoded polyprotein as characterized by the following formula:

$[N^{pro}]_4$-$[PS]_0$-[C-term]

and wherein the definitions are as defined above.

A specific example of BVDV is disclosed below, wherein the N-terminal methionine is followed by the $N^{pro}$ sequence ELF and the C-protein and any other protein present in the polyprotein including the carboxyterminal NS5B. Hence, most preferably, the invention relates to a BVDV according to the invention, wherein said mutation(s) in the coding sequence for $N^{pro}$ lead to an encoded polyprotein as characterized by the following formula:

MELF (SEQ ID NO:30)-[C-term].

and wherein the definitions are as defined above.

Also more preferably, the invention relates to pestivirus, in particular to BVDV according to the invention, wherein said mutation(s) in the coding sequence for $N^{pro}$ lead to an encoded polyprotein as characterized by the following formula:

$[N^{pro}]_6$-$[PS]_0$-[C-term]

and wherein the definitions are as defined above.

A specific example of BVDV is disclosed below, wherein the N-terminal methionine is followed by the $N^{pro}$ sequence ELFSN (SEQ ID NO:49) and the C-protein and any other protein present in the polyprotein including the carboxyterminal NS5B. Hence, most preferably, the invention relates to a BVDV according to the invention, wherein said mutation(s) in the coding sequence for $N^{pro}$ lead to an encoded polyprotein as characterized by the following formula:

MELFSN (SEQ ID NO:31)-[C-term].

and wherein the definitions are as defined above.

Also more preferably, the invention relates to a pestivirus, in particular to BVDV according to the invention, wherein said mutation(s) in the coding sequence for $N^{pro}$ lead to an encoded polyprotein as characterized by the following formula:

$[N^{pro}]_4$-$[PS]_0$-[C-term*]

and wherein the definitions are as defined above except for the fact that the aminoterminal part of the C-protein is changed.

A specific example of BVDV is disclosed below, wherein the N-terminal methionine is followed by the $N^{pro}$ sequence ELF and in the C-protein sequence, the amino acid at position 2 is changed from D to N. Therefore, the amino terminal C-protein sequence is SNEGSK (SEQ ID NO:21) . . . instead of SDEGSK (SEQ ID NO:22). Hence, most preferably, the invention relates to a BVDV according to the invention, wherein said mutation(s) in the coding sequence for $N^{pro}$ lead to an encoded polyprotein as characterized by the following formula:

MELF (SEQ ID NO:30)-[C-term*], wherein in the C-protein the amino acid at position 2 is changed from D to N, and wherein the definitions are as defined above.

Also more preferably, the invention relates to a pestivirus, in particular BVDV according to the invention, wherein said mutation(s) in the coding sequence for $N^{pro}$ lead to an encoded polyprotein as characterized by the following formula:

$[N^{pro}]_x$-$[PS]_1$-[C-term], wherein the definitions are as defined as above,
and wherein PS is any of the PS disclosed above, preferably selected from the group of ubiquitin or LC3.

A specific example of BVDV is disclosed below, wherein the N-terminal methionine is followed by any 21 or 28 $N^{pro}$ amino acids, ubiquitin or LC3 and the C-protein. Hence most preferably, the invention relates to a BVDV according to the invention, wherein said mutation(s) in the coding sequence for $N^{pro}$ lead to an encoded polyprotein as characterized by the following formula:

$[N^{pro}]_{22}$-$[PS]_1$-[C-term], wherein preferably, the PS is ubiquitin or LC3 or $[N^{pro}]_{29}$-$[PS]_1$-[C-term], wherein preferably, the PS is ubiquitin or LC3.

Ubiquitin is a well known highly conserved cellular protein of 76 amino acids. Among other functions, ubiquitin is a key player in protein catabolism since conjugation with ubiquitin can mark a protein for degradation via the proteasome. Ubiquitin conjugated with or fused to other proteins via the carboxyterminal glycin can be cleaved off by cellular ubiquitin-specific proteases. Thus, fusion of a protein to the carboxyterminus of ubiquitin will usually result in defined proteolytic cleavage of the fusion protein into its components when expressed within a cell.

LC3 (light chain 3 of microtubule associated proteins) represents a cellular protein of 125 amino acids that serves a variety of functions (length given for bovine LC3). Recently, a fundamental role of the protein in autophagy has been defined. During this process, LC3 is activated by carboxyterminal cleavage. Thereby, a new carboxyterminus is generated that consists of glycine. LC3 is then conjugated via the carboxyterminal glycine to phosphatidylethanolamine present in the membranes of autophagic vesicles. Because of this process, a protein fused to the carboxyterminus of LC3 will be cleaved off by a cellular protease at a defined position.

Also more preferably, the invention relates to a pestivirus, preferably to BVDV according to the invention, wherein said mutation(s) in the coding sequence for $N^{pro}$ lead to an encoded polyprotein as characterized by the following formula selected from the group of:

$[N^{pro}]_2$-$[PS]_y$-[C-term] and preferably ME-$[PS]_y$-[C-term];

$[N^{pro}]_5$-$[PS]_y$-[C-term] and preferably MELFS (SEQ ID NO:23)-$[PS]_y$-[C-term];

$[N^{pro}]_7$-$[PS]_y$-[C-term] and preferably MELFSNE (SEQ ID NO:24)-$[PS]_y$-[C-term];

$[N^{pro}]_8$-$[PS]_y$-[C-term] and preferably MELFSNEL (SEQ ID NO:25)-$[PS]_y$-[C-term];

[N$^{pro}$]$_9$-[PS]$_y$-[C-term] and preferably MELFSNELL (SEQ ID NO:26)-[PS]$_y$-[C-term];
[N$^{pro}$]$_{10}$-[PS]$_y$-[C-term] and preferably MELFSNELLY (SEQ ID NO:27)-[PS]$_y$-[C-term];
[N$^{pro}$]$_{11}$-[PS]$_y$-[C-term] and preferably MELFSNELLYK (SEQ II) NO:28)-[PS]$_y$-[C-term]; and
[N$^{pro}$]$_{12}$-[PS]$_y$-[C-term] and preferably MELFSNELLYKT (SEQ ID NO:29)-[PS]$_y$-[C-term]
and wherein the definitions are as defined as above. The preferably disclosed embodiments refer to BVDV.

Most preferably, y is 0 (no PS present).

According to a further aspect, the invention relates to a pestivirus, preferably to BVDV according to the invention, wherein said mutation(s) in the coding sequence for N$^{pro}$ lead to an encoded polyprotein as characterized by the following formula selected from the group of:

M-[PS]$_0$-[C-term];
MEL-[PS]$_0$-[C-term];
MELF (SEQ ID NO:30)-[PS]$_0$-[C-term];
MELFS (SEQ ID NO:23)-[PS]$_0$-[C-term];
MELFSN (SEQ ID NO:31)-[PS]$_0$-[C-term];
MELFSNE (SEQ ID NO:24)-[PS]$_0$-[C-term];
MELFSNEL (SEQ ID NO:25)-[PS]$_0$-[C-term];
MELFSNELL (SEQ ID NO:26)-[PS]$_0$-[C-term];
MELFSNELLY (SEQ ID NO:27)-[PS]$_0$-[C-term];
MELFSNELLYK (SEQ ID NO:28)-[PS]$_0$-[C-term];
MELFSNELLYKT (SEQ ID NO:29)-[PS]$_0$-[C-term].

According to a further aspect, the invention relates to a pestivirus, preferably to BVDV according to the invention, wherein said mutation(s) in the coding sequence for N$^{pro}$ lead to an encoded polyprotein as characterized by the following formula selected from the group of:

MELI (SEQ ID NO:32)-[PS]$_0$-[C-term];
MELIS (SEQ ID NO:33)-[PS]$_0$-[C-term];
MELISN (SEQ ID NO:34)-[PS]$_0$-[C-term];
MELISNE (SEQ ID NO:35)-[PS]$_0$-[C-term];
MELISNEL (SEQ ID NO:36)-[PS]$_0$-[C-term];
MELISNELL (SEQ ID NO:37)-[PS]$_0$-[C-term];
MELISNELLY (SEQ ID NO:38)-[PS]$_0$-[C-term];
MELISNELLYK (SEQ ID NO:39)-[PS]$_0$-[C-term];
MELISNELLYKT (SEQ ID NO:40)-[PS]$_0$-[C-term].

According to a further aspect, the invention relates to a pestivirus, preferably to BVDV according to the invention, wherein said mutation(s) in the coding sequence for N$^{pro}$ lead to an encoded polyprotein as characterized by the following formula selected from the group of:

MELIT (SEQ ID NO:41)-[PS]$_0$-[C-term];
MELITN (SEQ ID NO:42)-[PS]$_0$-[C-term];
MELITNE (SEQ ID NO:43)-[PS]$_0$-[C-term];
MELITNEL (SEQ ID NO:44)-[PS]$_0$-[C-term];
MELITNELL (SEQ ID NO:45)-[PS]$_0$-[C-term];
MELITNELLY (SEQ ID NO:46)-[PS]$_0$-[C-term];
MELITNELLYK (SEQ ID NO:47)-[PS]$_0$-[C-term];
MELITNELLYKT (SEQ ID NO:48)-[PS]$_0$-[C-term];

Another important aspect of the invention described herein are immunogenic compositions comprising a pestivirus, in particular a BVDV according to the invention, and a solution. The skilled person knows additional components which may be comprised in said composition (see also Remington's Pharmaceutical Sciences. (1990). 18th ed. Mack Publ., Easton). The expert may use known injectable, physiologically acceptable sterile solutions. For preparing a ready-to-use solution for parenteral injection or infusion, aqueous isotonic solutions, such as e.g. saline or corresponding plasma protein solutions are readily available. The pharmaceutical compositions may be present as lyophylisates or dry preparations, which can be reconstituted with a known injectable solution directly before use under sterile conditions, e.g. as a kit of parts.

The final preparation of the immunogenic compositions of the present invention are prepared for e.g. injection by mixing said pestivirus, preferably BVDV according to the invention with a sterile physiologically acceptable solution, that may be supplemented with known carrier substances or/and additives (e.g. serum albumin, dextrose, sodium bisulfite, EDTA). Said solution may be based on a physiologically acceptable solvent, e.g. an aqueous solution between pH 7 and 8. The pH may be stabilised by a pharmaceutically acceptable buffer. The solution may also contain further stabilising agents like a detergent like Tween 20, serum albumin such as BSA (bovine serum albumin), ascorbic acid, and/or spermidine. The composition may also comprise adjuvants, e.g. aluminiumhydroxide, mineral or other oils or ancillary molecules added to the vaccine or generated by the body after the respective induction by such additional components, like but not restricted to interferons, interleukins or growth factors.

For example, in an immunogenic composition according to the invention, the pestivirus, in particular BVDV may be solved in:

| Pestivirus (preferably BVDV) | 10$^2$-10$^8$ TCID$_{50}$ |
|---|---|
| SGS* | 25% v/v |
| Cell culture medium | qsp 1 dose |
| *SGS: | Composition per 2 ml |
| Sucrose | 75 mg |
| Gelatine | 20 mg |
| Potassium hydroxide | 0.274 mg |
| L-glutamic acid | 0.72 mg |
| Potassium dihydrogen phosphate | 0.516 mg |
| Dipotassium phosphate | 1.254 mg |
| Water for injection | qsp 2 ml |

If the immunogenic composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

The immunogenic composition according to the invention is capable to induce an immunological response in an animal. More preferred, the immunogenic composition according to the invention is a vaccine. A vaccine as understood herein comprises a pestivirus, in particular BVDV according to the invention and is defined above (section "definitions")

Most preferred, the immunogenic composition according to the invention further comprises a pharmaceutically acceptable carrier or excipient. Several carriers or excipients are disclosed above. The composition may comprise, if aimed at injections or infusion, substances for preparing isotonic solutions, preservatives such as p-hydroxybenzoates, stabilizers, such as alkalisalts of ethylendiamintetracetic acid, possibly also containing emulsifying and/or dispersing.

The immunogenic composition according to the invention may be applied intradermally, intratracheally, or intravaginally. The composition preferably may be applied intramuscularly or intranasally. In an animal body, it can prove advantageous to apply the immunogenic compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the immunogenic compositions according to the invention may be administered once or several times, also intermittently, for instance on a daily basis for several days, weeks or months and in different dosages.

The invention also relates to the use of a pestivirus, in particular BVDV according to the invention in the manufacture of a vaccine for the prophylaxis and treatment of pestiviral infections, in particular of BVDV infections.

Another important part of the invention is a polynucleotide molecule comprising the nucleic acid coding for a pestivirus, in particular for a BVDV according to the invention, or a fragment, functional variant, variant based on the degenerative nucleic acid code, fusion molecule or a chemical derivative thereof. Preferably, said polynucleotide molecule is DNA. Also preferably, said polynucleotide molecule is RNA. In a more preferred embodiment, said polynucleotide molecule also comprises the nucleotide sequence of a functional 5'- and/or 3'-non-translated region of a pestivirus, in particular of BVDV.

There are several nucleotide sequences known in the art, which represents the basis for the production of a polynucleotide molecule coding for a pestivirus attenuated according to the present invention. Examples of nuclecic acid sequences of wild-type sequences of several members of pestiviruses are listed below:

| Border disease virus | |
|---|---|
| Strain BD31 | NCBI GenBank Accession No. [U70263] |
| Strain X818 | NCBI GenBank Accession No. [AF037405] |
| Bovine viral diarrhea virus 1 | |
| Strain NADL | NCBI GenBank Accession No. [M31182] |
| Strain Osloss | NCBI GenBank Accession No. [M96687] |
| Strain SD-1 | NCBI GenBank Accession No. [M96751] |
| Strain CP7 | NCBI GenBank Accession No. [U63479] |
| Bovine viral diarrhea virus 2 | |
| Strain 890 | NCBI GenBank Accession No. [U18059] |
| Strain C413 | NCBI GenBank Accession No. [AF002227] |
| Strain New York'93 | NCBI GenBank Accession No. [AF502399] |
| Classical swine fever virus | |
| Strain Alfort/187 | NCBI GenBank Accession No. [X87939] |
| Strain Alfort-Tübingen | NCBI GenBank Accession No. [J04358] |
| Strain Brescia | NCBI GenBank Accession No. [M31768] |
| Strain C strain | NCBI GenBank Accession No. [Z46258] |

The mutations/modifications according to the invention relating to the coding sequence of $N^{pro}$ and $E^{rns}$ are described above more in detail. Having this information, a person skilled in the art is able to realize the manufacture of any polynucleotide/polynucleic acid coding for a pestivirus according to the present invention. Furthermore, this person is able to manufacture an attenuated pestivirus according to the invention. Molecular method for introducing a mutation into a polynucleotide sequence, cloning and amplification of said mutated polynucleotide are for example provided by Sambrook et 1989 or Ausubel et al. 1994.

Another important aspect of the invention is a method for attenuating a pestivirus which results in a pestivirus according to the invention, comprising modifying the $E^{rns}$ glycoprotein of said pestivirus in such that said attenuated pestivirus does not produce a dimeric $E^{rns}$ glycoprotein. According to further aspect, the carboxy-terminus of the $E^{rns}$ glycoprotein of said pestivirus is modified by a deletion, insertion or substitution. According to further aspect, at least the last C-terminal Cystein-residue of the $E^{rns}$ glyoprotein of said pestivirus is deleted or substituted by a non-Cys amino acid residue. According to further aspect, at least the last C-terminal Cystein-residue in the $E^{rns}$ glycoprotein of said pestivirus is deleted. According to further aspect, said pestivirus selected from the group consisting of CSFV, BVDV type 1 and/or 2, and BDV. According to further aspect, said attenunated pestivirus is a CSF pestivirus. According to a further aspect, at least the Cystein-residue at amino acid position 438 according to SEQ ID NO: 1 of the $E^{rns}$ glyoprotein of said CSFV pestivirus is deleted or is substituted by a non Cystein-residue. According to further aspect, said pestivirus is a BVD type 1 and/or 2 pestivirus. According to a further aspect, at least the Cystein-residue at amino acid position 441 according to SEQ ID NO: 4 (BVDV type 1) or SEQ ID NO:7 (BVDV type 2) of the $E^{rns}$ glyoprotein of said BVDV is deleted or substituted by a non Cystein-residue. According to further aspect, said pestivirus is a BD pestivirus. According to a further aspect, at least the Cystein-residue at amino acid position 439 according to SEQ ID NO: 10 of the $E^{rns}$ glyoprotein of said BDV is deleted or is substituted by a non Cystein-residue.

According to a further aspect the present invention provides a method for attenuating a pestivirus, characterized in that the glycoprotein $E^{rns}$ is modified in such that the RNAse activity residing within the $E^{rns}$ is inactivated by a deletion, insertion or substitution, and in such that said pestivirus is not capable to form any $E^{rns}$ dimer. According to a preferred embodiment, said pestivirus is selected from the group consisting of CSFV, BVDV, and BDV, including any subtypes thereof.

According to a further aspect, the present invention provides a method for attenuating a pestivirus, characterized in that glycoprotein $E^{rns}$ is modified by a deletion, insertion or substitution in such that said pestivirus is not capable to form any $E^{rns}$ dimer and by modifying the $N^{pro}$ protein by a deletion, insertion or substitution in such that the $N^{pro}$ protein is inactivated.

According to a further aspect, said method comprises the steps:

a) reverse transcription of a wild-type pestivirus nucleotide sequence into a cDNA;

b) cloning said cDNA;

c) introducing mutations selected from the group of deletions, insertion mutations and/or substitution mutations into said cDNA, wherein said mutations are located in the coding sequence encoding glycoprotein $E^{rns}$, or the coding sequence encoding glycoprotein $E^{rns}$ and the protease $N^{pro}$, d) incorporating the cDNA into a plasmid or into a DNA virus capable of directing the transcription of pestivirus cDNA into RNA in vitro or upon infection of suitable cells.

Yet another important embodiment of the invention is a method of treatment of disease caused by a pestivirus, wherein a pestivirus according to the invention or a composition according to the invention is administered to an animal in need thereof at a suitable dose as known to the skilled person and the reduction of symptoms of said pestivirus infection.

Yet another important embodiment of the invention is a method of treatment of disease caused by BVDV, wherein a BVDV according to the invention or a composition according to the invention is administered to an animal in need thereof at a suitable dose as known to the skilled person and the reduction of symptoms of BVDV infection such as viremia and leukopenia and/or pyrexia and/or diarrhea is monitored.

EXAMPLES

The following examples serve to further illustrate the present invention; but the same should not be construed as limiting the scope of the invention disclosed herein.

Example 1

The objective of the study TV#26 was to define the outcome of clinical signs after infection of pigs with a CSFV Alfort/Tübingen mutant exhibiting a deletion of the cysteine codon at position 438 in the polypeptide (171 in the $E^{rns}$ sequence). This mutation prevents $E^{rns}$ dimerization (EP #82 (4)). As controls an RNase negative variant of CSFV Alfort/Tübingen with mutation H297K and wt virus were used.

In this study, 12 animals with weight of about 20 kg were split in three groups of four animals each. The CSFV mutants (first group: TF #283(1)/second group: EP #82(4)) and CSFV wild type virus (third group: EP #98(1)) were applied via the intramuscular and intranasal route on day 0 (0 dpi). Each animal received $10^6$ $KID_{50}$ virus in 1.5 ml DMEM. After infection, animals were monitored for 22 days and rectal temperatures were recorded daily or every second day. A clinical score was determined according to Mittelholzer with modifications.

a) Viruses for the Animal Study
1. TF #283 (1): CSFV Alfort/Tübingen, RNase negative
2. EP#82(4): CSFV Alfort/Tübingen, incompetent for $E^{rns}$ dimerization
3. EP#98(1): CSFV Alfort/Tübingen, wild type virus.

The mutants show only a slightly reduced growth rate between 24 to 70 h p.i. in cell culture compared to the parental strain. It will have to be tested in further experiments whether this difference is significant (FIG. 1).

The CSFV mutants (first group: TF #283(1)/second group: EP #82 (4)) and CSFV wild type virus (EP #98(1)) were applied intramuscularly and intranasally on day 0 (0 dpi). Each animal received $10^6$ $KID_{50}$ virus in 1.5 ml DMEM. Two-thirds of the suspension were applied intranasally (0.5 ml per nostril). For better i.m. application the last 0.5 ml of virus was filled up to 2 ml with DMEM and were injected in the muscle brachiocephalicus.

For titre confirmation of challenge virus 1 ml virus suspension was collected after different dilution and transport steps:
a) original virus (stock solution)
b) first dilution step with DMEM as diluent to obtain a virus concentration of $10^{5.824}$ $KID_{50}$/ml ($10^6$ $KID_{50}$/1.5 ml) directly to −70° C.
c) This sample was taken along "on ice" with the inoculum and handled the same way. After returning from the stable this sample was frozen at −70° C. immediately.
d) second dilution step for i.m. application (see above) After returning from the stable this sample was frozen at −70° C. immediately.

Titre confirmation has not been finished yet.

TABLE 1

Titer of challenge virus preparations

|  | TF #283(1) 4. pas (14.12.07) | | EP #82(4) 7. pas (10.01.08) | | EP #98(1) 1. pas (14.12.07) | |
| --- | --- | --- | --- | --- | --- | --- |
|  | expected | determined | expected | determined | expected | determined |
| original virus | $10^6$ |  | $10^{6.25}$ |  | $10^{6.125}$ |  |
| b | $10^{5.8}$ |  | $10^{5.8}$ |  | $10^{5.8}$ |  |
| c | $10^{5.8}$ |  | $10^{5.8}$ |  | $10^{5.8}$ |  |
| d | $10^{5.22}$ |  | $10^{5.22}$ |  | $10^{5.22}$ |  | b = directly to −70° C. after first dilution step (for intranasal application)
c = return on ice
d = second dilution step (for i.m. application)

b) Operating Schedule

Blood was taken from the jugular vein for BC isolation, leukocyte counting, plasma isolation, FACS analysis and serum preparation according to table 3. After infection, animals were monitored for 22 days and rectal temperatures were recorded daily or, in the late stage of the experiment, every second day.

TABLE 2

Operating schedule for blood collection

|  | whole blood for BC isolation + leukocyte count + plasma | whole blood for FACS analysis | Serum (SNT) |
|---|---|---|---|
| −1 dpi | X | X | X |
| 0 dpi |  | Infektion |  |
| 2 dpi | X |  |  |
| 5 dpi | X |  |  |
| 8 dpi | X | X |  |
| 9 dpi = term (group 3) | X (group 3) | X (group 3) | X (group 3) |
| 12 dpi | X (group 1 + 2) | X (group 1 + 2) |  |
| 15 dpi | X (group 1 + 2) | X (group 1 + 2) |  |
| 22 dpi = term (group 1 + 2) 27.03.2008 | X (group 1 + 2) | X (group 1 + 2) | X (group 1 + 2) | c) Animals and Observation During the Experiment

Twelve animals with an average weight of 20 kg arrived at the institute on Mar. 28, 2008. The pigs were divided into three different groups of 4 animals. After six days of acclimatisation the animals were infected with the mutant and wild type viruses.

TABLE 3 allocation of the animals and challenge viruses to the 3 groups

|  | group | | |
|---|---|---|---|
|  | 1 | 2 | 3 |
| virus | TF #283 (1) | EP #82 (4) | EP #98 (1) |
| animal-ID | 841 | 847 | 574 |
|  | 842 | 848 | 576 |
|  | 843 | 849 | 593 |
|  | 844 | 850 | 598 |

Pigs were observed daily for general health status. The animals of group #3 challenged with the wild type virus had to be killed prematurely on day 9 p.i. because of considerable signs of CSF. In groups infected with the RNase negative mutant and the dimerization incompetent mutant all animals showed signs of disease typical for CSF. In comparison with the wild type infected animals (group 3) the severity of symptoms in group 1 and 2 were significantly less distinctive.

A clinical score according to Mittelholzer (with the following modifications: defecation: soft feces, normal amount=0; Reduced amount of feces, dry/thin feces=1; only small amount of dry, fibrin-covered feces, or diarrhea=2; no feces, mucus in rectum, or wat Rectal temperatures were recorded on −3 and −2 dpi and daily or every second day from 0 dpi up to 20 dpi. In group 1 and 2 every animal reached the critical temperature of 40° C. on 4/5 or 6 days post infection. The temperature recovered in all animals of these groups to normal values till 10 dpi or 11 dpi. In the wild type virus infected group body temperature increased from day 4 post infection and no descent was detectable until euthanasia.

d) Analysis of Buffy Coat Preparation

Detection of viremia through virus isolation in Buffy coat preparations has not been finished yet.

TABLE 5

| | buffy coat preparation | | | | | | | | | | | |
|---|---|---|---|---|---|---|---|---|---|---|---|---|
| | group 1 | | | | group 2 | | | | group 3 | | | |
| | 841 | 842 | 843 | 844 | 847 | 848 | 849 | 850 | 574 | 576 | 593 | 598 |
| −1 dpi | | | | | | | | | | | | |
| 2 dpi | | | | | | | | | | | | |
| 5 dpi | | | | | | | | | | | | |
| 8 dpi | | | | | | | | | | | | |
| 9 dpi | | | | | | | | | | | | |
| 12 dpi | | | | | | | | | | | | |
| 15 dpi | | | | | | | | | | | | |
| 22 dpi | | | | | | | | | | | | |

Animal was euthanised e) White Blood Cell Counts

WBC counts were determined in a haemocytometer, "Neubauer chamber", by standard laboratory procedure. For all animals a reduction of WBC was detectable during the study. The surviving animals showed an increase to almost normal values until study termination.

TABLE 6

| | | WBC counts | | | | | | | | | | | |
|---|---|---|---|---|---|---|---|---|---|---|---|---|---|
| | | group 1 | | | | group 2 | | | | group 3 | | | |
| | | 841 | 842 | 843 | 844 | 847 | 848 | 849 | 850 | 574 | 576 | 593 | 596 |
| days post infection | −1 | 11972 | 17527 | 11706 | 12722 | 19694 | 19694 | 19361 | 15944 | 20441 | 18371 | 20666 | 11361 |
| | 2 | 9896 | 9842 | 12027 | 9457 | 18194 | 15472 | 17333 | 9611 | 14555 | 16248 | 22055 | 12500 |
| | 5 | 6664 | 7194 | 7861 | 10111 | 9694 | 9051 | 13111 | 11944 | 12472 | 15055 | 10055 | 8030 |
| | 8 | 13321 | 12399 | 8852 | 11130 | 14609 | 14542 | 16828 | 7583 | 5190 | 7612 | 10611 | 6430 |
| | 9 | n.d. | n.d. | n.d. | n.d. | n.d. | n.d. | n.d. | n.d. | 3429 | 7555 | 7194 | 5171 |
| | 12 | 11138 | 13729 | 12611 | 13527 | 20277 | 15083 | 25611 | 10833 | | | | |
| | 15 | 12527 | 13861 | 18083 | 13722 | 22194 | 14906 | 27887 | 11194 | | | | |
| | 22 | 11080 | 11885 | 13634 | 8850 | 24392 | 14049 | 30146 | 11366 | | | | | n.d. = not determined

Animal was euthanised f) Serum Neutralisation Assay

Determination of antibody titers has not been finished yet.

Serum neutralisation assays will be performed using SP50 as test virus on day −1 before infection, 9 days post infection for group 3 and 22 dpi for group 1 and 2.

TABLE 7

Antibody titers against SP50 determined in SNT, n.d. = not determined

| | group 1 | | | | group 2 | | | | group 3 | | | |
|---|---|---|---|---|---|---|---|---|---|---|---|---|
| | 841 | 842 | 843 | 844 | 847 | 848 | 849 | 850 | 574 | 576 | 593 | 598 |
| −1 dpi | | | | | | | | | | | | |
| 9 dpi | n.d. | n.d. | n.d. | n.d. | n.d. | n.d. | n.d. | n.d. | | | | |
| 22 dpi | | | | | | | | | | | | |

The reciprocal values of serum dilutions that neutralise ca. 100 TCID50 of SP50 are given.

g) Conclusion

It is obvious that the deletion of cysteine #438 and thereby the prevention of $E^{rns}$ dimer formation (biochemical data available) leads to attenuation of CSFV. This attenuation can hardly be due to a general growth retardation of the virus mutant since only marginal differences between the growth rates of the mutant and wt viruses were observed. The development and intensity of the clinical scores and fever as well as the degree of the WBC number reduction are very similar between the virus mutant lacking the $E^{rns}$ RNase activity and the variant with the deletion preventing $E^{rns}$ dimer formation. Since the dimerization has been found to be crucial for the biological functions but not enzymatic activity of other RNases, it can be hypothesized that the attenuation of CSFV in consequence of the prevention of $E^{rns}$ dimer formation and the abrogation of the RNase activity rely on the same principles of the virus host interaction, namely the blockage of the $E^{rns}$ RNase effect. Thus, the prevention of dimer formation is most likely equivalent to blocking the RNase activity, even though the virus is able to express an active RNase.

REFERENCES

Ausubel, F. M. et al., Current Protocols in molecular biology. New York: Greene Publishing Associates and Wiley-Interscience. 1994 (updated)

Baker, J. C. 1987. Bovine viral diarrhea virus: a review. J. Am. Vet. Med. Assoc. 190: 1449-1458.

Becher, P., König, M., Paton, D. J., Thiel, H. J., 1995, Further characterization of border disease virus isolates: evidence for the presence of more than three species within the genus pesivirus. Virology 209 (1), 200-206.

Chong, S., Williams, K. S., Wotkowicz, C., and Xu, M. Q. 1998. Modulation of Protein Splicing of the *Saccharomyces cerevisiae* Vacuolar Membrane ATPase Intein. J. Biol. Chem. 273: 10567-10577. Donis, R. O., Corapi, W., and Dubovi, E. J. 1988. Neutralizing monoclonal antibodies to bovine viral diarrhea virus bind to the 56K to 58K glycoprotein. J. Gen. Virol. 69: 77-86.

Fuerst T. R. et al. 1986. Eukaryotic transient expression system based on recombinant vaccinia virus that synthesizes bacteriophage T7 RNA polymerase. Proc. Natl. Acad. Sci. 83: 8122-8126.

Heinz, F. X., Collett, M. S., Purcell., R. H., Cold, E. A., Howard, C. R., Houghton, M., Moormann, R. J. M., Rice, C. M., and Thiel, H.-J. 2000. Family Flaviviridae. PP 859-878. In: Virus Taxonomy (van Regenmortel., H. H. V., Fauquet, C. M., and Bishop, D. H. L, Eds.). Academic Press, San Diego.

Hulst, M. M., Himes, G., Newbigin, E., Moormann, R. J. M. 1994. Glycoprotein E2 of classical swine fever virus: expression in insect cells and identification as a ribonuclease. Virology 200: 558-565.

Hulst, M. M., F. E. Panoto, A. Hooekmann, H. G. P. van Gennip., and Moormann, R. J. M. 1998. Inactivation of the RNase activity of glycoprotein $E^{rns}$ of classical swine fever virus results in a cytopathogenic virus. J. Virol. 72: 151-157.

Kit, M. and S. Kit. 1991. Sensitive glycoprotein gIII blocking ELISA to distinguish between pseudorabies (Aujeszky's disease)-infected and vaccinated pigs. Veterinary Microbiology 28:141-155.

Kunkel, T. A., J. D. Roberts, and R. A. Zakour. 1987. Rapid and efficient site-specific mutagenesis without phenotypic selection. Methods Enzymol. 154:367-392.

König, Matthias, 1994, Virus der klassischen Schweinepest: Untersuchungen zur Pathogenese und zur Induktion einer protektiven Immunantwort. Dissertation, Tierärztliche Hochschule Hannover, Germany.

Lindenbach, B. D., and Rice, C. M. 2001. The pestiviruses. In Fields Virology, eds. Knipe, D. M., & Howley, P. M. (Lippincott-Raven, Philadelphia), pp. 991-1042. Mayer, D., Hofmann, M. A., and Tratschin, J. D. 2004. Attenuation of classical swine fever virus by deletion of the viral N(pro) gene. Vaccine. 22:317-328.

Meyers, G., Rümenapf, T. and Thiel, H.-J. 1989. Molecular cloning and nucleotide sequence of the genome of hog cholera virus. Virology 171: 555-567.

Meyers, G., Saalmüller, A., and Büttner, M. (1999). Mutations abrogating the RNase activity in glycoprotein e(ms) of the pestivirus classical swine fever virus lead to virus attenuation. J Virol 73: 10224-10235.

Meyers, G., Tautz, N., Becher, P., Thiel, H.-J., & Kümmerer, B. M. 1996b. Recovery of cytopathogenic and noncytopathogenic bovine viral diarrhea viruses from cDNA constructs. J. Virol., 70: 8606-8613.

Meyers, G., Thiel, H.-J., and Rümenapf, T. 1996a. Classical swine fever virus: Recovery of infectious viruses from cDNA constructs and generation of recombinant cytopathogenic swine fever virus. J. Virol. 67:7088-709526.

Meyers, G., Wirblich, C., Thiel. H.-J. and Thumfart, J. O. 2000. Rabbit hemorrhagic disease Virus: genome organization and polyprotein processing of a calicivirus studied after transient expression of cDNA constructs. Virology 276: 349-363.

Moennig, V. and Plagemann, J. 1992. The pestiviruses. Adv. Virus Res. 41: 53-91.

Paton, D. J., Lowings, J. P., Barrett, A. D. 1992. Epitope mapping of the gp53 envelope protein of bovine viral diarrhea virus. Virology 190: 763-772.

Pellerin, C. et. al. Identification of a new group of bovine viral diarrhea virus strains associated with severe outbreaks and high mortalities, Virology 203, 1994:260-268.

Porter, A. G. (1993). Picornavirus nonstructural proteins: emerging roles in virus replication and inhibition of host cell functions. *J. Virol.* 67, 6917-6921.

Rüggli, N., Tratschin, J. D., Schweizer, M., McCullough, K. C., Hofmann, M. A., Summerfield, A. 2003. Classical swine fever virus interferes with cellular antiviral defense: evidence for a novel function of N(pro). J. Virol. 77:7645-7654.

Rümenapf, T., Stark, R., Heimann, M., and Thiel, H.-J. 1998. N-terminal protease of pestiviruses: identification of putative catalytic residues by site directed mutagenesis. J. Virol. 72: 2544-2547.

Rümenapf, T., Unger, G., Strauss, J. H., and Thiel, H.-J. 1993. Processing of the evelope glycoproteins of pestiviruses. J. Virol. 67: 3288-3294. Schneider, R., G. Unger, R. Stark, E. Schneider-Scherzer, and H.-J. Thiel. 1993. Identification of a structural glycoprotein of an RNA virus as a ribonuclease. Science 261: 1169-1171.

Sambrook, J., Fritsch, E. F. & Maniatis, T., Molecular Cloning: A Laboratory Manual Cold Spring Harbor Laboratory, Cold Spring Harbor, N.Y., 1989

Stark, R., Meyers, G., Rümenapf, T., and Thiel, H.-J. (1993): Processing of pestivirus polyprotein: Cleavage site between autoprotease and nucleocapsid protein of classical swine fever virus. J. Virol., 67, 7088-7095. Thiel, H.-J., Plagemann, G. W., & Moennig, V. 1996. The pestiviruses. In Fields Virology, eds. Fields, B. N., Knipe, D. M., & Howley, P. M. (Lippincott-Raven, Philadelphia), pp. 1059-1073.

Thiel, H.-J., Stark, R., Weiland, E., Rümenapf, T. & Meyers, G. 1991. Hog cholera virus: molecular composition of virions from a pestivirus. J. Virol. 65: 4705-4712.31.

Tratschin, J.-D., Moser, C., Ruggli, N., and Hofmann, M. A. 1998. Classical swine fever virus leader proteinase Npro is not required for viral replication in cell culture. J. Virol. 72, 7681-7684. van Rijn, P. A., van Gennip, H. G., de Meijer, E. J., Moormann, R. J. 1993. Epitope mapping of envelope glycoprotein E1 of hog cholera virus strain Brescia. J. Gen. Virol. 74: 2053-2060.

Van Gennip H. G. P., Hesselink, A. T., Moormann, R. J. M., Hulst M. M. (2005). Dimerisation of glycoprotein Ems of classical swine fever virus is not essential for viral replication and infection. Arch. Virology 150, 2271-2286.

Weiland, E., Thiel, H.-J., Hess, G., and Weiland, F. (1989). Development of monoclonal neutralizing antibodies against bovine viral diarrhea virus after pretreatment of mice with normal bovine cells and cyclophosphamide. J. Virol. Methods 24: 237-244.

Weiland, E., Stark, R., Haas, B., Rümenapf, T., Meyers, G. and Thiel, H.-J. (1990). Pestivirus glycoprotein which induces neutralizing antibodies forms part of a disulfide-linked heterodimer. J. Virology 64, 3563-3569.

Weiland, E., Ahl, R., Stark, R., Weiland, F. and Thiel, H.-J. (1992). A second envelope glycoprotein mediates neutralization of a pestivirus, hog cholera virus. J. Virology 66, 3677-3682.

Windisch, J. M., Schneider, R., Stark, R., Weiland, E., Meyers, G., and Thiel, H.-J. 1996. RNase of classical swine fever virus: biochemical characterization and inhibition by virus-neutralizing monoclonal antibodies. J. Virol. 70: 352-358

Wiskerchen, M., Belzer, S. K., and Collett, M. S. 1991. Pestivirus gene expression: the first protein product of the bovine viral diarrhea virus large open reading frame, p20, possesses proteolytic activity J. Virol. 65:4508-4514.

---

The invention claimed is:

1. An immunogenic composition comprising an attenuated pestivirus, wherein the attenuated pestivirus does not produce a dimeric $E^{rns}$ glycoprotein, wherein at least the last cysteine residue of the $E^{rns}$ glycoprotein of the attenuated pestivirus is deleted or substituted by a non-cysteine amino acid residue.

2. The immunogenic composition according to claim 1, wherein the last cysteine residue of the $E^{rns}$ glycoprotein of the attenuated pestivirus is deleted.

3. The immunogenic composition according to claim 1, wherein the attenuated pestivirus is a Bovine viral diarrhea virus (BVDV), Classical swine fever virus (CSFV), or Border disease virus (BDV).

4. The immunogenic composition according to claim 3, wherein at least the last cysteine residue of the $E^{rns}$ glycoprotein is deleted or substituted by a non-cysteine residue, wherein the last cysteine residue of the $E^{rns}$ glycoprotein is corresponding to:

a. amino acid position 441 of the attenuated BVDV, when aligned with SEQ ID Nos: 4 or 7:

b. the homologous cysteine residue at amino acid position 438 according to SEQ ID NO: 1 of the attenuated CSFV. wherein homology is according to a sequence alignment of SEQ ID NO:1 with SEQ ID NOs:4 or 7: or c. the homologous cysteine residue at amino acid position 439 according to SEQ ID NO: 10 of the attenuated BDV, wherein homology is according to a sequence alignment of SEQ ID NO:10 with SEQ ID NOs: 4 or 7.

5. The immunogenic composition according to claim 1, further comprising at least a mutation in the N$^{pro}$ protein of the attenuated pestivirus, wherein the mutation in the N$^{pro}$ protein leads to inactivation of the N$^{pro}$ protein.

6. The immunogenic composition according to claim 5, wherein the mutation in the N$^{pro}$ protein of the attenuated pestivirus leads to an encoded polyprotein as characterized by the following formula:

[N$^{pro}$]$_x$-[PS]$_y$-[C-term]

wherein:
[N$^{pro}$] relates to the N$^{pro}$ portion of the polyprotein, wherein "x" represents the number of amino acids of the N$^{pro}$ portion present in the polyprotein; and wherein
[PS] relates to a processing signal selected from the group consisting of: ubiquitin, LC3, SUMO-1, NEDD8, GATE-16 or GABA(A)RAP), Intein, picornavirus 3C, caridovirus 2A, and p15 of rabbit hemorrhagic disease virus; and wherein
"Y" may be =0, which means that no processing signal is present, or "Y" may be =1, which means that a processing signal is present; and wherein
[C-term] relates to the complete virus polyprotein except for N$^{pro}$, but including the capsid (C)-protein, modified E$^{RNS}$ protein and any other protein present in the virus polyprotein including the carboxyterminal NS5B; and wherein
if "y" is =0, then "x" is 0 to 12, (meaning no N$^{pro}$ specific amino acid or 1 to 12 amino acids of N$^{pro}$ are present); and wherein
if "y" is =1, then "x" is 0 to 168; (meaning no N$^{pro}$ specific amino acid or 1 to all 168 amino acids of N$^{pro}$ are present).

7. The immunogenic composition according to claim 6, wherein the mutation in the N$^{pro}$ portion leads to an encoded polyprotein as characterized by the following formula:

[N$^{pro}$]-[PS]$_0$-[C-term].

8. The immunogenic composition according to claim 6, wherein the mutation in the N$^{pro}$ portion lead to an encoded polyprotein as characterized by the following formula:

[N$^{pro}$]$_4$-[PS]$_0$-[C-term*], wherein [C-term*] is =[C-term] wherein within the C-protein the amino acid at position 2 is changed from D to N.

9. The immunogenic composition according to claim 6, wherein the attenuated virus is BVDV, and wherein the mutation in the N$^{pro}$ leads to an encoded polyprotein as characterized by a formula selected from the group consisting of:

[N$^{pro}$]$_x$-[PS]$_0$-MELF-[PS]$_0$-[C-term*];

and wherein [C-term*] is =[C-term] wherein within the C-protein the amino acid at position 2 is changed from D to N.

10. The immunogenic composition according to claim 6, wherein the mutation in the N$^{pro}$ leads to an encoded polyprotein as characterized by a formula selected from the group consisting of:

N$^{Pro}$]$_2$-[PS]$_1$-[C-term], and wherein PS is ubiquitin or LC3.

11. The immunogenic composition according to claim 9, wherein the [PS]$_0$ is replaced by [PS]$_1$, and wherein the PS is selected from the group of consisting of: ubiquitin, LC3, SUMO-1, NEDD8, GATE-16, GABA(A)RAP, Intein, picornavirus 3C, caridovirus 2A, aphtovirus 2A, and p15 of rabbit hemorrhagic disease virus.

12. The immunogenic composition according to claim 1, wherein the composition further comprises a pharmaceutically acceptable carrier or excipients.

13. The immunogenic composition according to claim 1, wherein the composition comprises at least two attenuated pestiviruses of the same genus.

14. The immunogenic composition according to claim 13, wherein the attenuated pestiviruses are different isolates or subtypes of the same genus.

15. The immunogenic composition according to claim 13, wherein the attenuated pestiviruses are modified at same coding regions such that none of the attenuated viruses can revert to a pathogenic pestivirus by recombination.

16. An attenuated pestivirus, wherein the attenuated pestivirus does not produce a dimeric E$^{rns}$ glycoprotein and has at least one mutation in the N$^{pro}$ protein such that the N$^{pro}$ protein is inactivated wherein at least the last cysteine residue of the E$^{rns}$ glycoprotein is deleted or substituted by a non-cysteine amino acid residue.

17. The attenuated pestivirus according to claim 16, wherein the attenuated pestivirus is a Bovine viral diarrhea virus (BVDV), Classical swine fever virus (CSFV) or Border disease virus (BDV).

18. The attenuated pestivirus according claim 17, wherein at least the last cysteine residue of the E$^{rns}$ glycoprotein is deleted or substituted by a non-cysteine residue, wherein the last cysteine residue of the E$^{rns}$ glycoprotein is corresponding to:
 a. amino acid position 441 of the attenuated BVDV, when aligned with SEQ ID NOs: 4 or 7;
 b. the homologous cysteine residue at amino acid position 438 according to SEQ ID NO: 1 of the attenuated CSFV, wherein homology is according to a sequence alignment of SEQ ID NO:1 with SEQ ID NOs: 4 or 7; or
 c: the homologous cysteine residue at amino acid position 439 according to SEQ ID NO: 10 of the attenuated BDV, wherein homology is according to a sequence alignment of SEQ ID NO:10 with SEQ ID NOs.4 or 7.

19. The attenuated virus according to claim 16, wherein the mutation(s) in the N$^{pro}$ lead to an encoded polyprotein as characterized by the following formula:

[N$^{pro}$]$_x$-[PS]$_y$-[C-term]

and wherein:
[N$^{pro}$] relates to the N$^{pro}$ portion of the polyprotein, wherein "x" represents the number of amino acids of the N$^{pro}$ present in the polyprotein; and wherein
[PS] relates to a processing signal selected from the group consisting of: ubiquitin, LC3, SUMO-1, NEDD8, GATE-16 or GABA(A)RAP), Intein, picornavirus 3C, caridovirus 2A, aphtovirus 2A, and p15 of rabbit hemorrhagic disease virus; and wherein
"Y" may be =0, which means that no processing signal is present, or "Y" may be =1, which means that a processing signal is present; and wherein
[C-term] relates to the complete virus polyprotein except for N$^{pro}$, but including the region of capsid (C)-protein, modified E$^{RNS}$ protein and any other protein present in the virus polyprotein including the carboxyterminal NS5B; and wherein
if "y" is =0, then "x" is 0 to 12, (means no NP specific amino acid or 1 to 12 amino acids of N$^{pro}$ are present); and wherein if "y" is =1, then "x" is 0 to 168; (means no $N^{pro}$ specific amino acid or 1 to all 168 amino acids of NP are present).

20. The attenuated virus according to claim 19, wherein the mutation(s) in the $N^{pro}$ leads to an encoded polyprotein as characterized by the following formula:

$[N^{pro}]_4$-$[PS]_0$-[C-term].

21. The attenuated virus according to claim 19, wherein the mutation(s) in the $N^{pro}$ leads to an encoded polyprotein as characterized by the following formula:

$[N^{pro}]_4$-$[PS]_0$-[C-term*], and wherein [C-term*] is =[C-term] wherein in the C-protein the amino acid at position 2 is changed from D to N.

22. The attenuated virus according to claim 19, wherein the mutation(s) in the $N^{pro}$ leads to an encoded polyprotein as characterized by the following formula:

$[N^{pro}]_x$-$[PS]_1$-[C-term]

and wherein PS is selected from the group of ubiquitin or LC3.

23. A recombinant attenuated BVDV, wherein the attenuated BVDV does not produce a dimeric $E^{rns}$ glycoprotein wherein at least the last cysteine residue of the $E^{rns}$ glycoprotein of the attenuated BVDV is deleted or substituted by a non-cysteine amino acid residue.

24. The recombinant attenuated BVDV according to claim 23, wherein at least the last cysteine residue corresponding to amino acid position 441 when aligned with SEQ ID NOs: 4 or 7 is deleted or substituted by a non-cysteine residue.

25. A method for attenuating a pestivirus, comprising modifying the $E^{rns}$ glycoprotein of the pestivirus such that the attenuated pestivirus does not produce a dimeric $E^{rns}$ glycoprotein wherein at least the last cysteine residue of the $E^{rns}$ glycoprotein of the is deleted or substituted by a non-cysteine amino acid residue.

* * * * *

SEQUENCE LISTING

```
<160> NUMBER OF SEQ ID NOS: 49

<210> SEQ ID NO 1
<211> LENGTH: 3898
<212> TYPE: PRT
<213> ORGANISM: CSFV

<400> SEQUENCE: 1

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160
```

```
Cys Pro Leu Trp Val Thr Ser Cys Ser Asp Gly Ala Ser Gly Ser
                165                 170                 175

Lys Asp Lys Lys Pro Asp Arg Met Asn Lys Gly Lys Leu Lys Ile Ala
            180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
            245                 250                 255

Ile Thr Ile Leu Leu Tyr Gln Pro Val Ala Ala Glu Asn Ile Thr Gln
        260                 265                 270

Trp Asn Leu Ser Asp Asn Gly Thr Asn Gly Ile Gln Arg Ala Met Tyr
    275                 280                 285

Leu Arg Gly Val Asn Arg Ser Leu His Gly Ile Trp Pro Glu Lys Ile
290                 295                 300

Cys Lys Gly Val Pro Thr His Leu Ala Thr Asp Thr Glu Leu Lys Glu
305                 310                 315                 320

Ile Arg Gly Met Met Asp Ala Ser Glu Arg Thr Asn Tyr Thr Cys Cys
                325                 330                 335

Arg Leu Gln Arg His Glu Trp Asn Lys His Gly Trp Cys Asn Trp Tyr
            340                 345                 350

Asn Ile Asp Pro Trp Ile Gln Leu Met Asn Arg Thr Gln Thr Asn Leu
        355                 360                 365

Thr Glu Gly Pro Pro Asp Lys Glu Cys Ala Val Thr Cys Arg Tyr Asp
    370                 375                 380

Lys Asn Thr Asp Val Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
            420                 425                 430

Tyr Gly Asp His Glu Cys Gly Ser Leu Leu Gln Asp Thr Ala Leu Tyr
        435                 440                 445

Leu Leu Asp Gly Met Thr Asn Thr Ile Glu Asn Ala Arg Gln Gly Ala
450                 455                 460

Ala Arg Val Thr Ser Trp Leu Gly Arg Gln Leu Ser Thr Ala Gly Lys
465                 470                 475                 480

Lys Leu Glu Arg Arg Ser Lys Thr Trp Phe Gly Ala Tyr Ala Leu Ser
                485                 490                 495

Pro Tyr Cys Asn Val Thr Arg Lys Ile Gly Tyr Ile Trp Tyr Thr Asn
            500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
    530                 535                 540

Gly Gly His Leu Ser Glu Phe Leu Leu Leu Ser Leu Val Ile Leu Ser
545                 550                 555                 560

Asp Phe Ala Pro Glu Thr Ala Ser Thr Leu Tyr Leu Ile Leu His Tyr
                565                 570                 575
```

-continued

Ala Ile Pro Gln Ser His Glu Glu Pro Gly Cys Asp Thr Asn Gln
            580                 585                 590

Leu Asn Leu Thr Val Lys Leu Arg Thr Glu Asp Val Val Pro Ser Ser
            595                 600                 605

Val Trp Asn Ile Gly Lys Tyr Val Cys Val Arg Pro Asp Trp Trp Pro
            610                 615                 620

Tyr Glu Thr Lys Val Ala Leu Leu Phe Glu Glu Ala Gly Gln Val Ile
625                 630                 635                 640

Lys Leu Val Leu Arg Ala Leu Arg Asp Leu Thr Arg Val Trp Asn Ser
            645                 650                 655

Ala Ser Thr Thr Ala Phe Leu Ile Cys Leu Ile Lys Val Leu Arg Gly
            660                 665                 670

Gln Val Val Gln Gly Ile Ile Trp Leu Leu Leu Val Thr Gly Ala Gln
            675                 680                 685

Gly Arg Leu Ala Cys Lys Glu Asp Tyr Arg Tyr Ala Ile Ser Ser Thr
            690                 695                 700

Asn Glu Ile Gly Leu Leu Gly Ala Glu Gly Leu Thr Thr Thr Trp Lys
705                 710                 715                 720

Glu Tyr Ser His Gly Leu Gln Leu Asp Asp Gly Thr Val Lys Ala Val
            725                 730                 735

Cys Thr Ala Gly Ser Phe Lys Val Thr Ala Leu Asn Val Val Ser Arg
            740                 745                 750

Arg Tyr Leu Ala Ser Leu His Lys Arg Ala Leu Pro Thr Ser Val Thr
            755                 760                 765

Phe Glu Leu Leu Phe Asp Gly Thr Asn Pro Ala Ile Glu Glu Met Asp
            770                 775                 780

Asp Asp Phe Gly Phe Gly Leu Cys Pro Phe Asp Thr Ser Pro Val Ile
785                 790                 795                 800

Lys Gly Lys Tyr Asn Thr Thr Leu Leu Asn Gly Ser Ala Phe Tyr Leu
            805                 810                 815

Val Cys Pro Ile Gly Trp Thr Gly Val Val Glu Cys Thr Ala Val Ser
            820                 825                 830

Pro Thr Thr Leu Arg Thr Glu Val Val Lys Thr Phe Arg Arg Asp Lys
            835                 840                 845

Pro Phe Pro His Arg Val Asp Cys Val Thr Thr Ile Val Glu Lys Glu
            850                 855                 860

Asp Leu Phe His Cys Lys Leu Gly Gly Asn Trp Thr Cys Val Lys Gly
865                 870                 875                 880

Asp Pro Val Thr Tyr Lys Gly Gly Gln Val Lys Gln Cys Arg Trp Cys
            885                 890                 895

Gly Phe Glu Phe Lys Glu Pro Tyr Gly Leu Pro His Tyr Pro Ile Gly
            900                 905                 910

Lys Cys Ile Leu Thr Asn Glu Thr Gly Tyr Arg Val Val Asp Ser Thr
            915                 920                 925

Asp Cys Asn Arg Asp Gly Val Val Ile Ser Thr Glu Gly Glu His Glu
            930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Glu Gly
            965                 970                 975

Pro Val Arg Lys Thr Ser Cys Thr Phe Asn Tyr Thr Lys Thr Leu Arg
            980                 985                 990

Asn Lys Tyr Tyr Glu Pro Arg Asp  Ser Tyr Phe Gln Gln  Tyr Met Leu

```
              995                 1000               1005
Lys Gly Glu Tyr Gln Tyr Trp Phe Asn Leu Asp Val Thr Asp His
    1010                1015               1020

His Thr Asp Tyr Phe Ala Glu Phe Val Leu Val Val Val Ala
    1025                1030               1035

Leu Leu Gly Gly Arg Tyr Val Leu Trp Leu Ile Val Thr Tyr Ile
    1040                1045               1050

Ile Leu Thr Glu Gln Leu Ala Ala Gly Leu Gln Leu Gly Gln Gly
    1055                1060               1065

Glu Val Val Leu Ile Gly Asn Leu Ile Thr His Thr Asp Asn Glu
    1070                1075               1080

Val Val Val Tyr Phe Leu Leu Leu Tyr Leu Val Ile Arg Asp Glu
    1085                1090               1095

Pro Ile Lys Lys Trp Ile Leu Leu Leu Phe His Ala Met Thr Asn
    1100                1105               1110

Asn Pro Val Lys Thr Ile Thr Val Ala Leu Leu Met Ile Ser Gly
    1115                1120               1125

Val Ala Lys Gly Gly Lys Ile Asp Gly Gly Trp Gln Arg Gln Pro
    1130                1135               1140

Val Thr Ser Phe Asp Ile Gln Leu Ala Leu Ala Val Val Val Val
    1145                1150               1155

Val Val Met Leu Leu Ala Lys Arg Asp Pro Thr Thr Phe Pro Leu
    1160                1165               1170

Val Ile Thr Val Ala Thr Leu Arg Thr Ala Lys Ile Thr Asn Gly
    1175                1180               1185

Phe Ser Thr Asp Leu Val Ile Ala Thr Val Ser Ala Ala Leu Leu
    1190                1195               1200

Thr Trp Thr Tyr Ile Ser Asp Tyr Tyr Lys Tyr Lys Thr Trp Leu
    1205                1210               1215

Gln Tyr Leu Val Ser Thr Val Thr Gly Ile Phe Leu Ile Arg Val
    1220                1225               1230

Leu Lys Gly Ile Gly Glu Leu Asp Leu His Ala Pro Thr Leu Pro
    1235                1240               1245

Ser His Arg Pro Leu Phe Tyr Ile Leu Val Tyr Leu Ile Ser Thr
    1250                1255               1260

Ala Val Val Thr Arg Trp Asn Leu Asp Val Ala Gly Leu Leu Leu
    1265                1270               1275

Gln Cys Val Pro Thr Leu Leu Met Val Phe Thr Met Trp Ala Asp
    1280                1285               1290

Ile Leu Thr Leu Ile Leu Ile Leu Pro Thr Tyr Glu Leu Thr Lys
    1295                1300               1305

Leu Tyr Tyr Leu Lys Glu Val Lys Ile Gly Ala Glu Arg Gly Trp
    1310                1315               1320

Leu Trp Lys Thr Asn Tyr Lys Arg Val Asn Asp Ile Tyr Glu Val
    1325                1330               1335

Asp Gln Thr Ser Glu Gly Val Tyr Leu Phe Pro Ser Lys Gln Arg
    1340                1345               1350

Thr Ser Ala Ile Thr Ser Thr Met Leu Pro Leu Ile Lys Ala Ile
    1355                1360               1365

Leu Ile Ser Cys Ile Ser Asn Lys Trp Gln Leu Ile Tyr Leu Leu
    1370                1375               1380

Tyr Leu Ile Phe Glu Val Ser Tyr Tyr Leu His Lys Lys Val Ile
    1385                1390               1395
```

```
Asp Glu Ile Ala Gly Gly Thr Asn Phe Val Ser Arg Leu Val Ala
    1400            1405            1410

Ala Leu Ile Glu Val Asn Trp Ala Phe Asp Asn Glu Glu Val Lys
    1415            1420            1425

Gly Leu Lys Lys Phe Phe Leu Leu Ser Ser Arg Val Lys Glu Leu
    1430            1435            1440

Ile Ile Lys His Lys Val Arg Asn Glu Val Val Val Arg Trp Phe
    1445            1450            1455

Gly Asp Glu Glu Ile Tyr Gly Met Pro Lys Leu Ile Gly Leu Val
    1460            1465            1470

Lys Ala Ala Thr Leu Ser Arg Asn Lys His Cys Met Leu Cys Thr
    1475            1480            1485

Val Cys Glu Asp Arg Asp Trp Arg Gly Glu Thr Cys Pro Lys Cys
    1490            1495            1500

Gly Arg Phe Gly Pro Pro Val Val Cys Gly Met Thr Leu Ala Asp
    1505            1510            1515

Phe Glu Glu Lys His Tyr Lys Arg Ile Phe Ile Arg Glu Asp Gln
    1520            1525            1530

Ser Gly Gly Pro Leu Arg Glu Glu His Ala Gly Tyr Leu Gln Tyr
    1535            1540            1545

Lys Ala Arg Gly Gln Leu Phe Leu Arg Asn Leu Pro Val Leu Ala
    1550            1555            1560

Thr Lys Val Lys Met Leu Leu Val Gly Asn Leu Gly Thr Glu Ile
    1565            1570            1575

Gly Asp Leu Glu His Leu Gly Trp Val Leu Arg Gly Pro Ala Val
    1580            1585            1590

Cys Lys Lys Val Thr Glu His Glu Arg Cys Thr Thr Ser Ile Met
    1595            1600            1605

Asp Lys Leu Thr Ala Phe Pro Gly Val Met Pro Arg Gly Thr Thr
    1610            1615            1620

Pro Arg Ala Pro Val Arg Phe Pro Thr Ser Leu Leu Lys Ile Arg
    1625            1630            1635

Arg Gly Leu Glu Thr Gly Trp Ala Tyr Thr His Gln Gly Gly Ile
    1640            1645            1650

Ser Ser Val Asp His Val Thr Cys Gly Lys Asp Leu Leu Val Cys
    1655            1660            1665

Asp Thr Met Gly Arg Thr Arg Val Val Cys Gln Ser Asn Asn Lys
    1670            1675            1680

Met Thr Asp Glu Ser Glu Tyr Gly Val Lys Thr Asp Ser Gly Cys
    1685            1690            1695

Pro Glu Gly Ala Arg Cys Tyr Val Phe Asn Pro Glu Ala Val Asn
    1700            1705            1710

Ile Ser Gly Thr Lys Gly Ala Met Val His Leu Gln Lys Thr Gly
    1715            1720            1725

Gly Glu Phe Thr Cys Val Thr Ala Ser Gly Thr Pro Ala Phe Phe
    1730            1735            1740

Asp Leu Lys Asn Leu Lys Gly Trp Ser Gly Leu Pro Ile Phe Glu
    1745            1750            1755

Ala Ser Ser Gly Arg Val Val Gly Arg Val Lys Val Gly Lys Asn
    1760            1765            1770

Glu Asp Ser Lys Pro Thr Lys Leu Met Ser Gly Ile Gln Thr Val
    1775            1780            1785
```

-continued

```
Ser Lys Ser Ala Thr Asp Leu Thr Glu Met Val Lys Lys Ile Thr
    1790                1795                1800

Thr Met Asn Arg Gly Glu Phe Arg Gln Ile Thr Leu Ala Thr Gly
    1805                1810                1815

Ala Gly Lys Thr Thr Glu Leu Pro Arg Ser Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Gln Lys His Pro Ser Ile
    1850                1855                1860

Ala Phe Asn Leu Arg Ile Gly Glu Met Lys Glu Gly Asp Met Ala
    1865                1870                1875

Thr Gly Ile Thr Tyr Ala Ser Tyr Gly Tyr Phe Cys Gln Met Ser
    1880                1885                1890

Gln Pro Lys Leu Arg Ala Ala Met Val Glu Tyr Ser Phe Ile Phe
    1895                1900                1905

Leu Asp Glu Tyr His Cys Ala Thr Pro Glu Gln Leu Ala Ile Met
    1910                1915                1920

Gly Lys Ile His Arg Phe Ser Glu Asn Leu Arg Val Val Ala Met
    1925                1930                1935

Thr Ala Thr Pro Ala Gly Thr Val Thr Thr Thr Gly Gln Lys His
    1940                1945                1950

Pro Ile Glu Glu Phe Ile Ala Pro Glu Val Met Lys Gly Glu Asp
    1955                1960                1965

Leu Gly Ser Glu Tyr Leu Asp Ile Ala Gly Leu Lys Ile Pro Val
    1970                1975                1980

Glu Glu Met Lys Asn Asn Met Leu Val Phe Val Pro Thr Arg Asn
    1985                1990                1995

Met Ala Val Glu Ala Ala Lys Lys Leu Lys Ala Lys Gly Tyr Asn
    2000                2005                2010

Ser Gly Tyr Tyr Tyr Ser Gly Glu Asp Pro Ser Asn Leu Arg Val
    2015                2020                2025

Val Thr Ser Gln Ser Pro Tyr Val Val Val Ala Thr Asn Ala Ile
    2030                2035                2040

Glu Ser Gly Val Thr Leu Pro Asp Leu Asp Val Val Val Asp Thr
    2045                2050                2055

Gly Leu Lys Cys Glu Lys Arg Ile Arg Leu Ser Pro Lys Met Pro
    2060                2065                2070

Phe Ile Val Thr Gly Leu Lys Arg Met Ala Val Thr Ile Gly Glu
    2075                2080                2085

Gln Ala Gln Arg Arg Gly Arg Val Gly Arg Val Lys Pro Gly Arg
    2090                2095                2100

Tyr Tyr Arg Ser Gln Glu Thr Pro Val Gly Ser Lys Asp Tyr His
    2105                2110                2115

Tyr Asp Leu Leu Gln Ala Gln Arg Tyr Gly Ile Glu Asp Gly Ile
    2120                2125                2130

Asn Ile Thr Lys Ser Phe Arg Glu Met Asn Tyr Asp Trp Ser Leu
    2135                2140                2145

Tyr Glu Glu Asp Ser Leu Met Ile Thr Gln Leu Glu Ile Leu Asn
    2150                2155                2160

Asn Leu Leu Ile Ser Glu Glu Leu Pro Met Ala Val Lys Asn Ile
    2165                2170                2175

Met Ala Arg Thr Asp His Pro Glu Pro Ile Gln Leu Ala Tyr Asn
```

```
            2180                2185                2190

Ser Tyr Glu Thr Gln Val Pro Val Leu Phe Pro Lys Ile Arg Asn
    2195                2200                2205

Gly Glu Val Thr Asp Thr Tyr Asp Asn Tyr Thr Phe Leu Asn Ala
    2210                2215                2220

Arg Lys Leu Gly Asp Asp Val Pro Pro Tyr Val Tyr Ala Thr Glu
    2225                2230                2235

Asp Glu Asp Leu Ala Val Glu Leu Leu Gly Leu Asp Trp Pro Asp
    2240                2245                2250

Pro Gly Asn Gln Gly Thr Val Glu Ala Gly Arg Ala Leu Lys Gln
    2255                2260                2265

Val Val Gly Leu Ser Thr Ala Glu Asn Ala Leu Leu Val Ala Leu
    2270                2275                2280

Phe Gly Tyr Val Gly Tyr Gln Ala Leu Ser Lys Arg His Ile Pro
    2285                2290                2295

Val Val Thr Asp Ile Tyr Ser Val Glu Asp His Arg Leu Glu Asp
    2300                2305                2310

Thr Thr His Leu Gln Tyr Ala Pro Asn Ala Ile Lys Thr Glu Gly
    2315                2320                2325

Lys Glu Thr Glu Leu Lys Glu Leu Ala Gln Gly Asp Val Gln Arg
    2330                2335                2340

Cys Val Glu Ala Val Thr Asn Tyr Ala Arg Glu Gly Ile Gln Phe
    2345                2350                2355

Met Lys Ser Gln Ala Leu Lys Val Arg Glu Thr Pro Thr Tyr Lys
    2360                2365                2370

Glu Thr Met Asn Thr Val Ala Asp Tyr Val Lys Lys Phe Ile Glu
    2375                2380                2385

Ala Leu Thr Asp Ser Lys Asp Ile Ile Lys Tyr Gly Leu Trp
    2390                2395                2400

Gly Ala His Thr Ala Leu Tyr Lys Ser Ile Gly Ala Arg Leu Gly
    2405                2410                2415

His Glu Thr Ala Phe Ala Thr Leu Val Val Lys Trp Leu Ala Phe
    2420                2425                2430

Gly Gly Glu Ser Ile Ser Asp His Ile Lys Gln Ala Ala Thr Asp
    2435                2440                2445

Leu Val Val Tyr Tyr Ile Ile Asn Arg Pro Gln Phe Pro Gly Asp
    2450                2455                2460

Thr Glu Thr Gln Gln Glu Gly Arg Lys Phe Val Ala Ser Leu Leu
    2465                2470                2475

Val Ser Ala Leu Ala Thr Tyr Thr Tyr Lys Ser Trp Asn Tyr Asn
    2480                2485                2490

Asn Leu Ser Lys Ile Val Glu Pro Ala Leu Ala Thr Leu Pro Tyr
    2495                2500                2505

Ala Ala Lys Ala Leu Lys Leu Phe Ala Pro Thr Arg Leu Glu Ser
    2510                2515                2520

Val Val Ile Leu Ser Thr Ala Ile Tyr Lys Thr Tyr Leu Ser Ile
    2525                2530                2535

Arg Arg Gly Lys Ser Asp Gly Leu Leu Gly Thr Gly Val Ser Ala
    2540                2545                2550

Ala Met Glu Ile Met Ser Gln Asn Pro Val Ser Val Gly Ile Ala
    2555                2560                2565

Val Met Leu Gly Val Gly Ala Val Ala Ala His Asn Ala Ile Glu
    2570                2575                2580
```

-continued

Ala Ser Glu Gln Lys Arg Thr Leu Leu Met Lys Val Phe Val Lys
2585                2590                2595

Asn Phe Leu Asp Gln Ala Ala Thr Asp Glu Leu Val Lys Glu Ser
2600                2605                2610

Pro Glu Lys Ile Ile Met Ala Leu Phe Glu Ala Val Gln Thr Val
2615                2620                2625

Gly Asn Pro Leu Arg Leu Val Tyr His Leu Tyr Gly Val Phe Tyr
2630                2635                2640

Lys Gly Trp Glu Ala Lys Glu Leu Ala Gln Arg Thr Ala Gly Arg
2645                2650                2655

Asn Leu Phe Thr Leu Ile Met Phe Glu Ala Val Glu Leu Leu Gly
2660                2665                2670

Val Asp Ser Glu Gly Lys Ile Arg Gln Leu Ser Ser Asn Tyr Ile
2675                2680                2685

Leu Glu Leu Leu Tyr Lys Phe Arg Asp Asn Ile Lys Ser Ser Val
2690                2695                2700

Arg Glu Ile Ala Ile Ser Trp Ala Pro Ala Pro Phe Ser Cys Asp
2705                2710                2715

Trp Thr Pro Thr Asp Asp Arg Ile Gly Leu Pro His Asp Asn Tyr
2720                2725                2730

Leu Arg Val Glu Thr Lys Cys Pro Cys Gly Tyr Arg Met Lys Ala
2735                2740                2745

Val Lys Asn Cys Ala Gly Glu Leu Arg Leu Leu Glu Glu Gly Gly
2750                2755                2760

Ser Phe Leu Cys Arg Asn Lys Phe Gly Arg Gly Ser Gln Asn Tyr
2765                2770                2775

Arg Val Thr Lys Tyr Tyr Asp Asp Asn Leu Ser Glu Ile Lys Pro
2780                2785                2790

Val Ile Arg Met Glu Gly His Val Glu Leu Tyr Tyr Lys Gly Ala
2795                2800                2805

Thr Ile Lys Leu Asp Phe Asn Asn Ser Lys Thr Val Leu Ala Thr
2810                2815                2820

Asp Lys Trp Glu Val Asp His Ser Thr Leu Val Arg Ala Leu Lys
2825                2830                2835

Arg Tyr Thr Gly Ala Gly Tyr Arg Gly Ala Tyr Leu Gly Glu Lys
2840                2845                2850

Pro Asn His Lys His Leu Ile Gln Arg Asp Cys Ala Thr Leu Thr
2855                2860                2865

Lys Asp Lys Val Cys Phe Ile Lys Met Lys Arg Gly Cys Ala Phe
2870                2875                2880

Thr Tyr Asp Leu Ser Leu His Asn Leu Thr Arg Leu Ile Glu Leu
2885                2890                2895

Val His Lys Asn Asn Leu Glu Asp Arg Glu Ile Pro Ala Val Thr
2900                2905                2910

Val Thr Thr Trp Leu Ala Tyr Thr Phe Val Asn Glu Asp Ile Gly
2915                2920                2925

Thr Ile Lys Pro Thr Phe Gly Glu Lys Val Thr Pro Glu Lys Gln
2930                2935                2940

Glu Glu Val Val Leu Gln Pro Ala Val Val Val Asp Thr Thr Asp
2945                2950                2955

Val Ala Val Thr Val Val Gly Glu Thr Ser Thr Met Thr Thr Gly
2960                2965                2970

```
Glu Thr Pro Thr Thr Phe Thr Ser Leu Gly Ser Asp Ser Lys Val
2975                2980                2985

Arg Gln Val Leu Lys Leu Gly Val Asp Asp Gly Gln Tyr Pro Gly
2990                2995                3000

Pro Asn Gln Gln Arg Ala Ser Leu Leu Glu Ala Ile Gln Gly Val
3005                3010                3015

Asp Glu Arg Pro Ser Val Leu Ile Leu Gly Ser Asp Lys Ala Thr
3020                3025                3030

Ser Asn Arg Val Lys Thr Ala Lys Asn Val Lys Ile Tyr Arg Ser
3035                3040                3045

Arg Asp Pro Leu Glu Leu Arg Glu Met Met Lys Arg Gly Lys Ile
3050                3055                3060

Leu Val Val Ala Leu Ser Arg Val Asp Thr Ala Leu Leu Lys Phe
3065                3070                3075

Val Asp Tyr Lys Gly Thr Phe Leu Thr Arg Glu Thr Leu Glu Ala
3080                3085                3090

Leu Ser Leu Gly Lys Pro Lys Lys Arg Asp Ile Thr Lys Ala Glu
3095                3100                3105

Ala Gln Trp Leu Leu Arg Leu Glu Asp Gln Ile Glu Glu Leu Pro
3110                3115                3120

Asp Trp Phe Ala Ala Lys Glu Pro Ile Phe Leu Glu Ala Asn Ile
3125                3130                3135

Lys Arg Asp Lys Tyr His Leu Val Gly Asp Ile Ala Thr Ile Lys
3140                3145                3150

Glu Lys Ala Lys Gln Leu Gly Ala Thr Asp Ser Thr Lys Ile Ser
3155                3160                3165

Lys Glu Val Gly Ala Lys Val Tyr Ser Met Lys Leu Ser Asn Trp
3170                3175                3180

Val Ile Gln Glu Glu Asn Lys Gln Gly Ser Leu Ala Pro Leu Phe
3185                3190                3195

Glu Glu Leu Leu Gln Gln Cys Pro Pro Gly Gly Gln Asn Lys Thr
3200                3205                3210

Thr His Met Val Ser Ala Tyr Gln Leu Ala Gln Gly Asn Trp Val
3215                3220                3225

Pro Val Ser Cys His Val Phe Met Gly Thr Ile Pro Ala Arg Arg
3230                3235                3240

Thr Lys Thr His Pro Tyr Glu Ala Tyr Val Lys Leu Arg Glu Leu
3245                3250                3255

Val Asp Glu His Lys Met Lys Ala Leu Cys Gly Gly Ser Gly Leu
3260                3265                3270

Ser Lys His Asn Glu Trp Val Ile Gly Lys Val Lys Tyr Gln Gly
3275                3280                3285

Asn Leu Arg Thr Lys His Met Leu Asn Pro Gly Lys Val Ala Glu
3290                3295                3300

Gln Leu His Arg Glu Gly Tyr Arg His Asn Val Tyr Asn Lys Thr
3305                3310                3315

Ile Gly Ser Val Met Thr Ala Thr Gly Ile Arg Leu Glu Lys Leu
3320                3325                3330

Pro Val Val Arg Ala Gln Thr Asp Thr Thr Asn Phe His Gln Ala
3335                3340                3345

Ile Arg Asp Lys Ile Asp Lys Glu Glu Asn Leu Gln Thr Pro Gly
3350                3355                3360

Leu His Lys Lys Leu Met Glu Val Phe Asn Ala Leu Lys Arg Pro
```

```
            3365                3370                3375

Glu Leu Glu Ala Ser Tyr Asp Ala Val Asp Trp Glu Glu Leu Glu
    3380                3385                3390

Arg Gly Ile Asn Arg Lys Gly Ala Ala Gly Phe Phe Glu Arg Lys
    3395                3400                3405

Asn Ile Gly Glu Val Leu Asp Ser Glu Lys Asn Lys Val Glu Glu
    3410                3415                3420

Val Ile Asp Ser Leu Lys Lys Gly Arg Asn Ile Arg Tyr Tyr Glu
    3425                3430                3435

Thr Ala Ile Pro Lys Asn Glu Lys Arg Asp Val Asn Asp Asp Trp
    3440                3445                3450

Thr Ala Gly Asp Phe Val Asp Glu Lys Lys Pro Arg Val Ile Gln
    3455                3460                3465

Tyr Pro Glu Ala Lys Thr Arg Leu Ala Ile Thr Lys Val Met Tyr
    3470                3475                3480

Lys Trp Val Lys Gln Lys Pro Val Val Ile Pro Gly Tyr Glu Gly
    3485                3490                3495

Lys Thr Pro Leu Phe Gln Ile Phe Asp Lys Val Lys Lys Glu Trp
    3500                3505                3510

Asp Gln Phe Gln Asn Pro Val Ala Val Ser Phe Asp Thr Lys Ala
    3515                3520                3525

Trp Asp Thr Gln Val Thr Thr Arg Asp Leu Glu Leu Ile Arg Asp
    3530                3535                3540

Ile Gln Lys Phe Tyr Phe Lys Lys Lys Trp His Lys Phe Ile Asp
    3545                3550                3555

Thr Leu Thr Lys His Met Ser Glu Val Pro Val Ile Ser Ala Asp
    3560                3565                3570

Gly Glu Val Tyr Ile Arg Lys Gly Gln Arg Gly Ser Gly Gln Pro
    3575                3580                3585

Asp Thr Ser Ala Gly Asn Ser Met Leu Asn Val Leu Thr Met Val
    3590                3595                3600

Tyr Ala Phe Cys Glu Ala Thr Gly Val Pro Tyr Lys Ser Phe Asp
    3605                3610                3615

Arg Val Ala Lys Ile His Val Cys Gly Asp Asp Gly Phe Leu Ile
    3620                3625                3630

Thr Glu Arg Ala Leu Gly Glu Lys Phe Ala Ser Lys Gly Val Gln
    3635                3640                3645

Ile Leu Tyr Glu Ala Gly Lys Pro Gln Lys Ile Thr Glu Gly Asp
    3650                3655                3660

Lys Met Lys Val Ala Tyr Gln Phe Asp Asp Ile Glu Phe Cys Ser
    3665                3670                3675

His Thr Pro Val Gln Val Arg Trp Ser Asp Asn Thr Ser Ser Tyr
    3680                3685                3690

Met Pro Gly Arg Asn Thr Thr Thr Ile Leu Ala Lys Met Ala Thr
    3695                3700                3705

Arg Leu Asp Ser Ser Gly Glu Arg Gly Thr Ile Ala Tyr Glu Lys
    3710                3715                3720

Ala Val Ala Phe Ser Phe Leu Leu Met Tyr Ser Trp Asn Pro Leu
    3725                3730                3735

Ile Arg Arg Ile Cys Leu Leu Val Leu Ser Thr Glu Leu Gln Val
    3740                3745                3750

Arg Pro Gly Lys Ser Thr Thr Tyr Tyr Tyr Glu Gly Asp Pro Ile
    3755                3760                3765
```

```
Ser Ala Tyr Lys Glu Val Ile Gly His Asn Leu Phe Asp Leu Lys
    3770            3775            3780

Arg Thr Ser Phe Glu Lys Leu Ala Lys Leu Asn Leu Ser Met Ser
    3785            3790            3795

Thr Leu Gly Val Trp Thr Arg His Thr Ser Lys Arg Leu Leu Gln
    3800            3805            3810

Asp Cys Val Asn Val Gly Thr Lys Glu Gly Asn Trp Leu Val Asn
    3815            3820            3825

Ala Asp Arg Leu Val Ser Ser Lys Thr Gly Asn Arg Tyr Ile Pro
    3830            3835            3840

Gly Glu Gly His Thr Leu Gln Gly Lys His Tyr Glu Glu Leu Ile
    3845            3850            3855

Leu Ala Arg Lys Pro Ile Gly Asn Phe Glu Gly Thr Asp Arg Tyr
    3860            3865            3870

Asn Leu Gly Pro Ile Val Asn Val Val Leu Arg Arg Leu Lys Ile
    3875            3880            3885

Met Met Met Ala Leu Ile Gly Arg Gly Val
    3890            3895

<210> SEQ ID NO 2
<211> LENGTH: 3897
<212> TYPE: PRT
<213> ORGANISM: CSFV

<400> SEQUENCE: 2

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys Ser Asp Asp Gly Ala Ser Gly Ser
                165                 170                 175

Lys Asp Lys Lys Pro Asp Arg Met Asn Lys Gly Lys Leu Lys Ile Ala
            180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Lys Gly Lys Val
    210                 215                 220

Lys Gly Lys Asn Thr Gln Asp Gly Leu Tyr His Asn Lys Asn Lys Pro
```

```
                225                 230                 235                 240
Pro Glu Ser Arg Lys Lys Leu Glu Lys Ala Leu Leu Ala Trp Ala Val
                245                 250                 255

Ile Thr Ile Leu Leu Tyr Gln Pro Val Ala Ala Glu Asn Ile Thr Gln
                260                 265                 270

Trp Asn Leu Ser Asp Asn Gly Thr Asn Gly Ile Gln Arg Ala Met Tyr
                275                 280                 285

Leu Arg Gly Val Asn Arg Ser Leu His Gly Ile Trp Pro Glu Lys Ile
                290                 295                 300

Cys Lys Gly Val Pro Thr His Leu Ala Thr Asp Thr Glu Leu Lys Glu
305                 310                 315                 320

Ile Arg Gly Met Met Asp Ala Ser Glu Arg Thr Asn Tyr Thr Cys Cys
                325                 330                 335

Arg Leu Gln Arg His Glu Trp Asn Lys His Gly Trp Cys Asn Trp Tyr
                340                 345                 350

Asn Ile Asp Pro Trp Ile Gln Leu Met Asn Arg Thr Gln Thr Asn Leu
                355                 360                 365

Thr Glu Gly Pro Pro Asp Lys Glu Cys Ala Val Thr Cys Arg Tyr Asp
                370                 375                 380

Lys Asn Thr Asp Val Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
                420                 425                 430

Tyr Gly Asp His Glu Gly Ser Leu Leu Gln Asp Thr Ala Leu Tyr Leu
                435                 440                 445

Leu Asp Gly Met Thr Asn Thr Ile Glu Asn Ala Arg Gln Gly Ala Ala
                450                 455                 460

Arg Val Thr Ser Trp Leu Gly Arg Gln Leu Ser Thr Ala Gly Lys Lys
465                 470                 475                 480

Leu Glu Arg Arg Ser Lys Thr Trp Phe Gly Ala Tyr Ala Leu Ser Pro
                485                 490                 495

Tyr Cys Asn Val Thr Arg Lys Ile Gly Tyr Ile Trp Tyr Thr Asn Asn
                500                 505                 510

Cys Thr Pro Ala Cys Leu Pro Lys Asn Thr Lys Ile Ile Gly Pro Gly
                515                 520                 525

Lys Phe Asp Thr Asn Ala Glu Asp Gly Lys Ile Leu His Glu Met Gly
                530                 535                 540

Gly His Leu Ser Glu Phe Leu Leu Leu Ser Leu Val Ile Leu Ser Asp
545                 550                 555                 560

Phe Ala Pro Glu Thr Ala Ser Thr Leu Tyr Leu Ile Leu His Tyr Ala
                565                 570                 575

Ile Pro Gln Ser His Glu Glu Pro Glu Gly Cys Asp Thr Asn Gln Leu
                580                 585                 590

Asn Leu Thr Val Lys Leu Arg Thr Glu Asp Val Val Pro Ser Ser Val
                595                 600                 605

Trp Asn Ile Gly Lys Tyr Val Cys Val Arg Pro Asp Trp Trp Pro Tyr
                610                 615                 620

Glu Thr Lys Val Ala Leu Leu Phe Glu Glu Ala Gly Gln Val Ile Lys
625                 630                 635                 640

Leu Val Leu Arg Ala Leu Arg Asp Leu Thr Arg Val Trp Asn Ser Ala
                645                 650                 655
```

-continued

Ser Thr Thr Ala Phe Leu Ile Cys Leu Ile Lys Val Leu Arg Gly Gln
            660                 665                 670

Val Val Gln Gly Ile Ile Trp Leu Leu Val Thr Gly Ala Gln Gly
        675                 680                 685

Arg Leu Ala Cys Lys Glu Asp Tyr Arg Tyr Ala Ile Ser Ser Thr Asn
        690                 695                 700

Glu Ile Gly Leu Leu Gly Ala Glu Gly Leu Thr Thr Thr Trp Lys Glu
705                 710                 715                 720

Tyr Ser His Gly Leu Gln Leu Asp Asp Gly Thr Val Lys Ala Val Cys
                725                 730                 735

Thr Ala Gly Ser Phe Lys Val Thr Ala Leu Asn Val Val Ser Arg Arg
            740                 745                 750

Tyr Leu Ala Ser Leu His Lys Arg Ala Leu Pro Thr Ser Val Thr Phe
            755                 760                 765

Glu Leu Leu Phe Asp Gly Thr Asn Pro Ala Ile Glu Glu Met Asp Asp
        770                 775                 780

Asp Phe Gly Phe Gly Leu Cys Pro Phe Asp Thr Ser Pro Val Ile Lys
785                 790                 795                 800

Gly Lys Tyr Asn Thr Thr Leu Leu Asn Gly Ser Ala Phe Tyr Leu Val
                805                 810                 815

Cys Pro Ile Gly Trp Thr Gly Val Val Glu Cys Thr Ala Val Ser Pro
            820                 825                 830

Thr Thr Leu Arg Thr Glu Val Val Lys Thr Phe Arg Arg Asp Lys Pro
        835                 840                 845

Phe Pro His Arg Val Asp Cys Val Thr Thr Ile Val Glu Lys Glu Asp
        850                 855                 860

Leu Phe His Cys Lys Leu Gly Gly Asn Trp Thr Cys Val Lys Gly Asp
865                 870                 875                 880

Pro Val Thr Tyr Lys Gly Gly Gln Val Lys Gln Cys Arg Trp Cys Gly
                885                 890                 895

Phe Glu Phe Lys Glu Pro Tyr Gly Leu Pro His Tyr Pro Ile Gly Lys
            900                 905                 910

Cys Ile Leu Thr Asn Glu Thr Gly Tyr Arg Val Val Asp Ser Thr Asp
            915                 920                 925

Cys Asn Arg Asp Gly Val Val Ile Ser Thr Glu Gly Glu His Glu Cys
        930                 935                 940

Leu Ile Gly Asn Thr Thr Val Lys Val His Ala Leu Asp Glu Arg Leu
945                 950                 955                 960

Gly Pro Met Pro Cys Arg Pro Lys Glu Ile Val Ser Ser Glu Gly Pro
                965                 970                 975

Val Arg Lys Thr Ser Cys Thr Phe Asn Tyr Thr Lys Thr Leu Arg Asn
            980                 985                 990

Lys Tyr Tyr Glu Pro Arg Asp Ser Tyr Phe Gln Gln Tyr Met Leu Lys
        995                 1000                1005

Gly Glu Tyr Gln Tyr Trp Phe Asn Leu Asp Val Thr Asp His His
        1010                1015                1020

Thr Asp Tyr Phe Ala Glu Phe Val Val Leu Val Val Val Ala Leu
        1025                1030                1035

Leu Gly Gly Arg Tyr Val Leu Trp Leu Ile Val Thr Tyr Ile Ile
        1040                1045                1050

Leu Thr Glu Gln Leu Ala Ala Gly Leu Gln Leu Gly Gln Gly Glu
        1055                1060                1065

```
Val Val Leu Ile Gly Asn Leu Ile Thr His Thr Asp Asn Glu Val
1070                1075                1080

Val Val Tyr Phe Leu Leu Tyr Leu Val Ile Arg Asp Glu Pro
1085                1090                1095

Ile Lys Lys Trp Ile Leu Leu Leu Phe His Ala Met Thr Asn Asn
1100                1105                1110

Pro Val Lys Thr Ile Thr Val Ala Leu Leu Met Ile Ser Gly Val
1115                1120                1125

Ala Lys Gly Gly Lys Ile Asp Gly Gly Trp Gln Arg Gln Pro Val
1130                1135                1140

Thr Ser Phe Asp Ile Gln Leu Ala Leu Ala Val Val Val Val Val
1145                1150                1155

Val Met Leu Leu Ala Lys Arg Asp Pro Thr Thr Phe Pro Leu Val
1160                1165                1170

Ile Thr Val Ala Thr Leu Arg Thr Ala Lys Ile Thr Asn Gly Phe
1175                1180                1185

Ser Thr Asp Leu Val Ile Ala Thr Val Ser Ala Ala Leu Leu Thr
1190                1195                1200

Trp Thr Tyr Ile Ser Asp Tyr Tyr Lys Tyr Lys Thr Trp Leu Gln
1205                1210                1215

Tyr Leu Val Ser Thr Val Thr Gly Ile Phe Leu Ile Arg Val Leu
1220                1225                1230

Lys Gly Ile Gly Glu Leu Asp Leu His Ala Pro Thr Leu Pro Ser
1235                1240                1245

His Arg Pro Leu Phe Tyr Ile Leu Val Tyr Leu Ile Ser Thr Ala
1250                1255                1260

Val Val Thr Arg Trp Asn Leu Asp Val Ala Gly Leu Leu Leu Gln
1265                1270                1275

Cys Val Pro Thr Leu Leu Met Val Phe Thr Met Trp Ala Asp Ile
1280                1285                1290

Leu Thr Leu Ile Leu Ile Leu Pro Thr Tyr Glu Leu Thr Lys Leu
1295                1300                1305

Tyr Tyr Leu Lys Glu Val Lys Ile Gly Ala Glu Arg Gly Trp Leu
1310                1315                1320

Trp Lys Thr Asn Tyr Lys Arg Val Asn Asp Ile Tyr Glu Val Asp
1325                1330                1335

Gln Thr Ser Glu Gly Val Tyr Leu Phe Pro Ser Lys Gln Arg Thr
1340                1345                1350

Ser Ala Ile Thr Ser Thr Met Leu Pro Leu Ile Lys Ala Ile Leu
1355                1360                1365

Ile Ser Cys Ile Ser Asn Lys Trp Gln Leu Ile Tyr Leu Leu Tyr
1370                1375                1380

Leu Ile Phe Glu Val Ser Tyr Tyr Leu His Lys Lys Val Ile Asp
1385                1390                1395

Glu Ile Ala Gly Gly Thr Asn Phe Val Ser Arg Leu Val Ala Ala
1400                1405                1410

Leu Ile Glu Val Asn Trp Ala Phe Asp Asn Glu Val Lys Gly
1415                1420                1425

Leu Lys Lys Phe Phe Leu Leu Ser Ser Arg Val Lys Glu Leu Ile
1430                1435                1440

Ile Lys His Lys Val Arg Asn Glu Val Val Val Arg Trp Phe Gly
1445                1450                1455

Asp Glu Glu Ile Tyr Gly Met Pro Lys Leu Ile Gly Leu Val Lys
```

-continued

```
            1460                1465                1470

Ala Ala Thr Leu Ser Arg Asn Lys His Cys Met Leu Cys Thr Val
    1475                1480                1485

Cys Glu Asp Arg Asp Trp Arg Gly Glu Thr Cys Pro Lys Cys Gly
    1490                1495                1500

Arg Phe Gly Pro Pro Val Val Cys Gly Met Thr Leu Ala Asp Phe
    1505                1510                1515

Glu Glu Lys His Tyr Lys Arg Ile Phe Ile Arg Glu Asp Gln Ser
    1520                1525                1530

Gly Gly Pro Leu Arg Glu Glu His Ala Gly Tyr Leu Gln Tyr Lys
    1535                1540                1545

Ala Arg Gly Gln Leu Phe Leu Arg Asn Leu Pro Val Leu Ala Thr
    1550                1555                1560

Lys Val Lys Met Leu Leu Val Gly Asn Leu Gly Thr Glu Ile Gly
    1565                1570                1575

Asp Leu Glu His Leu Gly Trp Val Leu Arg Gly Pro Ala Val Cys
    1580                1585                1590

Lys Lys Val Thr Glu His Glu Arg Cys Thr Thr Ser Ile Met Asp
    1595                1600                1605

Lys Leu Thr Ala Phe Phe Gly Val Met Pro Arg Gly Thr Thr Pro
    1610                1615                1620

Arg Ala Pro Val Arg Phe Pro Thr Ser Leu Leu Lys Ile Arg Arg
    1625                1630                1635

Gly Leu Glu Thr Gly Trp Ala Tyr Thr His Gln Gly Gly Ile Ser
    1640                1645                1650

Ser Val Asp His Val Thr Cys Gly Lys Asp Leu Leu Val Cys Asp
    1655                1660                1665

Thr Met Gly Arg Thr Arg Val Val Cys Gln Ser Asn Asn Lys Met
    1670                1675                1680

Thr Asp Glu Ser Glu Tyr Gly Val Lys Thr Asp Ser Gly Cys Pro
    1685                1690                1695

Glu Gly Ala Arg Cys Tyr Val Phe Asn Pro Glu Ala Val Asn Ile
    1700                1705                1710

Ser Gly Thr Lys Gly Ala Met Val His Leu Gln Lys Thr Gly Gly
    1715                1720                1725

Glu Phe Thr Cys Val Thr Ala Ser Gly Thr Pro Ala Phe Phe Asp
    1730                1735                1740

Leu Lys Asn Leu Lys Gly Trp Ser Gly Leu Pro Ile Phe Glu Ala
    1745                1750                1755

Ser Ser Gly Arg Val Val Gly Arg Val Lys Val Gly Lys Asn Glu
    1760                1765                1770

Asp Ser Lys Pro Thr Lys Leu Met Ser Gly Ile Gln Thr Val Ser
    1775                1780                1785

Lys Ser Ala Thr Asp Leu Thr Glu Met Val Lys Lys Ile Thr Thr
    1790                1795                1800

Met Asn Arg Gly Glu Phe Arg Gln Ile Thr Leu Ala Thr Gly Ala
    1805                1810                1815

Gly Lys Thr Thr Glu Leu Pro Arg Ser Val Ile Glu Glu Ile Gly
    1820                1825                1830

Arg His Lys Arg Val Leu Val Leu Ile Pro Leu Arg Ala Ala Ala
    1835                1840                1845

Glu Ser Val Tyr Gln Tyr Met Arg Gln Lys His Pro Ser Ile Ala
    1850                1855                1860
```

```
Phe Asn Leu Arg Ile Gly Glu Met Lys Glu Gly Asp Met Ala Thr
    1865            1870            1875

Gly Ile Thr Tyr Ala Ser Tyr Gly Tyr Phe Cys Gln Met Ser Gln
    1880            1885            1890

Pro Lys Leu Arg Ala Ala Met Val Glu Tyr Ser Phe Ile Phe Leu
    1895            1900            1905

Asp Glu Tyr His Cys Ala Thr Pro Glu Gln Leu Ala Ile Met Gly
    1910            1915            1920

Lys Ile His Arg Phe Ser Glu Asn Leu Arg Val Val Ala Met Thr
    1925            1930            1935

Ala Thr Pro Ala Gly Thr Val Thr Thr Thr Gly Gln Lys His Pro
    1940            1945            1950

Ile Glu Glu Phe Ile Ala Pro Glu Val Met Lys Gly Glu Asp Leu
    1955            1960            1965

Gly Ser Glu Tyr Leu Asp Ile Ala Gly Leu Lys Ile Pro Val Glu
    1970            1975            1980

Glu Met Lys Asn Asn Met Leu Val Phe Val Pro Thr Arg Asn Met
    1985            1990            1995

Ala Val Glu Ala Ala Lys Lys Leu Lys Ala Lys Gly Tyr Asn Ser
    2000            2005            2010

Gly Tyr Tyr Tyr Ser Gly Glu Asp Pro Ser Asn Leu Arg Val Val
    2015            2020            2025

Thr Ser Gln Ser Pro Tyr Val Val Ala Thr Asn Ala Ile Glu
    2030            2035            2040

Ser Gly Val Thr Leu Pro Asp Leu Asp Val Val Val Asp Thr Gly
    2045            2050            2055

Leu Lys Cys Glu Lys Arg Ile Arg Leu Ser Pro Lys Met Pro Phe
    2060            2065            2070

Ile Val Thr Gly Leu Lys Arg Met Ala Val Thr Ile Gly Glu Gln
    2075            2080            2085

Ala Gln Arg Arg Gly Arg Val Gly Arg Val Lys Pro Gly Arg Tyr
    2090            2095            2100

Tyr Arg Ser Gln Glu Thr Pro Val Gly Ser Lys Asp Tyr His Tyr
    2105            2110            2115

Asp Leu Leu Gln Ala Gln Arg Tyr Gly Ile Glu Asp Gly Ile Asn
    2120            2125            2130

Ile Thr Lys Ser Phe Arg Glu Met Asn Tyr Asp Trp Ser Leu Tyr
    2135            2140            2145

Glu Glu Asp Ser Leu Met Ile Thr Gln Leu Glu Ile Leu Asn Asn
    2150            2155            2160

Leu Leu Ile Ser Glu Glu Leu Pro Met Ala Val Lys Asn Ile Met
    2165            2170            2175

Ala Arg Thr Asp His Pro Glu Pro Ile Gln Leu Ala Tyr Asn Ser
    2180            2185            2190

Tyr Glu Thr Gln Val Pro Val Leu Phe Pro Lys Ile Arg Asn Gly
    2195            2200            2205

Glu Val Thr Asp Thr Tyr Asp Asn Tyr Thr Phe Leu Asn Ala Arg
    2210            2215            2220

Lys Leu Gly Asp Asp Val Pro Pro Tyr Val Tyr Ala Thr Glu Asp
    2225            2230            2235

Glu Asp Leu Ala Val Glu Leu Leu Gly Leu Asp Trp Pro Asp Pro
    2240            2245            2250
```

```
Gly Asn  Gln Gly Thr Val  Glu Ala Gly Arg  Ala Leu Lys Gln  Val
    2255              2260              2265

Val Gly  Leu Ser Thr Ala  Glu Asn Ala Leu  Leu Val Ala Leu  Phe
    2270              2275              2280

Gly Tyr  Val Gly Tyr Gln  Ala Leu Ser Lys  Arg His Ile Pro  Val
    2285              2290              2295

Val Thr  Asp Ile Tyr Ser  Val Glu Asp His  Arg Leu Glu Asp  Thr
    2300              2305              2310

Thr His  Leu Gln Tyr Ala  Pro Asn Ala Ile  Lys Thr Glu Gly  Lys
    2315              2320              2325

Glu Thr  Glu Leu Lys Glu  Leu Ala Gln Gly  Asp Val Gln Arg  Cys
    2330              2335              2340

Val Glu  Ala Val Thr Asn  Tyr Ala Arg Glu  Gly Ile Gln Phe  Met
    2345              2350              2355

Lys Ser  Gln Ala Leu Lys  Val Arg Glu Thr  Pro Thr Tyr Lys  Glu
    2360              2365              2370

Thr Met  Asn Thr Val Ala  Asp Tyr Val Lys  Lys Phe Ile Glu  Ala
    2375              2380              2385

Leu Thr  Asp Ser Lys Glu  Asp Ile Ile Lys  Tyr Gly Leu Trp  Gly
    2390              2395              2400

Ala His  Thr Ala Leu Tyr  Lys Ser Ile Gly  Ala Arg Leu Gly  His
    2405              2410              2415

Glu Thr  Ala Phe Ala Thr  Leu Val Val Lys  Trp Leu Ala Phe  Gly
    2420              2425              2430

Gly Glu  Ser Ile Ser Asp  His Ile Lys Gln  Ala Ala Thr Asp  Leu
    2435              2440              2445

Val Val  Tyr Tyr Ile Ile  Asn Arg Pro Gln  Phe Pro Gly Asp  Thr
    2450              2455              2460

Glu Thr  Gln Gln Glu Gly  Arg Lys Phe Val  Ala Ser Leu Leu  Val
    2465              2470              2475

Ser Ala  Leu Ala Thr Tyr  Thr Tyr Lys Ser  Trp Asn Tyr Asn  Asn
    2480              2485              2490

Leu Ser  Lys Ile Val Glu  Pro Ala Leu Ala  Thr Leu Pro Tyr  Ala
    2495              2500              2505

Ala Lys  Ala Leu Lys Leu  Phe Ala Pro Thr  Arg Leu Glu Ser  Val
    2510              2515              2520

Val Ile  Leu Ser Thr Ala  Ile Tyr Lys Thr  Tyr Leu Ser Ile  Arg
    2525              2530              2535

Arg Gly  Lys Ser Asp Gly  Leu Leu Gly Thr  Gly Val Ser Ala  Ala
    2540              2545              2550

Met Glu  Ile Met Ser Gln  Asn Pro Val Ser  Val Gly Ile Ala  Val
    2555              2560              2565

Met Leu  Gly Val Gly Ala  Val Ala Ala His  Asn Ala Ile Glu  Ala
    2570              2575              2580

Ser Glu  Gln Lys Arg Thr  Leu Leu Met Lys  Val Phe Val Lys  Asn
    2585              2590              2595

Phe Leu  Asp Gln Ala Ala  Thr Asp Glu Leu  Val Lys Glu Ser  Pro
    2600              2605              2610

Glu Lys  Ile Ile Met Ala  Leu Phe Glu Ala  Val Gln Thr Val  Gly
    2615              2620              2625

Asn Pro  Leu Arg Leu Val  Tyr His Leu Tyr  Gly Val Phe Tyr  Lys
    2630              2635              2640

Gly Trp  Glu Ala Lys Glu  Leu Ala Gln Arg  Thr Ala Gly Arg  Asn
```

```
                    2645                2650                2655

Leu Phe Thr Leu Ile Met Phe Glu Ala Val Glu Leu Leu Gly Val
        2660                2665                2670

Asp Ser Glu Gly Lys Ile Arg Gln Leu Ser Ser Asn Tyr Ile Leu
        2675                2680                2685

Glu Leu Leu Tyr Lys Phe Arg Asp Asn Ile Lys Ser Ser Val Arg
        2690                2695                2700

Glu Ile Ala Ile Ser Trp Ala Pro Ala Pro Phe Ser Cys Asp Trp
        2705                2710                2715

Thr Pro Thr Asp Asp Arg Ile Gly Leu Pro His Asp Asn Tyr Leu
        2720                2725                2730

Arg Val Glu Thr Lys Cys Pro Cys Gly Tyr Arg Met Lys Ala Val
        2735                2740                2745

Lys Asn Cys Ala Gly Glu Leu Arg Leu Leu Glu Glu Gly Gly Ser
        2750                2755                2760

Phe Leu Cys Arg Asn Lys Phe Gly Arg Gly Ser Gln Asn Tyr Arg
        2765                2770                2775

Val Thr Lys Tyr Tyr Asp Asp Asn Leu Ser Glu Ile Lys Pro Val
        2780                2785                2790

Ile Arg Met Glu Gly His Val Glu Leu Tyr Tyr Lys Gly Ala Thr
        2795                2800                2805

Ile Lys Leu Asp Phe Asn Asn Ser Lys Thr Val Leu Ala Thr Asp
        2810                2815                2820

Lys Trp Glu Val Asp His Ser Thr Leu Val Arg Ala Leu Lys Arg
        2825                2830                2835

Tyr Thr Gly Ala Gly Tyr Arg Gly Ala Tyr Leu Gly Glu Lys Pro
        2840                2845                2850

Asn His Lys His Leu Ile Gln Arg Asp Cys Ala Thr Leu Thr Lys
        2855                2860                2865

Asp Lys Val Cys Phe Ile Lys Met Lys Arg Gly Cys Ala Phe Thr
        2870                2875                2880

Tyr Asp Leu Ser Leu His Asn Leu Thr Arg Leu Ile Glu Leu Val
        2885                2890                2895

His Lys Asn Asn Leu Glu Asp Arg Glu Ile Pro Ala Val Thr Val
        2900                2905                2910

Thr Thr Trp Leu Ala Tyr Thr Phe Val Asn Glu Asp Ile Gly Thr
        2915                2920                2925

Ile Lys Pro Thr Phe Gly Glu Lys Val Thr Pro Glu Lys Gln Glu
        2930                2935                2940

Glu Val Val Leu Gln Pro Ala Val Val Asp Thr Thr Asp Val
        2945                2950                2955

Ala Val Thr Val Val Gly Glu Thr Ser Thr Met Thr Thr Gly Glu
        2960                2965                2970

Thr Pro Thr Thr Phe Thr Ser Leu Gly Ser Asp Ser Lys Val Arg
        2975                2980                2985

Gln Val Leu Lys Leu Gly Val Asp Asp Gly Gln Tyr Pro Gly Pro
        2990                2995                3000

Asn Gln Gln Arg Ala Ser Leu Leu Glu Ala Ile Gln Gly Val Asp
        3005                3010                3015

Glu Arg Pro Ser Val Leu Ile Leu Gly Ser Asp Lys Ala Thr Ser
        3020                3025                3030

Asn Arg Val Lys Thr Ala Lys Asn Val Lys Ile Tyr Arg Ser Arg
        3035                3040                3045
```

```
Asp Pro Leu Glu Leu Arg Glu Met Met Lys Arg Gly Lys Ile Leu
3050                3055                3060

Val Val Ala Leu Ser Arg Val Asp Thr Ala Leu Leu Lys Phe Val
3065                3070                3075

Asp Tyr Lys Gly Thr Phe Leu Thr Arg Glu Thr Leu Glu Ala Leu
3080                3085                3090

Ser Leu Gly Lys Pro Lys Lys Arg Asp Ile Thr Lys Ala Glu Ala
3095                3100                3105

Gln Trp Leu Leu Arg Leu Glu Asp Gln Ile Glu Glu Leu Pro Asp
3110                3115                3120

Trp Phe Ala Ala Lys Glu Pro Ile Phe Leu Glu Ala Asn Ile Lys
3125                3130                3135

Arg Asp Lys Tyr His Leu Val Gly Asp Ile Ala Thr Ile Lys Glu
3140                3145                3150

Lys Ala Lys Gln Leu Gly Ala Thr Asp Ser Thr Lys Ile Ser Lys
3155                3160                3165

Glu Val Gly Ala Lys Val Tyr Ser Met Lys Leu Ser Asn Trp Val
3170                3175                3180

Ile Gln Glu Glu Asn Lys Gln Gly Ser Leu Ala Pro Leu Phe Glu
3185                3190                3195

Glu Leu Leu Gln Gln Cys Pro Pro Gly Gly Gln Asn Lys Thr Thr
3200                3205                3210

His Met Val Ser Ala Tyr Gln Leu Ala Gln Gly Asn Trp Val Pro
3215                3220                3225

Val Ser Cys His Val Phe Met Gly Thr Ile Pro Ala Arg Arg Thr
3230                3235                3240

Lys Thr His Pro Tyr Glu Ala Tyr Val Lys Leu Arg Glu Leu Val
3245                3250                3255

Asp Glu His Lys Met Lys Ala Leu Cys Gly Gly Ser Gly Leu Ser
3260                3265                3270

Lys His Asn Glu Trp Val Ile Gly Lys Val Lys Tyr Gln Gly Asn
3275                3280                3285

Leu Arg Thr Lys His Met Leu Asn Pro Gly Lys Val Ala Glu Gln
3290                3295                3300

Leu His Arg Glu Gly Tyr Arg His Asn Val Tyr Asn Lys Thr Ile
3305                3310                3315

Gly Ser Val Met Thr Ala Thr Gly Ile Arg Leu Glu Lys Leu Pro
3320                3325                3330

Val Val Arg Ala Gln Thr Asp Thr Thr Asn Phe His Gln Ala Ile
3335                3340                3345

Arg Asp Lys Ile Asp Lys Glu Glu Asn Leu Gln Thr Pro Gly Leu
3350                3355                3360

His Lys Lys Leu Met Glu Val Phe Asn Ala Leu Lys Arg Pro Glu
3365                3370                3375

Leu Glu Ala Ser Tyr Asp Ala Val Asp Trp Glu Glu Leu Glu Arg
3380                3385                3390

Gly Ile Asn Arg Lys Gly Ala Ala Gly Phe Phe Glu Arg Lys Asn
3395                3400                3405

Ile Gly Glu Val Leu Asp Ser Glu Lys Asn Lys Val Glu Glu Val
3410                3415                3420

Ile Asp Ser Leu Lys Lys Gly Arg Asn Ile Arg Tyr Tyr Glu Thr
3425                3430                3435
```

```
Ala Ile Pro Lys Asn Glu Lys Arg Asp Val Asn Asp Asp Trp Thr
3440                3445                3450

Ala Gly Asp Phe Val Asp Glu Lys Lys Pro Arg Val Ile Gln Tyr
3455                3460                3465

Pro Glu Ala Lys Thr Arg Leu Ala Ile Thr Lys Val Met Tyr Lys
3470                3475                3480

Trp Val Lys Gln Lys Pro Val Ile Pro Gly Tyr Glu Gly Lys
3485                3490                3495

Thr Pro Leu Phe Gln Ile Phe Asp Lys Val Lys Lys Glu Trp Asp
3500                3505                3510

Gln Phe Gln Asn Pro Val Ala Val Ser Phe Asp Thr Lys Ala Trp
3515                3520                3525

Asp Thr Gln Val Thr Thr Arg Asp Leu Glu Leu Ile Arg Asp Ile
3530                3535                3540

Gln Lys Phe Tyr Phe Lys Lys Lys Trp His Lys Phe Ile Asp Thr
3545                3550                3555

Leu Thr Lys His Met Ser Glu Val Pro Val Ile Ser Ala Asp Gly
3560                3565                3570

Glu Val Tyr Ile Arg Lys Gly Gln Arg Gly Ser Gly Gln Pro Asp
3575                3580                3585

Thr Ser Ala Gly Asn Ser Met Leu Asn Val Leu Thr Met Val Tyr
3590                3595                3600

Ala Phe Cys Glu Ala Thr Gly Val Pro Tyr Lys Ser Phe Asp Arg
3605                3610                3615

Val Ala Lys Ile His Val Cys Gly Asp Asp Gly Phe Leu Ile Thr
3620                3625                3630

Glu Arg Ala Leu Gly Glu Lys Phe Ala Ser Lys Gly Val Gln Ile
3635                3640                3645

Leu Tyr Glu Ala Gly Lys Pro Gln Lys Ile Thr Glu Gly Asp Lys
3650                3655                3660

Met Lys Val Ala Tyr Gln Phe Asp Asp Ile Glu Phe Cys Ser His
3665                3670                3675

Thr Pro Val Gln Val Arg Trp Ser Asp Asn Thr Ser Ser Tyr Met
3680                3685                3690

Pro Gly Arg Asn Thr Thr Thr Ile Leu Ala Lys Met Ala Thr Arg
3695                3700                3705

Leu Asp Ser Ser Gly Glu Arg Gly Thr Ile Ala Tyr Glu Lys Ala
3710                3715                3720

Val Ala Phe Ser Phe Leu Leu Met Tyr Ser Trp Asn Pro Leu Ile
3725                3730                3735

Arg Arg Ile Cys Leu Leu Val Leu Ser Thr Glu Leu Gln Val Arg
3740                3745                3750

Pro Gly Lys Ser Thr Thr Tyr Tyr Tyr Glu Gly Asp Pro Ile Ser
3755                3760                3765

Ala Tyr Lys Glu Val Ile Gly His Asn Leu Phe Asp Leu Lys Arg
3770                3775                3780

Thr Ser Phe Glu Lys Leu Ala Lys Leu Asn Leu Ser Met Ser Thr
3785                3790                3795

Leu Gly Val Trp Thr Arg His Thr Ser Lys Arg Leu Leu Gln Asp
3800                3805                3810

Cys Val Asn Val Gly Thr Lys Glu Gly Asn Trp Leu Val Asn Ala
3815                3820                3825

Asp Arg Leu Val Ser Ser Lys Thr Gly Asn Arg Tyr Ile Pro Gly
```

```
             3830                3835                3840
Glu Gly His Thr Leu Gln Gly Lys His Tyr Glu Leu Ile Leu
        3845                3850                3855

Ala Arg Lys Pro Ile Gly Asn Phe Glu Gly Thr Asp Arg Tyr Asn
        3860                3865                3870

Leu Gly Pro Ile Val Asn Val Val Leu Arg Arg Leu Lys Ile Met
        3875                3880                3885

Met Met Ala Leu Ile Gly Arg Gly Val
        3890                3895

<210> SEQ ID NO 3
<211> LENGTH: 3898
<212> TYPE: PRT
<213> ORGANISM: CSFV

<400> SEQUENCE: 3

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys Ser Asp Asp Gly Ala Ser Gly Ser
                165                 170                 175

Lys Asp Lys Lys Pro Asp Arg Met Asn Lys Gly Lys Leu Lys Ile Ala
            180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Thr Ile Leu Leu Tyr Gln Pro Val Ala Ala Glu Asn Ile Thr Gln
            260                 265                 270

Trp Asn Leu Ser Asp Asn Gly Thr Asn Gly Ile Gln Arg Ala Met Tyr
        275                 280                 285

Leu Arg Gly Val Asn Arg Ser Leu His Gly Ile Trp Pro Glu Lys Ile
    290                 295                 300
```

```
Cys Lys Gly Val Pro Thr His Leu Ala Thr Asp Thr Glu Leu Lys Glu
305                 310                 315                 320

Ile Arg Gly Met Met Asp Ala Ser Glu Arg Thr Asn Tyr Thr Cys Cys
                325                 330                 335

Arg Leu Gln Arg His Glu Trp Asn Lys His Gly Trp Cys Asn Trp Tyr
            340                 345                 350

Asn Ile Asp Pro Trp Ile Gln Leu Met Asn Arg Thr Gln Thr Asn Leu
        355                 360                 365

Thr Glu Gly Pro Pro Asp Lys Glu Cys Ala Val Thr Cys Arg Tyr Asp
    370                 375                 380

Lys Asn Thr Asp Val Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
                420                 425                 430

Tyr Gly Asp His Glu Ser Gly Ser Leu Leu Gln Asp Thr Ala Leu Tyr
            435                 440                 445

Leu Leu Asp Gly Met Thr Asn Thr Ile Glu Asn Ala Arg Gln Gly Ala
        450                 455                 460

Ala Arg Val Thr Ser Trp Leu Gly Arg Gln Leu Ser Thr Ala Gly Lys
465                 470                 475                 480

Lys Leu Glu Arg Arg Ser Lys Thr Trp Phe Gly Ala Tyr Ala Leu Ser
                485                 490                 495

Pro Tyr Cys Asn Val Thr Arg Lys Ile Gly Tyr Ile Trp Tyr Thr Asn
            500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
    530                 535                 540

Gly Gly His Leu Ser Glu Phe Leu Leu Leu Ser Leu Val Ile Leu Ser
545                 550                 555                 560

Asp Phe Ala Pro Glu Thr Ala Ser Thr Leu Tyr Leu Ile Leu His Tyr
                565                 570                 575

Ala Ile Pro Gln Ser His Glu Glu Pro Glu Gly Cys Asp Thr Asn Gln
            580                 585                 590

Leu Asn Leu Thr Val Lys Leu Arg Thr Glu Asp Val Val Pro Ser Ser
        595                 600                 605

Val Trp Asn Ile Gly Lys Tyr Val Cys Val Arg Pro Asp Trp Trp Pro
    610                 615                 620

Tyr Glu Thr Lys Val Ala Leu Leu Phe Glu Glu Ala Gly Gln Val Ile
625                 630                 635                 640

Lys Leu Val Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
            660                 665                 670

Gln Val Val Gln Gly Ile Ile Trp Leu Leu Leu Val Thr Gly Ala Gln
        675                 680                 685

Gly Arg Leu Ala Cys Lys Glu Asp Tyr Arg Tyr Ala Ile Ser Ser Thr
    690                 695                 700

Asn Glu Ile Gly Leu Leu Gly Ala Glu Gly Leu Thr Thr Thr Trp Lys
705                 710                 715                 720

Glu Tyr Ser His Gly Leu Gln Leu Asp Asp Gly Thr Val Lys Ala Val
```

```
                725                 730                 735
Cys Thr Ala Gly Ser Phe Lys Val Thr Ala Leu Asn Val Val Ser Arg
                740                 745                 750

Arg Tyr Leu Ala Ser Leu His Lys Arg Ala Leu Pro Thr Ser Val Thr
                755                 760                 765

Phe Glu Leu Leu Phe Asp Gly Thr Asn Pro Ala Ile Glu Glu Met Asp
                770                 775                 780

Asp Asp Phe Gly Phe Gly Leu Cys Pro Phe Asp Thr Ser Pro Val Ile
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Val Glu Cys Thr Ala Val Ser
                820                 825                 830

Pro Thr Thr Leu Arg Thr Glu Val Val Lys Thr Phe Arg Arg Asp Lys
                835                 840                 845

Pro Phe Pro His Arg Val Asp Cys Val Thr Thr Ile Val Glu Lys Glu
                850                 855                 860

Asp Leu Phe His Cys Lys Leu Gly Gly Asn Trp Thr Cys Val Lys Gly
865                 870                 875                 880

Asp Pro Val Thr Tyr Lys Gly Gly Gln Val Lys Gln Cys Arg Trp Cys
                885                 890                 895

Gly Phe Glu Phe Lys Glu Pro Tyr Gly Leu Pro His Tyr Pro Ile Gly
                900                 905                 910

Lys Cys Ile Leu Thr Asn Glu Thr Gly Tyr Arg Val Val Asp Ser Thr
                915                 920                 925

Asp Cys Asn Arg Asp Gly Val Val Ile Ser Thr Glu Gly Glu His Glu
                930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Glu Gly
                965                 970                 975

Pro Val Arg Lys Thr Ser Cys Thr Phe Asn Tyr Thr Lys Thr Leu Arg
                980                 985                 990

Asn Lys Tyr Tyr Glu Pro Arg Asp Ser Tyr Phe Gln Gln Tyr Met Leu
                995                 1000                1005

Lys Gly Glu Tyr Gln Tyr Trp Phe Asn Leu Asp Val Thr Asp His
                1010                1015                1020

His Thr Asp Tyr Phe Ala Glu Phe Val Val Leu Val Val Val Ala
                1025                1030                1035

Leu Leu Gly Gly Arg Tyr Val Leu Trp Leu Ile Val Thr Tyr Ile
                1040                1045                1050

Ile Leu Thr Glu Gln Leu Ala Ala Gly Leu Gln Leu Gly Gln Gly
                1055                1060                1065

Glu Val Val Leu Ile Gly Asn Leu Ile Thr His Thr Asp Asn Glu
                1070                1075                1080

Val Val Val Tyr Phe Leu Leu Leu Tyr Leu Val Ile Arg Asp Glu
                1085                1090                1095

Pro Ile Lys Lys Trp Ile Leu Leu Leu Phe His Ala Met Thr Asn
                1100                1105                1110

Asn Pro Val Lys Thr Ile Thr Val Ala Leu Leu Met Ile Ser Gly
                1115                1120                1125

Val Ala Lys Gly Gly Lys Ile Asp Gly Gly Trp Gln Arg Gln Pro
                1130                1135                1140
```

-continued

Val Thr Ser Phe Asp Ile Gln Leu Ala Leu Ala Val Val Val Val
1145                1150                1155

Val Val Met Leu Leu Ala Lys Arg Asp Pro Thr Thr Phe Pro Leu
1160                1165                1170

Val Ile Thr Val Ala Thr Leu Arg Thr Ala Lys Ile Thr Asn Gly
1175                1180                1185

Phe Ser Thr Asp Leu Val Ile Ala Thr Val Ser Ala Ala Leu Leu
1190                1195                1200

Thr Trp Thr Tyr Ile Ser Asp Tyr Tyr Lys Tyr Lys Thr Trp Leu
1205                1210                1215

Gln Tyr Leu Val Ser Thr Val Thr Gly Ile Phe Leu Ile Arg Val
1220                1225                1230

Leu Lys Gly Ile Gly Glu Leu Asp Leu His Ala Pro Thr Leu Pro
1235                1240                1245

Ser His Arg Pro Leu Phe Tyr Ile Leu Val Tyr Leu Ile Ser Thr
1250                1255                1260

Ala Val Val Thr Arg Trp Asn Leu Asp Val Ala Gly Leu Leu Leu
1265                1270                1275

Gln Cys Val Pro Thr Leu Leu Met Val Phe Thr Met Trp Ala Asp
1280                1285                1290

Ile Leu Thr Leu Ile Leu Ile Leu Pro Thr Tyr Glu Leu Thr Lys
1295                1300                1305

Leu Tyr Tyr Leu Lys Glu Val Lys Ile Gly Ala Glu Arg Gly Trp
1310                1315                1320

Leu Trp Lys Thr Asn Tyr Lys Arg Val Asn Asp Ile Tyr Glu Val
1325                1330                1335

Asp Gln Thr Ser Glu Gly Val Tyr Leu Phe Pro Ser Lys Gln Arg
1340                1345                1350

Thr Ser Ala Ile Thr Ser Thr Met Leu Pro Leu Ile Lys Ala Ile
1355                1360                1365

Leu Ile Ser Cys Ile Ser Asn Lys Trp Gln Leu Ile Tyr Leu Leu
1370                1375                1380

Tyr Leu Ile Phe Glu Val Ser Tyr Tyr Leu His Lys Lys Val Ile
1385                1390                1395

Asp Glu Ile Ala Gly Gly Thr Asn Phe Val Ser Arg Leu Val Ala
1400                1405                1410

Ala Leu Ile Glu Val Asn Trp Ala Phe Asp Asn Glu Glu Val Lys
1415                1420                1425

Gly Leu Lys Lys Phe Phe Leu Leu Ser Ser Arg Val Lys Glu Leu
1430                1435                1440

Ile Ile Lys His Lys Val Arg Asn Glu Val Val Val Arg Trp Phe
1445                1450                1455

Gly Asp Glu Glu Ile Tyr Gly Met Pro Lys Leu Ile Gly Leu Val
1460                1465                1470

Lys Ala Ala Thr Leu Ser Arg Asn Lys His Cys Met Leu Cys Thr
1475                1480                1485

Val Cys Glu Asp Arg Asp Trp Arg Gly Glu Thr Cys Pro Lys Cys
1490                1495                1500

Gly Arg Phe Gly Pro Pro Val Val Cys Gly Met Thr Leu Ala Asp
1505                1510                1515

Phe Glu Glu Lys His Tyr Lys Arg Ile Phe Ile Arg Glu Asp Gln
1520                1525                1530

```
Ser Gly Gly Pro Leu Arg Glu Glu His Ala Gly Tyr Leu Gln Tyr
1535                1540                1545

Lys Ala Arg Gly Gln Leu Phe Leu Arg Asn Leu Pro Val Leu Ala
1550                1555                1560

Thr Lys Val Lys Met Leu Leu Val Gly Asn Leu Gly Thr Glu Ile
1565                1570                1575

Gly Asp Leu Glu His Leu Gly Trp Val Leu Arg Gly Pro Ala Val
1580                1585                1590

Cys Lys Lys Val Thr Glu His Glu Arg Cys Thr Thr Ser Ile Met
1595                1600                1605

Asp Lys Leu Thr Ala Phe Phe Gly Val Met Pro Arg Gly Thr Thr
1610                1615                1620

Pro Arg Ala Pro Val Arg Phe Pro Thr Ser Leu Leu Lys Ile Arg
1625                1630                1635

Arg Gly Leu Glu Thr Gly Trp Ala Tyr Thr His Gln Gly Gly Ile
1640                1645                1650

Ser Ser Val Asp His Val Thr Cys Gly Lys Asp Leu Leu Val Cys
1655                1660                1665

Asp Thr Met Gly Arg Thr Arg Val Val Cys Gln Ser Asn Asn Lys
1670                1675                1680

Met Thr Asp Glu Ser Glu Tyr Gly Val Lys Thr Asp Ser Gly Cys
1685                1690                1695

Pro Glu Gly Ala Arg Cys Tyr Val Phe Asn Pro Glu Ala Val Asn
1700                1705                1710

Ile Ser Gly Thr Lys Gly Ala Met Val His Leu Gln Lys Thr Gly
1715                1720                1725

Gly Glu Phe Thr Cys Val Thr Ala Ser Gly Thr Pro Ala Phe Phe
1730                1735                1740

Asp Leu Lys Asn Leu Lys Gly Trp Ser Gly Leu Pro Ile Phe Glu
1745                1750                1755

Ala Ser Ser Gly Arg Val Val Gly Arg Val Lys Val Gly Lys Asn
1760                1765                1770

Glu Asp Ser Lys Pro Thr Lys Leu Met Ser Gly Ile Gln Thr Val
1775                1780                1785

Ser Lys Ser Ala Thr Asp Leu Thr Glu Met Val Lys Lys Ile Thr
1790                1795                1800

Thr Met Asn Arg Gly Glu Phe Arg Gln Ile Thr Leu Ala Thr Gly
1805                1810                1815

Ala Gly Lys Thr Thr Glu Leu Pro Arg Ser Val Ile Glu Glu Ile
1820                1825                1830

Gly Arg His Lys Arg Val Leu Val Leu Ile Pro Leu Arg Ala Ala
1835                1840                1845

Ala Glu Ser Val Tyr Gln Tyr Met Arg Gln Lys His Pro Ser Ile
1850                1855                1860

Ala Phe Asn Leu Arg Ile Gly Glu Met Lys Glu Gly Asp Met Ala
1865                1870                1875

Thr Gly Ile Thr Tyr Ala Ser Tyr Gly Tyr Phe Cys Gln Met Ser
1880                1885                1890

Gln Pro Lys Leu Arg Ala Ala Met Val Glu Tyr Ser Phe Ile Phe
1895                1900                1905

Leu Asp Glu Tyr His Cys Ala Thr Pro Glu Gln Leu Ala Ile Met
1910                1915                1920

Gly Lys Ile His Arg Phe Ser Glu Asn Leu Arg Val Val Ala Met
```

```
                  1925                1930                1935
Thr Ala Thr Pro Ala Gly Thr Val Thr Thr Thr Gly Gln Lys His
          1940                1945                1950

Pro Ile Glu Glu Phe Ile Ala Pro Glu Val Met Lys Gly Glu Asp
          1955                1960                1965

Leu Gly Ser Glu Tyr Leu Asp Ile Ala Gly Leu Lys Ile Pro Val
          1970                1975                1980

Glu Glu Met Lys Asn Asn Met Leu Val Phe Val Pro Thr Arg Asn
          1985                1990                1995

Met Ala Val Glu Ala Ala Lys Lys Leu Lys Ala Lys Gly Tyr Asn
          2000                2005                2010

Ser Gly Tyr Tyr Tyr Ser Gly Glu Asp Pro Ser Asn Leu Arg Val
          2015                2020                2025

Val Thr Ser Gln Ser Pro Tyr Val Val Ala Thr Asn Ala Ile
          2030                2035                2040

Glu Ser Gly Val Thr Leu Pro Asp Leu Asp Val Val Asp Thr
          2045                2050                2055

Gly Leu Lys Cys Glu Lys Arg Ile Arg Leu Ser Pro Lys Met Pro
          2060                2065                2070

Phe Ile Val Thr Gly Leu Lys Arg Met Ala Val Thr Ile Gly Glu
          2075                2080                2085

Gln Ala Gln Arg Arg Gly Arg Val Gly Arg Val Lys Pro Gly Arg
          2090                2095                2100

Tyr Tyr Arg Ser Gln Glu Thr Pro Val Gly Ser Lys Asp Tyr His
          2105                2110                2115

Tyr Asp Leu Leu Gln Ala Gln Arg Tyr Gly Ile Glu Asp Gly Ile
          2120                2125                2130

Asn Ile Thr Lys Ser Phe Arg Glu Met Asn Tyr Asp Trp Ser Leu
          2135                2140                2145

Tyr Glu Glu Asp Ser Leu Met Ile Thr Gln Leu Glu Ile Leu Asn
          2150                2155                2160

Asn Leu Leu Ile Ser Glu Glu Leu Pro Met Ala Val Lys Asn Ile
          2165                2170                2175

Met Ala Arg Thr Asp His Pro Glu Pro Ile Gln Leu Ala Tyr Asn
          2180                2185                2190

Ser Tyr Glu Thr Gln Val Pro Val Leu Phe Pro Lys Ile Arg Asn
          2195                2200                2205

Gly Glu Val Thr Asp Thr Tyr Asp Asn Tyr Thr Phe Leu Asn Ala
          2210                2215                2220

Arg Lys Leu Gly Asp Asp Val Pro Pro Tyr Val Tyr Ala Thr Glu
          2225                2230                2235

Asp Glu Asp Leu Ala Val Glu Leu Leu Gly Leu Asp Trp Pro Asp
          2240                2245                2250

Pro Gly Asn Gln Gly Thr Val Glu Ala Gly Arg Ala Leu Lys Gln
          2255                2260                2265

Val Val Gly Leu Ser Thr Ala Glu Asn Ala Leu Leu Val Ala Leu
          2270                2275                2280

Phe Gly Tyr Val Gly Tyr Gln Ala Leu Ser Lys Arg His Ile Pro
          2285                2290                2295

Val Val Thr Asp Ile Tyr Ser Val Glu Asp His Arg Leu Glu Asp
          2300                2305                2310

Thr Thr His Leu Gln Tyr Ala Pro Asn Ala Ile Lys Thr Glu Gly
          2315                2320                2325
```

```
Lys Glu Thr Glu Leu Lys Glu Leu Ala Gln Gly Asp Val Gln Arg
    2330            2335            2340

Cys Val Glu Ala Val Thr Asn Tyr Ala Arg Glu Gly Ile Gln Phe
    2345            2350            2355

Met Lys Ser Gln Ala Leu Lys Val Arg Glu Thr Pro Thr Tyr Lys
    2360            2365            2370

Glu Thr Met Asn Thr Val Ala Asp Tyr Val Lys Phe Ile Glu
    2375            2380            2385

Ala Leu Thr Asp Ser Lys Glu Asp Ile Ile Lys Tyr Gly Leu Trp
    2390            2395            2400

Gly Ala His Thr Ala Leu Tyr Lys Ser Ile Gly Ala Arg Leu Gly
    2405            2410            2415

His Glu Thr Ala Phe Ala Thr Leu Val Val Lys Trp Leu Ala Phe
    2420            2425            2430

Gly Gly Glu Ser Ile Ser Asp His Ile Lys Gln Ala Ala Thr Asp
    2435            2440            2445

Leu Val Val Tyr Tyr Ile Ile Asn Arg Pro Gln Phe Pro Gly Asp
    2450            2455            2460

Thr Glu Thr Gln Gln Glu Gly Arg Lys Phe Val Ala Ser Leu Leu
    2465            2470            2475

Val Ser Ala Leu Ala Thr Tyr Thr Tyr Lys Ser Trp Asn Tyr Asn
    2480            2485            2490

Asn Leu Ser Lys Ile Val Glu Pro Ala Leu Ala Thr Leu Pro Tyr
    2495            2500            2505

Ala Ala Lys Ala Leu Lys Leu Phe Ala Pro Thr Arg Leu Glu Ser
    2510            2515            2520

Val Val Ile Leu Ser Thr Ala Ile Tyr Lys Thr Tyr Leu Ser Ile
    2525            2530            2535

Arg Arg Gly Lys Ser Asp Gly Leu Leu Gly Thr Gly Val Ser Ala
    2540            2545            2550

Ala Met Glu Ile Met Ser Gln Asn Pro Val Ser Val Gly Ile Ala
    2555            2560            2565

Val Met Leu Gly Val Gly Ala Val Ala Ala His Asn Ala Ile Glu
    2570            2575            2580

Ala Ser Glu Gln Lys Arg Thr Leu Leu Met Lys Val Phe Val Lys
    2585            2590            2595

Asn Phe Leu Asp Gln Ala Ala Thr Asp Glu Leu Val Lys Glu Ser
    2600            2605            2610

Pro Glu Lys Ile Ile Met Ala Leu Phe Glu Ala Val Gln Thr Val
    2615            2620            2625

Gly Asn Pro Leu Arg Leu Val Tyr His Leu Tyr Gly Val Phe Tyr
    2630            2635            2640

Lys Gly Trp Glu Ala Lys Glu Leu Ala Gln Arg Thr Ala Gly Arg
    2645            2650            2655

Asn Leu Phe Thr Leu Ile Met Phe Glu Ala Val Glu Leu Leu Gly
    2660            2665            2670

Val Asp Ser Glu Gly Lys Ile Arg Gln Leu Ser Ser Asn Tyr Ile
    2675            2680            2685

Leu Glu Leu Leu Tyr Lys Phe Arg Asp Asn Ile Lys Ser Ser Val
    2690            2695            2700

Arg Glu Ile Ala Ile Ser Trp Ala Pro Ala Pro Phe Ser Cys Asp
    2705            2710            2715
```

-continued

```
Trp Thr Pro Thr Asp Asp Arg Ile Gly Leu Pro His Asp Asn Tyr
    2720                2725                2730

Leu Arg Val Glu Thr Lys Cys Pro Cys Gly Tyr Arg Met Lys Ala
    2735                2740                2745

Val Lys Asn Cys Ala Gly Glu Leu Arg Leu Leu Glu Glu Gly Gly
    2750                2755                2760

Ser Phe Leu Cys Arg Asn Lys Phe Gly Arg Gly Ser Gln Asn Tyr
    2765                2770                2775

Arg Val Thr Lys Tyr Tyr Asp Asp Asn Leu Ser Glu Ile Lys Pro
    2780                2785                2790

Val Ile Arg Met Glu Gly His Val Glu Leu Tyr Tyr Lys Gly Ala
    2795                2800                2805

Thr Ile Lys Leu Asp Phe Asn Asn Ser Lys Thr Val Leu Ala Thr
    2810                2815                2820

Asp Lys Trp Glu Val Asp His Ser Thr Leu Val Arg Ala Leu Lys
    2825                2830                2835

Arg Tyr Thr Gly Ala Gly Tyr Arg Gly Ala Tyr Leu Gly Glu Lys
    2840                2845                2850

Pro Asn His Lys His Leu Ile Gln Arg Asp Cys Ala Thr Leu Thr
    2855                2860                2865

Lys Asp Lys Val Cys Phe Ile Lys Met Lys Arg Gly Cys Ala Phe
    2870                2875                2880

Thr Tyr Asp Leu Ser Leu His Asn Leu Thr Arg Leu Ile Glu Leu
    2885                2890                2895

Val His Lys Asn Asn Leu Glu Asp Arg Glu Ile Pro Ala Val Thr
    2900                2905                2910

Val Thr Thr Trp Leu Ala Tyr Thr Phe Val Asn Glu Asp Ile Gly
    2915                2920                2925

Thr Ile Lys Pro Thr Phe Gly Glu Lys Val Thr Pro Glu Lys Gln
    2930                2935                2940

Glu Glu Val Val Leu Gln Pro Ala Val Val Val Asp Thr Thr Asp
    2945                2950                2955

Val Ala Val Thr Val Val Gly Glu Thr Ser Thr Met Thr Thr Gly
    2960                2965                2970

Glu Thr Pro Thr Thr Phe Thr Ser Leu Gly Ser Asp Ser Lys Val
    2975                2980                2985

Arg Gln Val Leu Lys Leu Gly Val Asp Asp Gly Gln Tyr Pro Gly
    2990                2995                3000

Pro Asn Gln Gln Arg Ala Ser Leu Leu Glu Ala Ile Gln Gly Val
    3005                3010                3015

Asp Glu Arg Pro Ser Val Leu Ile Leu Gly Ser Asp Lys Ala Thr
    3020                3025                3030

Ser Asn Arg Val Lys Thr Ala Lys Asn Val Lys Ile Tyr Arg Ser
    3035                3040                3045

Arg Asp Pro Leu Glu Leu Arg Glu Met Met Lys Arg Gly Lys Ile
    3050                3055                3060

Leu Val Val Ala Leu Ser Arg Val Asp Thr Ala Leu Leu Lys Phe
    3065                3070                3075

Val Asp Tyr Lys Gly Thr Phe Leu Thr Arg Glu Thr Leu Glu Ala
    3080                3085                3090

Leu Ser Leu Gly Lys Pro Lys Lys Arg Asp Ile Thr Lys Ala Glu
    3095                3100                3105

Ala Gln Trp Leu Leu Arg Leu Glu Asp Gln Ile Glu Glu Leu Pro
```

-continued

```
                3110                3115                3120
Asp Trp Phe Ala Ala Lys Glu Pro Ile Phe Leu Glu Ala Asn Ile
    3125                3130                3135
Lys Arg Asp Lys Tyr His Leu Val Gly Asp Ile Ala Thr Ile Lys
    3140                3145                3150
Glu Lys Ala Lys Gln Leu Gly Ala Thr Asp Ser Thr Lys Ile Ser
    3155                3160                3165
Lys Glu Val Gly Ala Lys Val Tyr Ser Met Lys Leu Ser Asn Trp
    3170                3175                3180
Val Ile Gln Glu Glu Asn Lys Gln Gly Ser Leu Ala Pro Leu Phe
    3185                3190                3195
Glu Glu Leu Leu Gln Gln Cys Pro Pro Gly Gly Gln Asn Lys Thr
    3200                3205                3210
Thr His Met Val Ser Ala Tyr Gln Leu Ala Gln Gly Asn Trp Val
    3215                3220                3225
Pro Val Ser Cys His Val Phe Met Gly Thr Ile Pro Ala Arg Arg
    3230                3235                3240
Thr Lys Thr His Pro Tyr Glu Ala Tyr Val Lys Leu Arg Glu Leu
    3245                3250                3255
Val Asp Glu His Lys Met Lys Ala Leu Cys Gly Gly Ser Gly Leu
    3260                3265                3270
Ser Lys His Asn Glu Trp Val Ile Gly Lys Val Lys Tyr Gln Gly
    3275                3280                3285
Asn Leu Arg Thr Lys His Met Leu Asn Pro Gly Lys Val Ala Glu
    3290                3295                3300
Gln Leu His Arg Glu Gly Tyr Arg His Asn Val Tyr Asn Lys Thr
    3305                3310                3315
Ile Gly Ser Val Met Thr Ala Thr Gly Ile Arg Leu Glu Lys Leu
    3320                3325                3330
Pro Val Val Arg Ala Gln Thr Asp Thr Thr Asn Phe His Gln Ala
    3335                3340                3345
Ile Arg Asp Lys Ile Asp Lys Glu Glu Asn Leu Gln Thr Pro Gly
    3350                3355                3360
Leu His Lys Lys Leu Met Glu Val Phe Asn Ala Leu Lys Arg Pro
    3365                3370                3375
Glu Leu Glu Ala Ser Tyr Asp Ala Val Asp Trp Glu Glu Leu Glu
    3380                3385                3390
Arg Gly Ile Asn Arg Lys Gly Ala Ala Gly Phe Phe Glu Arg Lys
    3395                3400                3405
Asn Ile Gly Glu Val Leu Asp Ser Glu Lys Asn Lys Val Glu Glu
    3410                3415                3420
Val Ile Asp Ser Leu Lys Lys Gly Arg Asn Ile Arg Tyr Tyr Glu
    3425                3430                3435
Thr Ala Ile Pro Lys Asn Glu Lys Arg Asp Val Asn Asp Asp Trp
    3440                3445                3450
Thr Ala Gly Asp Phe Val Asp Glu Lys Lys Pro Arg Val Ile Gln
    3455                3460                3465
Tyr Pro Glu Ala Lys Thr Arg Leu Ala Ile Thr Lys Val Met Tyr
    3470                3475                3480
Lys Trp Val Lys Gln Lys Pro Val Val Ile Pro Gly Tyr Glu Gly
    3485                3490                3495
Lys Thr Pro Leu Phe Gln Ile Phe Asp Lys Val Lys Lys Glu Trp
    3500                3505                3510
```

```
Asp Gln Phe Gln Asn Pro Val Ala Val Ser Phe Asp Thr Lys Ala
3515                3520                3525

Trp Asp Thr Gln Val Thr Thr Arg Asp Leu Glu Leu Ile Arg Asp
    3530                3535                3540

Ile Gln Lys Phe Tyr Phe Lys Lys Lys Trp His Lys Phe Ile Asp
    3545                3550                3555

Thr Leu Thr Lys His Met Ser Glu Val Pro Val Ile Ser Ala Asp
    3560                3565                3570

Gly Glu Val Tyr Ile Arg Lys Gly Gln Arg Gly Ser Gly Gln Pro
    3575                3580                3585

Asp Thr Ser Ala Gly Asn Ser Met Leu Asn Val Leu Thr Met Val
    3590                3595                3600

Tyr Ala Phe Cys Glu Ala Thr Gly Val Pro Tyr Lys Ser Phe Asp
    3605                3610                3615

Arg Val Ala Lys Ile His Val Cys Gly Asp Asp Gly Phe Leu Ile
    3620                3625                3630

Thr Glu Arg Ala Leu Gly Glu Lys Phe Ala Ser Lys Gly Val Gln
    3635                3640                3645

Ile Leu Tyr Glu Ala Gly Lys Pro Gln Lys Ile Thr Glu Gly Asp
    3650                3655                3660

Lys Met Lys Val Ala Tyr Gln Phe Asp Asp Ile Glu Phe Cys Ser
    3665                3670                3675

His Thr Pro Val Gln Val Arg Trp Ser Asp Asn Thr Ser Ser Tyr
    3680                3685                3690

Met Pro Gly Arg Asn Thr Thr Thr Ile Leu Ala Lys Met Ala Thr
    3695                3700                3705

Arg Leu Asp Ser Ser Gly Glu Arg Gly Thr Ile Ala Tyr Glu Lys
    3710                3715                3720

Ala Val Ala Phe Ser Phe Leu Leu Met Tyr Ser Trp Asn Pro Leu
    3725                3730                3735

Ile Arg Arg Ile Cys Leu Leu Val Leu Ser Thr Glu Leu Gln Val
    3740                3745                3750

Arg Pro Gly Lys Ser Thr Thr Tyr Tyr Tyr Glu Gly Asp Pro Ile
    3755                3760                3765

Ser Ala Tyr Lys Glu Val Ile Gly His Asn Leu Phe Asp Leu Lys
    3770                3775                3780

Arg Thr Ser Phe Glu Lys Leu Ala Lys Leu Asn Leu Ser Met Ser
    3785                3790                3795

Thr Leu Gly Val Trp Thr Arg His Thr Ser Lys Arg Leu Leu Gln
    3800                3805                3810

Asp Cys Val Asn Val Gly Thr Lys Glu Gly Asn Trp Leu Val Asn
    3815                3820                3825

Ala Asp Arg Leu Val Ser Ser Lys Thr Gly Asn Arg Tyr Ile Pro
    3830                3835                3840

Gly Glu Gly His Thr Leu Gln Gly Lys His Tyr Glu Glu Leu Ile
    3845                3850                3855

Leu Ala Arg Lys Pro Ile Gly Asn Phe Glu Gly Thr Asp Arg Tyr
    3860                3865                3870

Asn Leu Gly Pro Ile Val Asn Val Val Leu Arg Arg Leu Lys Ile
    3875                3880                3885

Met Met Met Ala Leu Ile Gly Arg Gly Val
    3890                3895
```

<210> SEQ ID NO 4
<211> LENGTH: 3898
<212> TYPE: PRT
<213> ORGANISM: BVDV

<400> SEQUENCE: 4

```
Met Glu Leu Ile Thr Asn Glu Leu Leu Tyr Lys Thr Tyr Lys Gln Lys
1               5                   10                  15

Pro Ala Gly Val Glu Glu Pro Val Tyr Asp Gln Ala Gly Asn Pro Leu
            20                  25                  30

Phe Gly Glu Arg Gly Val Val His Pro Gln Ala Thr Leu Lys Leu Pro
        35                  40                  45

His Lys Arg Gly Glu Ser Glu Val Pro Thr Asn Leu Ala Ser Leu Pro
    50                  55                  60

Lys Arg Gly Asp Cys Arg Ser Gly Asn Ser Lys Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Gln Glu Thr Ser Met Cys
            100                 105                 110

Glu Thr Thr Lys Arg Ile Gly Arg Val Thr Gly Ser Asp Ser Lys Leu
        115                 120                 125

Tyr His Ile Tyr Val Cys Ile Asp Gly Cys Ile Ile Lys Ser Ala
    130                 135                 140

Thr Lys Asp His Gln Lys Val Phe Lys Trp Val His Asn Lys Leu Asn
145                 150                 155                 160

Cys Pro Leu Trp Val Thr Ser Cys Ser Asp Thr Asn Ala Glu Gly Ala
                165                 170                 175

Thr Arg Lys Lys Gln Gln Lys Pro Asp Arg Leu Glu Lys Gly Arg Met
            180                 185                 190

Lys Ile Thr Pro Lys Glu Ser Glu Lys Asp Ser Lys Thr Lys Pro Pro
        195                 200                 205

Asp Ala Thr Ile Val Val Asp Gly Val Lys Tyr Gln Val Lys Lys Lys
    210                 215                 220

Gly Lys Val Lys Ser Lys Asn Thr Gln Asp Gly Leu Tyr His Asn Lys
225                 230                 235                 240

Asn Lys Pro Gln Glu Ser Arg Lys Lys Leu Glu Lys Ala Leu Leu Ala
                245                 250                 255

Trp Ala Ile Ile Ala Leu Val Leu Phe Asp Ile Ala Val Gly Glu Asn
            260                 265                 270

Ile Thr Gln Trp Asn Leu Gln Asp Asn Gly Thr Glu Gly Ile Gln Arg
        275                 280                 285

Ala Met Phe Gln Arg Gly Val Asn Arg Ser Leu His Gly Ile Trp Pro
    290                 295                 300

Glu Lys Ile Cys Thr Gly Val Pro Ser His Leu Ala Thr Asp Thr Glu
305                 310                 315                 320

Leu Lys Ala Ile His Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Tyr Asn Ile Glu Pro Trp Ile Leu Leu Met Asn Lys Thr Gln
        355                 360                 365

Ala Asn Leu Thr Glu Gly Gln Pro Pro Arg Glu Cys Ala Val Thr Cys
    370                 375                 380
```

```
Arg Tyr Asp Arg Asp Ser Asp Leu Asn Ile Val Thr Gln Ala Arg Asp
385                 390                 395                 400

Ser Pro Thr Pro Leu Thr Gly Cys Lys Lys Gly Lys Asn Phe Ser Phe
            405                 410                 415

Ala Gly Val Leu Val Gln Gly Pro Cys Asn Phe Glu Ile Ala Ala Ser
        420                 425                 430

Asp Val Leu Phe Lys Glu His Asp Cys Thr Gly Met Ile Gln Asp Thr
            435                 440                 445

Ala His Tyr Leu Val Asp Gly Leu Thr Asn Ser Leu Glu Ser Ala Arg
450                 455                 460

Gln Gly Thr Ala Lys Leu Thr Thr Trp Leu Gly Arg Gln Leu Arg Ile
465                 470                 475                 480

Leu Gly Lys Lys Leu Glu Asn Lys Ser Lys Thr Trp Phe Gly Ala Tyr
            485                 490                 495

Ala Ala Ser Pro Tyr Cys Glu Val Glu Arg Arg Leu Gly Tyr Ile Trp
        500                 505                 510

Tyr Thr Lys Asn Cys Thr Pro Ala Cys Leu Pro Lys Asn Thr Lys Ile
            515                 520                 525

Val Gly Pro Gly Lys Phe Asp Thr Asn Ala Glu Asp Gly Lys Leu Leu
530                 535                 540

His Glu Met Gly Gly His Leu Ser Glu Val Leu Leu Ser Val Val
545                 550                 555                 560

Val Leu Ser Asp Phe Ala Pro Glu Thr Ala Ser Ile Val Tyr Leu Ile
            565                 570                 575

Leu His Phe Thr Ile Pro Gln Gly His Thr Asp Ile Glu Asp Cys Asp
            580                 585                 590

Lys Asn Gln Leu Asn Leu Thr Val Gly Leu Thr Thr Ala Glu Val Val
            595                 600                 605

Pro Ser Ser Val Trp Asn Leu Gly Lys Tyr Val Cys Val Arg Pro Asp
610                 615                 620

Trp Trp Pro Tyr Glu Thr Ala Thr Val Leu Val Phe Glu Glu Val Gly
625                 630                 635                 640

Gln Val Ile Lys Leu Val Leu Arg Ala Leu Arg Asp Leu Thr Arg Ile
            645                 650                 655

Trp Thr Ala Ala Thr Thr Thr Ala Phe Leu Val Cys Met Val Lys Val
            660                 665                 670

Val Arg Gly Gln Val Leu Gln Gly Ile Leu Trp Leu Met Leu Ile Thr
            675                 680                 685

Gly Ala Gln Gly Tyr Pro Asp Cys Lys Pro Asp Phe Ser Tyr Ala Ile
            690                 695                 700

Ala Lys Asn Asp Glu Ile Gly Pro Leu Gly Ala Thr Gly Leu Thr Thr
705                 710                 715                 720

Gln Trp Tyr Lys Tyr Ser Asp Glu Met Arg Leu Gln Asp Thr Val Val
            725                 730                 735

Thr Val Trp Cys Lys Asn Gly Glu Phe Arg His Leu Ile Thr Cys Glu
            740                 745                 750

Arg Glu Ala Arg Tyr Leu Ala Ile Leu His Thr Arg Ala Leu Pro Thr
            755                 760                 765

Ser Val Val Phe Glu Lys Ile Ile Asn Gly Lys Glu Gln Glu Asp Ile
        770                 775                 780

Val Glu Met Ser Asp Asn Phe Glu Phe Gly Leu Cys Pro Cys Asp Ala
785                 790                 795                 800
```

-continued

Lys Pro Leu Val Arg Gly Lys Phe Asn Val Thr Leu Leu Asn Gly Pro
                805                 810                 815

Ala Phe Gln Met Val Cys Pro Ile Gly Trp Thr Gly Val Ser Cys
            820                 825                 830

Thr Leu Ala Asn Lys Asp Thr Leu Ala Thr Thr Val Val Arg Thr Tyr
            835                 840                 845

Lys Arg Asp Lys Pro Phe Pro Tyr Arg Gln Gly Cys Ile Thr Gln Lys
    850                 855                 860

Thr Ile Gly Glu Asp Leu Tyr Asp Cys Val Leu Gly Gly Asn Trp Thr
865                 870                 875                 880

Cys Val Pro Gly Asn Gln Leu Arg Tyr Val Gly Gly Pro Val Glu Ser
                885                 890                 895

Cys Lys Trp Cys Gly Tyr Lys Phe Asp Lys Ser Glu Gly Leu Pro His
            900                 905                 910

Phe Pro Ile Gly Lys Cys Lys Leu Lys Asn Glu Ser Gly Tyr Arg Gln
            915                 920                 925

Val Asp Glu Thr Ser Cys Asn Arg Asp Gly Val Ala Ile Val Pro Ser
    930                 935                 940

Gly Leu Val Lys Cys Lys Ile Gly Asn Thr Val Val Gln Val Ile Ala
945                 950                 955                 960

Met Asp Asp Lys Leu Gly Pro Met Pro Cys Arg Pro His Glu Ile Ile
                965                 970                 975

Ser Ser Glu Gly Pro Val Glu Lys Thr Ala Cys Thr Phe Asn Tyr Ala
            980                 985                 990

Arg Thr Leu Lys Asn Lys Tyr Phe Glu Pro Arg Asp Asn Tyr Phe Gln
            995                 1000                1005

Gln Tyr Met Leu Lys Gly Glu Tyr Gln Tyr Trp Phe Asp Leu Glu
    1010                1015                1020

Ile Thr Asp His His Arg Asp Tyr Phe Ala Glu Ser Leu Leu Val
    1025                1030                1035

Ile Val Val Ala Leu Leu Gly Gly Arg Tyr Val Leu Trp Leu Leu
    1040                1045                1050

Val Thr Tyr Met Ile Leu Ser Glu Gln Met Thr Leu Gly Ala Gln
    1055                1060                1065

Tyr Gly Ala Gly Glu Ile Val Met Met Gly Asn Leu Leu Thr His
    1070                1075                1080

Asp Ser Ile Glu Val Val Thr Tyr Phe Leu Leu Leu Tyr Leu Leu
    1085                1090                1095

Leu Arg Glu Glu Asn Ile Lys Lys Trp Val Ile Leu Ile Tyr His
    1100                1105                1110

Ile Ile Val Met His Pro Leu Lys Ser Met Thr Val Ile Leu Leu
    1115                1120                1125

Met Val Gly Gly Met Ala Lys Ala Glu Pro Asp Thr Gln Ser Tyr
    1130                1135                1140

Leu Glu Arg Val Asp Leu Ser Phe Thr Met Ile Thr Leu Ile Val
    1145                1150                1155

Val Gly Leu Val Ile Ala Arg Arg Asp Pro Thr Val Val Pro Leu
    1160                1165                1170

Val Thr Ile Val Ala Ala Leu Lys Ile Thr Gly Leu Gly Phe Gly
    1175                1180                1185

Pro Gly Val Asp Val Ala Met Ala Val Leu Thr Leu Thr Leu Leu
    1190                1195                1200

Met Val Ser Tyr Val Thr Asp Tyr Phe Arg Tyr Lys Arg Trp Leu

-continued

```
            1205                1210                1215
Gln Cys Ile Leu Ser Leu Val Ala Gly Val Phe Leu Ile Arg Ser
    1220                1225                1230
Leu Lys His Leu Gly Glu Ile Glu Thr Pro Glu Leu Thr Ile Pro
    1235                1240                1245
Asn Trp Arg Pro Leu Thr Phe Ile Leu Leu Tyr Leu Thr Ser Ala
    1250                1255                1260
Thr Val Val Thr Arg Trp Lys Val Asp Ile Ala Gly Ile Leu Leu
    1265                1270                1275
Gln Gly Ala Pro Ile Leu Leu Leu Ile Ala Thr Leu Trp Ala Asp
    1280                1285                1290
Phe Leu Thr Leu Val Leu Ile Leu Pro Thr Tyr Glu Leu Val Lys
    1295                1300                1305
Leu Tyr Tyr Leu Lys Asn Ile Lys Thr Asp Val Glu Arg Ser Trp
    1310                1315                1320
Leu Gly Gly Leu Asp Tyr Lys Thr Ile Asp Ser Val Tyr Asp Val
    1325                1330                1335
Asp Glu Ser Gly Glu Gly Val Tyr Leu Phe Pro Ser Arg Gln Asp
    1340                1345                1350
Gly Lys Lys Asn Thr Ser Ile Leu Leu Pro Leu Ile Arg Ala Thr
    1355                1360                1365
Leu Ile Ser Cys Val Ser Ser Lys Trp Gln Met Val Tyr Met Ala
    1370                1375                1380
Tyr Leu Thr Leu Asp Phe Met Tyr Tyr Met His Arg Lys Val Ile
    1385                1390                1395
Glu Glu Ile Ser Gly Gly Thr Asn Val Ile Ser Arg Val Ile Ala
    1400                1405                1410
Ala Leu Ile Glu Leu Asn Trp Ser Met Glu Glu Glu Ser Lys
    1415                1420                1425
Gly Leu Lys Lys Phe Phe Val Leu Ser Gly Arg Val Arg Asn Leu
    1430                1435                1440
Ile Ile Lys His Lys Val Arg Asn Gln Thr Val Ala Ser Trp Tyr
    1445                1450                1455
Gly Glu Glu Val Tyr Gly Leu Pro Lys Val Thr Ile Ile
    1460                1465                1470
Arg Ala Cys Thr Leu Asn Lys Asn Lys His Cys Ile Ile Cys Thr
    1475                1480                1485
Val Cys Glu Ala Lys Lys Trp Lys Gly Gly Asn Cys Pro Lys Cys
    1490                1495                1500
Gly Arg His Gly Lys Pro Ile Thr Cys Gly Met Thr Leu Ala Asp
    1505                1510                1515
Phe Glu Glu Arg His Tyr Lys Arg Ile Phe Ile Arg Glu Gly Thr
    1520                1525                1530
Phe Glu Gly Pro Phe Arg Gln Glu Tyr Asn Gly Phe Val Gln Tyr
    1535                1540                1545
Ala Ala Arg Gly Gln Leu Phe Leu Arg Asn Leu Pro Ile Leu Ala
    1550                1555                1560
Thr Lys Val Lys Met Leu Met Val Gly Asn Leu Gly Glu Glu Ile
    1565                1570                1575
Gly Asp Leu Glu His Leu Gly Trp Ile Leu Arg Gly Pro Ala Val
    1580                1585                1590
Cys Lys Lys Ile Thr Glu His Glu Lys Cys His Val Ser Ile Leu
    1595                1600                1605
```

-continued

```
Asp Lys Leu Thr Ala Phe Phe Gly Val Met Pro Arg Gly Thr Thr
    1610                1615                1620

Pro Arg Ala Pro Val Arg Phe Pro Thr Ala Leu Leu Lys Val Arg
    1625                1630                1635

Arg Gly Leu Glu Thr Gly Trp Ala Tyr Thr His Gln Gly Gly Ile
    1640                1645                1650

Ser Ser Val Asp His Val Thr Ala Gly Lys Asp Leu Leu Val Cys
    1655                1660                1665

Asp Ser Met Gly Arg Thr Arg Val Val Cys Gln Ser Asn Asn Lys
    1670                1675                1680

Leu Thr Asp Glu Thr Glu Tyr Gly Val Lys Thr Asp Ser Gly Cys
    1685                1690                1695

Pro Asp Gly Ala Arg Cys Tyr Val Leu Asn Pro Glu Ala Val Asn
    1700                1705                1710

Ile Ser Gly Ser Lys Gly Ala Val Val His Leu Gln Lys Thr Gly
    1715                1720                1725

Gly Glu Phe Thr Cys Val Thr Ala Ser Gly Thr Pro Ala Phe Phe
    1730                1735                1740

Asp Leu Lys Asn Leu Lys Gly Trp Ser Gly Leu Pro Ile Tyr Glu
    1745                1750                1755

Ala Ser Ser Gly Arg Val Val Gly Arg Val Lys Val Gly Lys Asn
    1760                1765                1770

Glu Glu Ser Lys Pro Thr Lys Leu Met Ser Gly Ile Gln Thr Val
    1775                1780                1785

Ser Lys Ser Thr Ala Asp Leu Thr Glu Met Val Lys Lys Ile Thr
    1790                1795                1800

Ser Met Asn Arg Gly Asp Phe Lys Gln Ile Thr Leu Ala Thr Gly
    1805                1810                1815

Ala Gly Lys Thr Thr Glu Leu Pro Lys Ala Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Leu Lys His Pro Ser Ile
    1850                1855                1860

Ser Phe Asn Leu Arg Ile Gly Asp Met Lys Glu Gly Asp Met Ala
    1865                1870                1875

Thr Gly Ile Thr Tyr Ala Ser Tyr Gly Tyr Phe Cys Gln Met Gln
    1880                1885                1890

Gln Pro Lys Leu Arg Ala Ala Met Val Glu Tyr Ser Tyr Ile Phe
    1895                1900                1905

Leu Asp Glu Tyr His Cys Ala Thr Pro Glu Gln Leu Ala Val Ile
    1910                1915                1920

Gly Lys Ile His Arg Phe Ser Glu Ser Ile Arg Val Val Ala Met
    1925                1930                1935

Thr Ala Thr Pro Ala Gly Ser Val Thr Thr Thr Gly Gln Lys His
    1940                1945                1950

Pro Ile Glu Glu Phe Ile Ala Pro Glu Val Met Lys Gly Glu Asp
    1955                1960                1965

Leu Gly Ser Gln Phe Leu Asp Ile Ala Gly Leu Lys Ile Pro Val
    1970                1975                1980

Glu Glu Met Lys Gly Asn Met Leu Val Phe Val Pro Thr Arg Asn
    1985                1990                1995
```

-continued

```
Met Ala Val Asp Val Ala Lys Lys Leu Lys Ala Lys Gly Tyr Asn
2000               2005                2010

Ser Gly Tyr Tyr Ser Gly Glu Asp Pro Ala Asn Leu Arg Val
2015               2020                2025

Val Thr Ser Gln Ser Pro Tyr Val Val Ala Thr Asn Ala Ile
2030               2035                2040

Glu Ser Gly Val Thr Leu Pro Asp Leu Asp Thr Val Val Asp Thr
2045               2050                2055

Gly Leu Lys Cys Glu Lys Arg Val Arg Val Ser Ser Lys Ile Pro
2060               2065                2070

Phe Ile Val Thr Gly Leu Lys Arg Met Ala Val Thr Val Gly Glu
2075               2080                2085

Gln Ala Gln Arg Arg Gly Arg Val Gly Arg Val Lys Pro Gly Arg
2090               2095                2100

Tyr Tyr Arg Ser Gln Glu Thr Ala Thr Gly Ser Lys Asp Tyr His
2105               2110                2115

Tyr Asp Leu Leu Gln Ala Gln Arg Tyr Gly Ile Glu Asp Gly Ile
2120               2125                2130

Asn Ile Thr Lys Ser Phe Arg Glu Met Asn Tyr Asp Trp Ser Leu
2135               2140                2145

Tyr Glu Glu Asp Ser Leu Leu Ile Thr Gln Leu Glu Ile Leu Asn
2150               2155                2160

Asn Leu Leu Ile Ser Glu Asp Leu Pro Ala Ala Val Lys Asn Ile
2165               2170                2175

Met Ala Arg Thr Asp His Pro Glu Pro Ile Gln Leu Ala Tyr Asn
2180               2185                2190

Ser Tyr Glu Val Gln Val Pro Val Leu Phe Pro Lys Ile Arg Asn
2195               2200                2205

Gly Glu Val Thr Asp Thr Tyr Glu Asn Tyr Ser Phe Leu Asn Ala
2210               2215                2220

Arg Lys Leu Gly Glu Asp Val Pro Thr Tyr Ile Tyr Ala Thr Glu
2225               2230                2235

Asp Glu Asp Leu Ala Val Asp Leu Leu Gly Leu Asp Trp Pro Asp
2240               2245                2250

Pro Gly Asn Gln Gln Val Val Glu Thr Gly Lys Ala Leu Lys Gln
2255               2260                2265

Val Val Gly Leu Ser Ser Ala Glu Asn Ala Leu Leu Ile Ala Leu
2270               2275                2280

Phe Gly Tyr Val Gly Tyr Gln Ala Leu Ser Lys Arg His Val Pro
2285               2290                2295

Met Ile Thr Asp Ile Tyr Thr Ile Glu Asp Gln Arg Leu Glu Asp
2300               2305                2310

Thr Thr His Leu Gln Tyr Ala Pro Asn Ala Ile Arg Thr Glu Gly
2315               2320                2325

Lys Glu Thr Glu Leu Lys Glu Leu Ala Val Gly Asp Leu Asp Lys
2330               2335                2340

Ile Met Gly Ser Ile Ser Asp Tyr Ala Ser Gly Leu Glu Phe
2345               2350                2355

Val Arg Ser Gln Ala Glu Lys Ile Arg Ser Ala Pro Thr Phe Lys
2360               2365                2370

Glu Asn Val Glu Thr Ala Lys Gly Tyr Val Gln Lys Phe Ile Asp
2375               2380                2385

Ala Leu Ile Glu Asn Lys Glu Thr Ile Ile Arg Tyr Gly Leu Trp
```

```
              2390                2395                2400
Gly Thr His Thr Ala Leu Tyr Lys Ser Ile Ala Ala Arg Leu Gly
    2405                2410                2415
His Glu Thr Ala Phe Ala Thr Leu Val Val Lys Trp Leu Ala Phe
    2420                2425                2430
Gly Gly Glu Ser Val Ser Asp His Val Arg Gln Ala Ala Val Asp
    2435                2440                2445
Leu Val Val Tyr Tyr Val Met Asn Lys Pro Ser Phe Pro Gly Asp
    2450                2455                2460
Ser Glu Thr Gln Gln Glu Gly Arg Arg Phe Val Ala Ser Leu Phe
    2465                2470                2475
Ile Ser Ala Leu Ala Thr Tyr Thr Tyr Lys Ser Trp Asn Tyr His
    2480                2485                2490
Asn Leu Ser Lys Val Val Glu Pro Ala Leu Ala Tyr Leu Pro Tyr
    2495                2500                2505
Ala Thr Ser Ala Leu Lys Met Phe Thr Pro Thr Arg Leu Glu Ser
    2510                2515                2520
Val Val Ile Leu Ser Thr Thr Ile Tyr Lys Thr Tyr Leu Ser Ile
    2525                2530                2535
Arg Lys Gly Lys Ser Asp Gly Leu Leu Gly Thr Gly Ile Ser Ala
    2540                2545                2550
Ala Met Glu Ile Leu Ser Gln Asn Pro Val Ser Val Gly Ile Ser
    2555                2560                2565
Val Met Leu Gly Val Gly Ala Ile Ala Ala His Asn Ala Ile Glu
    2570                2575                2580
Ser Ser Glu Gln Lys Arg Thr Leu Leu Met Lys Val Phe Val Lys
    2585                2590                2595
Asn Phe Leu Asp Gln Ala Ala Thr Asp Glu Leu Val Lys Glu Asn
    2600                2605                2610
Pro Glu Lys Ile Ile Met Ala Leu Phe Glu Ala Val Gln Thr Ile
    2615                2620                2625
Gly Asn Pro Leu Arg Leu Ile Tyr His Leu Tyr Gly Val Tyr Tyr
    2630                2635                2640
Lys Gly Trp Glu Ala Lys Glu Leu Ser Glu Arg Thr Ala Gly Arg
    2645                2650                2655
Asn Leu Phe Thr Leu Ile Met Phe Glu Ala Phe Glu Leu Leu Gly
    2660                2665                2670
Met Asp Ser Glu Gly Lys Ile Arg Asn Leu Ser Gly Asn Tyr Ile
    2675                2680                2685
Leu Asp Leu Ile Tyr Ser Leu His Lys Gln Ile Asn Arg Gly Leu
    2690                2695                2700
Lys Lys Ile Val Leu Gly Trp Ala Pro Ala Pro Phe Ser Cys Asp
    2705                2710                2715
Trp Thr Pro Ser Asp Gly Arg Ile Arg Leu Pro Thr Asp Asn Tyr
    2720                2725                2730
Leu Arg Val Glu Thr Lys Cys Pro Cys Gly Tyr Glu Met Lys Ala
    2735                2740                2745
Leu Arg Asn Val Ser Gly Ser Leu Thr Lys Val Glu Glu Lys Gly
    2750                2755                2760
Pro Phe Leu Cys Arg Asn Arg Pro Gly Arg Gly Pro Val Asn Tyr
    2765                2770                2775
Arg Val Thr Lys Tyr Tyr Asp Asp Asn Leu Thr Glu Ile Lys Pro
    2780                2785                2790
```

-continued

```
Val Ala Lys Leu Glu Gly Leu Val Glu His Tyr Tyr Lys Gly Val
            2795            2800            2805

Thr Ala Arg Ile Asp Tyr Asp Lys Gly Lys Met Leu Val Ala Thr
            2810            2815            2820

Asp Lys Trp Glu Val Glu His Gly Thr Val Thr Arg Leu Ala Lys
            2825            2830            2835

Arg Tyr Ser Gly Val Gly Phe Lys Gly Ala Tyr Leu Gly Asp Glu
            2840            2845            2850

Pro Asn Tyr Arg Asp Leu Val Glu Arg Asp Cys Ala Thr Ile Thr
            2855            2860            2865

Lys Asn Thr Val Gln Phe Leu Lys Met Lys Lys Gly Cys Ala Phe
            2870            2875            2880

Thr Tyr Asp Leu Thr Leu Ser Asn Leu Thr Arg Leu Ile Glu Leu
            2885            2890            2895

Val His Arg Asn Asn Leu Glu Glu Lys Asp Ile Pro Ala Ala Thr
            2900            2905            2910

Val Thr Thr Trp Leu Ala Tyr Thr Phe Val Asn Glu Asp Val Gly
            2915            2920            2925

Thr Ile Arg Pro Val Leu Gly Glu Arg Val Ile Ala Asp Pro Val
            2930            2935            2940

Val Asp Val Asn Leu Gln Pro Glu Val Gln Val Asp Thr Ser Glu
            2945            2950            2955

Val Gly Ile Thr Leu Val Gly Lys Ala Ala Leu Met Thr Thr Gly
            2960            2965            2970

Thr Thr Pro Val Val Glu Lys Thr Glu Pro Ser Ala Ser Ala Ser
            2975            2980            2985

Pro Ser Ser Ile Lys Ile Gly Leu Asp Gln Gly Ser Tyr Pro Gly
            2990            2995            3000

Pro Gly Leu Gln Asp Arg Thr Leu Val Asp Glu Ile His Ser Lys
            3005            3010            3015

Asp Glu Arg Pro Phe Val Leu Val Leu Gly Ser Lys Asn Ser Met
            3020            3025            3030

Ser Asn Arg Ala Lys Thr Ala Lys Asn Ile Asn Leu Tyr Thr Gly
            3035            3040            3045

Lys Asp Pro Arg Glu Ile Arg Asp Leu Met Ala Gln Gly Arg Met
            3050            3055            3060

Leu Val Val Ala Leu Arg Gly Phe Asn Pro Glu Leu Ser Glu Leu
            3065            3070            3075

Val Asp Phe Lys Gly Thr Phe Leu Asp Arg Glu Ala Leu Glu Ala
            3080            3085            3090

Leu Ser Leu Gly Arg Pro Arg Pro Lys Gln Val Thr Thr Ser Thr
            3095            3100            3105

Val Arg Glu Leu Leu Glu Gln Glu Glu Gln Val Glu Val Pro Asn
            3110            3115            3120

Trp Phe Gly Ala Asp Asp Pro Val Phe Leu Glu Val Ala Leu Lys
            3125            3130            3135

Gly Asp Lys Tyr His Leu Val Gly Asp Val Asp Lys Val Lys Asp
            3140            3145            3150

Gln Ala Lys Gly Leu Gly Ala Thr Asp Gln Thr Arg Ile Val Lys
            3155            3160            3165

Glu Val Gly Ala Arg Thr Tyr Thr Met Lys Leu Ser Ser Trp Phe
            3170            3175            3180
```

```
Leu Gln Ala Ser Asn Lys Gln Met Ser Leu Thr Pro Leu Phe Glu
3185                3190                3195

Glu Leu Leu Arg Cys Pro Pro Lys Ala Lys Asn Asn Lys Gly
3200                3205                3210

His Met Ala Ser Ala Tyr Gln Leu Ala Gln Gly Asn Trp Glu Pro
3215                3220                3225

Leu Asp Cys Gly Val Tyr Leu Gly Thr Ile Pro Ala Arg Arg Val
3230                3235                3240

Lys Ile His Pro Tyr Glu Ala Tyr Leu Lys Leu Lys Asp Leu Leu
3245                3250                3255

Glu Glu Glu Glu Lys Lys Pro Lys Ser Arg Asp Thr Val Ile Arg
3260                3265                3270

Glu His Asn Lys Trp Ile Leu Lys Lys Val Arg His Gln Gly Asn
3275                3280                3285

Leu Asn Thr Lys Lys Ile Leu Asn Pro Gly Lys Leu Ser Glu Gln
3290                3295                3300

Leu Asp Arg Glu Gly His Lys Arg Asn Ile Tyr Asn Asn Gln Ile
3305                3310                3315

Gly Thr Ile Leu Thr Gly Ala Gly Val Arg Leu Glu Lys Leu Pro
3320                3325                3330

Val Val Arg Ala Gln Thr Asp Thr Lys Ser Phe His Glu Ala Ile
3335                3340                3345

Arg Asp Lys Ile Asp Lys Asn Glu Asn Gln Gln Ser Pro Gly Leu
3350                3355                3360

His Gly Lys Leu Leu Glu Ile Phe His Thr Ile Ala Gln Pro Ser
3365                3370                3375

Leu Arg His Thr Tyr Gly Glu Val Thr Trp Glu Gln Leu Glu Ala
3380                3385                3390

Gly Ile Asn Arg Lys Gly Ala Ala Gly Phe Leu Glu Lys Lys Asn
3395                3400                3405

Val Gly Glu Val Leu Asp Ser Glu Lys His Leu Val Glu Gln Leu
3410                3415                3420

Ile Arg Asp Leu Lys Ala Gly Arg Lys Ile Arg Tyr Tyr Glu Thr
3425                3430                3435

Ala Ile Pro Lys Asn Glu Lys Arg Asp Val Ser Asp Asp Trp Gln
3440                3445                3450

Ala Gly Asp Leu Val Asp Glu Lys Lys Pro Arg Val Ile Gln Tyr
3455                3460                3465

Pro Glu Ala Lys Thr Arg Leu Ala Ile Thr Lys Val Met Tyr Asn
3470                3475                3480

Trp Val Lys Gln Gln Pro Val Val Ile Pro Gly Tyr Glu Gly Lys
3485                3490                3495

Thr Pro Leu Phe Asn Ile Phe Asn Lys Val Arg Lys Glu Trp Asp
3500                3505                3510

Leu Phe Asn Glu Pro Val Ala Val Ser Phe Asp Thr Lys Ala Trp
3515                3520                3525

Asp Thr Gln Val Thr Ser Lys Asp Leu Arg Leu Ile Gly Glu Ile
3530                3535                3540

Gln Lys Tyr Tyr Tyr Arg Lys Glu Trp His Lys Phe Ile Asp Thr
3545                3550                3555

Ile Thr Asp His Met Val Glu Val Pro Val Ile Thr Ala Asp Gly
3560                3565                3570

Glu Val Tyr Ile Arg Asn Gly Gln Arg Gly Ser Gly Gln Pro Asp
```

```
                3575                3580                3585

Thr Ser Ala Gly Asn Ser Met Leu Asn Val Leu Thr Met Met Tyr
        3590                3595                3600

Ala Phe Cys Glu Ser Thr Gly Ile Pro Tyr Lys Ser Phe Asn Arg
        3605                3610                3615

Val Ala Arg Ile His Val Cys Gly Asp Asp Gly Phe Leu Ile Thr
        3620                3625                3630

Glu Arg Gly Leu Gly Leu Lys Phe Ala Asn Asn Gly Met Gln Ile
        3635                3640                3645

Leu His Glu Ala Gly Lys Pro Gln Lys Ile Thr Glu Gly Glu Arg
        3650                3655                3660

Met Lys Val Ala Tyr Arg Phe Glu Asp Ile Glu Phe Cys Ser His
        3665                3670                3675

Thr Pro Val Pro Val Arg Trp Ser Asp Asn Thr Ser Ser Tyr Met
        3680                3685                3690

Ala Gly Arg Asp Thr Ala Ile Ile Leu Ser Lys Met Ala Thr Arg
        3695                3700                3705

Leu Asp Ser Ser Gly Glu Arg Gly Thr Thr Ala Tyr Glu Lys Ala
        3710                3715                3720

Val Ala Phe Ser Phe Leu Leu Met Tyr Ser Trp Asn Pro Leu Val
        3725                3730                3735

Arg Arg Ile Cys Leu Leu Val Leu Ser Gln Gln Pro Glu Thr Ala
        3740                3745                3750

Pro Ser Thr Gln Thr Thr Tyr Tyr Tyr Lys Gly Asp Pro Ile Gly
        3755                3760                3765

Ala Tyr Lys Asp Val Ile Gly Lys Asn Leu Ser Glu Leu Lys Arg
        3770                3775                3780

Thr Gly Phe Glu Lys Leu Ala Asn Leu Asn Leu Ser Leu Ser Thr
        3785                3790                3795

Leu Gly Ile Trp Ser Lys His Thr Ser Lys Arg Ile Ile Gln Asp
        3800                3805                3810

Cys Val Thr Ile Gly Lys Glu Glu Gly Asn Trp Leu Val Asn Ala
        3815                3820                3825

Asp Arg Leu Ile Ser Ser Lys Thr Gly His Leu Tyr Ile Pro Asp
        3830                3835                3840

Lys Gly Tyr Thr Leu Gln Gly Lys His Tyr Glu Gln Leu Gln Leu
        3845                3850                3855

Gln Ala Arg Thr Ser Pro Ile Met Gly Val Gly Thr Glu Arg Tyr
        3860                3865                3870

Lys Leu Gly Pro Ile Val Asn Leu Leu Leu Arg Arg Leu Lys Val
        3875                3880                3885

Leu Leu Met Ala Ala Val Gly Ala Ser Ser
        3890                3895

<210> SEQ ID NO 5
<211> LENGTH: 3897
<212> TYPE: PRT
<213> ORGANISM: BVDV

<400> SEQUENCE: 5

Met Glu Leu Ile Thr Asn Glu Leu Leu Tyr Lys Thr Tyr Lys Gln Lys
1               5                   10                  15

Pro Ala Gly Val Glu Glu Pro Val Tyr Asp Gln Ala Gly Asn Pro Leu
            20                  25                  30
```

-continued

Phe Gly Glu Arg Gly Val Val His Pro Gln Ala Thr Leu Lys Leu Pro
            35                  40                  45

His Lys Arg Gly Glu Ser Glu Val Pro Thr Asn Leu Ala Ser Leu Pro
 50                  55                  60

Lys Arg Gly Asp Cys Arg Ser Gly Asn Ser Lys Gly Pro Val Ser Gly
 65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Gln Glu Thr Ser Met Cys
            100                 105                 110

Glu Thr Thr Lys Arg Ile Gly Arg Val Thr Gly Ser Asp Ser Lys Leu
            115                 120                 125

Tyr His Ile Tyr Val Cys Ile Asp Gly Cys Ile Ile Ile Lys Ser Ala
            130                 135                 140

Thr Lys Asp His Gln Lys Val Phe Lys Trp Val His Asn Lys Leu Asn
145                 150                 155                 160

Cys Pro Leu Trp Val Thr Ser Cys Ser Asp Thr Asn Ala Glu Gly Ala
                165                 170                 175

Thr Arg Lys Lys Gln Gln Lys Pro Asp Arg Leu Glu Lys Gly Arg Met
            180                 185                 190

Lys Ile Thr Pro Lys Glu Ser Glu Lys Asp Ser Lys Thr Lys Pro Pro
            195                 200                 205

Asp Ala Thr Ile Val Val Asp Gly Val Lys Tyr Gln Val Lys Lys Lys
            210                 215                 220

Gly Lys Val Lys Ser Lys Asn Thr Gln Asp Gly Leu Tyr His Asn Lys
225                 230                 235                 240

Asn Lys Pro Gln Glu Ser Arg Lys Lys Leu Glu Lys Ala Leu Leu Ala
                245                 250                 255

Trp Ala Ile Ile Ala Leu Val Leu Phe Asp Ile Ala Val Gly Glu Asn
            260                 265                 270

Ile Thr Gln Trp Asn Leu Gln Asp Asn Gly Thr Glu Gly Ile Gln Arg
            275                 280                 285

Ala Met Phe Gln Arg Gly Val Asn Arg Ser Leu His Gly Ile Trp Pro
            290                 295                 300

Glu Lys Ile Cys Thr Gly Val Pro Ser His Leu Ala Thr Asp Thr Glu
305                 310                 315                 320

Leu Lys Ala Ile His Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Tyr Asn Ile Glu Pro Trp Ile Leu Leu Met Asn Lys Thr Gln
            355                 360                 365

Ala Asn Leu Thr Glu Gly Gln Pro Pro Arg Glu Cys Ala Val Thr Cys
            370                 375                 380

Arg Tyr Asp Arg Asp Ser Asp Leu Asn Ile Val Thr Gln Ala Arg Asp
385                 390                 395                 400

Ser Pro Thr Pro Leu Thr Gly Cys Lys Lys Gly Lys Asn Phe Ser Phe
                405                 410                 415

Ala Gly Val Leu Val Gln Gly Pro Cys Asn Phe Glu Ile Ala Ala Ser
            420                 425                 430

Asp Val Leu Phe Lys Glu His Asp Thr Gly Met Ile Gln Asp Thr Ala
            435                 440                 445

His Tyr Leu Val Asp Gly Leu Thr Asn Ser Leu Glu Ser Ala Arg Gln

```
              450                 455                 460
Gly Thr Ala Lys Leu Thr Thr Trp Leu Gly Arg Gln Leu Arg Ile Leu
465                 470                 475                 480

Gly Lys Lys Leu Glu Asn Lys Ser Lys Thr Trp Phe Gly Ala Tyr Ala
                485                 490                 495

Ala Ser Pro Tyr Cys Glu Val Glu Arg Arg Leu Gly Tyr Ile Trp Tyr
                500                 505                 510

Thr Lys Asn Cys Thr Pro Ala Cys Leu Pro Lys Asn Thr Lys Ile Val
                515                 520                 525

Gly Pro Gly Lys Phe Asp Thr Asn Ala Glu Asp Gly Lys Leu Leu His
                530                 535                 540

Glu Met Gly Gly His Leu Ser Glu Val Leu Leu Ser Val Val Val
545                 550                 555                 560

Leu Ser Asp Phe Ala Pro Glu Thr Ala Ser Ile Val Tyr Leu Ile Leu
                565                 570                 575

His Phe Thr Ile Pro Gln Gly His Thr Asp Ile Glu Asp Cys Asp Lys
                580                 585                 590

Asn Gln Leu Asn Leu Thr Val Gly Leu Thr Thr Ala Glu Val Val Pro
                595                 600                 605

Ser Ser Val Trp Asn Leu Gly Lys Tyr Val Cys Val Arg Pro Asp Trp
610                 615                 620

Trp Pro Tyr Glu Thr Ala Thr Val Leu Val Phe Glu Glu Val Gly Gln
625                 630                 635                 640

Val Ile Lys Leu Val Leu Arg Ala Leu Arg Asp Leu Thr Arg Ile Trp
                645                 650                 655

Thr Ala Ala Thr Thr Thr Ala Phe Leu Val Cys Met Val Lys Val Val
                660                 665                 670

Arg Gly Gln Val Leu Gln Gly Ile Leu Trp Leu Met Leu Ile Thr Gly
                675                 680                 685

Ala Gln Gly Tyr Pro Asp Cys Lys Pro Asp Phe Ser Tyr Ala Ile Ala
                690                 695                 700

Lys Asn Asp Glu Ile Gly Pro Leu Gly Ala Thr Gly Leu Thr Thr Gln
705                 710                 715                 720

Trp Tyr Lys Tyr Ser Asp Glu Met Arg Leu Gln Asp Thr Val Thr
                725                 730                 735

Val Trp Cys Lys Asn Gly Glu Phe Arg His Leu Ile Thr Cys Glu Arg
                740                 745                 750

Glu Ala Arg Tyr Leu Ala Ile Leu His Thr Arg Ala Leu Pro Thr Ser
                755                 760                 765

Val Val Phe Glu Lys Ile Ile Asn Gly Lys Glu Gln Glu Asp Ile Val
770                 775                 780

Glu Met Ser Asp Asn Phe Glu Phe Gly Leu Cys Pro Cys Asp Ala Lys
785                 790                 795                 800

Pro Leu Val Arg Gly Lys Phe Asn Val Thr Leu Leu Asn Gly Pro Ala
                805                 810                 815

Phe Gln Met Val Cys Pro Ile Gly Trp Thr Gly Thr Val Ser Cys Thr
                820                 825                 830

Leu Ala Asn Lys Asp Thr Leu Ala Thr Thr Val Val Arg Thr Tyr Lys
                835                 840                 845

Arg Asp Lys Pro Phe Pro Tyr Arg Gln Gly Cys Ile Thr Gln Lys Thr
                850                 855                 860

Ile Gly Glu Asp Leu Tyr Asp Cys Val Leu Gly Gly Asn Trp Thr Cys
865                 870                 875                 880
```

-continued

```
Val Pro Gly Asn Gln Leu Arg Tyr Val Gly Pro Val Glu Ser Cys
            885                 890                 895

Lys Trp Cys Gly Tyr Lys Phe Asp Lys Ser Glu Gly Leu Pro His Phe
            900                 905                 910

Pro Ile Gly Lys Cys Lys Leu Lys Asn Glu Ser Gly Tyr Arg Gln Val
            915                 920                 925

Asp Glu Thr Ser Cys Asn Arg Asp Gly Val Ala Ile Val Pro Ser Gly
            930                 935                 940

Leu Val Lys Cys Lys Ile Gly Asn Thr Val Val Gln Val Ile Ala Met
945                 950                 955                 960

Asp Asp Lys Leu Gly Pro Met Pro Cys Arg Pro His Glu Ile Ile Ser
            965                 970                 975

Ser Glu Gly Pro Val Glu Lys Thr Ala Cys Thr Phe Asn Tyr Ala Arg
            980                 985                 990

Thr Leu Lys Asn Lys Tyr Phe Glu Pro Arg Asp Asn Tyr Phe Gln Gln
            995                1000                1005

Tyr Met Leu Lys Gly Glu Tyr Gln Tyr Trp Phe Asp Leu Glu Ile
            1010               1015                1020

Thr Asp His His Arg Asp Tyr Phe Ala Glu Ser Leu Leu Val Ile
            1025               1030                1035

Val Val Ala Leu Leu Gly Gly Arg Tyr Val Leu Trp Leu Leu Val
            1040               1045                1050

Thr Tyr Met Ile Leu Ser Glu Gln Met Thr Leu Gly Ala Gln Tyr
            1055               1060                1065

Gly Ala Gly Glu Ile Val Met Met Gly Asn Leu Leu Thr His Asp
            1070               1075                1080

Ser Ile Glu Val Val Thr Tyr Phe Leu Leu Tyr Leu Leu Leu
            1085               1090                1095

Arg Glu Glu Asn Ile Lys Lys Trp Val Ile Leu Ile Tyr His Ile
            1100               1105                1110

Ile Val Met His Pro Leu Lys Ser Met Thr Val Ile Leu Leu Met
            1115               1120                1125

Val Gly Gly Met Ala Lys Ala Glu Pro Asp Thr Gln Ser Tyr Leu
            1130               1135                1140

Glu Arg Val Asp Leu Ser Phe Thr Met Ile Thr Leu Ile Val Val
            1145               1150                1155

Gly Leu Val Ile Ala Arg Arg Asp Pro Thr Val Pro Leu Val
            1160               1165                1170

Thr Ile Val Ala Ala Leu Lys Ile Thr Gly Leu Gly Phe Gly Pro
            1175               1180                1185

Gly Val Asp Val Ala Met Ala Val Leu Thr Leu Thr Leu Leu Met
            1190               1195                1200

Val Ser Tyr Val Thr Asp Tyr Phe Arg Tyr Lys Arg Trp Leu Gln
            1205               1210                1215

Cys Ile Leu Ser Leu Val Ala Gly Val Phe Leu Ile Arg Ser Leu
            1220               1225                1230

Lys His Leu Gly Glu Ile Glu Thr Pro Glu Leu Thr Ile Pro Asn
            1235               1240                1245

Trp Arg Pro Leu Thr Phe Ile Leu Leu Tyr Leu Thr Ser Ala Thr
            1250               1255                1260

Val Val Thr Arg Trp Lys Val Asp Ile Ala Gly Ile Leu Leu Gln
            1265               1270                1275
```

```
Gly Ala Pro Ile Leu Leu Leu Ile Ala Thr Leu Trp Ala Asp Phe
    1280                1285                1290

Leu Thr Leu Val Leu Ile Leu Pro Thr Tyr Glu Leu Val Lys Leu
    1295                1300                1305

Tyr Tyr Leu Lys Asn Ile Lys Thr Asp Val Glu Arg Ser Trp Leu
    1310                1315                1320

Gly Gly Leu Asp Tyr Lys Thr Ile Asp Ser Val Tyr Asp Val Asp
    1325                1330                1335

Glu Ser Gly Glu Gly Val Tyr Leu Phe Pro Ser Arg Gln Asp Gly
    1340                1345                1350

Lys Lys Asn Thr Ser Ile Leu Leu Pro Leu Ile Arg Ala Thr Leu
    1355                1360                1365

Ile Ser Cys Val Ser Ser Lys Trp Gln Met Val Tyr Met Ala Tyr
    1370                1375                1380

Leu Thr Leu Asp Phe Met Tyr Tyr Met His Arg Lys Val Ile Glu
    1385                1390                1395

Glu Ile Ser Gly Gly Thr Asn Val Ile Ser Arg Val Ile Ala Ala
    1400                1405                1410

Leu Ile Glu Leu Asn Trp Ser Met Glu Glu Glu Ser Lys Gly
    1415                1420                1425

Leu Lys Lys Phe Phe Val Leu Ser Gly Arg Val Arg Asn Leu Ile
    1430                1435                1440

Ile Lys His Lys Val Arg Asn Gln Thr Val Ala Ser Trp Tyr Gly
    1445                1450                1455

Glu Glu Glu Val Tyr Gly Leu Pro Lys Val Val Thr Ile Ile Arg
    1460                1465                1470

Ala Cys Thr Leu Asn Lys Asn Lys His Cys Ile Ile Cys Thr Val
    1475                1480                1485

Cys Glu Ala Lys Lys Trp Lys Gly Gly Asn Cys Pro Lys Cys Gly
    1490                1495                1500

Arg His Gly Lys Pro Ile Thr Cys Gly Met Thr Leu Ala Asp Phe
    1505                1510                1515

Glu Glu Arg His Tyr Lys Arg Ile Phe Ile Arg Glu Gly Thr Phe
    1520                1525                1530

Glu Gly Pro Phe Arg Gln Glu Tyr Asn Gly Phe Val Gln Tyr Ala
    1535                1540                1545

Ala Arg Gly Gln Leu Phe Leu Arg Asn Leu Pro Ile Leu Ala Thr
    1550                1555                1560

Lys Val Lys Met Leu Met Val Gly Asn Leu Gly Glu Glu Ile Gly
    1565                1570                1575

Asp Leu Glu His Leu Gly Trp Ile Leu Arg Gly Pro Ala Val Cys
    1580                1585                1590

Lys Lys Ile Thr Glu His Glu Lys Cys His Val Ser Ile Leu Asp
    1595                1600                1605

Lys Leu Thr Ala Phe Phe Gly Val Met Pro Arg Gly Thr Thr Pro
    1610                1615                1620

Arg Ala Pro Val Arg Phe Pro Thr Ala Leu Leu Lys Val Arg Arg
    1625                1630                1635

Gly Leu Glu Thr Gly Trp Ala Tyr Thr His Gln Gly Gly Ile Ser
    1640                1645                1650

Ser Val Asp His Val Thr Ala Gly Lys Asp Leu Leu Val Cys Asp
    1655                1660                1665

Ser Met Gly Arg Thr Arg Val Val Cys Gln Ser Asn Asn Lys Leu
```

```
                1670                1675                1680

Thr Asp Glu Thr Glu Tyr Gly Val Lys Thr Asp Ser Gly Cys Pro
        1685                1690                1695

Asp Gly Ala Arg Cys Tyr Val Leu Asn Pro Glu Ala Val Asn Ile
        1700                1705                1710

Ser Gly Ser Lys Gly Ala Val Val His Leu Gln Lys Thr Gly Gly
        1715                1720                1725

Glu Phe Thr Cys Val Thr Ala Ser Gly Thr Pro Ala Phe Phe Asp
        1730                1735                1740

Leu Lys Asn Leu Lys Gly Trp Ser Gly Leu Pro Ile Tyr Glu Ala
        1745                1750                1755

Ser Ser Gly Arg Val Val Gly Arg Val Lys Val Gly Lys Asn Glu
        1760                1765                1770

Glu Ser Lys Pro Thr Lys Leu Met Ser Gly Ile Gln Thr Val Ser
        1775                1780                1785

Lys Ser Thr Ala Asp Leu Thr Glu Met Val Lys Lys Ile Thr Ser
        1790                1795                1800

Met Asn Arg Gly Asp Phe Lys Gln Ile Thr Leu Ala Thr Gly Ala
        1805                1810                1815

Gly Lys Thr Thr Glu Leu Pro Lys Ala Val Ile Glu Glu Ile Gly
        1820                1825                1830

Arg His Lys Arg Val Leu Val Leu Ile Pro Leu Arg Ala Ala Ala
        1835                1840                1845

Glu Ser Val Tyr Gln Tyr Met Arg Leu Lys His Pro Ser Ile Ser
        1850                1855                1860

Phe Asn Leu Arg Ile Gly Asp Met Lys Glu Gly Asp Met Ala Thr
        1865                1870                1875

Gly Ile Thr Tyr Ala Ser Tyr Gly Tyr Phe Cys Gln Met Gln Gln
        1880                1885                1890

Pro Lys Leu Arg Ala Ala Met Val Glu Tyr Ser Tyr Ile Phe Leu
        1895                1900                1905

Asp Glu Tyr His Cys Ala Thr Pro Glu Gln Leu Ala Val Ile Gly
        1910                1915                1920

Lys Ile His Arg Phe Ser Glu Ser Ile Arg Val Val Ala Met Thr
        1925                1930                1935

Ala Thr Pro Ala Gly Ser Val Thr Thr Thr Gly Gln Lys His Pro
        1940                1945                1950

Ile Glu Glu Phe Ile Ala Pro Glu Val Met Lys Gly Glu Asp Leu
        1955                1960                1965

Gly Ser Gln Phe Leu Asp Ile Ala Gly Leu Lys Ile Pro Val Glu
        1970                1975                1980

Glu Met Lys Gly Asn Met Leu Val Phe Val Pro Thr Arg Asn Met
        1985                1990                1995

Ala Val Asp Val Ala Lys Lys Leu Lys Ala Lys Gly Tyr Asn Ser
        2000                2005                2010

Gly Tyr Tyr Tyr Ser Gly Glu Asp Pro Ala Asn Leu Arg Val Val
        2015                2020                2025

Thr Ser Gln Ser Pro Tyr Val Val Val Ala Thr Asn Ala Ile Glu
        2030                2035                2040

Ser Gly Val Thr Leu Pro Asp Leu Asp Thr Val Val Asp Thr Gly
        2045                2050                2055

Leu Lys Cys Glu Lys Arg Val Arg Val Ser Ser Lys Ile Pro Phe
        2060                2065                2070
```

```
Ile Val Thr Gly Leu Lys Arg Met Ala Val Thr Val Gly Glu Gln
2075                2080                2085

Ala Gln Arg Arg Gly Arg Val Gly Arg Val Lys Pro Gly Arg Tyr
2090                2095                2100

Tyr Arg Ser Gln Glu Thr Ala Thr Gly Ser Lys Asp Tyr His Tyr
2105                2110                2115

Asp Leu Leu Gln Ala Gln Arg Tyr Gly Ile Glu Asp Gly Ile Asn
2120                2125                2130

Ile Thr Lys Ser Phe Arg Glu Met Asn Tyr Asp Trp Ser Leu Tyr
2135                2140                2145

Glu Glu Asp Ser Leu Leu Ile Thr Gln Leu Glu Ile Leu Asn Asn
2150                2155                2160

Leu Leu Ile Ser Glu Asp Leu Pro Ala Ala Val Lys Asn Ile Met
2165                2170                2175

Ala Arg Thr Asp His Pro Glu Pro Ile Gln Leu Ala Tyr Asn Ser
2180                2185                2190

Tyr Glu Val Gln Val Pro Val Leu Phe Pro Lys Ile Arg Asn Gly
2195                2200                2205

Glu Val Thr Asp Thr Tyr Glu Asn Tyr Ser Phe Leu Asn Ala Arg
2210                2215                2220

Lys Leu Gly Glu Asp Val Pro Thr Tyr Ile Tyr Ala Thr Glu Asp
2225                2230                2235

Glu Asp Leu Ala Val Asp Leu Leu Gly Leu Asp Trp Pro Asp Pro
2240                2245                2250

Gly Asn Gln Gln Val Val Glu Thr Gly Lys Ala Leu Lys Gln Val
2255                2260                2265

Val Gly Leu Ser Ser Ala Glu Asn Ala Leu Leu Ile Ala Leu Phe
2270                2275                2280

Gly Tyr Val Gly Tyr Gln Ala Leu Ser Lys Arg His Val Pro Met
2285                2290                2295

Ile Thr Asp Ile Tyr Thr Ile Glu Asp Gln Arg Leu Glu Asp Thr
2300                2305                2310

Thr His Leu Gln Tyr Ala Pro Asn Ala Ile Arg Thr Glu Gly Lys
2315                2320                2325

Glu Thr Glu Leu Lys Glu Leu Ala Val Gly Asp Leu Asp Lys Ile
2330                2335                2340

Met Gly Ser Ile Ser Asp Tyr Ala Ser Gly Gly Leu Glu Phe Val
2345                2350                2355

Arg Ser Gln Ala Glu Lys Ile Arg Ser Ala Pro Thr Phe Lys Glu
2360                2365                2370

Asn Val Glu Thr Ala Lys Gly Tyr Val Gln Lys Phe Ile Asp Ala
2375                2380                2385

Leu Ile Glu Asn Lys Glu Thr Ile Ile Arg Tyr Gly Leu Trp Gly
2390                2395                2400

Thr His Thr Ala Leu Tyr Lys Ser Ile Ala Ala Arg Leu Gly His
2405                2410                2415

Glu Thr Ala Phe Ala Thr Leu Val Val Lys Trp Leu Ala Phe Gly
2420                2425                2430

Gly Glu Ser Val Ser Asp His Val Arg Gln Ala Ala Val Asp Leu
2435                2440                2445

Val Val Tyr Tyr Val Met Asn Lys Pro Ser Phe Pro Gly Asp Ser
2450                2455                2460
```

```
Glu Thr Gln Gln Glu Gly Arg Arg Phe Val Ala Ser Leu Phe Ile
2465                2470                2475

Ser Ala Leu Ala Thr Tyr Thr Tyr Lys Ser Trp Asn Tyr His Asn
    2480                2485                2490

Leu Ser Lys Val Val Glu Pro Ala Leu Ala Tyr Leu Pro Tyr Ala
    2495                2500                2505

Thr Ser Ala Leu Lys Met Phe Thr Pro Thr Arg Leu Glu Ser Val
    2510                2515                2520

Val Ile Leu Ser Thr Thr Ile Tyr Lys Thr Tyr Leu Ser Ile Arg
    2525                2530                2535

Lys Gly Lys Ser Asp Gly Leu Leu Gly Thr Gly Ile Ser Ala Ala
    2540                2545                2550

Met Glu Ile Leu Ser Gln Asn Pro Val Ser Val Gly Ile Ser Val
    2555                2560                2565

Met Leu Gly Val Gly Ala Ile Ala Ala His Asn Ala Ile Glu Ser
    2570                2575                2580

Ser Glu Gln Lys Arg Thr Leu Leu Met Lys Val Phe Val Lys Asn
    2585                2590                2595

Phe Leu Asp Gln Ala Ala Thr Asp Glu Leu Val Lys Glu Asn Pro
    2600                2605                2610

Glu Lys Ile Ile Met Ala Leu Phe Glu Ala Val Gln Thr Ile Gly
    2615                2620                2625

Asn Pro Leu Arg Leu Ile Tyr His Leu Tyr Gly Val Tyr Tyr Lys
    2630                2635                2640

Gly Trp Glu Ala Lys Glu Leu Ser Glu Arg Thr Ala Gly Arg Asn
    2645                2650                2655

Leu Phe Thr Leu Ile Met Phe Glu Ala Phe Glu Leu Leu Gly Met
    2660                2665                2670

Asp Ser Glu Gly Lys Ile Arg Asn Leu Ser Gly Asn Tyr Ile Leu
    2675                2680                2685

Asp Leu Ile Tyr Ser Leu His Lys Gln Ile Asn Arg Gly Leu Lys
    2690                2695                2700

Lys Ile Val Leu Gly Trp Ala Pro Ala Pro Phe Ser Cys Asp Trp
    2705                2710                2715

Thr Pro Ser Asp Gly Arg Ile Arg Leu Pro Thr Asp Asn Tyr Leu
    2720                2725                2730

Arg Val Glu Thr Lys Cys Pro Cys Gly Tyr Glu Met Lys Ala Leu
    2735                2740                2745

Arg Asn Val Ser Gly Ser Leu Thr Lys Val Glu Glu Lys Gly Pro
    2750                2755                2760

Phe Leu Cys Arg Asn Arg Pro Gly Arg Gly Pro Val Asn Tyr Arg
    2765                2770                2775

Val Thr Lys Tyr Tyr Asp Asp Asn Leu Thr Glu Ile Lys Pro Val
    2780                2785                2790

Ala Lys Leu Glu Gly Leu Val Glu His Tyr Tyr Lys Gly Val Thr
    2795                2800                2805

Ala Arg Ile Asp Tyr Asp Lys Gly Lys Met Leu Val Ala Thr Asp
    2810                2815                2820

Lys Trp Glu Val Glu His Gly Thr Val Thr Arg Leu Ala Lys Arg
    2825                2830                2835

Tyr Ser Gly Val Gly Phe Lys Gly Ala Tyr Leu Gly Asp Glu Pro
    2840                2845                2850

Asn Tyr Arg Asp Leu Val Glu Arg Asp Cys Ala Thr Ile Thr Lys
```

-continued

```
                2855                2860                2865
Asn Thr Val Gln Phe Leu Lys Met Lys Gly Cys Ala Phe Thr
    2870                2875                2880
Tyr Asp Leu Thr Leu Ser Asn Leu Thr Arg Leu Ile Glu Leu Val
    2885                2890                2895
His Arg Asn Asn Leu Glu Glu Lys Asp Ile Pro Ala Ala Thr Val
    2900                2905                2910
Thr Thr Trp Leu Ala Tyr Thr Phe Val Asn Glu Asp Val Gly Thr
    2915                2920                2925
Ile Arg Pro Val Leu Gly Glu Arg Val Ile Ala Asp Pro Val Val
    2930                2935                2940
Asp Val Asn Leu Gln Pro Glu Val Gln Val Asp Thr Ser Glu Val
    2945                2950                2955
Gly Ile Thr Leu Val Gly Lys Ala Ala Leu Met Thr Thr Gly Thr
    2960                2965                2970
Thr Pro Val Val Glu Lys Thr Glu Pro Ser Ala Ser Ala Ser Pro
    2975                2980                2985
Ser Ser Ile Lys Ile Gly Leu Asp Gln Gly Ser Tyr Pro Gly Pro
    2990                2995                3000
Gly Leu Gln Asp Arg Thr Leu Val Asp Glu Ile His Ser Lys Asp
    3005                3010                3015
Glu Arg Pro Phe Val Leu Val Leu Gly Ser Lys Asn Ser Met Ser
    3020                3025                3030
Asn Arg Ala Lys Thr Ala Lys Asn Ile Asn Leu Tyr Thr Gly Lys
    3035                3040                3045
Asp Pro Arg Glu Ile Arg Asp Leu Met Ala Gln Gly Arg Met Leu
    3050                3055                3060
Val Val Ala Leu Arg Gly Phe Asn Pro Glu Leu Ser Glu Leu Val
    3065                3070                3075
Asp Phe Lys Gly Thr Phe Leu Asp Arg Glu Ala Leu Glu Ala Leu
    3080                3085                3090
Ser Leu Gly Arg Pro Arg Pro Lys Gln Val Thr Thr Ser Thr Val
    3095                3100                3105
Arg Glu Leu Leu Glu Gln Glu Gln Val Glu Val Pro Asn Trp
    3110                3115                3120
Phe Gly Ala Asp Asp Pro Val Phe Leu Glu Val Ala Leu Lys Gly
    3125                3130                3135
Asp Lys Tyr His Leu Val Gly Asp Val Asp Lys Val Lys Asp Gln
    3140                3145                3150
Ala Lys Gly Leu Gly Ala Thr Asp Gln Thr Arg Ile Val Lys Glu
    3155                3160                3165
Val Gly Ala Arg Thr Tyr Thr Met Lys Leu Ser Ser Trp Phe Leu
    3170                3175                3180
Gln Ala Ser Asn Lys Gln Met Ser Leu Thr Pro Leu Phe Glu Glu
    3185                3190                3195
Leu Leu Leu Arg Cys Pro Pro Lys Ala Lys Asn Asn Lys Gly His
    3200                3205                3210
Met Ala Ser Ala Tyr Gln Leu Ala Gln Gly Asn Trp Glu Pro Leu
    3215                3220                3225
Asp Cys Gly Val Tyr Leu Gly Thr Ile Pro Ala Arg Arg Val Lys
    3230                3235                3240
Ile His Pro Tyr Glu Ala Tyr Leu Lys Leu Lys Asp Leu Leu Glu
    3245                3250                3255
```

```
Glu Glu Glu Lys Lys Pro Lys Ser Arg Asp Thr Val Ile Arg Glu
    3260            3265                3270

His Asn Lys Trp Ile Leu Lys Lys Val Arg His Gln Gly Asn Leu
    3275            3280                3285

Asn Thr Lys Lys Ile Leu Asn Pro Gly Lys Leu Ser Glu Gln Leu
    3290            3295                3300

Asp Arg Glu Gly His Lys Arg Asn Ile Tyr Asn Asn Gln Ile Gly
    3305            3310                3315

Thr Ile Leu Thr Gly Ala Gly Val Arg Leu Glu Lys Leu Pro Val
    3320            3325                3330

Val Arg Ala Gln Thr Asp Thr Lys Ser Phe His Glu Ala Ile Arg
    3335            3340                3345

Asp Lys Ile Asp Lys Asn Glu Asn Gln Gln Ser Pro Gly Leu His
    3350            3355                3360

Gly Lys Leu Leu Glu Ile Phe His Thr Ile Ala Gln Pro Ser Leu
    3365            3370                3375

Arg His Thr Tyr Gly Glu Val Thr Trp Glu Gln Leu Glu Ala Gly
    3380            3385                3390

Ile Asn Arg Lys Gly Ala Ala Gly Phe Leu Glu Lys Lys Asn Val
    3395            3400                3405

Gly Glu Val Leu Asp Ser Glu Lys His Leu Val Glu Gln Leu Ile
    3410            3415                3420

Arg Asp Leu Lys Ala Gly Arg Lys Ile Arg Tyr Tyr Glu Thr Ala
    3425            3430                3435

Ile Pro Lys Asn Glu Lys Arg Asp Val Ser Asp Asp Trp Gln Ala
    3440            3445                3450

Gly Asp Leu Val Asp Glu Lys Lys Pro Arg Val Ile Gln Tyr Pro
    3455            3460                3465

Glu Ala Lys Thr Arg Leu Ala Ile Thr Lys Val Met Tyr Asn Trp
    3470            3475                3480

Val Lys Gln Gln Pro Val Val Ile Pro Gly Tyr Glu Gly Lys Thr
    3485            3490                3495

Pro Leu Phe Asn Ile Phe Asn Lys Val Arg Lys Glu Trp Asp Leu
    3500            3505                3510

Phe Asn Glu Pro Val Ala Val Ser Phe Asp Thr Lys Ala Trp Asp
    3515            3520                3525

Thr Gln Val Thr Ser Lys Asp Leu Arg Leu Ile Gly Glu Ile Gln
    3530            3535                3540

Lys Tyr Tyr Tyr Arg Lys Glu Trp His Lys Phe Ile Asp Thr Ile
    3545            3550                3555

Thr Asp His Met Val Glu Val Pro Val Ile Thr Ala Asp Gly Glu
    3560            3565                3570

Val Tyr Ile Arg Asn Gly Gln Arg Gly Ser Gly Gln Pro Asp Thr
    3575            3580                3585

Ser Ala Gly Asn Ser Met Leu Asn Val Leu Thr Met Met Tyr Ala
    3590            3595                3600

Phe Cys Glu Ser Thr Gly Ile Pro Tyr Lys Ser Phe Asn Arg Val
    3605            3610                3615

Ala Arg Ile His Val Cys Gly Asp Asp Gly Phe Leu Ile Thr Glu
    3620            3625                3630

Arg Gly Leu Gly Leu Lys Phe Ala Asn Asn Gly Met Gln Ile Leu
    3635            3640                3645
```

```
His Glu Ala Gly Lys Pro Gln Lys Ile Thr Glu Gly Glu Arg Met
    3650                3655                3660

Lys Val Ala Tyr Arg Phe Glu Asp Ile Glu Phe Cys Ser His Thr
    3665                3670                3675

Pro Val Pro Val Arg Trp Ser Asp Asn Thr Ser Ser Tyr Met Ala
    3680                3685                3690

Gly Arg Asp Thr Ala Ile Ile Leu Ser Lys Met Ala Thr Arg Leu
    3695                3700                3705

Asp Ser Ser Gly Glu Arg Gly Thr Thr Ala Tyr Glu Lys Ala Val
    3710                3715                3720

Ala Phe Ser Phe Leu Leu Met Tyr Ser Trp Asn Pro Leu Val Arg
    3725                3730                3735

Arg Ile Cys Leu Leu Val Leu Ser Gln Gln Pro Glu Thr Ala Pro
    3740                3745                3750

Ser Thr Gln Thr Thr Tyr Tyr Tyr Lys Gly Asp Pro Ile Gly Ala
    3755                3760                3765

Tyr Lys Asp Val Ile Gly Lys Asn Leu Ser Glu Leu Lys Arg Thr
    3770                3775                3780

Gly Phe Glu Lys Leu Ala Asn Leu Asn Leu Ser Leu Ser Thr Leu
    3785                3790                3795

Gly Ile Trp Ser Lys His Thr Ser Lys Arg Ile Ile Gln Asp Cys
    3800                3805                3810

Val Thr Ile Gly Lys Glu Glu Gly Asn Trp Leu Val Asn Ala Asp
    3815                3820                3825

Arg Leu Ile Ser Ser Lys Thr Gly His Leu Tyr Ile Pro Asp Lys
    3830                3835                3840

Gly Tyr Thr Leu Gln Gly Lys His Tyr Glu Gln Leu Gln Leu Gln
    3845                3850                3855

Ala Arg Thr Ser Pro Ile Met Gly Val Gly Thr Glu Arg Tyr Lys
    3860                3865                3870

Leu Gly Pro Ile Val Asn Leu Leu Leu Arg Arg Leu Lys Val Leu
    3875                3880                3885

Leu Met Ala Ala Val Gly Ala Ser Ser
    3890                3895

<210> SEQ ID NO 6
<211> LENGTH: 3898
<212> TYPE: PRT
<213> ORGANISM: BVDV

<400> SEQUENCE: 6

Met Glu Leu Ile Thr Asn Glu Leu Leu Tyr Lys Thr Tyr Lys Gln Lys
1               5                   10                  15

Pro Ala Gly Val Glu Pro Val Tyr Asp Gln Ala Gly Asn Pro Leu
                20                  25                  30

Phe Gly Glu Arg Gly Val Val His Pro Gln Ala Thr Leu Lys Leu Pro
                35                  40                  45

His Lys Arg Gly Glu Ser Glu Val Pro Thr Asn Leu Ala Ser Leu Pro
    50                  55                  60

Lys Arg Gly Asp Cys Arg Ser Gly Asn Ser Lys Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Gln Glu Thr Ser Met Cys
                100                 105                 110
```

```
Glu Thr Thr Lys Arg Ile Gly Arg Val Thr Gly Ser Asp Ser Lys Leu
            115                 120                 125

Tyr His Ile Tyr Val Cys Ile Asp Gly Cys Ile Ile Ile Lys Ser Ala
            130                 135                 140

Thr Lys Asp His Gln Lys Val Phe Lys Trp Val His Asn Lys Leu Asn
145                 150                 155                 160

Cys Pro Leu Trp Val Thr Ser Cys Ser Asp Thr Asn Ala Glu Gly Ala
                    165                 170                 175

Thr Arg Lys Lys Gln Gln Lys Pro Asp Arg Leu Glu Lys Gly Arg Met
            180                 185                 190

Lys Ile Thr Pro Lys Glu Ser Glu Lys Asp Ser Lys Thr Lys Pro Pro
            195                 200                 205

Asp Ala Thr Ile Val Val Asp Gly Val Lys Tyr Gln Val Lys Lys Lys
            210                 215                 220

Gly Lys Val Lys Ser Lys Asn Thr Gln Asp Gly Leu Tyr His Asn Lys
225                 230                 235                 240

Asn Lys Pro Gln Glu Ser Arg Lys Lys Leu Glu Lys Ala Leu Leu Ala
                    245                 250                 255

Trp Ala Ile Ile Ala Leu Val Leu Phe Asp Ile Ala Val Gly Glu Asn
            260                 265                 270

Ile Thr Gln Trp Asn Leu Gln Asp Asn Gly Thr Glu Gly Ile Gln Arg
            275                 280                 285

Ala Met Phe Gln Arg Gly Val Asn Arg Ser Leu His Gly Ile Trp Pro
            290                 295                 300

Glu Lys Ile Cys Thr Gly Val Pro Ser His Leu Ala Thr Asp Thr Glu
305                 310                 315                 320

Leu Lys Ala Ile His Gly Met Met Asp Ala Ser Glu Lys Thr Asn Tyr
                    325                 330                 335

Thr Cys Cys Arg Leu Gln Arg His Glu Trp Asn Lys His Gly Trp Cys
            340                 345                 350

Asn Trp Tyr Asn Ile Glu Pro Trp Ile Leu Leu Met Asn Lys Thr Gln
            355                 360                 365

Ala Asn Leu Thr Glu Gly Gln Pro Pro Arg Glu Cys Ala Val Thr Cys
            370                 375                 380

Arg Tyr Asp Arg Asp Ser Asp Leu Asn Ile Val Thr Gln Ala Arg Asp
385                 390                 395                 400

Ser Pro Thr Pro Leu Thr Gly Cys Lys Lys Gly Lys Asn Phe Ser Phe
                    405                 410                 415

Ala Gly Val Leu Val Gln Gly Pro Cys Asn Phe Glu Ile Ala Ala Ser
            420                 425                 430

Asp Val Leu Phe Lys Glu His Asp Ser Thr Gly Met Ile Gln Asp Thr
            435                 440                 445

Ala His Tyr Leu Val Asp Gly Leu Thr Asn Ser Leu Glu Ser Ala Arg
450                 455                 460

Gln Gly Thr Ala Lys Leu Thr Thr Trp Leu Gly Arg Gln Leu Arg Ile
465                 470                 475                 480

Leu Gly Lys Lys Leu Glu Asn Lys Ser Lys Thr Trp Phe Gly Ala Tyr
                    485                 490                 495

Ala Ala Ser Pro Tyr Cys Glu Val Glu Arg Arg Leu Gly Tyr Ile Trp
            500                 505                 510

Tyr Thr Lys Asn Cys Thr Pro Ala Cys Leu Pro Lys Asn Thr Lys Ile
            515                 520                 525
```

-continued

Val Gly Pro Gly Lys Phe Asp Thr Asn Ala Glu Asp Gly Lys Leu Leu
    530                 535                 540

His Glu Met Gly Gly His Leu Ser Glu Val Leu Leu Ser Val Val
545                 550                 555                 560

Val Leu Ser Asp Phe Ala Pro Glu Thr Ala Ser Ile Val Tyr Leu Ile
                565                 570                 575

Leu His Phe Thr Ile Pro Gln Gly His Thr Asp Ile Glu Asp Cys Asp
            580                 585                 590

Lys Asn Gln Leu Asn Leu Thr Val Gly Leu Thr Thr Ala Glu Val Val
        595                 600                 605

Pro Ser Ser Val Trp Asn Leu Gly Lys Tyr Val Cys Val Arg Pro Asp
610                 615                 620

Trp Trp Pro Tyr Glu Thr Ala Thr Val Leu Val Phe Glu Glu Val Gly
625                 630                 635                 640

Gln Val Ile Lys Leu Val Leu Arg Ala Leu Arg Asp Leu Thr Arg Ile
                645                 650                 655

Trp Thr Ala Ala Thr Thr Thr Ala Phe Leu Val Cys Met Val Lys Val
            660                 665                 670

Val Arg Gly Gln Val Leu Gln Gly Ile Leu Trp Leu Met Leu Ile Thr
        675                 680                 685

Gly Ala Gln Gly Tyr Pro Asp Cys Lys Pro Asp Phe Ser Tyr Ala Ile
690                 695                 700

Ala Lys Asn Asp Glu Ile Gly Pro Leu Gly Ala Thr Gly Leu Thr Thr
705                 710                 715                 720

Gln Trp Tyr Lys Tyr Ser Asp Glu Met Arg Leu Gln Asp Thr Val Val
                725                 730                 735

Thr Val Trp Cys Lys Asn Gly Glu Phe Arg His Leu Ile Thr Cys Glu
            740                 745                 750

Arg Glu Ala Arg Tyr Leu Ala Ile Leu His Thr Arg Ala Leu Pro Thr
        755                 760                 765

Ser Val Val Phe Glu Lys Ile Ile Asn Gly Lys Glu Gln Glu Asp Ile
770                 775                 780

Val Glu Met Ser Asp Asn Phe Glu Phe Gly Leu Cys Pro Cys Asp Ala
785                 790                 795                 800

Lys Pro Leu Val Arg Gly Lys Phe Asn Val Thr Leu Leu Asn Gly Pro
                805                 810                 815

Ala Phe Gln Met Val Cys Pro Ile Gly Trp Thr Gly Thr Val Ser Cys
            820                 825                 830

Thr Leu Ala Asn Lys Asp Thr Leu Ala Thr Thr Val Val Arg Thr Tyr
        835                 840                 845

Lys Arg Asp Lys Pro Phe Pro Tyr Arg Gln Gly Cys Ile Thr Gln Lys
850                 855                 860

Thr Ile Gly Glu Asp Leu Tyr Asp Cys Val Leu Gly Gly Asn Trp Thr
865                 870                 875                 880

Cys Val Pro Gly Asn Gln Leu Arg Tyr Val Gly Gly Pro Val Glu Ser
                885                 890                 895

Cys Lys Trp Cys Gly Tyr Lys Phe Asp Lys Ser Glu Gly Leu Pro His
            900                 905                 910

Phe Pro Ile Gly Lys Cys Lys Leu Lys Asn Glu Ser Gly Tyr Arg Gln
        915                 920                 925

Val Asp Glu Thr Ser Cys Asn Arg Asp Gly Val Ala Ile Val Pro Ser
930                 935                 940

Gly Leu Val Lys Cys Lys Ile Gly Asn Thr Val Val Gln Val Ile Ala

-continued

```
                945                 950                 955                 960
            Met Asp Asp Lys Leu Gly Pro Met Pro Cys Arg Pro His Glu Ile Ile
                            965                 970                 975
            Ser Ser Glu Gly Pro Val Glu Lys Thr Ala Cys Thr Phe Asn Tyr Ala
                            980                 985                 990
            Arg Thr Leu Lys Asn Lys Tyr Phe Glu Pro Arg Asp Asn Tyr Phe Gln
                            995                 1000                1005
            Gln Tyr Met Leu Lys Gly Glu Tyr Gln Tyr Trp Phe Asp Leu Glu
                    1010                1015                1020
            Ile Thr Asp His His Arg Asp Tyr Phe Ala Glu Ser Leu Leu Val
                    1025                1030                1035
            Ile Val Val Ala Leu Leu Gly Gly Arg Tyr Val Leu Trp Leu Leu
                    1040                1045                1050
            Val Thr Tyr Met Ile Leu Ser Glu Gln Met Thr Leu Gly Ala Gln
                    1055                1060                1065
            Tyr Gly Ala Gly Glu Ile Val Met Met Gly Asn Leu Leu Thr His
                    1070                1075                1080
            Asp Ser Ile Glu Val Val Thr Tyr Phe Leu Leu Leu Tyr Leu Leu
                    1085                1090                1095
            Leu Arg Glu Glu Asn Ile Lys Lys Trp Val Ile Leu Ile Tyr His
                    1100                1105                1110
            Ile Ile Val Met His Pro Leu Lys Ser Met Thr Val Ile Leu Leu
                    1115                1120                1125
            Met Val Gly Gly Met Ala Lys Ala Glu Pro Asp Thr Gln Ser Tyr
                    1130                1135                1140
            Leu Glu Arg Val Asp Leu Ser Phe Thr Met Ile Thr Leu Ile Val
                    1145                1150                1155
            Val Gly Leu Val Ile Ala Arg Arg Asp Pro Thr Val Val Pro Leu
                    1160                1165                1170
            Val Thr Ile Val Ala Ala Leu Lys Ile Thr Gly Leu Gly Phe Gly
                    1175                1180                1185
            Pro Gly Val Asp Val Ala Met Ala Val Leu Thr Leu Thr Leu Leu
                    1190                1195                1200
            Met Val Ser Tyr Val Thr Asp Tyr Phe Arg Tyr Lys Arg Trp Leu
                    1205                1210                1215
            Gln Cys Ile Leu Ser Leu Val Ala Gly Val Phe Leu Ile Arg Ser
                    1220                1225                1230
            Leu Lys His Leu Gly Glu Ile Glu Thr Pro Glu Leu Thr Ile Pro
                    1235                1240                1245
            Asn Trp Arg Pro Leu Thr Phe Ile Leu Leu Tyr Leu Thr Ser Ala
                    1250                1255                1260
            Thr Val Val Thr Arg Trp Lys Val Asp Ile Ala Gly Ile Leu Leu
                    1265                1270                1275
            Gln Gly Ala Pro Ile Leu Leu Leu Ile Ala Thr Leu Trp Ala Asp
                    1280                1285                1290
            Phe Leu Thr Leu Val Leu Ile Leu Pro Thr Tyr Glu Leu Val Lys
                    1295                1300                1305
            Leu Tyr Tyr Leu Lys Asn Ile Lys Thr Asp Val Glu Arg Ser Trp
                    1310                1315                1320
            Leu Gly Gly Leu Asp Tyr Lys Thr Ile Asp Ser Val Tyr Asp Val
                    1325                1330                1335
            Asp Glu Ser Gly Glu Gly Val Tyr Leu Phe Pro Ser Arg Gln Asp
                    1340                1345                1350
```

```
Gly Lys Lys Asn Thr Ser Ile Leu Leu Pro Leu Ile Arg Ala Thr
1355                1360                1365

Leu Ile Ser Cys Val Ser Ser Lys Trp Gln Met Val Tyr Met Ala
1370                1375                1380

Tyr Leu Thr Leu Asp Phe Met Tyr Tyr Met His Arg Lys Val Ile
1385                1390                1395

Glu Glu Ile Ser Gly Gly Thr Asn Val Ile Ser Arg Val Ile Ala
1400                1405                1410

Ala Leu Ile Glu Leu Asn Trp Ser Met Glu Glu Glu Ser Lys
1415                1420                1425

Gly Leu Lys Lys Phe Phe Val Leu Ser Gly Arg Val Arg Asn Leu
1430                1435                1440

Ile Ile Lys His Lys Val Arg Asn Gln Thr Val Ala Ser Trp Tyr
1445                1450                1455

Gly Glu Glu Glu Val Tyr Gly Leu Pro Lys Val Val Thr Ile Ile
1460                1465                1470

Arg Ala Cys Thr Leu Asn Lys Asn Lys His Cys Ile Ile Cys Thr
1475                1480                1485

Val Cys Glu Ala Lys Lys Trp Lys Gly Gly Asn Cys Pro Lys Cys
1490                1495                1500

Gly Arg His Gly Lys Pro Ile Thr Cys Gly Met Thr Leu Ala Asp
1505                1510                1515

Phe Glu Glu Arg His Tyr Lys Arg Ile Phe Ile Arg Glu Gly Thr
1520                1525                1530

Phe Glu Gly Pro Phe Arg Gln Glu Tyr Asn Gly Phe Val Gln Tyr
1535                1540                1545

Ala Ala Arg Gly Gln Leu Phe Leu Arg Asn Leu Pro Ile Leu Ala
1550                1555                1560

Thr Lys Val Lys Met Leu Met Val Gly Asn Leu Gly Glu Glu Ile
1565                1570                1575

Gly Asp Leu Glu His Leu Gly Trp Ile Leu Arg Gly Pro Ala Val
1580                1585                1590

Cys Lys Lys Ile Thr Glu His Glu Lys Cys His Val Ser Ile Leu
1595                1600                1605

Asp Lys Leu Thr Ala Phe Phe Gly Val Met Pro Arg Gly Thr Thr
1610                1615                1620

Pro Arg Ala Pro Val Arg Phe Pro Thr Ala Leu Leu Lys Val Arg
1625                1630                1635

Arg Gly Leu Glu Thr Gly Trp Ala Tyr Thr His Gln Gly Gly Ile
1640                1645                1650

Ser Ser Val Asp His Val Thr Ala Gly Lys Asp Leu Leu Val Cys
1655                1660                1665

Asp Ser Met Gly Arg Thr Arg Val Val Cys Gln Ser Asn Asn Lys
1670                1675                1680

Leu Thr Asp Glu Thr Glu Tyr Gly Val Lys Thr Asp Ser Gly Cys
1685                1690                1695

Pro Asp Gly Ala Arg Cys Tyr Val Leu Asn Pro Glu Ala Val Asn
1700                1705                1710

Ile Ser Gly Ser Lys Gly Ala Val Val His Leu Gln Lys Thr Gly
1715                1720                1725

Gly Glu Phe Thr Cys Val Thr Ala Ser Gly Thr Pro Ala Phe Phe
1730                1735                1740
```

```
Asp Leu Lys Asn Leu Lys Gly Trp Ser Gly Leu Pro Ile Tyr Glu
    1745                1750                1755

Ala Ser Ser Gly Arg Val Val Gly Arg Val Lys Val Gly Lys Asn
    1760                1765                1770

Glu Glu Ser Lys Pro Thr Lys Leu Met Ser Gly Ile Gln Thr Val
    1775                1780                1785

Ser Lys Ser Thr Ala Asp Leu Thr Glu Met Val Lys Lys Ile Thr
    1790                1795                1800

Ser Met Asn Arg Gly Asp Phe Lys Gln Ile Thr Leu Ala Thr Gly
    1805                1810                1815

Ala Gly Lys Thr Thr Glu Leu Pro Lys Ala Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Leu Lys His Pro Ser Ile
    1850                1855                1860

Ser Phe Asn Leu Arg Ile Gly Asp Met Lys Glu Gly Asp Met Ala
    1865                1870                1875

Thr Gly Ile Thr Tyr Ala Ser Tyr Gly Tyr Phe Cys Gln Met Gln
    1880                1885                1890

Gln Pro Lys Leu Arg Ala Ala Met Val Glu Tyr Ser Tyr Ile Phe
    1895                1900                1905

Leu Asp Glu Tyr His Cys Ala Thr Pro Glu Gln Leu Ala Val Ile
    1910                1915                1920

Gly Lys Ile His Arg Phe Ser Glu Ser Ile Arg Val Val Ala Met
    1925                1930                1935

Thr Ala Thr Pro Ala Gly Ser Val Thr Thr Thr Gly Gln Lys His
    1940                1945                1950

Pro Ile Glu Glu Phe Ile Ala Pro Glu Val Met Lys Gly Glu Asp
    1955                1960                1965

Leu Gly Ser Gln Phe Leu Asp Ile Ala Gly Leu Lys Ile Pro Val
    1970                1975                1980

Glu Glu Met Lys Gly Asn Met Leu Val Phe Val Pro Thr Arg Asn
    1985                1990                1995

Met Ala Val Asp Val Ala Lys Lys Leu Lys Ala Lys Gly Tyr Asn
    2000                2005                2010

Ser Gly Tyr Tyr Tyr Ser Gly Glu Asp Pro Ala Asn Leu Arg Val
    2015                2020                2025

Val Thr Ser Gln Ser Pro Tyr Val Val Val Ala Thr Asn Ala Ile
    2030                2035                2040

Glu Ser Gly Val Thr Leu Pro Asp Leu Asp Thr Val Val Asp Thr
    2045                2050                2055

Gly Leu Lys Cys Glu Lys Arg Val Arg Val Ser Ser Lys Ile Pro
    2060                2065                2070

Phe Ile Val Thr Gly Leu Lys Arg Met Ala Val Thr Val Gly Glu
    2075                2080                2085

Gln Ala Gln Arg Arg Gly Arg Val Gly Arg Val Lys Pro Gly Arg
    2090                2095                2100

Tyr Tyr Arg Ser Gln Glu Thr Ala Thr Gly Ser Lys Asp Tyr His
    2105                2110                2115

Tyr Asp Leu Leu Gln Ala Gln Arg Tyr Gly Ile Glu Asp Gly Ile
    2120                2125                2130

Asn Ile Thr Lys Ser Phe Arg Glu Met Asn Tyr Asp Trp Ser Leu
```

```
                 2135                2140                2145
Tyr Glu Glu Asp Ser Leu Leu Ile Thr Gln Leu Glu Ile Leu Asn
    2150                2155                2160

Asn Leu Leu Ile Ser Glu Asp Leu Pro Ala Ala Val Lys Asn Ile
    2165                2170                2175

Met Ala Arg Thr Asp His Pro Glu Pro Ile Gln Leu Ala Tyr Asn
    2180                2185                2190

Ser Tyr Glu Val Gln Val Pro Val Leu Phe Pro Lys Ile Arg Asn
    2195                2200                2205

Gly Glu Val Thr Asp Thr Tyr Glu Asn Tyr Ser Phe Leu Asn Ala
    2210                2215                2220

Arg Lys Leu Gly Glu Asp Val Pro Thr Tyr Ile Tyr Ala Thr Glu
    2225                2230                2235

Asp Glu Asp Leu Ala Val Asp Leu Leu Gly Leu Asp Trp Pro Asp
    2240                2245                2250

Pro Gly Asn Gln Gln Val Val Glu Thr Gly Lys Ala Leu Lys Gln
    2255                2260                2265

Val Val Gly Leu Ser Ser Ala Glu Asn Ala Leu Leu Ile Ala Leu
    2270                2275                2280

Phe Gly Tyr Val Gly Tyr Gln Ala Leu Ser Lys Arg His Val Pro
    2285                2290                2295

Met Ile Thr Asp Ile Tyr Thr Ile Glu Asp Gln Arg Leu Glu Asp
    2300                2305                2310

Thr Thr His Leu Gln Tyr Ala Pro Asn Ala Ile Arg Thr Glu Gly
    2315                2320                2325

Lys Glu Thr Glu Leu Lys Glu Leu Ala Val Gly Asp Leu Asp Lys
    2330                2335                2340

Ile Met Gly Ser Ile Ser Asp Tyr Ala Ser Gly Gly Leu Glu Phe
    2345                2350                2355

Val Arg Ser Gln Ala Glu Lys Ile Arg Ser Ala Pro Thr Phe Lys
    2360                2365                2370

Glu Asn Val Glu Thr Ala Lys Gly Tyr Val Gln Lys Phe Ile Asp
    2375                2380                2385

Ala Leu Ile Glu Asn Lys Glu Thr Ile Ile Arg Tyr Gly Leu Trp
    2390                2395                2400

Gly Thr His Thr Ala Leu Tyr Lys Ser Ile Ala Ala Arg Leu Gly
    2405                2410                2415

His Glu Thr Ala Phe Ala Thr Leu Val Val Lys Trp Leu Ala Phe
    2420                2425                2430

Gly Gly Glu Ser Val Ser Asp His Val Arg Gln Ala Ala Val Asp
    2435                2440                2445

Leu Val Tyr Tyr Val Met Asn Lys Pro Ser Phe Pro Gly Asp
    2450                2455                2460

Ser Glu Thr Gln Gln Glu Gly Arg Arg Phe Val Ala Ser Leu Phe
    2465                2470                2475

Ile Ser Ala Leu Ala Thr Tyr Thr Tyr Lys Ser Trp Asn Tyr His
    2480                2485                2490

Asn Leu Ser Lys Val Val Glu Pro Ala Leu Ala Tyr Leu Pro Tyr
    2495                2500                2505

Ala Thr Ser Ala Leu Lys Met Phe Thr Pro Thr Arg Leu Glu Ser
    2510                2515                2520

Val Val Ile Leu Ser Thr Thr Ile Tyr Lys Thr Tyr Leu Ser Ile
    2525                2530                2535
```

```
Arg Lys Gly Lys Ser Asp Gly Leu Leu Thr Gly Ile Ser Ala
    2540            2545            2550

Ala Met Glu Ile Leu Ser Gln Asn Pro Val Ser Val Gly Ile Ser
    2555            2560            2565

Val Met Leu Gly Val Gly Ala Ile Ala Ala His Asn Ala Ile Glu
    2570            2575            2580

Ser Ser Glu Gln Lys Arg Thr Leu Leu Met Lys Val Phe Val Lys
    2585            2590            2595

Asn Phe Leu Asp Gln Ala Ala Thr Asp Glu Leu Val Lys Glu Asn
    2600            2605            2610

Pro Glu Lys Ile Ile Met Ala Leu Phe Glu Ala Val Gln Thr Ile
    2615            2620            2625

Gly Asn Pro Leu Arg Leu Ile Tyr His Leu Tyr Gly Val Tyr Tyr
    2630            2635            2640

Lys Gly Trp Glu Ala Lys Glu Leu Ser Glu Arg Thr Ala Gly Arg
    2645            2650            2655

Asn Leu Phe Thr Leu Ile Met Phe Glu Ala Phe Glu Leu Leu Gly
    2660            2665            2670

Met Asp Ser Glu Gly Lys Ile Arg Asn Leu Ser Gly Asn Tyr Ile
    2675            2680            2685

Leu Asp Leu Ile Tyr Ser Leu His Lys Gln Ile Asn Arg Gly Leu
    2690            2695            2700

Lys Lys Ile Val Leu Gly Trp Ala Pro Ala Pro Phe Ser Cys Asp
    2705            2710            2715

Trp Thr Pro Ser Asp Gly Arg Ile Arg Leu Pro Thr Asp Asn Tyr
    2720            2725            2730

Leu Arg Val Glu Thr Lys Cys Pro Cys Gly Tyr Glu Met Lys Ala
    2735            2740            2745

Leu Arg Asn Val Ser Gly Ser Leu Thr Lys Val Glu Glu Lys Gly
    2750            2755            2760

Pro Phe Leu Cys Arg Asn Arg Pro Gly Arg Gly Pro Val Asn Tyr
    2765            2770            2775

Arg Val Thr Lys Tyr Tyr Asp Asp Asn Leu Thr Glu Ile Lys Pro
    2780            2785            2790

Val Ala Lys Leu Glu Gly Leu Val Glu His Tyr Tyr Lys Gly Val
    2795            2800            2805

Thr Ala Arg Ile Asp Tyr Asp Lys Gly Lys Met Leu Val Ala Thr
    2810            2815            2820

Asp Lys Trp Glu Val Glu His Gly Thr Val Thr Arg Leu Ala Lys
    2825            2830            2835

Arg Tyr Ser Gly Val Gly Phe Lys Gly Ala Tyr Leu Gly Asp Glu
    2840            2845            2850

Pro Asn Tyr Arg Asp Leu Val Glu Arg Asp Cys Ala Thr Ile Thr
    2855            2860            2865

Lys Asn Thr Val Gln Phe Leu Lys Met Lys Lys Gly Cys Ala Phe
    2870            2875            2880

Thr Tyr Asp Leu Thr Leu Ser Asn Leu Thr Arg Leu Ile Glu Leu
    2885            2890            2895

Val His Arg Asn Asn Leu Glu Glu Lys Asp Ile Pro Ala Ala Thr
    2900            2905            2910

Val Thr Thr Trp Leu Ala Tyr Thr Phe Val Asn Glu Asp Val Gly
    2915            2920            2925
```

-continued

```
Thr Ile Arg Pro Val Leu Gly Glu Arg Val Ile Ala Asp Pro Val
2930                2935                2940

Val Asp Val Asn Leu Gln Pro Glu Val Gln Val Asp Thr Ser Glu
2945                2950                2955

Val Gly Ile Thr Leu Val Gly Lys Ala Ala Leu Met Thr Thr Gly
2960                2965                2970

Thr Thr Pro Val Val Glu Lys Thr Glu Pro Ser Ala Ser Ala Ser
2975                2980                2985

Pro Ser Ser Ile Lys Ile Gly Leu Asp Gln Gly Ser Tyr Pro Gly
2990                2995                3000

Pro Gly Leu Gln Asp Arg Thr Leu Val Asp Glu Ile His Ser Lys
3005                3010                3015

Asp Glu Arg Pro Phe Val Leu Val Leu Gly Ser Lys Asn Ser Met
3020                3025                3030

Ser Asn Arg Ala Lys Thr Ala Lys Asn Ile Asn Leu Tyr Thr Gly
3035                3040                3045

Lys Asp Pro Arg Glu Ile Arg Asp Leu Met Ala Gln Gly Arg Met
3050                3055                3060

Leu Val Val Ala Leu Arg Gly Phe Asn Pro Glu Leu Ser Glu Leu
3065                3070                3075

Val Asp Phe Lys Gly Thr Phe Leu Asp Arg Glu Ala Leu Glu Ala
3080                3085                3090

Leu Ser Leu Gly Arg Pro Arg Pro Lys Gln Val Thr Thr Ser Thr
3095                3100                3105

Val Arg Glu Leu Leu Glu Gln Glu Glu Gln Val Glu Val Pro Asn
3110                3115                3120

Trp Phe Gly Ala Asp Asp Pro Val Phe Leu Glu Val Ala Leu Lys
3125                3130                3135

Gly Asp Lys Tyr His Leu Val Gly Asp Val Asp Lys Val Lys Asp
3140                3145                3150

Gln Ala Lys Gly Leu Gly Ala Thr Asp Gln Thr Arg Ile Val Lys
3155                3160                3165

Glu Val Gly Ala Arg Thr Tyr Thr Met Lys Leu Ser Ser Trp Phe
3170                3175                3180

Leu Gln Ala Ser Asn Lys Gln Met Ser Leu Thr Pro Leu Phe Glu
3185                3190                3195

Glu Leu Leu Arg Cys Pro Pro Lys Ala Lys Asn Asn Lys Gly
3200                3205                3210

His Met Ala Ser Ala Tyr Gln Leu Ala Gln Gly Asn Trp Glu Pro
3215                3220                3225

Leu Asp Cys Gly Val Tyr Leu Gly Thr Ile Pro Ala Arg Arg Val
3230                3235                3240

Lys Ile His Pro Tyr Glu Ala Tyr Leu Lys Leu Lys Asp Leu Leu
3245                3250                3255

Glu Glu Glu Glu Lys Lys Pro Lys Ser Arg Asp Thr Val Ile Arg
3260                3265                3270

Glu His Asn Lys Trp Ile Leu Lys Lys Val Arg His Gln Gly Asn
3275                3280                3285

Leu Asn Thr Lys Lys Ile Leu Asn Pro Gly Lys Leu Ser Glu Gln
3290                3295                3300

Leu Asp Arg Glu Gly His Lys Arg Asn Ile Tyr Asn Asn Gln Ile
3305                3310                3315

Gly Thr Ile Leu Thr Gly Ala Gly Val Arg Leu Glu Lys Leu Pro
```

```
          3320                3325                3330

Val Val Arg Ala Gln Thr Asp Thr Lys Ser Phe His Glu Ala Ile
    3335                3340                3345

Arg Asp Lys Ile Asp Lys Asn Glu Asn Gln Gln Ser Pro Gly Leu
    3350                3355                3360

His Gly Lys Leu Leu Glu Ile Phe His Thr Ile Ala Gln Pro Ser
    3365                3370                3375

Leu Arg His Thr Tyr Gly Glu Val Thr Trp Glu Gln Leu Glu Ala
    3380                3385                3390

Gly Ile Asn Arg Lys Gly Ala Ala Gly Phe Leu Glu Lys Lys Asn
    3395                3400                3405

Val Gly Glu Val Leu Asp Ser Glu Lys His Leu Val Glu Gln Leu
    3410                3415                3420

Ile Arg Asp Leu Lys Ala Gly Arg Lys Ile Arg Tyr Tyr Glu Thr
    3425                3430                3435

Ala Ile Pro Lys Asn Glu Lys Arg Asp Val Ser Asp Asp Trp Gln
    3440                3445                3450

Ala Gly Asp Leu Val Asp Glu Lys Lys Pro Arg Val Ile Gln Tyr
    3455                3460                3465

Pro Glu Ala Lys Thr Arg Leu Ala Ile Thr Lys Val Met Tyr Asn
    3470                3475                3480

Trp Val Lys Gln Gln Pro Val Val Ile Pro Gly Tyr Glu Gly Lys
    3485                3490                3495

Thr Pro Leu Phe Asn Ile Phe Asn Lys Val Arg Lys Glu Trp Asp
    3500                3505                3510

Leu Phe Asn Glu Pro Val Ala Val Ser Phe Asp Thr Lys Ala Trp
    3515                3520                3525

Asp Thr Gln Val Thr Ser Lys Asp Leu Arg Leu Ile Gly Glu Ile
    3530                3535                3540

Gln Lys Tyr Tyr Tyr Arg Lys Glu Trp His Lys Phe Ile Asp Thr
    3545                3550                3555

Ile Thr Asp His Met Val Glu Val Pro Val Ile Thr Ala Asp Gly
    3560                3565                3570

Glu Val Tyr Ile Arg Asn Gly Gln Arg Gly Ser Gly Gln Pro Asp
    3575                3580                3585

Thr Ser Ala Gly Asn Ser Met Leu Asn Val Leu Thr Met Met Tyr
    3590                3595                3600

Ala Phe Cys Glu Ser Thr Gly Ile Pro Tyr Lys Ser Phe Asn Arg
    3605                3610                3615

Val Ala Arg Ile His Val Cys Gly Asp Asp Gly Phe Leu Ile Thr
    3620                3625                3630

Glu Arg Gly Leu Gly Leu Lys Phe Ala Asn Asn Gly Met Gln Ile
    3635                3640                3645

Leu His Glu Ala Gly Lys Pro Gln Lys Ile Thr Glu Gly Glu Arg
    3650                3655                3660

Met Lys Val Ala Tyr Arg Phe Glu Asp Ile Glu Phe Cys Ser His
    3665                3670                3675

Thr Pro Val Pro Val Arg Trp Ser Asp Asn Thr Ser Ser Tyr Met
    3680                3685                3690

Ala Gly Arg Asp Thr Ala Ile Ile Leu Ser Lys Met Ala Thr Arg
    3695                3700                3705

Leu Asp Ser Ser Gly Glu Arg Gly Thr Thr Ala Tyr Glu Lys Ala
    3710                3715                3720
```

```
Val Ala Phe Ser Phe Leu Leu Met Tyr Ser Trp Asn Pro Leu Val
            3725                3730                3735

Arg Arg Ile Cys Leu Leu Val Leu Ser Gln Gln Pro Glu Thr Ala
        3740                3745                3750

Pro Ser Thr Gln Thr Thr Tyr Tyr Tyr Lys Gly Asp Pro Ile Gly
    3755                3760                3765

Ala Tyr Lys Asp Val Ile Gly Lys Asn Leu Ser Glu Leu Lys Arg
3770                3775                3780

Thr Gly Phe Glu Lys Leu Ala Asn Leu Asn Leu Ser Leu Ser Thr
    3785                3790                3795

Leu Gly Ile Trp Ser Lys His Thr Ser Lys Arg Ile Ile Gln Asp
    3800                3805                3810

Cys Val Thr Ile Gly Lys Glu Glu Gly Asn Trp Leu Val Asn Ala
    3815                3820                3825

Asp Arg Leu Ile Ser Ser Lys Thr Gly His Leu Tyr Ile Pro Asp
    3830                3835                3840

Lys Gly Tyr Thr Leu Gln Gly Lys His Tyr Glu Gln Leu Gln Leu
    3845                3850                3855

Gln Ala Arg Thr Ser Pro Ile Met Gly Val Gly Thr Glu Arg Tyr
    3860                3865                3870

Lys Leu Gly Pro Ile Val Asn Leu Leu Leu Arg Arg Leu Lys Val
    3875                3880                3885

Leu Leu Met Ala Ala Val Gly Ala Ser Ser
    3890                3895

<210> SEQ ID NO 7
<211> LENGTH: 3913
<212> TYPE: PRT
<213> ORGANISM: BVDV

<400> SEQUENCE: 7

Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
                20                  25                  30

Phe Gly Glu Ser Ser Asp Leu His Pro Gln Ser Thr Leu Lys Leu Pro
            35                  40                  45

His Gln Arg Gly Ser Ala Asn Ile Leu Thr Asn Ala Arg Ser Leu Pro
        50                  55                  60

Arg Lys Gly Asp Cys Arg Arg Gly Asn Val Tyr Gly Pro Val Ser Gly
65                  70                  75                  80

Ile Tyr Ile Lys Pro Gly Pro Ile Tyr Tyr Gln Asp Tyr Val Gly Pro
                85                  90                  95

Val Tyr His Arg Ala Pro Leu Glu Leu Cys Arg Glu Ala Ser Met Cys
            100                 105                 110

Glu Thr Thr Arg Arg Val Gly Arg Val Thr Gly Ser Asp Gly Lys Leu
        115                 120                 125

Tyr His Ile Tyr Ile Cys Ile Asp Gly Cys Ile Leu Leu Lys Arg Ala
    130                 135                 140

Thr Arg Asn Gln Pro Glu Val Leu Lys Trp Val Tyr Asn Arg Leu Asn
145                 150                 155                 160

Cys Pro Leu Trp Val Thr Ser Cys Ser Asp Glu Gly Ser Lys Gly Ala
                165                 170                 175

Thr Ser Lys Lys Gln Pro Lys Pro Asp Arg Ile Glu Lys Gly Lys Met
```

```
                180             185             190
Lys Ile Ala Pro Lys Glu Thr Glu Lys Asp Cys Lys Thr Arg Pro Pro
            195                 200             205
Asp Ala Thr Ile Val Val Glu Gly Val Lys Tyr Gln Val Lys Lys Lys
    210             215                 220
Gly Lys Val Arg Gly Lys Asn Thr Gln Asp Gly Leu Tyr His Asn Lys
225             230                 235                 240
Asn Lys Pro Pro Glu Ser Arg Lys Lys Leu Glu Lys Ala Leu Leu Ala
                245                 250                 255
Trp Ala Ile Leu Ala Ala Val Leu Leu Gln Leu Val Thr Gly Glu Asn
            260                 265                 270
Ile Thr Gln Trp Asn Leu Met Asp Asn Gly Thr Glu Gly Ile Gln Gln
        275                 280                 285
Ala Met Phe Leu Arg Gly Val Asn Arg Ser Leu His Gly Ile Trp Pro
    290                 295                 300
Glu Lys Ile Cys Thr Gly Val Pro Thr His Leu Ala Thr Asp Tyr Glu
305                 310                 315                 320
Leu Lys Glu Ile Val Gly Met Met Asp Ala Ser Glu Lys Thr Asn Tyr
                325                 330                 335
Thr Cys Cys Arg Leu Gln Arg His Glu Trp Asn Lys His Gly Trp Cys
            340                 345                 350
Asn Trp Phe His Ile Glu Pro Trp Ile Trp Leu Met Asn Lys Thr Gln
        355                 360                 365
Asn Asn Leu Thr Glu Gly Gln Pro Leu Arg Glu Cys Ala Val Thr Cys
    370                 375                 380
Arg Tyr Asp Lys Glu Thr Glu Leu Asn Ile Val Thr Gln Ala Arg Asp
385                 390                 395                 400
Arg Pro Thr Thr Leu Thr Gly Cys Lys Lys Gly Lys Asn Phe Ser Phe
                405                 410                 415
Ala Gly Val Ile Leu Asp Gly Pro Cys Asn Phe Lys Val Ser Val Glu
            420                 425                 430
Asp Val Leu Phe Lys Glu His Asp Cys Gly Asn Met Leu Gln Glu Thr
        435                 440                 445
Ala Ile Gln Leu Leu Asp Gly Ala Thr Asn Thr Ile Glu Gly Ala Arg
    450                 455                 460
Val Gly Thr Ala Lys Leu Thr Thr Trp Leu Gly Lys Gln Leu Gly Ile
465                 470                 475                 480
Leu Gly Lys Lys Leu Glu Asn Lys Ser Lys Ala Trp Phe Gly Ala His
                485                 490                 495
Ala Ala Ser Pro Tyr Cys Gly Val Glu Arg Lys Ile Gly Tyr Val Trp
            500                 505                 510
Tyr Thr Lys Asn Cys Thr Pro Ala Cys Leu Pro Arg Asn Thr Arg Ile
        515                 520                 525
Ile Gly Pro Gly Lys Phe Asp Thr Asn Ala Glu Asp Gly Lys Ile Leu
    530                 535                 540
His Glu Met Gly Gly His Leu Ser Glu Phe Val Leu Leu Ser Leu Val
545                 550                 555                 560
Val Leu Ser Asp Phe Ala Pro Glu Thr Ala Ser Val Ile Tyr Leu Val
                565                 570                 575
Leu His Phe Ala Ile Pro Gln Ser His Val Asp Val Asp Thr Cys Asp
            580                 585                 590
Lys Asn Gln Leu Asn Leu Thr Val Ala Thr Thr Val Ala Glu Val Ile
        595                 600                 605
```

```
Pro Gly Thr Val Trp Asn Leu Gly Lys Tyr Val Cys Ile Arg Pro Asp
    610                 615                 620

Trp Trp Pro Tyr Glu Thr Thr Thr Val Phe Val Ile Glu Glu Ala Gly
625                 630                 635                 640

Gln Val Ile Lys Leu Met Leu Arg Ala Ile Arg Asp Leu Thr Arg Ile
                645                 650                 655

Trp Asn Ala Ala Thr Thr Thr Ala Phe Leu Ile Phe Leu Val Lys Ala
                660                 665                 670

Leu Arg Gly Gln Leu Ile Gln Gly Leu Leu Trp Leu Met Leu Ile Thr
            675                 680                 685

Gly Ala Gln Gly Phe Pro Glu Cys Lys Glu Gly Phe Gln Tyr Ala Ile
690                 695                 700

Ser Lys Asp Arg Lys Met Gly Leu Leu Gly Pro Glu Ser Leu Thr Thr
705                 710                 715                 720

Thr Trp His Leu Pro Thr Lys Lys Ile Val Asp Ser Met Val His Val
                725                 730                 735

Trp Cys Glu Gly Lys Asp Leu Lys Ile Leu Lys Met Cys Thr Lys Glu
                740                 745                 750

Glu Arg Tyr Leu Val Ala Val His Glu Arg Ala Leu Ser Thr Ser Ala
        755                 760                 765

Glu Phe Met Gln Ile Ser Asp Gly Thr Ile Gly Pro Asp Val Ile Asp
770                 775                 780

Met Pro Asp Asp Phe Glu Phe Gly Leu Cys Pro Cys Asp Ser Lys Pro
785                 790                 795                 800

Val Ile Lys Gly Lys Phe Asn Ala Ser Leu Leu Asn Gly Pro Ala Phe
                805                 810                 815

Gln Met Val Cys Pro Gln Gly Trp Thr Gly Thr Ile Glu Cys Thr Leu
                820                 825                 830

Ala Asn Gln Asp Thr Leu Asp Thr Thr Val Ile Arg Thr Tyr Arg Arg
            835                 840                 845

Thr Thr Pro Phe Gln Arg Arg Lys Trp Cys Thr Tyr Glu Lys Ile Ile
        850                 855                 860

Gly Glu Asp Ile Tyr Glu Cys Ile Leu Gly Gly Asn Trp Thr Cys Ile
865                 870                 875                 880

Thr Gly Asp His Ser Arg Leu Lys Asp Gly Pro Ile Lys Lys Cys Lys
                885                 890                 895

Trp Cys Gly His Asp Phe Val Asn Ser Glu Gly Leu Pro His Tyr Pro
                900                 905                 910

Ile Gly Lys Cys Met Leu Ile Asn Glu Ser Gly Tyr Arg Tyr Val Asp
            915                 920                 925

Asp Thr Ser Cys Asp Arg Gly Gly Val Ala Ile Val Pro Ser Gly Thr
930                 935                 940

Val Lys Cys Arg Ile Gly Asn Val Thr Val Gln Val Ile Ala Thr Asn
945                 950                 955                 960

Asn Asp Leu Gly Pro Met Pro Cys Ser Pro Ala Glu Val Ile Ala Ser
                965                 970                 975

Glu Gly Pro Val Glu Lys Thr Ala Cys Thr Phe Asn Tyr Ser Arg Thr
                980                 985                 990

Leu Pro Asn Lys Tyr Tyr Glu Pro Arg Asp Arg Tyr Phe Gln Gln Tyr
            995                 1000                1005

Met Leu Lys Gly Glu Trp Gln Tyr Trp Phe Asp Leu Asp Ser Val
    1010                1015                1020
```

```
Asp His His Lys Asp Tyr Phe Ser Glu Phe Ile Ile Ile Ala Val
    1025                1030               1035

Val Ala Leu Leu Gly Gly Lys Tyr Val Leu Trp Leu Leu Ile Thr
    1040                1045               1050

Tyr Thr Ile Leu Ser Glu Gln Met Ala Met Gly Ala Gly Val Asn
    1055                1060               1065

Thr Glu Glu Ile Val Met Ile Gly Asn Leu Leu Thr Asp Ser Asp
    1070                1075               1080

Ile Glu Val Val Val Tyr Phe Leu Leu Leu Tyr Leu Ile Val Lys
    1085                1090               1095

Glu Glu Leu Ala Arg Lys Trp Ile Ile Leu Val Tyr His Ile Leu
    1100                1105               1110

Val Ala Asn Pro Met Lys Thr Ile Gly Val Val Leu Leu Met Leu
    1115                1120               1125

Gly Gly Val Val Lys Ala Ser Arg Ile Asn Ala Asp Asp Gln Ser
    1130                1135               1140

Ala Met Asp Pro Cys Phe Leu Leu Val Thr Gly Val Val Ala Val
    1145                1150               1155

Leu Met Ile Ala Arg Arg Glu Pro Ala Thr Leu Pro Leu Ile Val
    1160                1165               1170

Ala Leu Leu Ala Ile Arg Thr Ser Gly Phe Leu Leu Pro Ala Ser
    1175                1180               1185

Ile Asp Val Thr Val Ala Val Val Leu Ile Val Leu Leu Leu Ala
    1190                1195               1200

Ser Tyr Ile Thr Asp Tyr Phe Arg Tyr Lys Lys Trp Leu Gln Leu
    1205                1210               1215

Leu Phe Ser Leu Ile Ala Gly Ile Phe Ile Ile Arg Ser Leu Lys
    1220                1225               1230

His Ile Asn Gln Met Glu Val Pro Glu Ile Ser Met Pro Ser Trp
    1235                1240               1245

Arg Pro Leu Ala Leu Val Leu Phe Tyr Ile Thr Ser Thr Ala Ile
    1250                1255               1260

Thr Thr Asn Trp Asp Ile Asp Leu Ala Gly Phe Leu Leu Gln Trp
    1265                1270               1275

Ala Pro Ala Val Ile Met Met Ala Thr Met Trp Ala Asp Phe Leu
    1280                1285               1290

Thr Leu Ile Ile Val Leu Pro Ser Tyr Glu Leu Ser Lys Leu Tyr
    1295                1300               1305

Phe Leu Lys Asn Val Arg Thr Asp Val Glu Lys Asn Trp Leu Gly
    1310                1315               1320

Lys Val Lys Tyr Arg Gln Ile Ser Ser Val Tyr Asp Ile Cys Asp
    1325                1330               1335

Ser Glu Glu Ala Val Tyr Leu Phe Pro Ser Arg His Lys Ser Gly
    1340                1345               1350

Ser Arg Pro Asp Phe Ile Leu Pro Phe Leu Lys Ala Val Leu Ile
    1355                1360               1365

Ser Cys Ile Ser Ser Gln Trp Gln Val Val Tyr Ile Ser Tyr Leu
    1370                1375               1380

Ile Leu Glu Ile Thr Tyr Tyr Met His Arg Lys Ile Ile Asp Glu
    1385                1390               1395

Val Ser Gly Gly Ala Asn Phe Leu Ser Arg Leu Ile Ala Ala Ile
    1400                1405               1410

Ile Glu Leu Asn Trp Ala Ile Asp Asp Glu Glu Cys Lys Gly Leu
```

```
                 1415                1420                1425
Lys  Lys  Leu  Tyr  Leu  Leu  Ser  Gly  Arg  Val  Lys  Asn  Leu  Ile  Val
     1430                1435                1440

Lys  His  Lys  Val  Arg  Asn  Glu  Ala  Val  His  Arg  Trp  Phe  Gly  Glu
     1445                1450                1455

Glu  Glu  Ile  Tyr  Gly  Ala  Pro  Lys  Val  Ile  Thr  Ile  Ile  Lys  Ala
     1460                1465                1470

Ser  Thr  Leu  Ser  Lys  Asn  Arg  His  Cys  Ile  Ile  Cys  Thr  Ile  Cys
     1475                1480                1485

Glu  Gly  Lys  Glu  Trp  Asn  Gly  Ala  Asn  Cys  Pro  Lys  Cys  Gly  Arg
     1490                1495                1500

Gln  Gly  Lys  Pro  Ile  Thr  Cys  Gly  Met  Thr  Leu  Ala  Asp  Phe  Glu
     1505                1510                1515

Glu  Lys  His  Tyr  Lys  Lys  Ile  Phe  Ile  Arg  Glu  Glu  Ser  Ser  Cys
     1520                1525                1530

Pro  Val  Pro  Phe  Asp  Pro  Ser  Cys  His  Cys  Asn  Tyr  Phe  Arg  His
     1535                1540                1545

Asp  Gly  Pro  Phe  Arg  Lys  Glu  Tyr  Lys  Gly  Tyr  Val  Gln  Tyr  Thr
     1550                1555                1560

Ala  Arg  Gly  Gln  Leu  Phe  Leu  Arg  Asn  Leu  Pro  Ile  Leu  Ala  Thr
     1565                1570                1575

Lys  Met  Lys  Leu  Leu  Met  Val  Gly  Asn  Leu  Gly  Ala  Glu  Ile  Gly
     1580                1585                1590

Asp  Leu  Glu  His  Leu  Gly  Trp  Val  Leu  Arg  Gly  Pro  Ala  Val  Cys
     1595                1600                1605

Lys  Lys  Ile  Thr  Asn  His  Glu  Lys  Cys  His  Val  Asn  Ile  Met  Asp
     1610                1615                1620

Lys  Leu  Thr  Ala  Phe  Phe  Gly  Ile  Met  Pro  Arg  Gly  Thr  Thr  Pro
     1625                1630                1635

Arg  Ala  Pro  Val  Arg  Phe  Pro  Thr  Ala  Leu  Leu  Lys  Val  Arg  Arg
     1640                1645                1650

Gly  Leu  Glu  Thr  Gly  Trp  Ala  Tyr  Thr  His  Gln  Gly  Gly  Ile  Ser
     1655                1660                1665

Ser  Val  Asp  His  Val  Thr  Ala  Gly  Lys  Asp  Leu  Leu  Val  Cys  Asp
     1670                1675                1680

Ser  Met  Gly  Arg  Thr  Arg  Val  Val  Cys  His  Ser  Asn  Asn  Lys  Met
     1685                1690                1695

Thr  Asp  Glu  Thr  Glu  Tyr  Gly  Ile  Lys  Thr  Asp  Ser  Gly  Cys  Pro
     1700                1705                1710

Glu  Gly  Ala  Arg  Cys  Tyr  Val  Leu  Asn  Pro  Glu  Ala  Val  Asn  Ile
     1715                1720                1725

Ser  Gly  Thr  Lys  Gly  Ala  Met  Val  His  Leu  Gln  Lys  Thr  Gly  Gly
     1730                1735                1740

Glu  Phe  Thr  Cys  Val  Thr  Ala  Ser  Gly  Thr  Pro  Ala  Phe  Phe  Asp
     1745                1750                1755

Leu  Lys  Asn  Leu  Lys  Gly  Trp  Ser  Gly  Leu  Pro  Ile  Phe  Glu  Ala
     1760                1765                1770

Ser  Ser  Gly  Arg  Val  Val  Gly  Arg  Val  Lys  Val  Gly  Lys  Asn  Glu
     1775                1780                1785

Asp  Ser  Lys  Pro  Thr  Lys  Leu  Met  Ser  Gly  Ile  Gln  Thr  Val  Ser
     1790                1795                1800

Lys  Asn  Gln  Thr  Asp  Leu  Ala  Asp  Ile  Val  Lys  Lys  Leu  Thr  Ser
     1805                1810                1815
```

-continued

```
Met Asn Arg Gly Glu Phe Lys Gln Ile Thr Leu Ala Thr Gly Ala
    1820                1825                1830

Gly Lys Thr Thr Glu Leu Pro Arg Ser Val Ile Glu Glu Ile Gly
    1835                1840                1845

Arg His Lys Arg Val Leu Val Leu Ile Pro Leu Arg Ala Ala Ala
    1850                1855                1860

Glu Ser Val Tyr Gln Tyr Met Arg Val Lys Tyr Pro Ser Ile Ser
    1865                1870                1875

Phe Asn Leu Arg Ile Gly Asp Met Lys Glu Gly Asp Met Ala Thr
    1880                1885                1890

Gly Ile Thr Tyr Ala Ser Tyr Gly Tyr Phe Cys Gln Leu Pro Gln
    1895                1900                1905

Pro Lys Leu Arg Ala Ala Met Val Glu Tyr Ser Tyr Ile Phe Leu
    1910                1915                1920

Asp Glu Tyr His Cys Ala Thr Pro Glu Gln Leu Ala Ile Ile Gly
    1925                1930                1935

Lys Ile His Arg Phe Ala Glu Asn Leu Arg Val Val Ala Met Thr
    1940                1945                1950

Ala Thr Pro Ala Gly Thr Val Thr Thr Thr Gly Gln Lys His Pro
    1955                1960                1965

Ile Glu Glu Phe Ile Ala Pro Glu Val Met Lys Gly Glu Asp Leu
    1970                1975                1980

Gly Ser Glu Tyr Leu Asp Ile Ala Gly Leu Lys Ile Pro Thr Glu
    1985                1990                1995

Glu Met Lys Gly Asn Met Leu Val Phe Ala Pro Thr Arg Asn Met
    2000                2005                2010

Ala Val Glu Thr Ala Lys Lys Leu Lys Ala Lys Gly Tyr Asn Ser
    2015                2020                2025

Gly Tyr Tyr Tyr Ser Gly Glu Asn Pro Glu Asn Leu Arg Val Val
    2030                2035                2040

Thr Ser Gln Ser Pro Tyr Val Val Ala Thr Asn Ala Ile Glu
    2045                2050                2055

Ser Gly Val Thr Leu Pro Asp Leu Asp Thr Val Val Asp Thr Gly
    2060                2065                2070

Leu Lys Cys Glu Lys Arg Val Arg Ile Ser Ser Lys Met Pro Phe
    2075                2080                2085

Ile Val Thr Gly Leu Lys Arg Met Ala Val Thr Ile Gly Glu Gln
    2090                2095                2100

Ala Gln Arg Arg Gly Arg Val Gly Arg Val Lys Pro Gly Arg Tyr
    2105                2110                2115

Tyr Arg Ser Gln Glu Thr Ala Ser Gly Ser Lys Asp Tyr His Tyr
    2120                2125                2130

Asp Leu Leu Gln Ala Gln Arg Tyr Gly Ile Glu Asp Gly Ile Asn
    2135                2140                2145

Val Thr Lys Ser Phe Arg Glu Met Asn Tyr Asp Trp Ser Leu Tyr
    2150                2155                2160

Glu Glu Asp Ser Leu Met Ile Thr Gln Leu Glu Val Leu Asn Asn
    2165                2170                2175

Leu Leu Ile Ser Glu Asp Leu Pro Ala Ala Val Lys Asn Ile Met
    2180                2185                2190

Ala Arg Thr Asp His Pro Glu Pro Ile Gln Leu Ala Tyr Asn Ser
    2195                2200                2205
```

```
Tyr Glu Asn Gln Ile Pro Val Leu Phe Pro Lys Ile Lys Asn Gly
2210                2215                2220

Glu Val Thr Asp Ser Tyr Glu Asn Tyr Thr Tyr Leu Asn Ala Arg
2225                2230                2235

Lys Leu Gly Glu Asp Val Pro Ala Tyr Val Tyr Ala Thr Glu Asp
2240                2245                2250

Glu Asp Leu Ala Val Asp Leu Leu Gly Met Asp Trp Pro Asp Pro
2255                2260                2265

Gly Asn Gln Gln Val Val Glu Thr Gly Arg Ala Leu Lys Gln Val
2270                2275                2280

Thr Gly Leu Ser Thr Ala Glu Asn Ala Leu Leu Ile Ala Leu Phe
2285                2290                2295

Gly Tyr Val Gly Tyr Gln Thr Leu Ser Lys Arg His Ile Pro Met
2300                2305                2310

Ile Thr Asp Ile Tyr Thr Leu Glu Asp His Arg Leu Glu Asp Thr
2315                2320                2325

Thr His Leu Gln Phe Ala Pro Asn Ala Ile Arg Thr Asp Gly Lys
2330                2335                2340

Asp Ser Glu Leu Lys Glu Leu Ala Val Gly Asp Leu Asp Lys Tyr
2345                2350                2355

Val Asp Ala Leu Val Asp Tyr Ser Lys Gln Gly Met Lys Phe Ile
2360                2365                2370

Lys Val Gln Ala Glu Lys Val Arg Asp Ser Gln Ser Thr Lys Glu
2375                2380                2385

Gly Leu Gln Thr Ile Lys Glu Tyr Val Asp Lys Phe Ile Gln Ser
2390                2395                2400

Leu Thr Glu Asn Lys Glu Glu Ile Ile Arg Tyr Gly Leu Trp Gly
2405                2410                2415

Val His Thr Ala Leu Tyr Lys Ser Leu Ala Ala Arg Leu Gly His
2420                2425                2430

Glu Thr Ala Phe Ala Thr Leu Val Val Lys Trp Leu Ala Phe Gly
2435                2440                2445

Gly Glu Thr Val Ser Ala His Ile Lys Gln Val Ala Val Asp Leu
2450                2455                2460

Val Val Tyr Tyr Ile Ile Asn Lys Pro Ser Phe Pro Gly Asp Thr
2465                2470                2475

Glu Thr Gln Gln Glu Gly Arg Arg Phe Val Ala Ser Leu Phe Ile
2480                2485                2490

Ser Ala Leu Ala Thr Tyr Thr Tyr Lys Thr Trp Asn Tyr Asn Asn
2495                2500                2505

Leu Gln Arg Val Val Glu Pro Ala Leu Ala Tyr Leu Pro Tyr Ala
2510                2515                2520

Thr Ser Ala Leu Lys Leu Phe Thr Pro Thr Arg Leu Glu Ser Val
2525                2530                2535

Val Ile Leu Ser Ser Thr Ile Tyr Lys Thr Tyr Leu Ser Ile Arg
2540                2545                2550

Lys Gly Lys Ser Asp Gly Leu Leu Gly Thr Gly Ile Ser Ala Ala
2555                2560                2565

Met Glu Ile Leu Asn Gln Asn Pro Ile Ser Val Gly Ile Ser Val
2570                2575                2580

Met Leu Gly Val Gly Ala Ile Ala Ala His Asn Ala Ile Glu Ser
2585                2590                2595

Ser Glu Gln Lys Arg Thr Leu Leu Met Lys Val Phe Val Lys Asn
```

```
                 2600                2605                2610
Phe Leu Asp Gln Ala Ala Thr Asp Glu Leu Val Lys Glu Asn Pro
             2615                2620                2625
Glu Lys Ile Ile Met Ala Leu Phe Glu Ala Val Gln Thr Ile Gly
             2630                2635                2640
Asn Pro Leu Arg Leu Ile Tyr His Leu Tyr Gly Val Tyr Tyr Lys
             2645                2650                2655
Gly Trp Glu Ala Lys Glu Leu Ala Glu Lys Thr Ala Gly Arg Asn
             2660                2665                2670
Leu Phe Thr Leu Ile Met Phe Glu Ala Phe Glu Leu Leu Gly Met
             2675                2680                2685
Asp Ser Glu Gly Lys Ile Arg Asn Leu Ser Gly Asn Tyr Ile Leu
             2690                2695                2700
Asp Leu Ile Phe Asn Leu His Asn Lys Leu Asn Lys Gly Leu Lys
             2705                2710                2715
Lys Leu Val Leu Gly Trp Ala Pro Ala Pro Leu Ser Cys Asp Trp
             2720                2725                2730
Thr Pro Ser Asp Glu Arg Ile Ser Leu Pro His Asn Asn Tyr Leu
             2735                2740                2745
Arg Val Glu Thr Arg Cys Pro Cys Gly Tyr Glu Met Lys Ala Ile
             2750                2755                2760
Lys Asn Val Ala Gly Lys Leu Thr Lys Val Glu Glu Lys Gly Ser
             2765                2770                2775
Phe Leu Cys Arg Asn Arg Leu Gly Arg Gly Pro Pro Asn Phe Lys
             2780                2785                2790
Val Thr Lys Phe Tyr Asp Asp Asn Leu Ile Glu Val Lys Pro Val
             2795                2800                2805
Ala Arg Leu Glu Gly Gln Val Asp Leu Tyr Tyr Lys Gly Val Thr
             2810                2815                2820
Ala Lys Leu Asp Tyr Asn Asn Gly Lys Val Leu Leu Ala Thr Asn
             2825                2830                2835
Lys Trp Glu Val Asp His Ala Phe Leu Thr Arg Leu Val Lys Lys
             2840                2845                2850
His Thr Gly Ile Gly Phe Lys Gly Ala Tyr Leu Gly Asp Arg Pro
             2855                2860                2865
Asp His Gln Asp Leu Val Asp Arg Asp Cys Ala Thr Ile Thr Lys
             2870                2875                2880
Asn Ser Val Gln Phe Leu Lys Met Lys Lys Gly Cys Ala Phe Thr
             2885                2890                2895
Tyr Asp Leu Thr Ile Ser Asn Leu Val Arg Leu Ile Glu Leu Val
             2900                2905                2910
His Lys Asn Asn Leu Gln Glu Arg Glu Ile Pro Thr Val Thr Val
             2915                2920                2925
Thr Thr Trp Leu Ala Tyr Ser Phe Val Asn Glu Asp Leu Gly Thr
             2930                2935                2940
Ile Lys Pro Val Leu Gly Glu Lys Val Ile Pro Glu Pro Pro Glu
             2945                2950                2955
Glu Leu Ser Leu Gln Pro Thr Val Arg Leu Val Thr Thr Glu Thr
             2960                2965                2970
Ala Ile Thr Ile Thr Gly Glu Ala Glu Val Met Thr Thr Gly Ile
             2975                2980                2985
Thr Pro Val Val Glu Met Lys Glu Glu Pro Gln Leu Asp His Gln
             2990                2995                3000
```

```
Ser Thr Thr Leu Lys Val Gly Leu Lys Glu Gly Glu Tyr Pro Gly
    3005                3010                3015

Pro Gly Val Asn Pro Asn His Leu Ala Glu Val Ile Asp Glu Lys
    3020                3025                3030

Asp Asp Arg Pro Phe Val Leu Ile Ile Gly Asn Lys Gly Ser Thr
    3035                3040                3045

Ser Asn Arg Ala Arg Thr Ala Lys Asn Ile Arg Leu Tyr Lys Gly
    3050                3055                3060

Asn Asn Pro Arg Glu Ile Arg Asp Leu Met Ser Gln Gly Arg Ile
    3065                3070                3075

Leu Thr Val Ala Leu Lys Glu Leu Asp Pro Glu Leu Lys Glu Leu
    3080                3085                3090

Val Asp Tyr Lys Gly Thr Phe Leu Asn Arg Glu Ala Leu Glu Ala
    3095                3100                3105

Leu Ser Leu Gly Lys Pro Ile Lys Arg Lys Thr Thr Thr Ala Met
    3110                3115                3120

Ile Arg Arg Leu Ile Glu Pro Glu Val Glu Glu Glu Leu Pro Asp
    3125                3130                3135

Trp Phe Gln Ala Glu Glu Pro Leu Phe Leu Glu Ala Lys Ile Gln
    3140                3145                3150

Asn Asp Leu Tyr His Leu Ile Gly Ser Val Asp Ser Ile Lys Ser
    3155                3160                3165

Lys Ala Lys Glu Leu Gly Ala Thr Asp Asn Thr Lys Ile Val Lys
    3170                3175                3180

Glu Val Gly Ala Arg Thr Tyr Thr Met Lys Leu Ser Ser Trp Ser
    3185                3190                3195

Thr Gln Val Thr Lys Lys Gln Met Ser Leu Ala Pro Leu Phe Glu
    3200                3205                3210

Glu Leu Leu Leu Lys Cys Pro Pro Cys Ser Lys Ile Ser Lys Gly
    3215                3220                3225

His Met Val Ser Ala Tyr Gln Leu Ala Gln Gly Asn Trp Glu Pro
    3230                3235                3240

Leu Gly Cys Gly Val Tyr Met Gly Thr Ile Pro Ala Arg Arg Leu
    3245                3250                3255

Lys Ile His Pro Tyr Glu Ala Tyr Leu Lys Leu Lys Glu Leu Val
    3260                3265                3270

Glu Val Glu Ser Ser Arg Ala Thr Ala Lys Glu Ser Ile Ile Arg
    3275                3280                3285

Glu His Asn Thr Trp Ile Leu Arg Lys Val Arg His Glu Gly Asn
    3290                3295                3300

Leu Arg Thr Lys Ser Met Ile Asn Pro Gly Lys Ile Ser Asp Gln
    3305                3310                3315

Leu Cys Arg Asp Gly His Lys Arg Asn Ile Tyr Asn Lys Ile Ile
    3320                3325                3330

Gly Ser Thr Met Ala Ser Ala Gly Ile Arg Leu Glu Lys Leu Pro
    3335                3340                3345

Val Val Arg Ala Gln Thr Asp Thr Thr Ser Phe His Gln Ala Ile
    3350                3355                3360

Arg Glu Lys Ile Asp Lys Thr Glu Asn Lys Gln Thr Pro Glu Leu
    3365                3370                3375

His Glu Glu Leu Met Lys Val Phe Asp Cys Leu Lys Ile Pro Glu
    3380                3385                3390
```

-continued

```
Leu Lys Glu Ser Tyr Asp Glu Val Ser Trp Glu Gln Leu Glu Ala
    3395                3400                3405

Gly Ile Asn Arg Lys Gly Ala Ala Gly Tyr Leu Glu Ser Lys Asn
    3410                3415                3420

Ile Gly Glu Val Leu Asp Thr Glu Lys His Ile Val Glu Gln Leu
    3425                3430                3435

Ile Lys Asp Leu Arg Lys Gly Lys Lys Ile Arg Tyr Tyr Glu Thr
    3440                3445                3450

Ala Ile Pro Lys Asn Glu Lys Arg Asp Val Ser Asp Asp Trp Glu
    3455                3460                3465

Ala Gly Glu Phe Val Asp Glu Lys Lys Pro Arg Val Ile Gln Tyr
    3470                3475                3480

Pro Asp Ala Lys Val Arg Leu Ala Ile Thr Lys Val Met Tyr Lys
    3485                3490                3495

Trp Val Lys Gln Lys Pro Val Val Ile Pro Gly Tyr Glu Gly Lys
    3500                3505                3510

Thr Pro Leu Phe Asp Ile Phe Asn Lys Val Lys Lys Glu Trp Asp
    3515                3520                3525

Ser Phe Gln Asp Pro Val Ala Val Ser Phe Asp Thr Lys Ala Trp
    3530                3535                3540

Asp Thr Gln Val Thr Ser Arg Asp Leu Met Leu Ile Lys Asp Ile
    3545                3550                3555

Gln Lys Tyr Tyr Phe Lys Arg Ser Ile His Lys Phe Leu Asp Thr
    3560                3565                3570

Ile Thr Glu His Met Val Glu Val Pro Val Ile Thr Ala Asp Gly
    3575                3580                3585

Glu Val Tyr Ile Arg Asn Gly Gln Arg Gly Ser Gly Gln Pro Asp
    3590                3595                3600

Thr Ser Ala Gly Asn Ser Met Leu Asn Val Leu Thr Met Ile Tyr
    3605                3610                3615

Ala Phe Cys Lys Ser Thr Gly Ile Pro Tyr Arg Gly Phe Ser Arg
    3620                3625                3630

Val Ala Arg Ile His Val Cys Gly Asp Asp Gly Phe Leu Ile Thr
    3635                3640                3645

Glu Arg Gly Leu Gly Leu Lys Phe Ser Glu Lys Gly Met Gln Ile
    3650                3655                3660

Leu His Glu Ala Gly Lys Pro Gln Lys Ile Thr Glu Gly Asp Lys
    3665                3670                3675

Met Lys Val Ala Tyr Arg Phe Glu Asp Ile Glu Phe Cys Ser His
    3680                3685                3690

Thr Pro Val Pro Val Arg Trp Ala Asp Asn Thr Ser Ser Tyr Met
    3695                3700                3705

Ala Gly Arg Ser Thr Ala Thr Ile Leu Ala Lys Met Ala Thr Arg
    3710                3715                3720

Leu Asp Ser Ser Gly Glu Arg Gly Ser Thr Ala Tyr Glu Lys Ala
    3725                3730                3735

Val Ala Phe Ser Phe Leu Leu Met Tyr Ser Trp Asn Pro Val Val
    3740                3745                3750

Arg Arg Ile Cys Leu Leu Val Leu Ser Gln Phe Pro Glu Ile Ser
    3755                3760                3765

Pro Ser Lys Asn Thr Ile Tyr Tyr Tyr Gln Gly Asp Pro Ile Ala
    3770                3775                3780

Ala Tyr Arg Glu Val Ile Gly Lys Gln Leu Cys Glu Leu Lys Arg
```

```
                    3785                3790                3795
Thr Gly Phe Glu Lys Leu Ala Gly Leu Asn Leu Ser Met Thr Thr
    3800                3805                3810

Leu Gly Ile Trp Thr Lys His Thr Ser Lys Arg Leu Ile Gln Asp
    3815                3820                3825

Cys Val Glu Ile Gly Lys Arg Glu Gly Asn Trp Leu Val Asn Ala
    3830                3835                3840

Asp Arg Leu Ile Ala Gly Lys Thr Gly Lys Phe Tyr Ile Pro Ser
    3845                3850                3855

Thr Gly Val Thr Leu Leu Gly Lys His Tyr Glu Glu Ile Asn Leu
    3860                3865                3870

Lys Gln Lys Ala Ala Gln Pro Pro Ile Glu Gly Val Asp Arg Tyr
    3875                3880                3885

Lys Leu Gly Pro Ile Val Asn Val Ile Leu Arg Arg Leu Arg Val
    3890                3895                3900

Met Leu Met Thr Val Ala Ser Gly Ser Trp
    3905                3910

<210> SEQ ID NO 8
<211> LENGTH: 3912
<212> TYPE: PRT
<213> ORGANISM: BVDV

<400> SEQUENCE: 8

Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
            20                  25                  30

Phe Gly Glu Ser Ser Asp Leu His Pro Gln Ser Thr Leu Lys Leu Pro
        35                  40                  45

His Gln Arg Gly Ser Ala Asn Ile Leu Thr Asn Ala Arg Ser Leu Pro
    50                  55                  60

Arg Lys Gly Asp Cys Arg Arg Gly Asn Val Tyr Gly Pro Val Ser Gly
65                  70                  75                  80

Ile Tyr Ile Lys Pro Gly Pro Ile Tyr Tyr Gln Asp Tyr Val Gly Pro
                85                  90                  95

Val Tyr His Arg Ala Pro Leu Glu Leu Cys Arg Glu Ala Ser Met Cys
            100                 105                 110

Glu Thr Thr Arg Arg Val Gly Arg Val Thr Gly Ser Asp Gly Lys Leu
        115                 120                 125

Tyr His Ile Tyr Ile Cys Ile Asp Gly Cys Ile Leu Leu Lys Arg Ala
    130                 135                 140

Thr Arg Asn Gln Pro Glu Val Leu Lys Trp Val Tyr Asn Arg Leu Asn
145                 150                 155                 160

Cys Pro Leu Trp Val Thr Ser Cys Ser Asp Glu Gly Ser Lys Gly Ala
                165                 170                 175

Thr Ser Lys Lys Gln Pro Lys Pro Asp Arg Ile Glu Lys Gly Lys Met
            180                 185                 190

Lys Ile Ala Pro Lys Glu Thr Glu Lys Asp Cys Lys Thr Arg Pro Pro
        195                 200                 205

Asp Ala Thr Ile Val Val Glu Gly Val Lys Tyr Gln Val Lys Lys Lys
    210                 215                 220

Gly Lys Val Arg Gly Lys Asn Thr Gln Asp Gly Leu Tyr His Asn Lys
225                 230                 235                 240
```

-continued

```
Asn Lys Pro Pro Glu Ser Arg Lys Lys Leu Glu Lys Ala Leu Leu Ala
            245                 250                 255
Trp Ala Ile Leu Ala Ala Val Leu Leu Gln Leu Val Thr Gly Glu Asn
        260                 265                 270
Ile Thr Gln Trp Asn Leu Met Asp Asn Gly Thr Glu Gly Ile Gln Gln
    275                 280                 285
Ala Met Phe Leu Arg Gly Val Asn Arg Ser Leu His Gly Ile Trp Pro
290                 295                 300
Glu Lys Ile Cys Thr Gly Val Pro Thr His Leu Ala Thr Asp Tyr Glu
305                 310                 315                 320
Leu Lys Glu Ile Val Gly Met Met Asp Ala Ser Glu Lys Thr Asn Tyr
                325                 330                 335
Thr Cys Cys Arg Leu Gln Arg His Glu Trp Asn Lys His Gly Trp Cys
            340                 345                 350
Asn Trp Phe His Ile Glu Pro Trp Ile Trp Leu Met Asn Lys Thr Gln
        355                 360                 365
Asn Asn Leu Thr Glu Gly Gln Pro Leu Arg Glu Cys Ala Val Thr Cys
    370                 375                 380
Arg Tyr Asp Lys Glu Thr Glu Leu Asn Ile Val Thr Gln Ala Arg Asp
385                 390                 395                 400
Arg Pro Thr Thr Leu Thr Gly Cys Lys Lys Gly Lys Asn Phe Ser Phe
                405                 410                 415
Ala Gly Val Ile Leu Asp Gly Pro Cys Asn Phe Lys Val Ser Val Glu
            420                 425                 430
Asp Val Leu Phe Lys Glu His Asp Gly Asn Met Leu Gln Glu Thr Ala
        435                 440                 445
Ile Gln Leu Leu Asp Gly Ala Thr Asn Thr Ile Glu Gly Ala Arg Val
    450                 455                 460
Gly Thr Ala Lys Leu Thr Thr Trp Leu Gly Lys Gln Leu Gly Ile Leu
465                 470                 475                 480
Gly Lys Lys Leu Glu Asn Lys Ser Lys Ala Trp Phe Gly Ala His Ala
                485                 490                 495
Ala Ser Pro Tyr Cys Gly Val Glu Arg Lys Ile Gly Tyr Val Trp Tyr
            500                 505                 510
Thr Lys Asn Cys Thr Pro Ala Cys Leu Pro Arg Asn Thr Arg Ile Ile
        515                 520                 525
Gly Pro Gly Lys Phe Asp Thr Asn Ala Glu Asp Gly Lys Ile Leu His
    530                 535                 540
Glu Met Gly Gly His Leu Ser Glu Phe Val Leu Leu Ser Leu Val Val
545                 550                 555                 560
Leu Ser Asp Phe Ala Pro Glu Thr Ala Ser Val Ile Tyr Leu Val Leu
                565                 570                 575
His Phe Ala Ile Pro Gln Ser His Val Asp Val Asp Thr Cys Asp Lys
            580                 585                 590
Asn Gln Leu Asn Leu Thr Val Ala Thr Val Ala Glu Val Ile Pro
        595                 600                 605
Gly Thr Val Trp Asn Leu Gly Lys Tyr Val Cys Ile Arg Pro Asp Trp
    610                 615                 620
Trp Pro Tyr Glu Thr Thr Val Phe Val Ile Glu Glu Ala Gly Gln
625                 630                 635                 640
Val Ile Lys Leu Met Leu Arg Ala Ile Arg Asp Leu Thr Arg Ile Trp
                645                 650                 655
Asn Ala Ala Thr Thr Thr Ala Phe Leu Ile Phe Leu Val Lys Ala Leu
```

```
                660             665             670
Arg Gly Gln Leu Ile Gln Gly Leu Leu Trp Leu Met Leu Ile Thr Gly
            675             680             685

Ala Gln Gly Phe Pro Glu Cys Lys Glu Gly Phe Gln Tyr Ala Ile Ser
    690             695             700

Lys Asp Arg Lys Met Gly Leu Leu Gly Pro Glu Ser Leu Thr Thr Thr
705             710             715             720

Trp His Leu Pro Thr Lys Lys Ile Val Asp Ser Met Val His Val Trp
                725             730             735

Cys Glu Gly Lys Asp Leu Lys Ile Leu Lys Met Cys Thr Lys Glu Glu
            740             745             750

Arg Tyr Leu Val Ala Val His Glu Arg Ala Leu Ser Thr Ser Ala Glu
        755             760             765

Phe Met Gln Ile Ser Asp Gly Thr Ile Gly Pro Asp Val Ile Asp Met
    770             775             780

Pro Asp Asp Phe Glu Phe Gly Leu Cys Pro Cys Asp Ser Lys Pro Val
785             790             795             800

Ile Lys Gly Lys Phe Asn Ala Ser Leu Leu Asn Gly Pro Ala Phe Gln
                805             810             815

Met Val Cys Pro Gln Gly Trp Thr Gly Thr Ile Glu Cys Thr Leu Ala
            820             825             830

Asn Gln Asp Thr Leu Asp Thr Thr Val Ile Arg Thr Tyr Arg Arg Thr
        835             840             845

Thr Pro Phe Gln Arg Arg Lys Trp Cys Thr Tyr Glu Lys Ile Ile Gly
    850             855             860

Glu Asp Ile Tyr Glu Cys Ile Leu Gly Gly Asn Trp Thr Cys Ile Thr
865             870             875             880

Gly Asp His Ser Arg Leu Lys Asp Gly Pro Ile Lys Lys Cys Lys Trp
                885             890             895

Cys Gly His Asp Phe Val Asn Ser Glu Gly Leu Pro His Tyr Pro Ile
            900             905             910

Gly Lys Cys Met Leu Ile Asn Glu Ser Gly Tyr Arg Tyr Val Asp Asp
        915             920             925

Thr Ser Cys Asp Arg Gly Gly Val Ala Ile Val Pro Ser Gly Thr Val
    930             935             940

Lys Cys Arg Ile Gly Asn Val Thr Val Gln Val Ile Ala Thr Asn Asn
945             950             955             960

Asp Leu Gly Pro Met Pro Cys Ser Pro Ala Glu Val Ile Ala Ser Glu
                965             970             975

Gly Pro Val Glu Lys Thr Ala Cys Thr Phe Asn Tyr Ser Arg Thr Leu
            980             985             990

Pro Asn Lys Tyr Tyr Glu Pro Arg  Asp Arg Tyr Phe Gln  Gln Tyr Met
        995             1000             1005

Leu Lys  Gly Glu Trp Gln Tyr  Trp Phe Asp Leu Asp  Ser Val Asp
        1010             1015             1020

His His  Lys Asp Tyr Phe Ser  Glu Phe Ile Ile Ile  Ala Val Val
        1025             1030             1035

Ala Leu  Leu Gly Gly Lys Tyr  Val Leu Trp Leu Leu  Ile Thr Tyr
        1040             1045             1050

Thr Ile  Leu Ser Glu Gln Met  Ala Met Gly Ala Gly  Val Asn Thr
        1055             1060             1065

Glu Glu  Ile Val Met Ile Gly  Asn Leu Leu Thr Asp  Ser Asp Ile
        1070             1075             1080
```

-continued

Glu Val Val Val Tyr Phe Leu Leu Leu Tyr Leu Ile Val Lys Glu
1085                1090                1095

Glu Leu Ala Arg Lys Trp Ile Ile Leu Val Tyr His Ile Leu Val
1100                1105                1110

Ala Asn Pro Met Lys Thr Ile Gly Val Val Leu Leu Met Leu Gly
1115                1120                1125

Gly Val Val Lys Ala Ser Arg Ile Asn Ala Asp Asp Gln Ser Ala
1130                1135                1140

Met Asp Pro Cys Phe Leu Leu Val Thr Gly Val Val Ala Val Leu
1145                1150                1155

Met Ile Ala Arg Arg Glu Pro Ala Thr Leu Pro Leu Ile Val Ala
1160                1165                1170

Leu Leu Ala Ile Arg Thr Ser Gly Phe Leu Leu Pro Ala Ser Ile
1175                1180                1185

Asp Val Thr Val Ala Val Val Leu Ile Val Leu Leu Leu Ala Ser
1190                1195                1200

Tyr Ile Thr Asp Tyr Phe Arg Tyr Lys Lys Trp Leu Gln Leu Leu
1205                1210                1215

Phe Ser Leu Ile Ala Gly Ile Phe Ile Ile Arg Ser Leu Lys His
1220                1225                1230

Ile Asn Gln Met Glu Val Pro Glu Ile Ser Met Pro Ser Trp Arg
1235                1240                1245

Pro Leu Ala Leu Val Leu Phe Tyr Ile Thr Ser Thr Ala Ile Thr
1250                1255                1260

Thr Asn Trp Asp Ile Asp Leu Ala Gly Phe Leu Leu Gln Trp Ala
1265                1270                1275

Pro Ala Val Ile Met Met Ala Thr Met Trp Ala Asp Phe Leu Thr
1280                1285                1290

Leu Ile Ile Val Leu Pro Ser Tyr Glu Leu Ser Lys Leu Tyr Phe
1295                1300                1305

Leu Lys Asn Val Arg Thr Asp Val Glu Lys Asn Trp Leu Gly Lys
1310                1315                1320

Val Lys Tyr Arg Gln Ile Ser Ser Val Tyr Asp Ile Cys Asp Ser
1325                1330                1335

Glu Glu Ala Val Tyr Leu Phe Pro Ser Arg His Lys Ser Gly Ser
1340                1345                1350

Arg Pro Asp Phe Ile Leu Pro Phe Leu Lys Ala Val Leu Ile Ser
1355                1360                1365

Cys Ile Ser Ser Gln Trp Gln Val Val Tyr Ile Ser Tyr Leu Ile
1370                1375                1380

Leu Glu Ile Thr Tyr Tyr Met His Arg Lys Ile Ile Asp Glu Val
1385                1390                1395

Ser Gly Gly Ala Asn Phe Leu Ser Arg Leu Ile Ala Ala Ile Ile
1400                1405                1410

Glu Leu Asn Trp Ala Ile Asp Asp Glu Glu Cys Lys Gly Leu Lys
1415                1420                1425

Lys Leu Tyr Leu Leu Ser Gly Arg Val Lys Asn Leu Ile Val Lys
1430                1435                1440

His Lys Val Arg Asn Glu Ala Val His Arg Trp Phe Gly Glu Glu
1445                1450                1455

Glu Ile Tyr Gly Ala Pro Lys Val Ile Thr Ile Ile Lys Ala Ser
1460                1465                1470

```
Thr Leu Ser Lys Asn Arg His Cys Ile Ile Cys Thr Ile Cys Glu
1475                1480                1485

Gly Lys Glu Trp Asn Gly Ala Asn Cys Pro Lys Cys Gly Arg Gln
1490                1495                1500

Gly Lys Pro Ile Thr Cys Gly Met Thr Leu Ala Asp Phe Glu Glu
1505                1510                1515

Lys His Tyr Lys Lys Ile Phe Ile Arg Glu Glu Ser Ser Cys Pro
1520                1525                1530

Val Pro Phe Asp Pro Ser Cys His Cys Asn Tyr Phe Arg His Asp
1535                1540                1545

Gly Pro Phe Arg Lys Glu Tyr Lys Gly Tyr Val Gln Tyr Thr Ala
1550                1555                1560

Arg Gly Gln Leu Phe Leu Arg Asn Leu Pro Ile Leu Ala Thr Lys
1565                1570                1575

Met Lys Leu Leu Met Val Gly Asn Leu Gly Ala Glu Ile Gly Asp
1580                1585                1590

Leu Glu His Leu Gly Trp Val Leu Arg Gly Pro Ala Val Cys Lys
1595                1600                1605

Lys Ile Thr Asn His Glu Lys Cys His Val Asn Ile Met Asp Lys
1610                1615                1620

Leu Thr Ala Phe Phe Gly Ile Met Pro Arg Gly Thr Thr Pro Arg
1625                1630                1635

Ala Pro Val Arg Phe Pro Thr Ala Leu Leu Lys Val Arg Arg Gly
1640                1645                1650

Leu Glu Thr Gly Trp Ala Tyr Thr His Gln Gly Gly Ile Ser Ser
1655                1660                1665

Val Asp His Val Thr Ala Gly Lys Asp Leu Leu Val Cys Asp Ser
1670                1675                1680

Met Gly Arg Thr Arg Val Val Cys His Ser Asn Asn Lys Met Thr
1685                1690                1695

Asp Glu Thr Glu Tyr Gly Ile Lys Thr Asp Ser Gly Cys Pro Glu
1700                1705                1710

Gly Ala Arg Cys Tyr Val Leu Asn Pro Glu Ala Val Asn Ile Ser
1715                1720                1725

Gly Thr Lys Gly Ala Met Val His Leu Gln Lys Thr Gly Gly Glu
1730                1735                1740

Phe Thr Cys Val Thr Ala Ser Gly Thr Pro Ala Phe Phe Asp Leu
1745                1750                1755

Lys Asn Leu Lys Gly Trp Ser Gly Leu Pro Ile Phe Glu Ala Ser
1760                1765                1770

Ser Gly Arg Val Val Gly Arg Val Lys Val Gly Lys Asn Glu Asp
1775                1780                1785

Ser Lys Pro Thr Lys Leu Met Ser Gly Ile Gln Thr Val Ser Lys
1790                1795                1800

Asn Gln Thr Asp Leu Ala Asp Ile Val Lys Lys Leu Thr Ser Met
1805                1810                1815

Asn Arg Gly Glu Phe Lys Gln Ile Thr Leu Ala Thr Gly Ala Gly
1820                1825                1830

Lys Thr Thr Glu Leu Pro Arg Ser Val Ile Glu Glu Ile Gly Arg
1835                1840                1845

His Lys Arg Val Leu Val Leu Ile Pro Leu Arg Ala Ala Ala Glu
1850                1855                1860

Ser Val Tyr Gln Tyr Met Arg Val Lys Tyr Pro Ser Ile Ser Phe
```

```
                      1865                1870                1875
Asn Leu Arg Ile Gly Asp Met Lys Glu Gly Asp Met Ala Thr Gly
                1880                1885                1890
Ile Thr Tyr Ala Ser Tyr Gly Tyr Phe Cys Gln Leu Pro Gln Pro
                1895                1900                1905
Lys Leu Arg Ala Ala Met Val Glu Tyr Ser Tyr Ile Phe Leu Asp
                1910                1915                1920
Glu Tyr His Cys Ala Thr Pro Glu Gln Leu Ala Ile Ile Gly Lys
                1925                1930                1935
Ile His Arg Phe Ala Glu Asn Leu Arg Val Val Ala Met Thr Ala
                1940                1945                1950
Thr Pro Ala Gly Thr Val Thr Thr Gly Gln Lys His Pro Ile
                1955                1960                1965
Glu Glu Phe Ile Ala Pro Val Met Lys Gly Glu Asp Leu Gly
                1970                1975                1980
Ser Glu Tyr Leu Asp Ile Ala Gly Leu Lys Ile Pro Thr Glu Glu
                1985                1990                1995
Met Lys Gly Asn Met Leu Val Phe Ala Pro Thr Arg Asn Met Ala
                2000                2005                2010
Val Glu Thr Ala Lys Lys Leu Lys Ala Lys Gly Tyr Asn Ser Gly
                2015                2020                2025
Tyr Tyr Tyr Ser Gly Glu Asn Pro Glu Asn Leu Arg Val Val Thr
                2030                2035                2040
Ser Gln Ser Pro Tyr Val Val Ala Thr Asn Ala Ile Glu Ser
                2045                2050                2055
Gly Val Thr Leu Pro Asp Leu Asp Thr Val Val Asp Thr Gly Leu
                2060                2065                2070
Lys Cys Glu Lys Arg Val Arg Ile Ser Ser Lys Met Pro Phe Ile
                2075                2080                2085
Val Thr Gly Leu Lys Arg Met Ala Val Thr Ile Gly Glu Gln Ala
                2090                2095                2100
Gln Arg Arg Gly Arg Val Gly Arg Val Lys Pro Gly Arg Tyr Tyr
                2105                2110                2115
Arg Ser Gln Glu Thr Ala Ser Gly Ser Lys Asp Tyr His Tyr Asp
                2120                2125                2130
Leu Leu Gln Ala Gln Arg Tyr Gly Ile Glu Asp Gly Ile Asn Val
                2135                2140                2145
Thr Lys Ser Phe Arg Glu Met Asn Tyr Asp Trp Ser Leu Tyr Glu
                2150                2155                2160
Glu Asp Ser Leu Met Ile Thr Gln Leu Glu Val Leu Asn Asn Leu
                2165                2170                2175
Leu Ile Ser Glu Asp Leu Pro Ala Ala Val Lys Asn Ile Met Ala
                2180                2185                2190
Arg Thr Asp His Pro Glu Pro Ile Gln Leu Ala Tyr Asn Ser Tyr
                2195                2200                2205
Glu Asn Gln Ile Pro Val Leu Phe Pro Lys Ile Lys Asn Gly Glu
                2210                2215                2220
Val Thr Asp Ser Tyr Glu Asn Tyr Thr Tyr Leu Asn Ala Arg Lys
                2225                2230                2235
Leu Gly Glu Asp Val Pro Ala Tyr Val Tyr Ala Thr Glu Asp Glu
                2240                2245                2250
Asp Leu Ala Val Asp Leu Leu Gly Met Asp Trp Pro Asp Pro Gly
                2255                2260                2265
```

```
Asn Gln Gln Val Val Glu Thr Gly Arg Ala Leu Lys Gln Val Thr
    2270                2275                2280

Gly Leu Ser Thr Ala Glu Asn Ala Leu Leu Ile Ala Leu Phe Gly
    2285                2290                2295

Tyr Val Gly Tyr Gln Thr Leu Ser Lys Arg His Ile Pro Met Ile
    2300                2305                2310

Thr Asp Ile Tyr Thr Leu Glu Asp His Arg Leu Glu Asp Thr Thr
    2315                2320                2325

His Leu Gln Phe Ala Pro Asn Ala Ile Arg Thr Asp Gly Lys Asp
    2330                2335                2340

Ser Glu Leu Lys Glu Leu Ala Val Gly Asp Leu Asp Lys Tyr Val
    2345                2350                2355

Asp Ala Leu Val Asp Tyr Ser Lys Gln Gly Met Lys Phe Ile Lys
    2360                2365                2370

Val Gln Ala Glu Lys Val Arg Asp Ser Gln Ser Thr Lys Glu Gly
    2375                2380                2385

Leu Gln Thr Ile Lys Glu Tyr Val Asp Lys Phe Ile Gln Ser Leu
    2390                2395                2400

Thr Glu Asn Lys Glu Glu Ile Ile Arg Tyr Gly Leu Trp Gly Val
    2405                2410                2415

His Thr Ala Leu Tyr Lys Ser Leu Ala Ala Arg Leu Gly His Glu
    2420                2425                2430

Thr Ala Phe Ala Thr Leu Val Val Lys Trp Leu Ala Phe Gly Gly
    2435                2440                2445

Glu Thr Val Ser Ala His Ile Lys Gln Val Ala Val Asp Leu Val
    2450                2455                2460

Val Tyr Tyr Ile Ile Asn Lys Pro Ser Phe Pro Gly Asp Thr Glu
    2465                2470                2475

Thr Gln Gln Glu Gly Arg Arg Phe Val Ala Ser Leu Phe Ile Ser
    2480                2485                2490

Ala Leu Ala Thr Tyr Thr Tyr Lys Thr Trp Asn Tyr Asn Asn Leu
    2495                2500                2505

Gln Arg Val Val Glu Pro Ala Leu Ala Tyr Leu Pro Tyr Ala Thr
    2510                2515                2520

Ser Ala Leu Lys Leu Phe Thr Pro Thr Arg Leu Glu Ser Val Val
    2525                2530                2535

Ile Leu Ser Ser Thr Ile Tyr Lys Thr Tyr Leu Ser Ile Arg Lys
    2540                2545                2550

Gly Lys Ser Asp Gly Leu Leu Gly Thr Gly Ile Ser Ala Ala Met
    2555                2560                2565

Glu Ile Leu Asn Gln Asn Pro Ile Ser Val Gly Ile Ser Val Met
    2570                2575                2580

Leu Gly Val Gly Ala Ile Ala Ala His Asn Ala Ile Glu Ser Ser
    2585                2590                2595

Glu Gln Lys Arg Thr Leu Leu Met Lys Val Phe Val Lys Asn Phe
    2600                2605                2610

Leu Asp Gln Ala Ala Thr Asp Glu Leu Val Lys Glu Asn Pro Glu
    2615                2620                2625

Lys Ile Ile Met Ala Leu Phe Glu Ala Val Gln Thr Ile Gly Asn
    2630                2635                2640

Pro Leu Arg Leu Ile Tyr His Leu Tyr Gly Val Tyr Tyr Lys Gly
    2645                2650                2655
```

```
Trp Glu Ala Lys Glu Leu Ala Glu Lys Thr Ala Gly Arg Asn Leu
2660            2665                2670

Phe Thr Leu Ile Met Phe Glu Ala Phe Glu Leu Leu Gly Met Asp
2675            2680                2685

Ser Glu Gly Lys Ile Arg Asn Leu Ser Gly Asn Tyr Ile Leu Asp
2690            2695                2700

Leu Ile Phe Asn Leu His Asn Lys Leu Asn Lys Gly Leu Lys Lys
2705            2710                2715

Leu Val Leu Gly Trp Ala Pro Ala Pro Leu Ser Cys Asp Trp Thr
2720            2725                2730

Pro Ser Asp Glu Arg Ile Ser Leu Pro His Asn Asn Tyr Leu Arg
2735            2740                2745

Val Glu Thr Arg Cys Pro Cys Gly Tyr Glu Met Lys Ala Ile Lys
2750            2755                2760

Asn Val Ala Gly Lys Leu Thr Lys Val Glu Glu Lys Gly Ser Phe
2765            2770                2775

Leu Cys Arg Asn Arg Leu Gly Arg Gly Pro Pro Asn Phe Lys Val
2780            2785                2790

Thr Lys Phe Tyr Asp Asp Asn Leu Ile Glu Val Lys Pro Val Ala
2795            2800                2805

Arg Leu Glu Gly Gln Val Asp Leu Tyr Tyr Lys Gly Val Thr Ala
2810            2815                2820

Lys Leu Asp Tyr Asn Asn Gly Lys Val Leu Leu Ala Thr Asn Lys
2825            2830                2835

Trp Glu Val Asp His Ala Phe Leu Thr Arg Leu Val Lys Lys His
2840            2845                2850

Thr Gly Ile Gly Phe Lys Gly Ala Tyr Leu Gly Asp Arg Pro Asp
2855            2860                2865

His Gln Asp Leu Val Asp Arg Asp Cys Ala Thr Ile Thr Lys Asn
2870            2875                2880

Ser Val Gln Phe Leu Lys Met Lys Lys Gly Cys Ala Phe Thr Tyr
2885            2890                2895

Asp Leu Thr Ile Ser Asn Leu Val Arg Leu Ile Glu Leu Val His
2900            2905                2910

Lys Asn Asn Leu Gln Glu Arg Glu Ile Pro Thr Val Thr Val Thr
2915            2920                2925

Thr Trp Leu Ala Tyr Ser Phe Val Asn Glu Asp Leu Gly Thr Ile
2930            2935                2940

Lys Pro Val Leu Gly Glu Lys Val Ile Pro Glu Pro Pro Glu Glu
2945            2950                2955

Leu Ser Leu Gln Pro Thr Val Arg Leu Val Thr Thr Glu Thr Ala
2960            2965                2970

Ile Thr Ile Thr Gly Glu Ala Glu Val Met Thr Thr Gly Ile Thr
2975            2980                2985

Pro Val Val Glu Met Lys Glu Glu Pro Gln Leu Asp His Gln Ser
2990            2995                3000

Thr Thr Leu Lys Val Gly Leu Lys Glu Gly Glu Tyr Pro Gly Pro
3005            3010                3015

Gly Val Asn Pro Asn His Leu Ala Glu Val Ile Asp Glu Lys Asp
3020            3025                3030

Asp Arg Pro Phe Val Leu Ile Ile Gly Asn Lys Gly Ser Thr Ser
3035            3040                3045

Asn Arg Ala Arg Thr Ala Lys Asn Ile Arg Leu Tyr Lys Gly Asn
```

```
                3050                3055                3060
Asn Pro Arg Glu Ile Arg Asp Leu Met Ser Gln Gly Arg Ile Leu
    3065                3070                3075
Thr Val Ala Leu Lys Glu Leu Asp Pro Glu Leu Lys Glu Leu Val
    3080                3085                3090
Asp Tyr Lys Gly Thr Phe Leu Asn Arg Glu Ala Leu Glu Ala Leu
    3095                3100                3105
Ser Leu Gly Lys Pro Ile Lys Arg Lys Thr Thr Thr Ala Met Ile
    3110                3115                3120
Arg Arg Leu Ile Glu Pro Glu Val Glu Glu Leu Pro Asp Trp
    3125                3130                3135
Phe Gln Ala Glu Glu Pro Leu Phe Leu Glu Ala Lys Ile Gln Asn
    3140                3145                3150
Asp Leu Tyr His Leu Ile Gly Ser Val Asp Ser Ile Lys Ser Lys
    3155                3160                3165
Ala Lys Glu Leu Gly Ala Thr Asp Asn Thr Lys Ile Val Lys Glu
    3170                3175                3180
Val Gly Ala Arg Thr Tyr Thr Met Lys Leu Ser Ser Trp Ser Thr
    3185                3190                3195
Gln Val Thr Lys Lys Gln Met Ser Leu Ala Pro Leu Phe Glu Glu
    3200                3205                3210
Leu Leu Leu Lys Cys Pro Pro Cys Ser Lys Ile Ser Lys Gly His
    3215                3220                3225
Met Val Ser Ala Tyr Gln Leu Ala Gln Gly Asn Trp Glu Pro Leu
    3230                3235                3240
Gly Cys Gly Val Tyr Met Gly Thr Ile Pro Ala Arg Arg Leu Lys
    3245                3250                3255
Ile His Pro Tyr Glu Ala Tyr Leu Lys Leu Lys Glu Leu Val Glu
    3260                3265                3270
Val Glu Ser Ser Arg Ala Thr Ala Lys Glu Ser Ile Ile Arg Glu
    3275                3280                3285
His Asn Thr Trp Ile Leu Arg Lys Val Arg His Glu Gly Asn Leu
    3290                3295                3300
Arg Thr Lys Ser Met Ile Asn Pro Gly Lys Ile Ser Asp Gln Leu
    3305                3310                3315
Cys Arg Asp Gly His Lys Arg Asn Ile Tyr Asn Lys Ile Ile Gly
    3320                3325                3330
Ser Thr Met Ala Ser Ala Gly Ile Arg Leu Glu Lys Leu Pro Val
    3335                3340                3345
Val Arg Ala Gln Thr Asp Thr Thr Ser Phe His Gln Ala Ile Arg
    3350                3355                3360
Glu Lys Ile Asp Lys Thr Glu Asn Lys Gln Thr Pro Glu Leu His
    3365                3370                3375
Glu Glu Leu Met Lys Val Phe Asp Cys Leu Lys Ile Pro Glu Leu
    3380                3385                3390
Lys Glu Ser Tyr Asp Glu Val Ser Trp Glu Gln Leu Glu Ala Gly
    3395                3400                3405
Ile Asn Arg Lys Gly Ala Ala Gly Tyr Leu Glu Ser Lys Asn Ile
    3410                3415                3420
Gly Glu Val Leu Asp Thr Glu Lys His Ile Val Glu Gln Leu Ile
    3425                3430                3435
Lys Asp Leu Arg Lys Gly Lys Lys Ile Arg Tyr Tyr Glu Thr Ala
    3440                3445                3450
```

```
Ile Pro Lys Asn Glu Lys Arg Asp Val Ser Asp Trp Glu Ala
3455              3460              3465

Gly Glu Phe Val Asp Glu Lys Lys Pro Arg Val Ile Gln Tyr Pro
3470              3475              3480

Asp Ala Lys Val Arg Leu Ala Ile Thr Lys Val Met Tyr Lys Trp
3485              3490              3495

Val Lys Gln Lys Pro Val Val Ile Pro Gly Tyr Glu Gly Lys Thr
3500              3505              3510

Pro Leu Phe Asp Ile Phe Asn Lys Val Lys Lys Glu Trp Asp Ser
3515              3520              3525

Phe Gln Asp Pro Val Ala Val Ser Phe Asp Thr Lys Ala Trp Asp
3530              3535              3540

Thr Gln Val Thr Ser Arg Asp Leu Met Leu Ile Lys Asp Ile Gln
3545              3550              3555

Lys Tyr Tyr Phe Lys Arg Ser Ile His Lys Phe Leu Asp Thr Ile
3560              3565              3570

Thr Glu His Met Val Glu Val Pro Val Ile Thr Ala Asp Gly Glu
3575              3580              3585

Val Tyr Ile Arg Asn Gly Gln Arg Gly Ser Gly Gln Pro Asp Thr
3590              3595              3600

Ser Ala Gly Asn Ser Met Leu Asn Val Leu Thr Met Ile Tyr Ala
3605              3610              3615

Phe Cys Lys Ser Thr Gly Ile Pro Tyr Arg Gly Phe Ser Arg Val
3620              3625              3630

Ala Arg Ile His Val Cys Gly Asp Asp Gly Phe Leu Ile Thr Glu
3635              3640              3645

Arg Gly Leu Gly Leu Lys Phe Ser Glu Lys Gly Met Gln Ile Leu
3650              3655              3660

His Glu Ala Gly Lys Pro Gln Lys Ile Thr Glu Gly Asp Lys Met
3665              3670              3675

Lys Val Ala Tyr Arg Phe Glu Asp Ile Glu Phe Cys Ser His Thr
3680              3685              3690

Pro Val Pro Val Arg Trp Ala Asp Asn Thr Ser Ser Tyr Met Ala
3695              3700              3705

Gly Arg Ser Thr Ala Thr Ile Leu Ala Lys Met Ala Thr Arg Leu
3710              3715              3720

Asp Ser Ser Gly Glu Arg Gly Ser Thr Ala Tyr Glu Lys Ala Val
3725              3730              3735

Ala Phe Ser Phe Leu Leu Met Tyr Ser Trp Asn Pro Val Val Arg
3740              3745              3750

Arg Ile Cys Leu Leu Val Leu Ser Gln Phe Pro Glu Ile Ser Pro
3755              3760              3765

Ser Lys Asn Thr Ile Tyr Tyr Tyr Gln Gly Asp Pro Ile Ala Ala
3770              3775              3780

Tyr Arg Glu Val Ile Gly Lys Gln Leu Cys Glu Leu Lys Arg Thr
3785              3790              3795

Gly Phe Glu Lys Leu Ala Gly Leu Asn Leu Ser Met Thr Thr Leu
3800              3805              3810

Gly Ile Trp Thr Lys His Thr Ser Lys Arg Leu Ile Gln Asp Cys
3815              3820              3825

Val Glu Ile Gly Lys Arg Glu Gly Asn Trp Leu Val Asn Ala Asp
3830              3835              3840
```

```
Arg Leu Ile Ala Gly Lys Thr Gly Lys Phe Tyr Ile Pro Ser Thr
    3845            3850            3855

Gly Val Thr Leu Leu Gly Lys His Tyr Glu Glu Ile Asn Leu Lys
    3860            3865            3870

Gln Lys Ala Ala Gln Pro Pro Ile Glu Gly Val Asp Arg Tyr Lys
    3875            3880            3885

Leu Gly Pro Ile Val Asn Val Ile Leu Arg Arg Leu Arg Val Met
    3890            3895            3900

Leu Met Thr Val Ala Ser Gly Ser Trp
    3905            3910

<210> SEQ ID NO 9
<211> LENGTH: 3913
<212> TYPE: PRT
<213> ORGANISM: BVDV

<400> SEQUENCE: 9

Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
                20                  25                  30

Phe Gly Glu Ser Ser Asp Leu His Pro Gln Ser Thr Leu Lys Leu Pro
            35                  40                  45

His Gln Arg Gly Ser Ala Asn Ile Leu Thr Asn Ala Arg Ser Leu Pro
        50                  55                  60

Arg Lys Gly Asp Cys Arg Arg Gly Asn Val Tyr Gly Pro Val Ser Gly
65                  70                  75                  80

Ile Tyr Ile Lys Pro Gly Pro Ile Tyr Tyr Gln Asp Tyr Val Gly Pro
                85                  90                  95

Val Tyr His Arg Ala Pro Leu Glu Leu Cys Arg Glu Ala Ser Met Cys
            100                 105                 110

Glu Thr Thr Arg Arg Val Gly Arg Val Thr Gly Ser Asp Gly Lys Leu
        115                 120                 125

Tyr His Ile Tyr Ile Cys Ile Asp Gly Cys Ile Leu Leu Lys Arg Ala
    130                 135                 140

Thr Arg Asn Gln Pro Glu Val Leu Lys Trp Val Tyr Asn Arg Leu Asn
145                 150                 155                 160

Cys Pro Leu Trp Val Thr Ser Cys Ser Asp Glu Gly Lys Gly Ala
                165                 170                 175

Thr Ser Lys Lys Gln Pro Lys Pro Asp Arg Ile Glu Lys Gly Lys Met
            180                 185                 190

Lys Ile Ala Pro Lys Glu Thr Glu Lys Asp Cys Lys Thr Arg Pro Pro
        195                 200                 205

Asp Ala Thr Ile Val Val Glu Gly Val Lys Tyr Gln Val Lys Lys Lys
    210                 215                 220

Gly Lys Val Arg Gly Lys Asn Thr Gln Asp Gly Leu Tyr His Asn Lys
225                 230                 235                 240

Asn Lys Pro Pro Glu Ser Arg Lys Lys Leu Glu Lys Ala Leu Leu Ala
                245                 250                 255

Trp Ala Ile Leu Ala Ala Val Leu Leu Gln Leu Val Thr Gly Glu Asn
            260                 265                 270

Ile Thr Gln Trp Asn Leu Met Asp Asn Gly Thr Glu Gly Ile Gln Gln
        275                 280                 285

Ala Met Phe Leu Arg Gly Val Asn Arg Ser Leu His Gly Ile Trp Pro
    290                 295                 300
```

-continued

```
Glu Lys Ile Cys Thr Gly Val Pro Thr His Leu Ala Thr Asp Tyr Glu
305                 310                 315                 320

Leu Lys Glu Ile Val Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Phe His Ile Glu Pro Trp Ile Trp Leu Met Asn Lys Thr Gln
        355                 360                 365

Asn Asn Leu Thr Glu Gly Gln Pro Leu Arg Glu Cys Ala Val Thr Cys
370                 375                 380

Arg Tyr Asp Lys Glu Thr Glu Leu Asn Ile Val Thr Gln Ala Arg Asp
385                 390                 395                 400

Arg Pro Thr Thr Leu Thr Gly Cys Lys Lys Gly Lys Asn Phe Ser Phe
                405                 410                 415

Ala Gly Val Ile Leu Asp Gly Pro Cys Asn Phe Lys Val Ser Val Glu
            420                 425                 430

Asp Val Leu Phe Lys Glu His Asp Ser Gly Asn Met Leu Gln Glu Thr
        435                 440                 445

Ala Ile Gln Leu Leu Asp Gly Ala Thr Asn Thr Ile Glu Gly Ala Arg
450                 455                 460

Val Gly Thr Ala Lys Leu Thr Thr Trp Leu Gly Lys Gln Leu Gly Ile
465                 470                 475                 480

Leu Gly Lys Lys Leu Glu Asn Lys Ser Lys Ala Trp Phe Gly Ala His
                485                 490                 495

Ala Ala Ser Pro Tyr Cys Gly Val Glu Arg Lys Ile Gly Tyr Val Trp
            500                 505                 510

Tyr Thr Lys Asn Cys Thr Pro Ala Cys Leu Pro Arg Asn Thr Arg Ile
        515                 520                 525

Ile Gly Pro Gly Lys Phe Asp Thr Asn Ala Glu Asp Gly Lys Ile Leu
530                 535                 540

His Glu Met Gly Gly His Leu Ser Glu Phe Val Leu Leu Ser Leu Val
545                 550                 555                 560

Val Leu Ser Asp Phe Ala Pro Glu Thr Ala Ser Val Ile Tyr Leu Val
                565                 570                 575

Leu His Phe Ala Ile Pro Gln Ser His Val Asp Val Asp Thr Cys Asp
            580                 585                 590

Lys Asn Gln Leu Asn Leu Thr Val Ala Thr Thr Val Ala Glu Val Ile
        595                 600                 605

Pro Gly Thr Val Trp Asn Leu Gly Lys Tyr Val Cys Ile Arg Pro Asp
                615                 620

Trp Trp Pro Tyr Glu Thr Thr Val Phe Val Ile Glu Glu Ala Gly
625                 630                 635                 640

Gln Val Ile Lys Leu Met Leu Arg Ala Ile Arg Asp Leu Thr Arg Ile
                645                 650                 655

Trp Asn Ala Ala Thr Thr Thr Ala Phe Leu Ile Phe Leu Val Lys Ala
            660                 665                 670

Leu Arg Gly Gln Leu Ile Gln Gly Leu Leu Trp Leu Met Leu Ile Thr
        675                 680                 685

Gly Ala Gln Gly Phe Pro Glu Cys Lys Glu Gly Phe Gln Tyr Ala Ile
690                 695                 700

Ser Lys Asp Arg Lys Met Gly Leu Leu Gly Pro Glu Ser Leu Thr Thr
705                 710                 715                 720
```

```
Thr Trp His Leu Pro Thr Lys Lys Ile Val Asp Ser Met Val His Val
            725                 730                 735

Trp Cys Glu Gly Lys Asp Leu Lys Ile Leu Lys Met Cys Thr Lys Glu
        740                 745                 750

Glu Arg Tyr Leu Val Ala Val His Glu Arg Ala Leu Ser Thr Ser Ala
            755                 760                 765

Glu Phe Met Gln Ile Ser Asp Gly Thr Ile Gly Pro Asp Val Ile Asp
        770                 775                 780

Met Pro Asp Asp Phe Glu Phe Gly Leu Cys Pro Cys Asp Ser Lys Pro
785                 790                 795                 800

Val Ile Lys Gly Lys Phe Asn Ala Ser Leu Leu Asn Gly Pro Ala Phe
            805                 810                 815

Gln Met Val Cys Pro Gln Gly Trp Thr Gly Thr Ile Glu Cys Thr Leu
            820                 825                 830

Ala Asn Gln Asp Thr Leu Asp Thr Thr Val Ile Arg Thr Tyr Arg Arg
            835                 840                 845

Thr Thr Pro Phe Gln Arg Arg Lys Trp Cys Thr Tyr Glu Lys Ile Ile
            850                 855                 860

Gly Glu Asp Ile Tyr Glu Cys Ile Leu Gly Gly Asn Trp Thr Cys Ile
865                 870                 875                 880

Thr Gly Asp His Ser Arg Leu Lys Asp Gly Pro Ile Lys Lys Cys Lys
            885                 890                 895

Trp Cys Gly His Asp Phe Val Asn Ser Glu Gly Leu Pro His Tyr Pro
            900                 905                 910

Ile Gly Lys Cys Met Leu Ile Asn Glu Ser Gly Tyr Arg Tyr Val Asp
            915                 920                 925

Asp Thr Ser Cys Asp Arg Gly Gly Val Ala Ile Val Pro Ser Gly Thr
            930                 935                 940

Val Lys Cys Arg Ile Gly Asn Val Thr Val Gln Val Ile Ala Thr Asn
945                 950                 955                 960

Asn Asp Leu Gly Pro Met Pro Cys Ser Pro Ala Glu Val Ile Ala Ser
                        965                 970                 975

Glu Gly Pro Val Glu Lys Thr Ala Cys Thr Phe Asn Tyr Ser Arg Thr
            980                 985                 990

Leu Pro Asn Lys Tyr Tyr Glu Pro Arg Asp Arg Tyr Phe Gln Gln Tyr
            995                 1000                1005

Met Leu Lys Gly Glu Trp Gln Tyr Trp Phe Asp Leu Asp Ser Val
        1010                1015                1020

Asp His His Lys Asp Tyr Phe Ser Glu Phe Ile Ile Ile Ala Val
        1025                1030                1035

Val Ala Leu Leu Gly Gly Lys Tyr Val Leu Trp Leu Leu Ile Thr
        1040                1045                1050

Tyr Thr Ile Leu Ser Glu Gln Met Ala Met Gly Ala Gly Val Asn
        1055                1060                1065

Thr Glu Glu Ile Val Met Ile Gly Asn Leu Leu Thr Asp Ser Asp
        1070                1075                1080

Ile Glu Val Val Val Tyr Phe Leu Leu Leu Tyr Leu Ile Val Lys
        1085                1090                1095

Glu Glu Leu Ala Arg Lys Trp Ile Ile Leu Val Tyr His Ile Leu
        1100                1105                1110

Val Ala Asn Pro Met Lys Thr Ile Gly Val Val Leu Leu Met Leu
        1115                1120                1125

Gly Gly Val Val Lys Ala Ser Arg Ile Asn Ala Asp Asp Gln Ser
```

-continued

```
                1130                1135                1140
Ala Met Asp Pro Cys Phe Leu Leu Val Thr Gly Val Val Ala Val
       1145                1150                1155
Leu Met Ile Ala Arg Arg Glu Pro Ala Thr Leu Pro Leu Ile Val
       1160                1165                1170
Ala Leu Leu Ala Ile Arg Thr Ser Gly Phe Leu Leu Pro Ala Ser
       1175                1180                1185
Ile Asp Val Thr Val Ala Val Val Leu Ile Val Leu Leu Leu Ala
       1190                1195                1200
Ser Tyr Ile Thr Asp Tyr Phe Arg Tyr Lys Lys Trp Leu Gln Leu
       1205                1210                1215
Leu Phe Ser Leu Ile Ala Gly Ile Phe Ile Ile Arg Ser Leu Lys
       1220                1225                1230
His Ile Asn Gln Met Glu Val Pro Glu Ile Ser Met Pro Ser Trp
       1235                1240                1245
Arg Pro Leu Ala Leu Val Leu Phe Tyr Ile Thr Ser Thr Ala Ile
       1250                1255                1260
Thr Thr Asn Trp Asp Ile Asp Leu Ala Gly Phe Leu Leu Gln Trp
       1265                1270                1275
Ala Pro Ala Val Ile Met Met Ala Thr Met Trp Ala Asp Phe Leu
       1280                1285                1290
Thr Leu Ile Ile Val Leu Pro Ser Tyr Glu Leu Ser Lys Leu Tyr
       1295                1300                1305
Phe Leu Lys Asn Val Arg Thr Asp Val Glu Lys Asn Trp Leu Gly
       1310                1315                1320
Lys Val Lys Tyr Arg Gln Ile Ser Ser Val Tyr Asp Ile Cys Asp
       1325                1330                1335
Ser Glu Glu Ala Val Tyr Leu Phe Pro Ser Arg His Lys Ser Gly
       1340                1345                1350
Ser Arg Pro Asp Phe Ile Leu Pro Phe Leu Lys Ala Val Leu Ile
       1355                1360                1365
Ser Cys Ile Ser Ser Gln Trp Gln Val Val Tyr Ile Ser Tyr Leu
       1370                1375                1380
Ile Leu Glu Ile Thr Tyr Tyr Met His Arg Lys Ile Ile Asp Glu
       1385                1390                1395
Val Ser Gly Gly Ala Asn Phe Leu Ser Arg Leu Ile Ala Ala Ile
       1400                1405                1410
Ile Glu Leu Asn Trp Ala Ile Asp Asp Glu Glu Cys Lys Gly Leu
       1415                1420                1425
Lys Lys Leu Tyr Leu Leu Ser Gly Arg Val Lys Asn Leu Ile Val
       1430                1435                1440
Lys His Lys Val Arg Asn Glu Ala Val His Arg Trp Phe Gly Glu
       1445                1450                1455
Glu Glu Ile Tyr Gly Ala Pro Lys Val Ile Thr Ile Ile Lys Ala
       1460                1465                1470
Ser Thr Leu Ser Lys Asn Arg His Cys Ile Ile Cys Thr Ile Cys
       1475                1480                1485
Glu Gly Lys Glu Trp Asn Gly Ala Asn Cys Pro Lys Cys Gly Arg
       1490                1495                1500
Gln Gly Lys Pro Ile Thr Cys Gly Met Thr Leu Ala Asp Phe Glu
       1505                1510                1515
Glu Lys His Tyr Lys Lys Ile Phe Ile Arg Glu Glu Ser Ser Cys
       1520                1525                1530
```

-continued

Pro Val Pro Phe Asp Pro Ser Cys His Cys Asn Tyr Phe Arg His
    1535            1540                1545

Asp Gly Pro Phe Arg Lys Glu Tyr Lys Gly Tyr Val Gln Tyr Thr
    1550            1555                1560

Ala Arg Gly Gln Leu Phe Leu Arg Asn Leu Pro Ile Leu Ala Thr
    1565            1570                1575

Lys Met Lys Leu Leu Met Val Gly Asn Leu Gly Ala Glu Ile Gly
    1580            1585                1590

Asp Leu Glu His Leu Gly Trp Val Leu Arg Gly Pro Ala Val Cys
    1595            1600                1605

Lys Lys Ile Thr Asn His Glu Lys Cys His Val Asn Ile Met Asp
    1610            1615                1620

Lys Leu Thr Ala Phe Phe Gly Ile Met Pro Arg Gly Thr Thr Pro
    1625            1630                1635

Arg Ala Pro Val Arg Phe Pro Thr Ala Leu Leu Lys Val Arg Arg
    1640            1645                1650

Gly Leu Glu Thr Gly Trp Ala Tyr Thr His Gln Gly Gly Ile Ser
    1655            1660                1665

Ser Val Asp His Val Thr Ala Gly Lys Asp Leu Leu Val Cys Asp
    1670            1675                1680

Ser Met Gly Arg Thr Arg Val Val Cys His Ser Asn Asn Lys Met
    1685            1690                1695

Thr Asp Glu Thr Glu Tyr Gly Ile Lys Thr Asp Ser Gly Cys Pro
    1700            1705                1710

Glu Gly Ala Arg Cys Tyr Val Leu Asn Pro Glu Ala Val Asn Ile
    1715            1720                1725

Ser Gly Thr Lys Gly Ala Met Val His Leu Gln Lys Thr Gly Gly
    1730            1735                1740

Glu Phe Thr Cys Val Thr Ala Ser Gly Thr Pro Ala Phe Phe Asp
    1745            1750                1755

Leu Lys Asn Leu Lys Gly Trp Ser Gly Leu Pro Ile Phe Glu Ala
    1760            1765                1770

Ser Ser Gly Arg Val Val Gly Arg Val Lys Val Gly Lys Asn Glu
    1775            1780                1785

Asp Ser Lys Pro Thr Lys Leu Met Ser Gly Ile Gln Thr Val Ser
    1790            1795                1800

Lys Asn Gln Thr Asp Leu Ala Asp Ile Val Lys Lys Leu Thr Ser
    1805            1810                1815

Met Asn Arg Gly Glu Phe Lys Gln Ile Thr Leu Ala Thr Gly Ala
    1820            1825                1830

Gly Lys Thr Thr Glu Leu Pro Arg Ser Val Ile Glu Glu Ile Gly
    1835            1840                1845

Arg His Lys Arg Val Leu Val Leu Ile Pro Leu Arg Ala Ala Ala
    1850            1855                1860

Glu Ser Val Tyr Gln Tyr Met Arg Val Lys Tyr Pro Ser Ile Ser
    1865            1870                1875

Phe Asn Leu Arg Ile Gly Asp Met Lys Glu Gly Asp Met Ala Thr
    1880            1885                1890

Gly Ile Thr Tyr Ala Ser Tyr Gly Tyr Phe Cys Gln Leu Pro Gln
    1895            1900                1905

Pro Lys Leu Arg Ala Ala Met Val Glu Tyr Ser Tyr Ile Phe Leu
    1910            1915                1920

```
Asp Glu Tyr His Cys Ala Thr Pro Glu Gln Leu Ala Ile Ile Gly
1925                1930                1935

Lys Ile His Arg Phe Ala Glu Asn Leu Arg Val Val Ala Met Thr
1940                1945                1950

Ala Thr Pro Ala Gly Thr Val Thr Thr Thr Gly Gln Lys His Pro
1955                1960                1965

Ile Glu Glu Phe Ile Ala Pro Glu Val Met Lys Gly Glu Asp Leu
1970                1975                1980

Gly Ser Glu Tyr Leu Asp Ile Ala Gly Leu Lys Ile Pro Thr Glu
1985                1990                1995

Glu Met Lys Gly Asn Met Leu Val Phe Ala Pro Thr Arg Asn Met
2000                2005                2010

Ala Val Glu Thr Ala Lys Lys Leu Lys Ala Lys Gly Tyr Asn Ser
2015                2020                2025

Gly Tyr Tyr Tyr Ser Gly Glu Asn Pro Glu Asn Leu Arg Val Val
2030                2035                2040

Thr Ser Gln Ser Pro Tyr Val Val Ala Thr Asn Ala Ile Glu
2045                2050                2055

Ser Gly Val Thr Leu Pro Asp Leu Asp Thr Val Val Asp Thr Gly
2060                2065                2070

Leu Lys Cys Glu Lys Arg Val Arg Ile Ser Ser Lys Met Pro Phe
2075                2080                2085

Ile Val Thr Gly Leu Lys Arg Met Ala Val Thr Ile Gly Glu Gln
2090                2095                2100

Ala Gln Arg Arg Gly Arg Val Gly Arg Val Lys Pro Gly Arg Tyr
2105                2110                2115

Tyr Arg Ser Gln Glu Thr Ala Ser Gly Ser Lys Asp Tyr His Tyr
2120                2125                2130

Asp Leu Leu Gln Ala Gln Arg Tyr Gly Ile Glu Asp Gly Ile Asn
2135                2140                2145

Val Thr Lys Ser Phe Arg Glu Met Asn Tyr Asp Trp Ser Leu Tyr
2150                2155                2160

Glu Glu Asp Ser Leu Met Ile Thr Gln Leu Glu Val Leu Asn Asn
2165                2170                2175

Leu Leu Ile Ser Glu Asp Leu Pro Ala Ala Val Lys Asn Ile Met
2180                2185                2190

Ala Arg Thr Asp His Pro Glu Pro Ile Gln Leu Ala Tyr Asn Ser
2195                2200                2205

Tyr Glu Asn Gln Ile Pro Val Leu Phe Pro Lys Ile Lys Asn Gly
2210                2215                2220

Glu Val Thr Asp Ser Tyr Glu Asn Tyr Thr Tyr Leu Asn Ala Arg
2225                2230                2235

Lys Leu Gly Glu Asp Val Pro Ala Tyr Val Tyr Ala Thr Glu Asp
2240                2245                2250

Glu Asp Leu Ala Val Asp Leu Leu Gly Met Asp Trp Pro Asp Pro
2255                2260                2265

Gly Asn Gln Gln Val Val Glu Thr Gly Arg Ala Leu Lys Gln Val
2270                2275                2280

Thr Gly Leu Ser Thr Ala Glu Asn Ala Leu Leu Ile Ala Leu Phe
2285                2290                2295

Gly Tyr Val Gly Tyr Gln Thr Leu Ser Lys Arg His Ile Pro Met
2300                2305                2310

Ile Thr Asp Ile Tyr Thr Leu Glu Asp His Arg Leu Glu Asp Thr
```

-continued

```
            2315                2320                2325
Thr His Leu Gln Phe Ala Pro Asn Ala Ile Arg Thr Asp Gly Lys
    2330                2335                2340
Asp Ser Glu Leu Lys Glu Leu Ala Val Gly Asp Leu Asp Lys Tyr
    2345                2350                2355
Val Asp Ala Leu Val Asp Tyr Ser Lys Gln Gly Met Lys Phe Ile
    2360                2365                2370
Lys Val Gln Ala Glu Lys Val Arg Asp Ser Gln Ser Thr Lys Glu
    2375                2380                2385
Gly Leu Gln Thr Ile Lys Glu Tyr Val Asp Lys Phe Ile Gln Ser
    2390                2395                2400
Leu Thr Glu Asn Lys Glu Glu Ile Ile Arg Tyr Gly Leu Trp Gly
    2405                2410                2415
Val His Thr Ala Leu Tyr Lys Ser Leu Ala Ala Arg Leu Gly His
    2420                2425                2430
Glu Thr Ala Phe Ala Thr Leu Val Val Lys Trp Leu Ala Phe Gly
    2435                2440                2445
Gly Glu Thr Val Ser Ala His Ile Lys Gln Val Ala Val Asp Leu
    2450                2455                2460
Val Val Tyr Tyr Ile Ile Asn Lys Pro Ser Phe Pro Gly Asp Thr
    2465                2470                2475
Glu Thr Gln Gln Glu Gly Arg Arg Phe Val Ala Ser Leu Phe Ile
    2480                2485                2490
Ser Ala Leu Ala Thr Tyr Thr Tyr Lys Thr Trp Asn Tyr Asn Asn
    2495                2500                2505
Leu Gln Arg Val Val Glu Pro Ala Leu Ala Tyr Leu Pro Tyr Ala
    2510                2515                2520
Thr Ser Ala Leu Lys Leu Phe Thr Pro Thr Arg Leu Glu Ser Val
    2525                2530                2535
Val Ile Leu Ser Ser Thr Ile Tyr Lys Thr Tyr Leu Ser Ile Arg
    2540                2545                2550
Lys Gly Lys Ser Asp Gly Leu Leu Gly Thr Gly Ile Ser Ala Ala
    2555                2560                2565
Met Glu Ile Leu Asn Gln Asn Pro Ile Ser Val Gly Ile Ser Val
    2570                2575                2580
Met Leu Gly Val Gly Ala Ile Ala Ala His Asn Ala Ile Glu Ser
    2585                2590                2595
Ser Glu Gln Lys Arg Thr Leu Leu Met Lys Val Phe Val Lys Asn
    2600                2605                2610
Phe Leu Asp Gln Ala Ala Thr Asp Glu Leu Val Lys Glu Asn Pro
    2615                2620                2625
Glu Lys Ile Ile Met Ala Leu Phe Glu Ala Val Gln Thr Ile Gly
    2630                2635                2640
Asn Pro Leu Arg Leu Ile Tyr His Leu Tyr Gly Val Tyr Tyr Lys
    2645                2650                2655
Gly Trp Glu Ala Lys Glu Leu Ala Glu Lys Thr Ala Gly Arg Asn
    2660                2665                2670
Leu Phe Thr Leu Ile Met Phe Glu Ala Phe Glu Leu Leu Gly Met
    2675                2680                2685
Asp Ser Glu Gly Lys Ile Arg Asn Leu Ser Gly Asn Tyr Ile Leu
    2690                2695                2700
Asp Leu Ile Phe Asn Leu His Asn Lys Leu Asn Lys Gly Leu Lys
    2705                2710                2715
```

-continued

Lys Leu Val Leu Gly Trp Ala Pro Ala Pro Leu Ser Cys Asp Trp
2720                2725                2730

Thr Pro Ser Asp Glu Arg Ile Ser Leu Pro His Asn Asn Tyr Leu
2735                2740                2745

Arg Val Glu Thr Arg Cys Pro Cys Gly Tyr Glu Met Lys Ala Ile
2750                2755                2760

Lys Asn Val Ala Gly Lys Leu Thr Lys Val Glu Lys Gly Ser
2765                2770                2775

Phe Leu Cys Arg Asn Arg Leu Gly Arg Gly Pro Pro Asn Phe Lys
2780                2785                2790

Val Thr Lys Phe Tyr Asp Asp Asn Leu Ile Glu Val Lys Pro Val
2795                2800                2805

Ala Arg Leu Glu Gly Gln Val Asp Leu Tyr Tyr Lys Gly Val Thr
2810                2815                2820

Ala Lys Leu Asp Tyr Asn Asn Gly Lys Val Leu Leu Ala Thr Asn
2825                2830                2835

Lys Trp Glu Val Asp His Ala Phe Leu Thr Arg Leu Val Lys Lys
2840                2845                2850

His Thr Gly Ile Gly Phe Lys Gly Ala Tyr Leu Gly Asp Arg Pro
2855                2860                2865

Asp His Gln Asp Leu Val Asp Arg Asp Cys Ala Thr Ile Thr Lys
2870                2875                2880

Asn Ser Val Gln Phe Leu Lys Met Lys Lys Gly Cys Ala Phe Thr
2885                2890                2895

Tyr Asp Leu Thr Ile Ser Asn Leu Val Arg Leu Ile Glu Leu Val
2900                2905                2910

His Lys Asn Asn Leu Gln Glu Arg Glu Ile Pro Thr Val Thr Val
2915                2920                2925

Thr Thr Trp Leu Ala Tyr Ser Phe Val Asn Glu Asp Leu Gly Thr
2930                2935                2940

Ile Lys Pro Val Leu Gly Glu Lys Val Ile Pro Glu Pro Pro Glu
2945                2950                2955

Glu Leu Ser Leu Gln Pro Thr Val Arg Leu Val Thr Thr Glu Thr
2960                2965                2970

Ala Ile Thr Ile Thr Gly Glu Ala Glu Val Met Thr Thr Gly Ile
2975                2980                2985

Thr Pro Val Val Glu Met Lys Glu Glu Pro Gln Leu Asp His Gln
2990                2995                3000

Ser Thr Thr Leu Lys Val Gly Leu Lys Glu Gly Glu Tyr Pro Gly
3005                3010                3015

Pro Gly Val Asn Pro Asn His Leu Ala Glu Val Ile Asp Glu Lys
3020                3025                3030

Asp Asp Arg Pro Phe Val Leu Ile Ile Gly Asn Lys Gly Ser Thr
3035                3040                3045

Ser Asn Arg Ala Arg Thr Ala Lys Asn Ile Arg Leu Tyr Lys Gly
3050                3055                3060

Asn Asn Pro Arg Glu Ile Arg Asp Leu Met Ser Gln Gly Arg Ile
3065                3070                3075

Leu Thr Val Ala Leu Lys Glu Leu Asp Pro Glu Leu Lys Glu Leu
3080                3085                3090

Val Asp Tyr Lys Gly Thr Phe Leu Asn Arg Glu Ala Leu Glu Ala
3095                3100                3105

-continued

```
Leu Ser  Leu Gly Lys Pro Ile Lys Arg Lys Thr Thr  Thr Ala Met
    3110            3115            3120

Ile Arg  Arg Leu Ile Glu Pro Glu Val Glu Glu Glu  Leu Pro Asp
    3125            3130            3135

Trp Phe  Gln Ala Glu Pro Leu Phe Leu Glu Ala      Lys Ile Gln
    3140            3145            3150

Asn Asp  Leu Tyr His Leu Ile Gly Ser Val Asp Ser  Ile Lys Ser
    3155            3160            3165

Lys Ala  Lys Glu Leu Gly Ala Thr Asp Asn Thr Lys  Ile Val Lys
    3170            3175            3180

Glu Val  Gly Ala Arg Thr Tyr Thr Met Lys Leu Ser  Ser Trp Ser
    3185            3190            3195

Thr Gln  Val Thr Lys Lys Gln Met Ser Leu Ala Pro  Leu Phe Glu
    3200            3205            3210

Glu Leu  Leu Leu Lys Cys Pro Pro Cys Ser Lys Ile  Ser Lys Gly
    3215            3220            3225

His Met  Val Ser Ala Tyr Gln Leu Ala Gln Gly Asn  Trp Glu Pro
    3230            3235            3240

Leu Gly  Cys Gly Val Tyr Met Gly Thr Ile Pro Ala  Arg Arg Leu
    3245            3250            3255

Lys Ile  His Pro Tyr Glu Ala Tyr Leu Lys Leu Lys  Glu Leu Val
    3260            3265            3270

Glu Val  Glu Ser Ser Arg Ala Thr Ala Lys Glu Ser  Ile Ile Arg
    3275            3280            3285

Glu His  Asn Thr Trp Ile Leu Arg Lys Val Arg His  Glu Gly Asn
    3290            3295            3300

Leu Arg  Thr Lys Ser Met Ile Asn Pro Gly Lys Ile  Ser Asp Gln
    3305            3310            3315

Leu Cys  Arg Asp Gly His Lys Arg Asn Ile Tyr Asn  Lys Ile Ile
    3320            3325            3330

Gly Ser  Thr Met Ala Ser Ala Gly Ile Arg Leu Glu  Lys Leu Pro
    3335            3340            3345

Val Val  Arg Ala Gln Thr Asp Thr Thr Ser Phe His  Gln Ala Ile
    3350            3355            3360

Arg Glu  Lys Ile Asp Lys Thr Glu Asn Lys Gln Thr  Pro Glu Leu
    3365            3370            3375

His Glu  Glu Leu Met Lys Val Phe Asp Cys Leu Lys  Ile Pro Glu
    3380            3385            3390

Leu Lys  Glu Ser Tyr Asp Glu Val Ser Trp Glu Gln  Leu Glu Ala
    3395            3400            3405

Gly Ile  Asn Arg Lys Gly Ala Ala Gly Tyr Leu Glu  Ser Lys Asn
    3410            3415            3420

Ile Gly  Glu Val Leu Asp Thr Glu Lys His Ile Val  Glu Gln Leu
    3425            3430            3435

Ile Lys  Asp Leu Arg Lys Gly Lys Lys Ile Arg Tyr  Tyr Glu Thr
    3440            3445            3450

Ala Ile  Pro Lys Asn Glu Lys Arg Asp Val Ser Asp  Asp Trp Glu
    3455            3460            3465

Ala Gly  Glu Phe Val Asp Glu Lys Lys Pro Arg Val  Ile Gln Tyr
    3470            3475            3480

Pro Asp  Ala Lys Val Arg Leu Ala Ile Thr Lys Val  Met Tyr Lys
    3485            3490            3495

Trp Val  Lys Gln Lys Pro Val Val Ile Pro Gly Tyr  Glu Gly Lys
```

-continued

```
            3500                3505                3510
Thr Pro Leu Phe Asp Ile Phe Asn Lys Val Lys Glu Trp Asp
            3515                3520                3525
Ser Phe Gln Asp Pro Val Ala Val Ser Phe Asp Thr Lys Ala Trp
            3530                3535                3540
Asp Thr Gln Val Thr Ser Arg Asp Leu Met Leu Ile Lys Asp Ile
            3545                3550                3555
Gln Lys Tyr Tyr Phe Lys Arg Ser Ile His Lys Phe Leu Asp Thr
            3560                3565                3570
Ile Thr Glu His Met Val Glu Val Pro Val Ile Thr Ala Asp Gly
            3575                3580                3585
Glu Val Tyr Ile Arg Asn Gly Gln Arg Gly Ser Gly Gln Pro Asp
            3590                3595                3600
Thr Ser Ala Gly Asn Ser Met Leu Asn Val Leu Thr Met Ile Tyr
            3605                3610                3615
Ala Phe Cys Lys Ser Thr Gly Ile Pro Tyr Arg Gly Phe Ser Arg
            3620                3625                3630
Val Ala Arg Ile His Val Cys Gly Asp Asp Gly Phe Leu Ile Thr
            3635                3640                3645
Glu Arg Gly Leu Gly Leu Lys Phe Ser Glu Lys Gly Met Gln Ile
            3650                3655                3660
Leu His Glu Ala Gly Lys Pro Gln Lys Ile Thr Glu Gly Asp Lys
            3665                3670                3675
Met Lys Val Ala Tyr Arg Phe Glu Asp Ile Glu Phe Cys Ser His
            3680                3685                3690
Thr Pro Val Pro Val Arg Trp Ala Asp Asn Thr Ser Ser Tyr Met
            3695                3700                3705
Ala Gly Arg Ser Thr Ala Thr Ile Leu Ala Lys Met Ala Thr Arg
            3710                3715                3720
Leu Asp Ser Ser Gly Glu Arg Gly Ser Thr Ala Tyr Glu Lys Ala
            3725                3730                3735
Val Ala Phe Ser Phe Leu Leu Met Tyr Ser Trp Asn Pro Val Val
            3740                3745                3750
Arg Arg Ile Cys Leu Leu Val Leu Ser Gln Phe Pro Glu Ile Ser
            3755                3760                3765
Pro Ser Lys Asn Thr Ile Tyr Tyr Tyr Gln Gly Asp Pro Ile Ala
            3770                3775                3780
Ala Tyr Arg Glu Val Ile Gly Lys Gln Leu Cys Glu Leu Lys Arg
            3785                3790                3795
Thr Gly Phe Glu Lys Leu Ala Gly Leu Asn Leu Ser Met Thr Thr
            3800                3805                3810
Leu Gly Ile Trp Thr Lys His Thr Ser Lys Arg Leu Ile Gln Asp
            3815                3820                3825
Cys Val Glu Ile Gly Lys Arg Glu Gly Asn Trp Leu Val Asn Ala
            3830                3835                3840
Asp Arg Leu Ile Ala Gly Lys Thr Gly Lys Phe Tyr Ile Pro Ser
            3845                3850                3855
Thr Gly Val Thr Leu Leu Gly Lys His Tyr Glu Glu Ile Asn Leu
            3860                3865                3870
Lys Gln Lys Ala Ala Gln Pro Pro Ile Glu Gly Val Asp Arg Tyr
            3875                3880                3885
Lys Leu Gly Pro Ile Val Asn Val Ile Leu Arg Arg Leu Arg Val
            3890                3895                3900
```

```
Met Leu  Met Thr Val Ala Ser  Gly Ser Trp
    3905                 3910

<210> SEQ ID NO 10
<211> LENGTH: 3895
<212> TYPE: PRT
<213> ORGANISM: BVDV

<400> SEQUENCE: 10

Met Glu Leu Asn Lys Phe Glu Leu Leu Tyr Lys Thr Ser Lys Gln Lys
1               5                   10                  15

Pro Val Gly Val Thr Glu Pro Ile Tyr Asp Ser Ala Gly Asn Pro Ile
            20                  25                  30

Tyr Gly Glu Arg Ser Thr Ile His Pro Gln Ser Thr Leu Lys Leu Pro
        35                  40                  45

His Glu Arg Gly Val Ala Glu Val Val Thr Thr Leu Arg Asp Leu Pro
    50                  55                  60

Lys Lys Gly Asp Cys Arg Ser Gly Asn His Arg Gly Pro Val Ser Gly
65                  70                  75                  80

Ile Tyr Ile Lys Pro Gly Pro Val Leu Tyr Gln Asp Tyr Lys Gly Pro
                85                  90                  95

Val Tyr His Arg Ala Pro Leu Glu Leu Phe Val Glu Thr Gln Phe Cys
            100                 105                 110

Glu Val Thr Lys Arg Ile Gly Arg Val Thr Gly Ser Asp Gly Arg Leu
        115                 120                 125

Tyr His Leu Tyr Ile Cys Ser Asp Gly Cys Ile Leu Leu Lys Thr Ala
    130                 135                 140

Ser Lys Thr Arg Ser Ala Val Leu Lys Trp Thr Arg Asn Ile Leu Asp
145                 150                 155                 160

Cys Pro Leu Trp Val Thr Ser Cys Ser Asp Asp Asn Lys Ser Glu Lys
                165                 170                 175

Thr Asn Glu Lys Lys Pro Asp Arg Val Arg Arg Gly Ala Met Lys Ile
            180                 185                 190

Thr Pro Lys Glu Ser Glu Lys Asp Ser Arg Ser Lys Pro Pro Asp Ala
        195                 200                 205

Thr Ile Val Val Glu Gly Ile Lys Tyr Gln Val Lys Lys Lys Gly Lys
    210                 215                 220

Val Lys Gly Lys Asn Thr Gln Asp Gly Leu Tyr His Asn Lys Asn Lys
225                 230                 235                 240

Pro Pro Glu Ser Arg Lys Lys Leu Glu Lys Ala Leu Leu Ala Trp Ala
                245                 250                 255

Ile Ile Ala Ile Phe Met Trp Glu Pro Val Ala Pro Glu Asn Val Thr
            260                 265                 270

Gln Trp Asn Leu Ser Asp Asn Gly Thr Thr Gly Ile Gln Leu Leu Met
        275                 280                 285

Phe Gln Arg Gly Val Asn Arg Ser Leu His Gly Ile Trp Pro Glu Lys
    290                 295                 300

Ile Cys Thr Gly Val Pro Thr His Leu Ala Thr Asp Ala Glu Leu Lys
305                 310                 315                 320

Gly Ile Gln Gly Met Met Asp Ala Ser Glu Lys Thr Asn Tyr Thr Cys
                325                 330                 335

Cys Arg Leu Gln Arg His Glu Trp Asn Lys Tyr Gly Trp Cys Asn Trp
            340                 345                 350

Tyr Asn Ile Asn Pro Trp Ile Trp Leu Met Asn Lys Thr Gln Ala Asn
```

-continued

```
            355                 360                 365
Leu Thr Glu Gly Pro Glu Lys Glu Cys Ala Val Thr Cys Arg Phe
370                 375                 380

Asp Lys Glu Ala Asp Ile Asn Ile Val Thr Gln Ala Arg Asp Arg Pro
385                 390                 395                 400

Thr Thr Leu Thr Gly Cys Lys Gly Lys Lys Phe Ser Phe Ala Gly
                405                 410                 415

Met Ile Ile Glu Gly Pro Cys Asn Phe Asn Val Ser Val Glu Asp Ile
                420                 425                 430

Leu Phe Gly Asp Asn Glu Cys Ser Ser Leu Phe Gln Asp Thr Ala Leu
            435                 440                 445

Tyr Val Val Asp Gly Val Thr Asn Thr Val Glu Asn Ala Arg Gln Gly
        450                 455                 460

Ala Ala Lys Leu Thr Ser Trp Leu Gly Lys Gln Leu Gly Ile Met Gly
465                 470                 475                 480

Lys Lys Leu Glu His Lys Ser Lys Thr Trp Phe Gly Ala Asn Ala Gln
                485                 490                 495

Ser Pro Tyr Cys Asn Val Thr Arg Lys Ile Gly Tyr Val Trp Tyr Thr
                500                 505                 510

Asn Asn Cys Thr Pro Ala Cys Leu Pro Lys Asn Thr Lys Ile Ile Gly
            515                 520                 525

Pro Gly Lys Phe Asp Thr Asn Ala Glu Asp Gly Lys Ile Leu His Glu
        530                 535                 540

Met Arg Gly His Ile Ser Glu Phe Ile Leu Leu Ser Leu Val Val Leu
545                 550                 555                 560

Ser Asp Phe Ala Pro Glu Thr Ala Ser Thr Leu Tyr Leu Val Leu His
                565                 570                 575

Phe Ala Leu Pro Gln Thr His Glu Val Pro Ser Val Cys Asp Thr Asn
            580                 585                 590

Gln Leu Asn Leu Thr Val Ser Leu Arg Val Asp Asp Val Ile Pro Ser
        595                 600                 605

Ser Val Trp Asn Leu Gly Lys Tyr Val Cys Val Arg Pro Asp Trp Trp
        610                 615                 620

Pro Tyr Glu Thr Thr Met Val Leu Leu Phe Glu Glu Ala Gly Gln Val
625                 630                 635                 640

Val Lys Leu Val Leu Arg Ala Ile Arg Asp Leu Thr Arg Val Trp Asn
                645                 650                 655

Ser Ala Ser Thr Thr Ala Phe Leu Ile Cys Leu Val Lys Val Leu Arg
                660                 665                 670

Gly Gln Val Val Gln Gly Leu Val Trp Leu Leu Leu Val Thr Gly Ala
            675                 680                 685

Gln Gly Gln Phe Ala Cys Arg Glu Asp Tyr Arg Tyr Ala Leu Ala Arg
        690                 695                 700

Thr Lys Glu Ile Gly Ala Leu Gly Ala Glu Ser Leu Thr Thr Thr Trp
705                 710                 715                 720

Thr Asp Tyr Arg Gly Asn Leu Glu Leu Asp Asp Gly Thr Val Arg Ala
                725                 730                 735

Thr Cys Ser Arg Gly Phe Phe Arg Phe Arg Gly His Cys Met Ile Gly
                740                 745                 750

Pro Arg Tyr Leu Ala Ser Leu His Leu Arg Ala Leu Pro Thr Ser Val
            755                 760                 765

Thr Phe Glu Leu Ile Pro Gly Gly Ser Ala Met Thr Glu Glu Glu Met
770                 775                 780
```

```
Gly Asp Asp Phe Glu Phe Gly Leu Cys Pro Cys Asp Ser Arg Pro Val
785                 790                 795                 800

Val Lys Gly Lys Tyr Asn Thr Thr Leu Leu Asn Gly Ser Ala Phe Gln
            805                 810                 815

Leu Ile Cys Pro Tyr Gly Trp Val Gly Arg Val Glu Cys Thr Thr Val
            820                 825                 830

Ser Lys Ser Thr Leu Ala Thr Glu Val Val Lys Ile Tyr Lys Lys Thr
            835                 840                 845

Lys Pro Phe Pro Gln Arg Val Gly Cys Asp His Thr Thr Val Tyr Lys
850                 855                 860

Gln Asp Leu Tyr His Cys Gln Met Gly Gly Asn Trp Thr Cys Met Arg
865                 870                 875                 880

Gly Glu Val Val Lys Tyr Val Gly Gly Pro Val Lys Lys Cys Glu Trp
                885                 890                 895

Cys Gly Tyr Val Phe Lys Lys Arg Glu Gly Leu Pro His Tyr Pro Ile
                900                 905                 910

Gly Arg Cys Met Leu Arg Asn Glu Thr Gly Tyr Arg Ser Val Asp Asp
            915                 920                 925

Thr Pro Cys Asp Arg Gly Gly Val Val Ile Ser Lys Thr Gly Glu Leu
930                 935                 940

Glu Cys Leu Ile Gly Lys Thr Thr Val Lys Val Phe Ser Ser Asp Lys
945                 950                 955                 960

Lys Leu Gly Pro Met Pro Cys Arg Pro Lys Glu Val Ile Ser Ser Glu
                965                 970                 975

Gly Pro Val Ser Lys Ile Ala Cys Thr Phe Asn Tyr Ser Lys Thr Leu
            980                 985                 990

Glu Asn Lys Tyr Tyr Glu Pro Arg Asp Ser Tyr Phe Gln Gln Tyr Met
            995                 1000                1005

Leu Lys Gly Gln Tyr Gln Tyr Trp Phe Asp Leu Glu Ala Thr Asp
        1010                1015                1020

His His Ser Asp Tyr Phe Ala Glu Phe Ile Met Leu Ala Val Val
        1025                1030                1035

Ala Leu Leu Gly Gly Arg Tyr Val Leu Trp Leu Met Val Val Tyr
        1040                1045                1050

Met Ile Leu Ala Asp Gln Met Thr Ser Ala Ile Asn Leu Gly Gln
        1055                1060                1065

Gly Glu Val Val Leu Ile Gly Asn Leu Ile Thr His Glu Asp His
        1070                1075                1080

Glu Val Val Tyr Phe Leu Leu Leu Tyr Leu Ile Val Lys Asp
        1085                1090                1095

Glu Pro Val Lys Lys Trp Ile Leu Phe Leu Phe His Ala Met Thr
        1100                1105                1110

Asn Asn Pro Val Lys Thr Ile Ser Val Gly Leu Leu Met Leu Ser
        1115                1120                1125

Gly Leu Val Lys Gly Glu Gly Ala Gly Met Thr Tyr Trp Glu Gly
        1130                1135                1140

Leu Asp Leu Gln Phe Thr Leu Leu Val Met Ile Thr Ala Ser Leu
        1145                1150                1155

Leu Val Ala Arg Arg Asp Val Thr Thr Tyr Pro Leu Ile Ile Thr
        1160                1165                1170

Val Ile Ala Leu Lys Thr Thr Trp Val Asn Ser Gly Pro Gly Ile
        1175                1180                1185
```

```
Asp Ala Ala Ile Ala Thr Ile Thr Thr Gly Leu Leu Met Trp Thr
    1190            1195                1200

Phe Ile Ser Asp Tyr Tyr Lys Tyr Lys Gln Trp Thr Gln Phe Leu
    1205            1210                1215

Ile Ser Ile Val Ser Gly Ile Phe Leu Ile Arg Thr Leu Lys Trp
    1220            1225                1230

Ile Gly Gly Leu Glu Leu His Ala Pro Glu Leu Pro Ser Tyr Arg
    1235            1240                1245

Pro Leu Phe Phe Ile Leu Thr Tyr Leu Ile Ser Ala Ala Ile Val
    1250            1255                1260

Thr Arg Trp Asn Leu Asp Ile Ala Gly Val Leu Leu Gln Cys Val
    1265            1270                1275

Pro Thr Ile Leu Met Val Leu Thr Leu Trp Ala Asp Leu Leu Thr
    1280            1285                1290

Leu Ile Leu Ile Leu Pro Thr Tyr Glu Leu Ala Lys Leu Tyr Tyr
    1295            1300                1305

Leu Lys Gly Val Lys Asn Gly Met Glu Arg Asn Trp Leu Gly Arg
    1310            1315                1320

Ile Thr Tyr Lys Arg Val Ser Asp Val Tyr Glu Ile Asp Glu Ser
    1325            1330                1335

Gln Glu Ala Val Tyr Leu Phe Pro Ser Lys Gln Lys Glu Gly Thr
    1340            1345                1350

Ile Thr Gly Gly Leu Leu Pro Leu Ile Lys Ala Ile Leu Ile Ser
    1355            1360                1365

Cys Ile Ser Ser Lys Trp Gln Cys Phe Tyr Leu Leu Tyr Leu Val
    1370            1375                1380

Val Glu Val Ser Tyr Tyr Leu His Lys Lys Ile Ile Glu Glu Val
    1385            1390                1395

Ala Gly Gly Thr Asn Leu Ile Ser Arg Leu Val Ala Ala Leu Leu
    1400            1405                1410

Glu Val Asn Trp Arg Phe Asp Asn Glu Glu Thr Lys Gly Leu Lys
    1415            1420                1425

Lys Phe Tyr Leu Ile Ser Gly Gln Val Lys Asn Leu Ile Ile Lys
    1430            1435                1440

His Lys Val Arg Asn Glu Val Val Ala His Trp Phe Asn Glu Glu
    1445            1450                1455

Glu Val Tyr Gly Met Pro Lys Leu Val Ser Val Lys Ala Ala
    1460            1465                1470

Thr Leu Asn Arg Ser Arg His Cys Ile Leu Cys Thr Val Cys Glu
    1475            1480                1485

Ser Arg Asp Trp Lys Gly Glu Thr Cys Pro Lys Cys Gly Arg Phe
    1490            1495                1500

Gly Pro Ser Leu Ser Cys Gly Met Thr Leu Ser Asp Phe Glu Glu
    1505            1510                1515

Arg His Tyr Lys Lys Ile Phe Ile Arg Glu Asp Gln Ser Asp Gly
    1520            1525                1530

Pro Phe Arg Glu Glu Tyr Lys Gly Tyr Leu Gln Tyr Lys Ala Arg
    1535            1540                1545

Gly Gln Leu Phe Leu Arg Asn Leu Pro Ile Leu Ala Thr Lys Val
    1550            1555                1560

Lys Leu Leu Leu Val Gly Asn Leu Gly Ser Glu Val Gly Asp Leu
    1565            1570                1575

Glu His Leu Gly Trp Ile Leu Arg Gly Pro Ala Val Cys Lys Lys
```

-continued

```
            1580                1585                1590
Ile Ile Asp His Glu Arg Cys His Val Ser Ile Met Asp Lys Leu
    1595                1600                1605

Thr Ala Phe Phe Gly Ile Met Pro Arg Gly Thr Thr Pro Arg Ala
    1610                1615                1620

Pro Ile Arg Phe Pro Thr Ser Leu Leu Arg Ile Arg Arg Gly Leu
    1625                1630                1635

Glu Thr Gly Trp Ala Tyr Thr His Gln Gly Gly Ile Ser Ser Val
    1640                1645                1650

Asp His Val Thr Ala Gly Lys Asp Leu Leu Val Cys Asp Ser Met
    1655                1660                1665

Gly Arg Thr Arg Val Val Cys Gln Ser Asn Asn Arg Met Thr Asp
    1670                1675                1680

Glu Thr Glu Tyr Gly Val Lys Thr Asp Ser Gly Cys Pro Glu Gly
    1685                1690                1695

Ala Arg Cys Tyr Val Phe Asn Pro Glu Ala Val Asn Ile Ser Gly
    1700                1705                1710

Thr Lys Gly Ala Met Val His Leu Gln Lys Thr Gly Gly Glu Phe
    1715                1720                1725

Thr Cys Val Thr Ala Ser Gly Thr Pro Ala Phe Phe Asp Leu Lys
    1730                1735                1740

Asn Leu Lys Gly Trp Ser Gly Leu Pro Ile Phe Glu Ala Ser Ser
    1745                1750                1755

Gly Arg Val Val Gly Arg Val Lys Val Gly Lys Asn Glu Glu Ser
    1760                1765                1770

Lys Pro Thr Lys Leu Met Ser Gly Ile Gln Thr Val Ser Lys Ser
    1775                1780                1785

Thr Thr Asp Leu Thr Asp Met Val Lys Lys Ile Thr Thr Met Asn
    1790                1795                1800

Arg Gly Glu Phe Lys Gln Ile Thr Leu Ala Thr Gly Ala Gly Lys
    1805                1810                1815

Thr Thr Glu Leu Pro Arg Ala Val Ile Glu Glu Ile Gly Arg His
    1820                1825                1830

Lys Arg Val Leu Val Leu Ile Pro Leu Arg Ala Ala Ala Glu Ser
    1835                1840                1845

Val Tyr Gln Tyr Met Arg Gln Lys His Pro Ser Ile Ala Phe Asn
    1850                1855                1860

Leu Arg Ile Gly Glu Met Lys Glu Gly Asp Met Ala Thr Gly Ile
    1865                1870                1875

Thr Tyr Ala Ser Tyr Gly Tyr Phe Cys Gln Met Pro Gln Pro Lys
    1880                1885                1890

Leu Arg Ala Ala Met Val Glu Tyr Ser Tyr Ile Phe Leu Asp Glu
    1895                1900                1905

Tyr His Cys Ala Thr Pro Glu Gln Leu Ala Ile Ile Gly Lys Ile
    1910                1915                1920

His Arg Phe Ser Glu Gln Leu Arg Val Val Ala Met Thr Ala Thr
    1925                1930                1935

Pro Ala Gly Thr Val Thr Thr Thr Gly Gln Lys His Pro Ile Glu
    1940                1945                1950

Glu Phe Ile Ala Pro Glu Val Met Lys Gly Glu Asp Leu Gly Ser
    1955                1960                1965

Glu Phe Leu Glu Ile Ala Gly Leu Lys Ile Pro Thr Glu Glu Met
    1970                1975                1980
```

-continued

```
Lys Gly Asn Met Leu Val Phe Val Pro Thr Arg Asn Met Ala Val
1985                1990                1995

Glu Thr Ala Lys Lys Leu Lys Ala Lys Gly Tyr Asn Ser Gly Tyr
2000                2005                2010

Tyr Tyr Ser Gly Glu Asp Pro Ala Asn Leu Arg Val Val Thr Ser
2015                2020                2025

Gln Ser Pro Tyr Val Val Val Ala Thr Asn Ala Ile Glu Ser Gly
2030                2035                2040

Val Thr Leu Pro Asp Leu Asp Val Val Asp Thr Gly Leu Lys
2045                2050                2055

Cys Glu Lys Arg Ile Arg Leu Ser Ser Lys Met Pro Phe Ile Val
2060                2065                2070

Thr Gly Leu Lys Arg Met Ala Val Thr Ile Gly Glu Gln Ala Gln
2075                2080                2085

Arg Arg Gly Arg Val Gly Arg Val Lys Pro Gly Arg Tyr Tyr Arg
2090                2095                2100

Ser Gln Glu Thr Ala Val Gly Ser Lys Asp Tyr His Tyr Asp Leu
2105                2110                2115

Leu Gln Ala Gln Arg Tyr Gly Ile Glu Asp Gly Ile Asn Ile Thr
2120                2125                2130

Lys Ser Phe Arg Glu Met Asn Tyr Asp Trp Ser Leu Tyr Glu Glu
2135                2140                2145

Asp Ser Leu Met Ile Thr Gln Leu Glu Ile Leu Asn Asn Leu Leu
2150                2155                2160

Ile Ser Glu Glu Leu Pro Val Ala Val Lys Asn Ile Met Ala Arg
2165                2170                2175

Thr Asp His Pro Glu Pro Ile Gln Leu Ala Tyr Asn Ser Tyr Glu
2180                2185                2190

Val Gln Val Pro Val Leu Phe Pro Lys Ile Arg Asn Gly Glu Val
2195                2200                2205

Thr Asp Ser Tyr Asp Ser Tyr Ser Phe Leu Asn Ala Arg Lys Leu
2210                2215                2220

Gly Asp Asp Val Pro Ala Tyr Val Tyr Ala Thr Glu Asp Glu Asp
2225                2230                2235

Leu Ala Val Glu Leu Leu Gly Met Asp Trp Pro Asp Pro Gly Asn
2240                2245                2250

Gln Gly Thr Val Glu Thr Gly Arg Ala Leu Lys Gln Val Thr Gly
2255                2260                2265

Leu Ser Ala Ala Glu Asn Ala Leu Leu Val Ala Leu Phe Gly Tyr
2270                2275                2280

Val Gly Tyr Gln Ala Leu Ser Lys Arg His Val Pro Met Val Thr
2285                2290                2295

Asp Ile Tyr Ser Ile Glu Asp His Arg Leu Glu Asp Thr Thr His
2300                2305                2310

Leu Gln Phe Ala Pro Asn Ala Ile Arg Thr Asp Gly Lys Glu Thr
2315                2320                2325

Glu Leu Lys Glu Leu Ala Gln Gly Asp Ile Gln Arg Cys Ala Glu
2330                2335                2340

Ala Met Val Gly Tyr Ala Gln Gln Gly Val Gln Phe Ile Lys Thr
2345                2350                2355

Gln Ala Leu Lys Val Gln Glu Asn His Val Phe Lys Asp Ser Ala
2360                2365                2370
```

-continued

| | | | | | | | | | | | |
|---|---|---|---|---|---|---|---|---|---|---|---|
|Asp|Thr|Ile|Val|Glu|Tyr|Val|Asp|Lys|Phe|Met|Lys|Ala|Ile|Ala|
| |2375| | | |2380| | | |2385| | | | | |

Asp Thr Ile Val Glu Tyr Val Asp Lys Phe Met Lys Ala Ile Ala
     2375              2380              2385

Glu Ser Lys Asp Asp Ile Leu Arg Tyr Gly Leu Trp Gly Ala His
     2390              2395              2400

Thr Ala Leu Tyr Lys Ser Ile Gly Ala Arg Leu Gly Tyr Glu Thr
     2405              2410              2415

Ala Phe Ala Thr Leu Val Ile Lys Trp Leu Ala Phe Gly Gly Glu
     2420              2425              2430

Ser Ile Asn Asp His Val Lys Gln Ala Ala Thr Asp Leu Val Val
     2435              2440              2445

Tyr Tyr Ile Ile Asn Arg Pro Gln Phe Pro Gly Asp Thr Glu Thr
     2450              2455              2460

Gln Gln Glu Gly Arg Lys Phe Val Ala Ser Leu Leu Val Ser Ala
     2465              2470              2475

Leu Ala Thr Tyr Thr Tyr Lys Ser Trp Asn Tyr Ser Asn Leu Ser
     2480              2485              2490

Lys Val Val Glu Pro Ala Leu Ala Cys Leu Pro Tyr Ala Ser Gln
     2495              2500              2505

Ala Leu Lys Leu Phe Ala Pro Thr Arg Leu Glu Ser Val Val Ile
     2510              2515              2520

Leu Ser Thr Ala Ile Tyr Lys Thr Tyr Leu Ala Ile Arg Arg Gly
     2525              2530              2535

Arg Ser Asp Gly Leu Leu Gly Thr Gly Val Ser Ala Ala Met Glu
     2540              2545              2550

Ile Met Ser Gln Asn Pro Val Ser Val Gly Ile Ala Val Met Leu
     2555              2560              2565

Gly Val Gly Ala Val Ala Ala His Asn Ala Ile Glu Ser Ser Glu
     2570              2575              2580

Gln Lys Arg Thr Leu Leu Met Lys Val Phe Val Lys Asn Phe Leu
     2585              2590              2595

Asp Gln Ala Ala Thr Asp Glu Leu Val Lys Glu Ser Pro Glu Lys
     2600              2605              2610

Ile Ile Thr Ala Leu Phe Glu Ala Val Gln Thr Val Gly Asn Pro
     2615              2620              2625

Leu Arg Leu Ile Tyr His Leu Tyr Gly Val Phe Tyr Lys Gly Trp
     2630              2635              2640

Glu Ala Lys Glu Val Ala Glu Lys Thr Ala Gly Arg Asn Leu Phe
     2645              2650              2655

Thr Leu Ile Met Phe Glu Ala Val Glu Leu Leu Gly Val Asp Ser
     2660              2665              2670

Glu Gly Lys Met Arg Arg Leu Ser Gly Asn Tyr Leu Ile Glu Leu
     2675              2680              2685

Leu Gln Lys Leu His Asp Gly Phe Arg Ile Ser Ile Lys Lys Phe
     2690              2695              2700

Ala Leu Gly Trp Ala Pro Gly Pro Phe Ser Cys Asn Trp Thr Pro
     2705              2710              2715

Ala Asp Asn Arg Ile Arg Leu Pro His Glu Asn Tyr Leu Arg Val
     2720              2725              2730

Val Thr Arg Cys Arg Cys Gly Tyr Arg Thr Lys Ala Val Lys Asn
     2735              2740              2745

Cys Ala Gly Glu Leu Ile Leu Glu Glu Glu Glu Gly Ser Phe Phe
     2750              2755              2760

Cys Arg Asn Lys Phe Gly Arg Gly Ala Pro Asn Tyr Lys Val Thr

```
            2765                2770                2775

Lys Phe Tyr Asp Gly Asn Leu Glu Glu Ile Arg Ala Arg Leu Lys
        2780                2785                2790

Leu Glu Gly Gln Val Glu Met Tyr Tyr Lys Gly Ala Thr Ile Lys
        2795                2800                2805

Ile Asp Tyr Ser Asn Asn Lys Leu Ile Leu Ala Thr Asp Lys Trp
        2810                2815                2820

Glu Val Glu His Ser Tyr Ile Thr Arg Leu Thr Lys Arg Tyr Thr
        2825                2830                2835

Gly Ala Gly Tyr Lys Gly Ala Phe Leu Gly Asp Glu Pro Asn His
        2840                2845                2850

Lys Ser Leu Ile Glu Arg Thr Cys Ala Thr Val Cys Lys Asp Lys
        2855                2860                2865

Ile Tyr Phe Ser Lys Met Lys Lys Gly Cys Ala Phe Thr Tyr Asp
        2870                2875                2880

Leu Ser Leu Ser Asn Leu Val Arg Leu Val Asp Leu Val His Arg
        2885                2890                2895

Asn Lys Leu Glu Glu Lys Asp Ile Pro Glu Arg Thr Val Thr Thr
        2900                2905                2910

Trp Leu Ala Tyr Thr Phe Val Asn Glu Asp Val Gly Thr Ile Lys
        2915                2920                2925

Pro Val Leu Gly Glu Lys Val Ile Pro Glu Glu Ser Asp Glu Ile
        2930                2935                2940

Asn Leu Gln Pro Thr Val Thr Val Asn Met Ser Lys Cys Gln Val
        2945                2950                2955

Thr Val Val Gly Glu Ala Lys Asn Met Thr Thr Gly Val Val Pro
        2960                2965                2970

Leu Thr Val Thr Lys Glu Ala Cys Asn Gly Gln Asp Arg Ser Val
        2975                2980                2985

Leu Asn Ile Gly Met Glu Glu Gly Glu Tyr Pro Gly Pro Ala Val
        2990                2995                3000

Ser Thr Val Thr Val Gly Glu Ala Val Gln Ser Lys Asp Val Arg
        3005                3010                3015

Pro Tyr Val Leu Val Ile Gly Ser Asn Lys Ala Thr Ser Asn Arg
        3020                3025                3030

Ala Lys Thr Ala Lys Asn Val Lys Leu Tyr Lys Gly Gly Asp Ala
        3035                3040                3045

Val Glu Val Arg Asp Leu Ile Lys Lys Gly Glu Met Leu Val Val
        3050                3055                3060

Ala Leu Ala Asp Val Glu Gln Asp Leu Leu Glu Tyr Val Asp Tyr
        3065                3070                3075

Lys Gly Thr Phe Leu Thr Arg Glu Thr Leu Glu Ala Leu Ser Leu
        3080                3085                3090

Gly Lys Pro Lys Ala Lys Asn Ile Thr Lys Ala Asp Ala His Arg
        3095                3100                3105

Leu Leu Asn Pro Glu Lys Glu Gln Ile Gly Leu Pro Asp Trp Phe
        3110                3115                3120

Thr Ala Thr Glu Pro Ile Phe Leu Glu Ala Met Ile Lys Gln Glu
        3125                3130                3135

Lys Tyr His Ile Thr Gly Asp Val Ala Thr Val Lys Asp Lys Ala
        3140                3145                3150

Lys Gln Leu Gly Ala Thr Asp Ser Thr Arg Ile Val Lys Glu Val
        3155                3160                3165
```

-continued

Gly Ala Arg Val Tyr Thr Met Lys Leu Asn Ser Trp Ala Leu Gln
3170                3175                3180

Ala Glu Arg Gly Asp Ala Asn Leu Lys Pro Leu Phe Glu Glu Leu
3185                3190                3195

Leu Leu Gln Cys Pro Pro Gly Arg Thr Val Lys Gly Gly Thr Met
3200                3205                3210

Val Ser Ala Tyr Gln Leu Ala Gln Gly Asn Trp Thr Pro Thr Ser
3215                3220                3225

Cys Lys Val Tyr Met Gly Thr Ile Thr Ala Lys Arg Val Lys Ile
3230                3235                3240

His Pro Tyr Glu Ala Tyr Ile Lys Leu Lys Glu Leu Ile Glu Glu
3245                3250                3255

Tyr Asn Met Lys Arg Val Thr Gly Asp Thr Gly Leu Lys Arg His
3260                3265                3270

Asn Glu Trp Ile Leu Lys Arg Ile Lys His His Gly Asn Leu Arg
3275                3280                3285

Thr Lys Lys Ile Leu Asn Pro Gly Lys Val Ala Glu Gln Leu Ser
3290                3295                3300

Arg Glu Gly His Lys His Asn Val Tyr Asn Lys Ile Ile Gly Ser
3305                3310                3315

Thr Met Ala Ser Val Gly Ile Lys Leu Glu Lys Leu Pro Val Val
3320                3325                3330

Arg Ala Gln Thr Asp Thr Thr Phe Phe His Gln Ala Ile Arg Asp
3335                3340                3345

Lys Ile Asp Lys Glu Glu Asn Pro Gln Thr Pro Asp Leu His Lys
3350                3355                3360

Glu Leu Lys Glu Val Phe Asn Ala Leu Lys Ile Pro Glu Leu Ala
3365                3370                3375

Ala Thr Tyr Asp Ala Val Glu Trp Glu Glu Leu Glu Thr Gly Ile
3380                3385                3390

Asn Arg Lys Gly Ala Ala Gly Phe Phe Glu Arg Lys Asn Ile Gly
3395                3400                3405

Glu Ile Leu Asp Thr Glu Lys Asn Lys Val Glu Asp Ile Ile Arg
3410                3415                3420

Asp Leu Lys Ser Gly Arg Pro Ile Lys Tyr Tyr Glu Thr Ala Ile
3425                3430                3435

Pro Lys Asn Glu Lys Arg Asp Val Asn Asp Trp Glu Ser Gly
3440                3445                3450

Asp Phe Val Asp Glu Lys Lys Pro Arg Val Ile Gln Tyr Pro Glu
3455                3460                3465

Ala Lys Val Arg Leu Ala Ile Thr Lys Val Met Tyr Lys Trp Val
3470                3475                3480

Lys Gln Lys Pro Val Val Ile Pro Gly Tyr Glu Gly Lys Thr Pro
3485                3490                3495

Leu Phe Glu Ile Phe Asp Lys Val Lys Lys Glu Trp Gly Ser Phe
3500                3505                3510

Asp Asn Pro Val Ala Val Ser Phe Asp Thr Lys Ala Trp Asp Thr
3515                3520                3525

Gln Val Thr Ser Lys Ser Leu Glu Leu Ile Arg Asp Ile Gln Lys
3530                3535                3540

Tyr Tyr Phe Lys Lys Glu Trp His Lys Phe Ile Glu Thr Ile Thr
3545                3550                3555

```
Glu His Met Val Glu Val Pro Val Val Thr Ala Asp Gly Glu Val
3560            3565                3570

Tyr Ile Ser Glu Gly Gln Arg Gly Ser Gly Gln Pro Asp Thr Ser
3575            3580                3585

Ala Gly Asn Ser Met Leu Asn Val Leu Thr Met Val Tyr Ala Phe
3590            3595                3600

Cys Arg Ala Thr Gly Val Pro Tyr Lys Ser Phe Lys Arg Val Ala
3605            3610                3615

Lys Ile His Val Cys Gly Asp Asp Gly Phe Leu Ile Thr Glu Lys
3620            3625                3630

Ser Leu Gly Glu Lys Phe Ala Ser Lys Gly Ile Gln Ile Leu His
3635            3640                3645

Glu Ala Gly Lys Pro Gln Lys Ile Thr Glu Gly Asp Arg Met Lys
3650            3655                3660

Val Ala Tyr Lys Phe Glu Asp Ile Glu Phe Cys Ser His Thr Pro
3665            3670                3675

Val Pro Val Arg Trp Ser Asp Asn Thr Thr Ser Tyr Met Pro Gly
3680            3685                3690

Arg Asn Thr Ala Thr Ile Leu Ala Lys Met Ala Thr Arg Leu Asp
3695            3700                3705

Ser Ser Gly Glu Arg Gly Thr Thr Ala Tyr Glu Lys Ala Val Ala
3710            3715                3720

Phe Ser Phe Leu Leu Met Tyr Ser Trp Asn Pro Leu Val Arg Arg
3725            3730                3735

Ile Cys Leu Leu Thr Leu Ser Ser Glu Leu Gly Thr Lys Pro Ser
3740            3745                3750

Lys Arg Thr Thr Tyr Tyr Glu Gly Asp Pro Ile Ser Ala Tyr
3755            3760                3765

Arg Glu Val Ile Gly His Asn Leu Leu Asp Leu Lys Arg Thr Gly
3770            3775                3780

Leu Glu Lys Leu Ala Leu Leu Asn Leu Ser Met Ser Thr Leu Gly
3785            3790                3795

Ile Trp Thr Lys His Ile Ser Lys Arg Leu Leu Gln Asp Cys Val
3800            3805                3810

Asp Val Gly Ser Lys Asp Gly Asn Trp Leu Val Asn Ala Asp Arg
3815            3820                3825

Pro Glu Ser Arg Lys Thr Gly Lys Val Tyr Leu Gln Ser Gly Gly
3830            3835                3840

His Thr Val Arg Gly Arg His Tyr Glu Asp Leu Ile Leu Pro Arg
3845            3850                3855

Met Val Lys Pro Thr Phe Gln Gly Val Asp Arg Tyr Lys Leu Gly
3860            3865                3870

Pro Ile Val Asn Val Ile Phe Arg Arg Leu Arg Val Met Met Met
3875            3880                3885

Ala Leu Val Gly Arg Gly Met
3890            3895

<210> SEQ ID NO 11
<211> LENGTH: 3894
<212> TYPE: PRT
<213> ORGANISM: BVDV

<400> SEQUENCE: 11

Met Glu Leu Asn Lys Phe Glu Leu Leu Tyr Lys Thr Ser Lys Gln Lys
1               5                   10                  15
```

-continued

```
Pro Val Gly Val Thr Glu Pro Ile Tyr Asp Ser Ala Gly Asn Pro Ile
             20                  25                  30

Tyr Gly Glu Arg Ser Thr Ile His Pro Gln Ser Thr Leu Lys Leu Pro
         35                  40                  45

His Glu Arg Gly Val Ala Glu Val Val Thr Thr Leu Arg Asp Leu Pro
 50                  55                  60

Lys Lys Gly Asp Cys Arg Ser Gly Asn His Arg Gly Pro Val Ser Gly
 65                  70                  75                  80

Ile Tyr Ile Lys Pro Gly Pro Val Leu Tyr Gln Asp Tyr Lys Gly Pro
                 85                  90                  95

Val Tyr His Arg Ala Pro Leu Glu Leu Phe Val Glu Thr Gln Phe Cys
             100                 105                 110

Glu Val Thr Lys Arg Ile Gly Arg Val Thr Gly Ser Asp Gly Arg Leu
         115                 120                 125

Tyr His Leu Tyr Ile Cys Ser Asp Gly Cys Ile Leu Leu Lys Thr Ala
 130                 135                 140

Ser Lys Thr Arg Ser Ala Val Leu Lys Trp Thr Arg Asn Ile Leu Asp
145                 150                 155                 160

Cys Pro Leu Trp Val Thr Ser Cys Ser Asp Asp Asn Lys Ser Glu Lys
                165                 170                 175

Thr Asn Glu Lys Lys Pro Asp Arg Val Arg Arg Gly Ala Met Lys Ile
            180                 185                 190

Thr Pro Lys Glu Ser Glu Lys Asp Ser Arg Ser Lys Pro Pro Asp Ala
        195                 200                 205

Thr Ile Val Val Glu Gly Ile Lys Tyr Gln Val Lys Lys Gly Lys
    210                 215                 220

Val Lys Gly Lys Asn Thr Gln Asp Gly Leu Tyr His Asn Lys Asn Lys
225                 230                 235                 240

Pro Pro Glu Ser Arg Lys Lys Leu Glu Lys Ala Leu Leu Ala Trp Ala
                245                 250                 255

Ile Ile Ala Ile Phe Met Trp Glu Pro Val Ala Pro Glu Asn Val Thr
            260                 265                 270

Gln Trp Asn Leu Ser Asp Asn Gly Thr Thr Gly Ile Gln Leu Leu Met
        275                 280                 285

Phe Gln Arg Gly Val Asn Arg Ser Leu His Gly Ile Trp Pro Glu Lys
    290                 295                 300

Ile Cys Thr Gly Val Pro Thr His Leu Ala Thr Asp Ala Glu Leu Lys
305                 310                 315                 320

Gly Ile Gln Gly Met Met Asp Ala Ser Glu Lys Thr Asn Tyr Thr Cys
                325                 330                 335

Cys Arg Leu Gln Arg His Glu Trp Asn Lys Tyr Gly Cys Asn Trp
            340                 345                 350

Tyr Asn Ile Asn Pro Trp Ile Trp Leu Met Asn Lys Thr Gln Ala Asn
        355                 360                 365

Leu Thr Glu Gly Pro Pro Glu Lys Glu Cys Ala Val Thr Cys Arg Phe
    370                 375                 380

Asp Lys Glu Ala Asp Ile Asn Ile Val Thr Gln Ala Arg Asp Arg Pro
385                 390                 395                 400

Thr Thr Leu Thr Gly Cys Lys Lys Gly Lys Lys Phe Ser Phe Ala Gly
                405                 410                 415

Met Ile Ile Glu Gly Pro Cys Asn Phe Asn Val Ser Val Glu Asp Ile
            420                 425                 430
```

-continued

```
Leu Phe Gly Asp Asn Glu Ser Ser Leu Phe Gln Asp Thr Ala Leu Tyr
            435                 440                 445
Val Val Asp Gly Val Thr Asn Thr Val Glu Asn Ala Arg Gln Gly Ala
450                 455                 460
Ala Lys Leu Thr Ser Trp Leu Gly Lys Gln Leu Gly Ile Met Gly Lys
465                 470                 475                 480
Lys Leu Glu His Lys Ser Lys Thr Trp Phe Gly Ala Asn Ala Gln Ser
                485                 490                 495
Pro Tyr Cys Asn Val Thr Arg Lys Ile Gly Tyr Val Trp Tyr Thr Asn
            500                 505                 510
Asn Cys Thr Pro Ala Cys Leu Pro Lys Asn Thr Lys Ile Ile Gly Pro
            515                 520                 525
Gly Lys Phe Asp Thr Asn Ala Glu Asp Gly Lys Ile Leu His Glu Met
        530                 535                 540
Arg Gly His Ile Ser Glu Phe Ile Leu Leu Ser Leu Val Val Leu Ser
545                 550                 555                 560
Asp Phe Ala Pro Glu Thr Ala Ser Thr Leu Tyr Leu Val Leu His Phe
                565                 570                 575
Ala Leu Pro Gln Thr His Glu Val Pro Ser Val Cys Asp Thr Asn Gln
            580                 585                 590
Leu Asn Leu Thr Val Ser Leu Arg Val Asp Asp Val Ile Pro Ser Ser
        595                 600                 605
Val Trp Asn Leu Gly Lys Tyr Val Cys Val Arg Pro Asp Trp Trp Pro
610                 615                 620
Tyr Glu Thr Thr Met Val Leu Leu Phe Glu Glu Ala Gly Gln Val Val
625                 630                 635                 640
Lys Leu Val Leu Arg Ala Ile Arg Asp Leu Thr Arg Val Trp Asn Ser
                645                 650                 655
Ala Ser Thr Thr Ala Phe Leu Ile Cys Leu Val Lys Val Leu Arg Gly
            660                 665                 670
Gln Val Val Gln Gly Leu Val Trp Leu Leu Leu Val Thr Gly Ala Gln
        675                 680                 685
Gly Gln Phe Ala Cys Arg Glu Asp Tyr Arg Tyr Ala Leu Ala Arg Thr
690                 695                 700
Lys Glu Ile Gly Ala Leu Gly Ala Glu Ser Leu Thr Thr Thr Trp Thr
705                 710                 715                 720
Asp Tyr Arg Gly Asn Leu Glu Leu Asp Asp Gly Thr Val Arg Ala Thr
                725                 730                 735
Cys Ser Arg Gly Phe Phe Arg Phe Arg Gly His Cys Met Ile Gly Pro
            740                 745                 750
Arg Tyr Leu Ala Ser Leu His Leu Arg Ala Leu Pro Thr Ser Val Thr
        755                 760                 765
Phe Glu Leu Ile Pro Gly Gly Ser Ala Met Thr Glu Glu Met Gly
770                 775                 780
Asp Asp Phe Glu Phe Gly Leu Cys Pro Cys Asp Ser Arg Pro Val Val
785                 790                 795                 800
Lys Gly Lys Tyr Asn Thr Thr Leu Leu Asn Gly Ser Ala Phe Gln Leu
                805                 810                 815
Ile Cys Pro Tyr Gly Trp Val Gly Arg Val Glu Cys Thr Thr Val Ser
            820                 825                 830
Lys Ser Thr Leu Ala Thr Glu Val Val Lys Ile Tyr Lys Lys Thr Lys
        835                 840                 845
Pro Phe Pro Gln Arg Val Gly Cys Asp His Thr Thr Val Tyr Lys Gln
```

```
                  850                 855                 860
Asp Leu Tyr His Cys Gln Met Gly Gly Asn Trp Thr Cys Met Arg Gly
865                 870                 875                 880

Glu Val Val Lys Tyr Val Gly Gly Pro Val Lys Lys Cys Glu Trp Cys
                    885                 890                 895

Gly Tyr Val Phe Lys Lys Arg Glu Gly Leu Pro His Tyr Pro Ile Gly
                900                 905                 910

Arg Cys Met Leu Arg Asn Glu Thr Gly Tyr Arg Ser Val Asp Asp Thr
            915                 920                 925

Pro Cys Asp Arg Gly Val Val Ile Ser Lys Thr Gly Glu Leu Glu
        930                 935                 940

Cys Leu Ile Gly Lys Thr Thr Val Lys Val Phe Ser Ser Asp Lys Lys
945                 950                 955                 960

Leu Gly Pro Met Pro Cys Arg Pro Lys Glu Val Ile Ser Ser Glu Gly
                965                 970                 975

Pro Val Ser Lys Ile Ala Cys Thr Phe Asn Tyr Ser Lys Thr Leu Glu
                980                 985                 990

Asn Lys Tyr Tyr Glu Pro Arg Asp Ser Tyr Phe Gln Gln Tyr Met Leu
            995                 1000                1005

Lys Gly Gln Tyr Gln Tyr Trp Phe Asp Leu Glu Ala Thr Asp His
    1010                1015                1020

His Ser Asp Tyr Phe Ala Glu Phe Ile Met Leu Ala Val Val Ala
    1025                1030                1035

Leu Leu Gly Gly Arg Tyr Val Leu Trp Leu Met Val Val Tyr Met
    1040                1045                1050

Ile Leu Ala Asp Gln Met Thr Ser Ala Ile Asn Leu Gly Gln Gly
    1055                1060                1065

Glu Val Val Leu Ile Gly Asn Leu Ile Thr His Glu Asp His Glu
    1070                1075                1080

Val Val Val Tyr Phe Leu Leu Leu Tyr Leu Ile Val Lys Asp Glu
    1085                1090                1095

Pro Val Lys Lys Trp Ile Leu Phe Leu Phe His Ala Met Thr Asn
    1100                1105                1110

Asn Pro Val Lys Thr Ile Ser Val Gly Leu Leu Met Leu Ser Gly
    1115                1120                1125

Leu Val Lys Gly Glu Gly Ala Gly Met Thr Tyr Trp Glu Gly Leu
    1130                1135                1140

Asp Leu Gln Phe Thr Leu Leu Val Met Ile Thr Ala Ser Leu Leu
    1145                1150                1155

Val Ala Arg Arg Asp Val Thr Thr Tyr Pro Leu Ile Ile Thr Val
    1160                1165                1170

Ile Ala Leu Lys Thr Thr Trp Val Asn Ser Gly Pro Gly Ile Asp
    1175                1180                1185

Ala Ala Ile Ala Thr Ile Thr Gly Leu Leu Met Trp Thr Phe
    1190                1195                1200

Ile Ser Asp Tyr Tyr Lys Tyr Lys Gln Trp Thr Gln Phe Leu Ile
    1205                1210                1215

Ser Ile Val Ser Gly Ile Phe Leu Ile Arg Thr Leu Lys Trp Ile
    1220                1225                1230

Gly Gly Leu Glu Leu His Ala Pro Glu Leu Pro Ser Tyr Arg Pro
    1235                1240                1245

Leu Phe Phe Ile Leu Thr Tyr Leu Ile Ser Ala Ala Ile Val Thr
    1250                1255                1260
```

-continued

```
Arg Trp Asn Leu Asp Ile Ala Gly Val Leu Leu Gln Cys Val Pro
    1265                1270                1275

Thr Ile Leu Met Val Leu Thr Leu Trp Ala Asp Leu Leu Thr Leu
    1280                1285                1290

Ile Leu Ile Leu Pro Thr Tyr Glu Leu Ala Lys Leu Tyr Tyr Leu
    1295                1300                1305

Lys Gly Val Lys Asn Gly Met Glu Arg Asn Trp Leu Gly Arg Ile
    1310                1315                1320

Thr Tyr Lys Arg Val Ser Asp Val Tyr Glu Ile Asp Glu Ser Gln
    1325                1330                1335

Glu Ala Val Tyr Leu Phe Pro Ser Lys Leu Lys Glu Gly Thr Ile
    1340                1345                1350

Thr Gly Gly Leu Leu Pro Leu Ile Lys Ala Ile Leu Ile Ser Cys
    1355                1360                1365

Ile Ser Ser Lys Trp Gln Cys Phe Tyr Leu Leu Tyr Leu Val Val
    1370                1375                1380

Glu Val Ser Tyr Tyr Leu His Lys Lys Ile Ile Glu Glu Val Ala
    1385                1390                1395

Gly Gly Thr Asn Leu Ile Ser Arg Leu Val Ala Ala Leu Leu Glu
    1400                1405                1410

Val Asn Trp Arg Phe Asp Asn Glu Glu Thr Lys Gly Leu Lys Lys
    1415                1420                1425

Phe Tyr Leu Ile Ser Gly Gln Val Lys Asn Leu Ile Ile Lys His
    1430                1435                1440

Lys Val Arg Asn Glu Val Val Ala His Trp Phe Asn Glu Glu Glu
    1445                1450                1455

Val Tyr Gly Met Pro Lys Leu Val Ser Val Val Lys Ala Ala Thr
    1460                1465                1470

Leu Asn Arg Ser Arg His Cys Ile Leu Cys Thr Val Cys Glu Ser
    1475                1480                1485

Arg Asp Trp Lys Gly Glu Thr Cys Pro Lys Cys Gly Arg Phe Gly
    1490                1495                1500

Pro Ser Leu Ser Cys Gly Met Thr Leu Ser Asp Phe Glu Glu Arg
    1505                1510                1515

His Tyr Lys Lys Ile Phe Ile Arg Glu Asp Gln Ser Asp Gly Pro
    1520                1525                1530

Phe Arg Glu Glu Tyr Lys Gly Tyr Leu Gln Tyr Lys Ala Arg Gly
    1535                1540                1545

Gln Leu Phe Leu Arg Asn Leu Pro Ile Leu Ala Thr Lys Val Lys
    1550                1555                1560

Leu Leu Leu Val Gly Asn Leu Gly Ser Glu Val Gly Asp Leu Glu
    1565                1570                1575

His Leu Gly Trp Ile Leu Arg Gly Pro Ala Val Cys Lys Lys Ile
    1580                1585                1590

Ile Asp His Glu Arg Cys His Val Ser Ile Met Asp Lys Leu Thr
    1595                1600                1605

Ala Phe Phe Gly Ile Met Pro Arg Gly Thr Thr Pro Arg Ala Pro
    1610                1615                1620

Ile Arg Phe Pro Thr Ser Leu Leu Arg Ile Arg Arg Gly Leu Glu
    1625                1630                1635

Thr Gly Trp Ala Tyr Thr His Gln Gly Gly Ile Ser Ser Val Asp
    1640                1645                1650
```

His Val Thr Ala Gly Lys Asp Leu Leu Val Cys Asp Ser Met Gly
1655                1660                1665

Arg Thr Arg Val Val Cys Gln Ser Asn Asn Arg Met Thr Asp Glu
1670                1675                1680

Thr Glu Tyr Gly Val Lys Thr Asp Ser Gly Cys Pro Glu Gly Ala
1685                1690                1695

Arg Cys Tyr Val Phe Asn Pro Glu Ala Val Asn Ile Ser Gly Thr
1700                1705                1710

Lys Gly Ala Met Val His Leu Gln Lys Thr Gly Gly Glu Phe Thr
1715                1720                1725

Cys Val Thr Ala Ser Gly Thr Pro Ala Phe Phe Asp Leu Lys Asn
1730                1735                1740

Leu Lys Gly Trp Ser Gly Leu Pro Ile Phe Glu Ala Ser Ser Gly
1745                1750                1755

Arg Val Val Gly Arg Val Lys Val Gly Lys Asn Glu Glu Ser Lys
1760                1765                1770

Pro Thr Lys Leu Met Ser Gly Ile Gln Thr Val Ser Lys Ser Thr
1775                1780                1785

Thr Asp Leu Thr Asp Met Val Lys Lys Ile Thr Thr Met Asn Arg
1790                1795                1800

Gly Glu Phe Lys Gln Ile Thr Leu Ala Thr Gly Ala Gly Lys Thr
1805                1810                1815

Thr Glu Leu Pro Arg Ala Val Ile Glu Glu Ile Gly Arg His Lys
1820                1825                1830

Arg Val Leu Val Leu Ile Pro Leu Arg Ala Ala Ala Glu Ser Val
1835                1840                1845

Tyr Gln Tyr Met Arg Gln Lys His Pro Ser Ile Ala Phe Asn Leu
1850                1855                1860

Arg Ile Gly Glu Met Lys Glu Gly Asp Met Ala Thr Gly Ile Thr
1865                1870                1875

Tyr Ala Ser Tyr Gly Tyr Phe Cys Gln Met Pro Gln Pro Lys Leu
1880                1885                1890

Arg Ala Ala Met Val Glu Tyr Ser Tyr Ile Phe Leu Asp Glu Tyr
1895                1900                1905

His Cys Ala Thr Pro Glu Gln Leu Ala Ile Ile Gly Lys Ile His
1910                1915                1920

Arg Phe Ser Glu Gln Leu Arg Val Val Ala Met Thr Ala Thr Pro
1925                1930                1935

Ala Gly Thr Val Thr Thr Thr Gly Gln Lys His Pro Ile Glu Glu
1940                1945                1950

Phe Ile Ala Pro Glu Val Met Lys Gly Glu Asp Leu Gly Ser Glu
1955                1960                1965

Phe Leu Glu Ile Ala Gly Leu Lys Ile Pro Thr Glu Glu Met Lys
1970                1975                1980

Gly Asn Met Leu Val Phe Val Pro Thr Arg Asn Met Ala Val Glu
1985                1990                1995

Thr Ala Lys Lys Leu Lys Ala Lys Gly Tyr Asn Ser Gly Tyr Tyr
2000                2005                2010

Tyr Ser Gly Glu Asp Pro Ala Asn Leu Arg Val Val Thr Ser Gln
2015                2020                2025

Ser Pro Tyr Val Val Val Ala Thr Asn Ala Ile Glu Ser Gly Val
2030                2035                2040

Thr Leu Pro Asp Leu Asp Val Val Val Asp Thr Gly Leu Lys Cys

-continued

```
            2045                2050                2055
Glu Lys Arg Ile Arg Leu Ser Ser Lys Met Pro Phe Ile Val Thr
            2060                2065                2070
Gly Leu Lys Arg Met Ala Val Thr Ile Gly Glu Gln Ala Gln Arg
            2075                2080                2085
Arg Gly Arg Val Gly Arg Val Lys Pro Gly Arg Tyr Tyr Arg Ser
            2090                2095                2100
Gln Glu Thr Ala Val Gly Ser Lys Asp Tyr His Tyr Asp Leu Leu
            2105                2110                2115
Gln Ala Gln Arg Tyr Gly Ile Glu Asp Gly Ile Asn Ile Thr Lys
            2120                2125                2130
Ser Phe Arg Glu Met Asn Tyr Asp Trp Ser Leu Tyr Glu Glu Asp
            2135                2140                2145
Ser Leu Met Ile Thr Gln Leu Glu Ile Leu Asn Asn Leu Leu Ile
            2150                2155                2160
Ser Glu Glu Leu Pro Val Ala Val Lys Asn Ile Met Ala Arg Thr
            2165                2170                2175
Asp His Pro Glu Pro Ile Gln Leu Ala Tyr Asn Ser Tyr Glu Val
            2180                2185                2190
Gln Val Pro Val Leu Phe Pro Lys Ile Arg Asn Gly Glu Val Thr
            2195                2200                2205
Asp Ser Tyr Asp Ser Tyr Ser Phe Leu Asn Ala Arg Lys Leu Gly
            2210                2215                2220
Asp Asp Val Pro Ala Tyr Val Tyr Ala Thr Glu Asp Glu Asp Leu
            2225                2230                2235
Ala Val Glu Leu Leu Gly Met Asp Trp Pro Asp Pro Gly Asn Gln
            2240                2245                2250
Gly Thr Val Glu Thr Gly Arg Ala Leu Lys Gln Val Thr Gly Leu
            2255                2260                2265
Ser Ala Ala Glu Asn Ala Leu Leu Val Ala Leu Phe Gly Tyr Val
            2270                2275                2280
Gly Tyr Gln Ala Leu Ser Lys Arg His Val Pro Met Val Thr Asp
            2285                2290                2295
Ile Tyr Ser Ile Glu Asp His Arg Leu Glu Asp Thr Thr His Leu
            2300                2305                2310
Gln Phe Ala Pro Asn Ala Ile Arg Thr Asp Gly Lys Glu Thr Glu
            2315                2320                2325
Leu Lys Glu Leu Ala Gln Gly Asp Ile Gln Arg Cys Ala Glu Ala
            2330                2335                2340
Met Val Gly Tyr Ala Gln Gln Gly Val Gln Phe Ile Lys Thr Gln
            2345                2350                2355
Ala Leu Lys Val Gln Glu Asn His Val Phe Lys Asp Ser Ala Asp
            2360                2365                2370
Thr Ile Val Glu Tyr Val Asp Lys Phe Met Lys Ala Ile Ala Glu
            2375                2380                2385
Ser Lys Asp Asp Ile Leu Arg Tyr Gly Leu Trp Gly Ala His Thr
            2390                2395                2400
Ala Leu Tyr Lys Ser Ile Gly Ala Arg Leu Gly Tyr Glu Thr Ala
            2405                2410                2415
Phe Ala Thr Leu Val Ile Lys Trp Leu Ala Phe Gly Gly Glu Ser
            2420                2425                2430
Ile Asn Asp His Val Lys Gln Ala Ala Thr Asp Leu Val Val Tyr
            2435                2440                2445
```

```
Tyr Ile Ile Asn Arg Pro Gln Phe Pro Gly Asp Thr Glu Thr Gln
        2450                2455                2460

Gln Glu Gly Arg Lys Phe Val Ala Ser Leu Leu Val Ser Ala Leu
        2465                2470                2475

Ala Thr Tyr Thr Tyr Lys Ser Trp Asn Tyr Ser Asn Leu Ser Lys
        2480                2485                2490

Val Val Glu Pro Ala Leu Ala Cys Leu Pro Tyr Ala Ser Gln Ala
        2495                2500                2505

Leu Lys Leu Phe Ala Pro Thr Arg Leu Glu Ser Val Val Ile Leu
        2510                2515                2520

Ser Thr Ala Ile Tyr Lys Thr Tyr Leu Ala Ile Arg Arg Gly Arg
        2525                2530                2535

Ser Asp Gly Leu Leu Gly Thr Gly Val Ser Ala Ala Met Glu Ile
        2540                2545                2550

Met Ser Gln Asn Pro Val Ser Val Gly Ile Ala Val Met Leu Gly
        2555                2560                2565

Val Gly Ala Val Ala Ala His Asn Ala Ile Glu Ser Ser Glu Gln
        2570                2575                2580

Lys Arg Thr Leu Leu Met Lys Val Phe Val Lys Asn Phe Leu Asp
        2585                2590                2595

Gln Ala Ala Thr Asp Glu Leu Val Lys Glu Ser Pro Glu Lys Ile
        2600                2605                2610

Ile Thr Ala Leu Phe Glu Ala Val Gln Thr Val Gly Asn Pro Leu
        2615                2620                2625

Arg Leu Ile Tyr His Leu Tyr Gly Val Phe Tyr Lys Gly Trp Glu
        2630                2635                2640

Ala Lys Glu Val Ala Glu Lys Thr Ala Gly Arg Asn Leu Phe Thr
        2645                2650                2655

Leu Ile Met Phe Glu Ala Val Glu Leu Leu Gly Val Asp Ser Glu
        2660                2665                2670

Gly Lys Met Arg Arg Leu Ser Gly Asn Tyr Leu Ile Glu Leu Leu
        2675                2680                2685

Gln Lys Leu His Asp Gly Phe Arg Ile Ser Ile Lys Lys Phe Ala
        2690                2695                2700

Leu Gly Trp Ala Pro Gly Pro Phe Ser Cys Asn Trp Thr Pro Ala
        2705                2710                2715

Asp Asn Arg Ile Arg Leu Pro His Glu Asn Tyr Leu Arg Val Val
        2720                2725                2730

Thr Arg Cys Arg Cys Gly Tyr Arg Thr Lys Ala Val Lys Asn Cys
        2735                2740                2745

Ala Gly Glu Leu Ile Leu Glu Glu Glu Gly Ser Phe Phe Cys
        2750                2755                2760

Arg Asn Lys Phe Gly Arg Gly Ala Pro Asn Tyr Lys Val Thr Lys
        2765                2770                2775

Phe Tyr Asp Gly Asn Leu Glu Glu Ile Arg Ala Arg Leu Lys Leu
        2780                2785                2790

Glu Gly Gln Val Glu Met Tyr Tyr Lys Gly Ala Thr Ile Lys Ile
        2795                2800                2805

Asp Tyr Ser Asn Asn Lys Leu Ile Leu Ala Thr Asp Lys Trp Glu
        2810                2815                2820

Val Glu His Ser Tyr Ile Thr Arg Leu Thr Lys Arg Tyr Thr Gly
        2825                2830                2835
```

-continued

```
Ala Gly Tyr Lys Gly Ala Phe Leu Gly Asp Glu Pro  Asn His Lys
2840                2845                2850

Ser Leu Ile Glu Arg Thr Cys Ala Thr Val Cys Lys  Asp Lys Ile
2855                2860                2865

Tyr Phe Ser Lys Met Lys Lys Gly Cys Ala Phe Thr  Tyr Asp Leu
2870                2875                2880

Ser Leu Ser Asn Leu Val Arg Leu Val Asp Leu Val  His Arg Asn
2885                2890                2895

Lys Leu Glu Glu Lys Asp Ile Pro Glu Arg Thr Val  Thr Thr Trp
2900                2905                2910

Leu Ala Tyr Thr Phe Val Asn Glu Asp Val Gly Thr  Ile Lys Pro
2915                2920                2925

Val Leu Gly Glu Lys Val Ile Pro Glu Glu Ser Asp  Glu Ile Asn
2930                2935                2940

Leu Gln Pro Thr Val Thr Val Asn Met Ser Lys Cys  Gln Val Thr
2945                2950                2955

Val Val Gly Glu Ala Lys Asn Met Thr Thr Gly Val  Val Pro Leu
2960                2965                2970

Thr Val Thr Lys Glu Ala Cys Asn Gly Gln Asp Arg  Ser Val Leu
2975                2980                2985

Asn Ile Gly Met Glu Glu Gly Glu Tyr Pro Gly Pro  Ala Val Ser
2990                2995                3000

Thr Val Thr Val Gly Glu Ala Val Gln Ser Lys Asp  Val Arg Pro
3005                3010                3015

Tyr Val Leu Val Ile Gly Ser Asn Lys Ala Thr Ser  Asn Arg Ala
3020                3025                3030

Lys Thr Ala Lys Asn Val Lys Leu Tyr Lys Gly Gly  Asp Ala Val
3035                3040                3045

Glu Val Arg Asp Leu Ile Lys Lys Gly Glu Met Leu  Val Val Ala
3050                3055                3060

Leu Ala Asp Val Glu Gln Asp Leu Leu Glu Tyr Val  Asp Tyr Lys
3065                3070                3075

Gly Thr Phe Leu Thr Arg Glu Thr Leu Glu Ala Leu  Ser Leu Gly
3080                3085                3090

Lys Pro Lys Ala Lys Asn Ile Thr Lys Ala Asp Ala  His Arg Leu
3095                3100                3105

Leu Asn Pro Glu Lys Glu Gln Ile Gly Leu Pro Asp  Trp Phe Thr
3110                3115                3120

Ala Thr Glu Pro Ile Phe Leu Glu Ala Met Ile Lys  Gln Glu Lys
3125                3130                3135

Tyr His Ile Thr Gly Asp Val Ala Thr Val Lys Asp  Lys Ala Lys
3140                3145                3150

Gln Leu Gly Ala Thr Asp Ser Thr Arg Ile Val Lys  Glu Val Gly
3155                3160                3165

Ala Arg Val Tyr Thr Met Lys Leu Asn Ser Trp Ala  Leu Gln Ala
3170                3175                3180

Glu Arg Gly Asp Ala Asn Leu Lys Pro Leu Phe Glu  Glu Leu Leu
3185                3190                3195

Leu Gln Cys Pro Pro Gly Arg Thr Val Lys Gly Gly  Thr Met Val
3200                3205                3210

Ser Ala Tyr Gln Leu Ala Gln Gly Asn Trp Thr Pro  Thr Ser Cys
3215                3220                3225

Lys Val Tyr Met Gly Thr Ile Thr Ala Lys Arg Val  Lys Ile His
```

```
                    3230              3235              3240

Pro Tyr Glu Ala Tyr Ile Lys Leu Lys Glu Leu Ile Glu Glu Tyr
    3245              3250              3255

Asn Met Lys Arg Val Thr Gly Asp Thr Gly Leu Lys Arg His Asn
    3260              3265              3270

Glu Trp Ile Leu Lys Arg Ile Lys His His Gly Asn Leu Arg Thr
    3275              3280              3285

Lys Lys Ile Leu Asn Pro Gly Lys Val Ala Glu Gln Leu Ser Arg
    3290              3295              3300

Glu Gly His Lys His Asn Val Tyr Asn Lys Ile Gly Ser Thr
    3305              3310              3315

Met Ala Ser Val Gly Ile Lys Leu Glu Lys Leu Pro Val Val Arg
    3320              3325              3330

Ala Gln Thr Asp Thr Thr Phe Phe His Gln Ala Ile Arg Asp Lys
    3335              3340              3345

Ile Asp Lys Glu Glu Asn Pro Gln Thr Pro Asp Leu His Lys Glu
    3350              3355              3360

Leu Lys Glu Val Phe Asn Ala Leu Lys Ile Pro Glu Leu Ala Ala
    3365              3370              3375

Thr Tyr Asp Ala Val Glu Trp Glu Glu Leu Glu Thr Gly Ile Asn
    3380              3385              3390

Arg Lys Gly Ala Ala Gly Phe Phe Glu Arg Lys Asn Ile Gly Glu
    3395              3400              3405

Ile Leu Asp Thr Glu Lys Asn Lys Val Glu Asp Ile Ile Arg Asp
    3410              3415              3420

Leu Lys Ser Gly Arg Pro Ile Lys Tyr Tyr Glu Thr Ala Ile Pro
    3425              3430              3435

Lys Asn Glu Lys Arg Asp Val Asn Asp Asp Trp Glu Ser Gly Asp
    3440              3445              3450

Phe Val Asp Glu Lys Lys Pro Arg Val Ile Gln Tyr Pro Glu Ala
    3455              3460              3465

Lys Val Arg Leu Ala Ile Thr Lys Val Met Tyr Lys Trp Val Lys
    3470              3475              3480

Gln Lys Pro Val Val Ile Pro Gly Tyr Glu Gly Lys Thr Pro Leu
    3485              3490              3495

Phe Glu Ile Phe Asp Lys Val Lys Lys Trp Gly Ser Phe Asp
    3500              3505              3510

Asn Pro Val Ala Val Ser Phe Asp Thr Lys Ala Trp Asp Thr Gln
    3515              3520              3525

Val Thr Ser Lys Ser Leu Glu Leu Ile Arg Asp Ile Gln Lys Tyr
    3530              3535              3540

Tyr Phe Lys Lys Glu Trp His Lys Phe Ile Glu Thr Ile Thr Glu
    3545              3550              3555

His Met Val Glu Val Pro Val Val Thr Ala Asp Gly Glu Val Tyr
    3560              3565              3570

Ile Ser Glu Gly Gln Arg Gly Ser Gly Gln Pro Asp Thr Ser Ala
    3575              3580              3585

Gly Asn Ser Met Leu Asn Val Leu Thr Met Val Tyr Ala Phe Cys
    3590              3595              3600

Arg Ala Thr Gly Val Pro Tyr Lys Ser Phe Lys Arg Val Ala Lys
    3605              3610              3615

Ile His Val Cys Gly Asp Asp Gly Phe Leu Ile Thr Glu Lys Ser
    3620              3625              3630
```

```
Leu Gly Glu Lys Phe Ala Ser Lys Gly Ile Gln Ile Leu His Glu
    3635                3640                3645

Ala Gly Lys Pro Gln Lys Ile Thr Glu Gly Asp Arg Met Lys Val
    3650                3655                3660

Ala Tyr Lys Phe Glu Asp Ile Glu Phe Cys Ser His Thr Pro Val
    3665                3670                3675

Pro Val Arg Trp Ser Asp Asn Thr Thr Ser Tyr Met Pro Gly Arg
    3680                3685                3690

Asn Thr Ala Thr Ile Leu Ala Lys Met Ala Thr Arg Leu Asp Ser
    3695                3700                3705

Ser Gly Glu Arg Gly Thr Thr Ala Tyr Glu Lys Ala Val Ala Phe
    3710                3715                3720

Ser Phe Leu Leu Met Tyr Ser Trp Asn Pro Leu Val Arg Arg Ile
    3725                3730                3735

Cys Leu Leu Thr Leu Ser Ser Glu Leu Gly Thr Lys Pro Ser Lys
    3740                3745                3750

Arg Thr Thr Tyr Tyr Tyr Glu Gly Asp Pro Ile Ser Ala Tyr Arg
    3755                3760                3765

Glu Val Ile Gly His Asn Leu Leu Asp Leu Lys Arg Thr Gly Leu
    3770                3775                3780

Glu Lys Leu Ala Leu Leu Asn Leu Ser Met Ser Thr Leu Gly Ile
    3785                3790                3795

Trp Thr Lys His Ile Ser Lys Arg Leu Leu Gln Asp Cys Val Asp
    3800                3805                3810

Val Gly Ser Lys Asp Gly Asn Trp Leu Val Asn Ala Asp Arg Pro
    3815                3820                3825

Glu Ser Arg Lys Thr Gly Lys Val Tyr Leu Gln Ser Gly Gly His
    3830                3835                3840

Thr Val Arg Gly Arg His Tyr Glu Asp Leu Ile Leu Pro Arg Met
    3845                3850                3855

Val Lys Pro Thr Phe Gln Gly Val Asp Arg Tyr Lys Leu Gly Pro
    3860                3865                3870

Ile Val Asn Val Ile Phe Arg Arg Leu Arg Val Met Met Met Ala
    3875                3880                3885

Leu Val Gly Arg Gly Met
    3890

<210> SEQ ID NO 12
<211> LENGTH: 3895
<212> TYPE: PRT
<213> ORGANISM: BVDV

<400> SEQUENCE: 12

Met Glu Leu Asn Lys Phe Glu Leu Leu Tyr Lys Thr Ser Lys Gln Lys
1               5                   10                  15

Pro Val Gly Val Thr Glu Pro Ile Tyr Asp Ser Ala Gly Asn Pro Ile
            20                  25                  30

Tyr Gly Glu Arg Ser Thr Ile His Pro Gln Ser Thr Leu Lys Leu Pro
        35                  40                  45

His Glu Arg Gly Val Ala Glu Val Val Thr Thr Leu Arg Asp Leu Pro
    50                  55                  60

Lys Lys Gly Asp Cys Arg Ser Gly Asn His Arg Gly Pro Val Ser Gly
65                  70                  75                  80

Ile Tyr Ile Lys Pro Gly Pro Val Leu Tyr Gln Asp Tyr Lys Gly Pro
```

```
                85                  90                  95
Val Tyr His Arg Ala Pro Leu Glu Leu Phe Val Glu Thr Gln Phe Cys
                100                 105                 110

Glu Val Thr Lys Arg Ile Gly Arg Val Thr Gly Ser Asp Gly Arg Leu
        115                 120                 125

Tyr His Leu Tyr Ile Cys Ser Asp Gly Cys Ile Leu Leu Lys Thr Ala
    130                 135                 140

Ser Lys Thr Arg Ser Ala Val Leu Lys Trp Thr Arg Asn Ile Leu Asp
145                 150                 155                 160

Cys Pro Leu Trp Val Thr Ser Cys Ser Asp Asp Asn Lys Ser Glu Lys
                165                 170                 175

Thr Asn Glu Lys Lys Pro Asp Arg Val Arg Arg Gly Ala Met Lys Ile
                180                 185                 190

Thr Pro Lys Glu Ser Glu Lys Asp Ser Arg Ser Lys Pro Pro Asp Ala
                195                 200                 205

Thr Ile Val Val Glu Gly Ile Lys Tyr Gln Val Lys Lys Gly Lys
        210                 215                 220

Val Lys Gly Lys Asn Thr Gln Asp Gly Leu Tyr His Asn Lys Asn Lys
225                 230                 235                 240

Pro Pro Glu Ser Arg Lys Lys Leu Glu Lys Ala Leu Leu Ala Trp Ala
                245                 250                 255

Ile Ile Ala Ile Phe Met Trp Glu Pro Val Ala Pro Glu Asn Val Thr
                260                 265                 270

Gln Trp Asn Leu Ser Asp Asn Gly Thr Thr Gly Ile Gln Leu Leu Met
                275                 280                 285

Phe Gln Arg Gly Val Asn Arg Ser Leu His Gly Ile Trp Pro Glu Lys
                290                 295                 300

Ile Cys Thr Gly Val Pro Thr His Leu Ala Thr Asp Ala Glu Leu Lys
305                 310                 315                 320

Gly Ile Gln Gly Met Met Asp Ala Ser Glu Lys Thr Asn Tyr Thr Cys
                325                 330                 335

Cys Arg Leu Gln Arg His Glu Trp Asn Lys Tyr Gly Trp Cys Asn Trp
                340                 345                 350

Tyr Asn Ile Asn Pro Trp Ile Trp Leu Met Asn Lys Thr Gln Ala Asn
                355                 360                 365

Leu Thr Glu Gly Pro Pro Glu Lys Glu Cys Ala Val Thr Cys Arg Phe
            370                 375                 380

Asp Lys Glu Ala Asp Ile Asn Ile Val Thr Gln Ala Arg Asp Arg Pro
385                 390                 395                 400

Thr Thr Leu Thr Gly Cys Lys Lys Gly Lys Lys Phe Ser Phe Ala Gly
                405                 410                 415

Met Ile Ile Glu Gly Pro Cys Asn Phe Asn Val Ser Val Glu Asp Ile
                420                 425                 430

Leu Phe Gly Asp Asn Glu Ser Ser Ser Leu Phe Gln Asp Thr Ala Leu
                435                 440                 445

Tyr Val Val Asp Gly Val Thr Asn Thr Val Glu Asn Ala Arg Gln Gly
            450                 455                 460

Ala Ala Lys Leu Thr Ser Trp Leu Gly Lys Gln Leu Gly Ile Met Gly
465                 470                 475                 480

Lys Lys Leu Glu His Lys Ser Lys Thr Trp Phe Gly Ala Asn Ala Gln
                485                 490                 495

Ser Pro Tyr Cys Asn Val Thr Arg Lys Ile Gly Tyr Val Trp Tyr Thr
                500                 505                 510
```

```
Asn Asn Cys Thr Pro Ala Cys Leu Pro Lys Asn Thr Lys Ile Ile Gly
        515                 520                 525

Pro Gly Lys Phe Asp Thr Asn Ala Glu Asp Gly Lys Ile Leu His Glu
530                 535                 540

Met Arg Gly His Ile Ser Glu Phe Ile Leu Leu Ser Leu Val Val Leu
545                 550                 555                 560

Ser Asp Phe Ala Pro Glu Thr Ala Ser Thr Leu Tyr Leu Val Leu His
                565                 570                 575

Phe Ala Leu Pro Gln Thr His Glu Val Pro Ser Val Cys Asp Thr Asn
                580                 585                 590

Gln Leu Asn Leu Thr Val Ser Leu Arg Val Asp Val Ile Pro Ser
            595                 600                 605

Ser Val Trp Asn Leu Gly Lys Tyr Val Cys Val Arg Pro Asp Trp Trp
        610                 615                 620

Pro Tyr Glu Thr Thr Met Val Leu Leu Phe Glu Ala Gly Gln Val
625                 630                 635                 640

Val Lys Leu Val Leu Arg Ala Ile Arg Asp Leu Thr Arg Val Trp Asn
                645                 650                 655

Ser Ala Ser Thr Thr Ala Phe Leu Ile Cys Leu Val Lys Val Leu Arg
            660                 665                 670

Gly Gln Val Val Gln Gly Leu Val Trp Leu Leu Val Thr Gly Ala
        675                 680                 685

Gln Gly Gln Phe Ala Cys Arg Glu Asp Tyr Arg Tyr Ala Leu Ala Arg
690                 695                 700

Thr Lys Glu Ile Gly Ala Leu Gly Ala Glu Ser Leu Thr Thr Thr Trp
705                 710                 715                 720

Thr Asp Tyr Arg Gly Asn Leu Glu Leu Asp Asp Gly Thr Val Arg Ala
                725                 730                 735

Thr Cys Ser Arg Gly Phe Phe Arg Phe Arg Gly His Cys Met Ile Gly
            740                 745                 750

Pro Arg Tyr Leu Ala Ser Leu His Leu Arg Ala Leu Pro Thr Ser Val
        755                 760                 765

Thr Phe Glu Leu Ile Pro Gly Gly Ser Ala Met Thr Glu Glu Met
770                 775                 780

Gly Asp Asp Phe Glu Phe Gly Leu Cys Pro Cys Asp Ser Arg Pro Val
785                 790                 795                 800

Val Lys Gly Lys Tyr Asn Thr Thr Leu Leu Asn Gly Ser Ala Phe Gln
                805                 810                 815

Leu Ile Cys Pro Tyr Gly Trp Val Gly Arg Val Glu Cys Thr Thr Val
            820                 825                 830

Ser Lys Ser Thr Leu Ala Thr Glu Val Val Lys Ile Tyr Lys Lys Thr
        835                 840                 845

Lys Pro Phe Pro Gln Arg Val Gly Cys Asp His Thr Thr Val Tyr Lys
850                 855                 860

Gln Asp Leu Tyr His Cys Gln Met Gly Gly Asn Trp Thr Cys Met Arg
865                 870                 875                 880

Gly Glu Val Val Lys Tyr Val Gly Gly Pro Val Lys Lys Cys Glu Trp
                885                 890                 895

Cys Gly Tyr Val Phe Lys Lys Arg Glu Gly Leu Pro His Tyr Pro Ile
            900                 905                 910

Gly Arg Cys Met Leu Arg Asn Glu Thr Gly Tyr Arg Ser Val Asp Asp
        915                 920                 925
```

```
Thr Pro Cys Asp Arg Gly Gly Val Val Ile Ser Lys Thr Gly Glu Leu
930                 935                 940

Glu Cys Leu Ile Gly Lys Thr Thr Val Lys Val Phe Ser Ser Asp Lys
945                 950                 955                 960

Lys Leu Gly Pro Met Pro Cys Arg Pro Lys Glu Val Ile Ser Ser Glu
                965                 970                 975

Gly Pro Val Ser Lys Ile Ala Cys Thr Phe Asn Tyr Ser Lys Thr Leu
                980                 985                 990

Glu Asn Lys Tyr Tyr Glu Pro Arg Asp Ser Tyr Phe Gln Gln Tyr Met
            995                 1000                1005

Leu Lys Gly Gln Tyr Gln Tyr Trp Phe Asp Leu Glu Ala Thr Asp
    1010            1015            1020

His His Ser Asp Tyr Phe Ala Glu Phe Ile Met Leu Ala Val Val
    1025            1030            1035

Ala Leu Leu Gly Gly Arg Tyr Val Leu Trp Leu Met Val Val Tyr
    1040            1045            1050

Met Ile Leu Ala Asp Gln Met Thr Ser Ala Ile Asn Leu Gly Gln
    1055            1060            1065

Gly Glu Val Val Leu Ile Gly Asn Leu Ile Thr His Glu Asp His
    1070            1075            1080

Glu Val Val Val Tyr Phe Leu Leu Leu Tyr Leu Ile Val Lys Asp
    1085            1090            1095

Glu Pro Val Lys Lys Trp Ile Leu Phe Leu Phe His Ala Met Thr
    1100            1105            1110

Asn Asn Pro Val Lys Thr Ile Ser Val Gly Leu Leu Met Leu Ser
    1115            1120            1125

Gly Leu Val Lys Gly Glu Gly Ala Gly Met Thr Tyr Trp Glu Gly
    1130            1135            1140

Leu Asp Leu Gln Phe Thr Leu Leu Val Met Ile Thr Ala Ser Leu
    1145            1150            1155

Leu Val Ala Arg Arg Asp Val Thr Thr Tyr Pro Leu Ile Ile Thr
    1160            1165            1170

Val Ile Ala Leu Lys Thr Thr Trp Val Asn Ser Gly Pro Gly Ile
    1175            1180            1185

Asp Ala Ala Ile Ala Thr Ile Thr Thr Gly Leu Leu Met Trp Thr
    1190            1195            1200

Phe Ile Ser Asp Tyr Tyr Lys Tyr Lys Gln Trp Thr Gln Phe Leu
    1205            1210            1215

Ile Ser Ile Val Ser Gly Ile Phe Leu Ile Arg Thr Leu Lys Trp
    1220            1225            1230

Ile Gly Gly Leu Glu Leu His Ala Pro Glu Leu Pro Ser Tyr Arg
    1235            1240            1245

Pro Leu Phe Phe Ile Leu Thr Tyr Leu Ile Ser Ala Ala Ile Val
    1250            1255            1260

Thr Arg Trp Asn Leu Asp Ile Ala Gly Val Leu Leu Gln Cys Val
    1265            1270            1275

Pro Thr Ile Leu Met Val Leu Thr Leu Trp Ala Asp Leu Leu Thr
    1280            1285            1290

Leu Ile Leu Ile Leu Pro Thr Tyr Glu Leu Ala Lys Leu Tyr Tyr
    1295            1300            1305

Leu Lys Gly Val Lys Asn Gly Met Glu Arg Asn Trp Leu Gly Arg
    1310            1315            1320

Ile Thr Tyr Lys Arg Val Ser Asp Val Tyr Glu Ile Asp Glu Ser
```

-continued

```
            1325                1330                1335
Gln Glu Ala Val Tyr Leu Phe Pro Ser Lys Gln Lys Glu Gly Thr
    1340                1345                1350
Ile Thr Gly Gly Leu Leu Pro Leu Ile Lys Ala Ile Leu Ile Ser
    1355                1360                1365
Cys Ile Ser Ser Lys Trp Gln Cys Phe Tyr Leu Leu Tyr Leu Val
    1370                1375                1380
Val Glu Val Ser Tyr Tyr Leu His Lys Lys Ile Ile Glu Glu Val
    1385                1390                1395
Ala Gly Gly Thr Asn Leu Ile Ser Arg Leu Val Ala Ala Leu Leu
    1400                1405                1410
Glu Val Asn Trp Arg Phe Asp Asn Glu Thr Lys Gly Leu Lys
    1415                1420                1425
Lys Phe Tyr Leu Ile Ser Gly Gln Val Lys Asn Leu Ile Ile Lys
    1430                1435                1440
His Lys Val Arg Asn Glu Val Val Ala His Trp Phe Asn Glu Glu
    1445                1450                1455
Glu Val Tyr Gly Met Pro Lys Leu Val Ser Val Val Lys Ala Ala
    1460                1465                1470
Thr Leu Asn Arg Ser Arg His Cys Ile Leu Cys Thr Val Cys Glu
    1475                1480                1485
Ser Arg Asp Trp Lys Gly Glu Thr Cys Pro Lys Cys Gly Arg Phe
    1490                1495                1500
Gly Pro Ser Leu Ser Cys Gly Met Thr Leu Ser Asp Phe Glu Glu
    1505                1510                1515
Arg His Tyr Lys Lys Ile Phe Ile Arg Glu Asp Gln Ser Asp Gly
    1520                1525                1530
Pro Phe Arg Glu Glu Tyr Lys Gly Tyr Leu Gln Tyr Lys Ala Arg
    1535                1540                1545
Gly Gln Leu Phe Leu Arg Asn Leu Pro Ile Leu Ala Thr Lys Val
    1550                1555                1560
Lys Leu Leu Leu Val Gly Asn Leu Gly Ser Glu Val Gly Asp Leu
    1565                1570                1575
Glu His Leu Gly Trp Ile Leu Arg Gly Pro Ala Val Cys Lys Lys
    1580                1585                1590
Ile Ile Asp His Glu Arg Cys His Val Ser Ile Met Asp Lys Leu
    1595                1600                1605
Thr Ala Phe Phe Gly Ile Met Pro Arg Gly Thr Thr Pro Arg Ala
    1610                1615                1620
Pro Ile Arg Phe Pro Thr Ser Leu Leu Arg Ile Arg Arg Gly Leu
    1625                1630                1635
Glu Thr Gly Trp Ala Tyr Thr His Gln Gly Gly Ile Ser Ser Val
    1640                1645                1650
Asp His Val Thr Ala Gly Lys Asp Leu Leu Val Cys Asp Ser Met
    1655                1660                1665
Gly Arg Thr Arg Val Val Cys Gln Ser Asn Asn Arg Met Thr Asp
    1670                1675                1680
Glu Thr Glu Tyr Gly Val Lys Thr Asp Ser Gly Cys Pro Glu Gly
    1685                1690                1695
Ala Arg Cys Tyr Val Phe Asn Pro Glu Ala Val Asn Ile Ser Gly
    1700                1705                1710
Thr Lys Gly Ala Met Val His Leu Gln Lys Thr Gly Gly Glu Phe
    1715                1720                1725
```

```
Thr Cys Val Thr Ala Ser Gly Thr Pro Ala Phe Phe Asp Leu Lys
    1730            1735            1740

Asn Leu Lys Gly Trp Ser Gly Leu Pro Ile Phe Glu Ala Ser Ser
    1745            1750            1755

Gly Arg Val Val Gly Arg Val Lys Val Gly Lys Asn Glu Glu Ser
    1760            1765            1770

Lys Pro Thr Lys Leu Met Ser Gly Ile Gln Thr Val Ser Lys Ser
    1775            1780            1785

Thr Thr Asp Leu Thr Asp Met Val Lys Lys Ile Thr Thr Met Asn
    1790            1795            1800

Arg Gly Glu Phe Lys Gln Ile Thr Leu Ala Thr Gly Ala Gly Lys
    1805            1810            1815

Thr Thr Glu Leu Pro Arg Ala Val Ile Glu Glu Ile Gly Arg His
    1820            1825            1830

Lys Arg Val Leu Val Leu Ile Pro Leu Arg Ala Ala Ala Glu Ser
    1835            1840            1845

Val Tyr Gln Tyr Met Arg Gln Lys His Pro Ser Ile Ala Phe Asn
    1850            1855            1860

Leu Arg Ile Gly Glu Met Lys Glu Gly Asp Met Ala Thr Gly Ile
    1865            1870            1875

Thr Tyr Ala Ser Tyr Gly Tyr Phe Cys Gln Met Pro Gln Pro Lys
    1880            1885            1890

Leu Arg Ala Ala Met Val Glu Tyr Ser Tyr Ile Phe Leu Asp Glu
    1895            1900            1905

Tyr His Cys Ala Thr Pro Glu Gln Leu Ala Ile Ile Gly Lys Ile
    1910            1915            1920

His Arg Phe Ser Glu Gln Leu Arg Val Val Ala Met Thr Ala Thr
    1925            1930            1935

Pro Ala Gly Thr Val Thr Thr Thr Gly Gln Lys His Pro Ile Glu
    1940            1945            1950

Glu Phe Ile Ala Pro Glu Val Met Lys Gly Glu Asp Leu Gly Ser
    1955            1960            1965

Glu Phe Leu Glu Ile Ala Gly Leu Lys Ile Pro Thr Glu Glu Met
    1970            1975            1980

Lys Gly Asn Met Leu Val Phe Val Pro Thr Arg Asn Met Ala Val
    1985            1990            1995

Glu Thr Ala Lys Lys Leu Lys Ala Lys Gly Tyr Asn Ser Gly Tyr
    2000            2005            2010

Tyr Tyr Ser Gly Glu Asp Pro Ala Asn Leu Arg Val Val Thr Ser
    2015            2020            2025

Gln Ser Pro Tyr Val Val Val Ala Thr Asn Ala Ile Glu Ser Gly
    2030            2035            2040

Val Thr Leu Pro Asp Leu Asp Val Val Val Asp Thr Gly Leu Lys
    2045            2050            2055

Cys Glu Lys Arg Ile Arg Leu Ser Ser Lys Met Pro Phe Ile Val
    2060            2065            2070

Thr Gly Leu Lys Arg Met Ala Val Thr Ile Gly Glu Gln Ala Gln
    2075            2080            2085

Arg Arg Gly Arg Val Gly Arg Val Lys Pro Gly Arg Tyr Tyr Arg
    2090            2095            2100

Ser Gln Glu Thr Ala Val Gly Ser Lys Asp Tyr His Tyr Asp Leu
    2105            2110            2115
```

-continued

Leu Gln Ala Gln Arg Tyr Gly Ile Glu Asp Gly Ile Asn Ile Thr
2120                     2125                2130

Lys Ser Phe Arg Glu Met Asn Tyr Asp Trp Ser Leu Tyr Glu Glu
2135                     2140                2145

Asp Ser Leu Met Ile Thr Gln Leu Glu Ile Leu Asn Asn Leu Leu
2150                     2155                2160

Ile Ser Glu Glu Leu Pro Val Ala Val Lys Asn Ile Met Ala Arg
2165                     2170                2175

Thr Asp His Pro Glu Pro Ile Gln Leu Ala Tyr Asn Ser Tyr Glu
2180                     2185                2190

Val Gln Val Pro Val Leu Phe Pro Lys Ile Arg Asn Gly Glu Val
2195                     2200                2205

Thr Asp Ser Tyr Asp Ser Tyr Ser Phe Leu Asn Ala Arg Lys Leu
2210                     2215                2220

Gly Asp Asp Val Pro Ala Tyr Val Tyr Ala Thr Glu Asp Glu Asp
2225                     2230                2235

Leu Ala Val Glu Leu Leu Gly Met Asp Trp Pro Asp Pro Gly Asn
2240                     2245                2250

Gln Gly Thr Val Glu Thr Gly Arg Ala Leu Lys Gln Val Thr Gly
2255                     2260                2265

Leu Ser Ala Ala Glu Asn Ala Leu Leu Val Ala Leu Phe Gly Tyr
2270                     2275                2280

Val Gly Tyr Gln Ala Leu Ser Lys Arg His Val Pro Met Val Thr
2285                     2290                2295

Asp Ile Tyr Ser Ile Glu Asp His Arg Leu Glu Asp Thr Thr His
2300                     2305                2310

Leu Gln Phe Ala Pro Asn Ala Ile Arg Thr Asp Gly Lys Glu Thr
2315                     2320                2325

Glu Leu Lys Glu Leu Ala Gln Gly Asp Ile Gln Arg Cys Ala Glu
2330                     2335                2340

Ala Met Val Gly Tyr Ala Gln Gln Gly Val Gln Phe Ile Lys Thr
2345                     2350                2355

Gln Ala Leu Lys Val Gln Glu Asn His Val Phe Lys Asp Ser Ala
2360                     2365                2370

Asp Thr Ile Val Glu Tyr Val Asp Lys Phe Met Lys Ala Ile Ala
2375                     2380                2385

Glu Ser Lys Asp Asp Ile Leu Arg Tyr Gly Leu Trp Gly Ala His
2390                     2395                2400

Thr Ala Leu Tyr Lys Ser Ile Gly Ala Arg Leu Gly Tyr Glu Thr
2405                     2410                2415

Ala Phe Ala Thr Leu Val Ile Lys Trp Leu Ala Phe Gly Gly Glu
2420                     2425                2430

Ser Ile Asn Asp His Val Lys Gln Ala Ala Thr Asp Leu Val Val
2435                     2440                2445

Tyr Tyr Ile Ile Asn Arg Pro Gln Phe Pro Gly Asp Thr Glu Thr
2450                     2455                2460

Gln Gln Glu Gly Arg Lys Phe Val Ala Ser Leu Leu Val Ser Ala
2465                     2470                2475

Leu Ala Thr Tyr Thr Tyr Lys Ser Trp Asn Tyr Ser Asn Leu Ser
2480                     2485                2490

Lys Val Val Glu Pro Ala Leu Ala Cys Leu Pro Tyr Ala Ser Gln
2495                     2500                2505

Ala Leu Lys Leu Phe Ala Pro Thr Arg Leu Glu Ser Val Val Ile

-continued

```
                    2510                2515                2520
Leu Ser Thr Ala Ile Tyr Lys Thr Tyr Leu Ala Ile Arg Arg Gly
    2525                2530                2535
Arg Ser Asp Gly Leu Leu Gly Thr Gly Val Ser Ala Ala Met Glu
    2540                2545                2550
Ile Met Ser Gln Asn Pro Val Ser Val Gly Ile Ala Val Met Leu
    2555                2560                2565
Gly Val Gly Ala Val Ala Ala His Asn Ala Ile Glu Ser Ser Glu
    2570                2575                2580
Gln Lys Arg Thr Leu Leu Met Lys Val Phe Val Lys Asn Phe Leu
    2585                2590                2595
Asp Gln Ala Ala Thr Asp Glu Leu Val Lys Glu Ser Pro Glu Lys
    2600                2605                2610
Ile Ile Thr Ala Leu Phe Glu Ala Val Gln Thr Val Gly Asn Pro
    2615                2620                2625
Leu Arg Leu Ile Tyr His Leu Tyr Gly Val Phe Tyr Lys Gly Trp
    2630                2635                2640
Glu Ala Lys Glu Val Ala Glu Lys Thr Ala Gly Arg Asn Leu Phe
    2645                2650                2655
Thr Leu Ile Met Phe Glu Ala Val Glu Leu Leu Gly Val Asp Ser
    2660                2665                2670
Glu Gly Lys Met Arg Arg Leu Ser Gly Asn Tyr Leu Ile Glu Leu
    2675                2680                2685
Leu Gln Lys Leu His Asp Gly Phe Arg Ile Ser Ile Lys Lys Phe
    2690                2695                2700
Ala Leu Gly Trp Ala Pro Gly Pro Phe Ser Cys Asn Trp Thr Pro
    2705                2710                2715
Ala Asp Asn Arg Ile Arg Leu Pro His Glu Asn Tyr Leu Arg Val
    2720                2725                2730
Val Thr Arg Cys Arg Cys Gly Tyr Arg Thr Lys Ala Val Lys Asn
    2735                2740                2745
Cys Ala Gly Glu Leu Ile Leu Glu Glu Glu Gly Ser Phe Phe
    2750                2755                2760
Cys Arg Asn Lys Phe Gly Arg Gly Ala Pro Asn Tyr Lys Val Thr
    2765                2770                2775
Lys Phe Tyr Asp Gly Asn Leu Glu Glu Ile Arg Ala Arg Leu Lys
    2780                2785                2790
Leu Glu Gly Gln Val Glu Met Tyr Tyr Lys Gly Ala Thr Ile Lys
    2795                2800                2805
Ile Asp Tyr Ser Asn Asn Lys Leu Ile Leu Ala Thr Asp Lys Trp
    2810                2815                2820
Glu Val Glu His Ser Tyr Ile Thr Arg Leu Thr Lys Arg Tyr Thr
    2825                2830                2835
Gly Ala Gly Tyr Lys Gly Ala Phe Leu Gly Asp Glu Pro Asn His
    2840                2845                2850
Lys Ser Leu Ile Glu Arg Thr Cys Ala Thr Val Cys Lys Asp Lys
    2855                2860                2865
Ile Tyr Phe Ser Lys Met Lys Lys Gly Cys Ala Phe Thr Tyr Asp
    2870                2875                2880
Leu Ser Leu Ser Asn Leu Val Arg Leu Val Asp Leu Val His Arg
    2885                2890                2895
Asn Lys Leu Glu Glu Lys Asp Ile Pro Glu Arg Thr Val Thr Thr
    2900                2905                2910
```

```
Trp Leu Ala Tyr Thr Phe Val Asn Glu Asp Val Gly Thr Ile Lys
2915                 2920                 2925

Pro Val Leu Gly Glu Lys Val Ile Pro Glu Glu Ser Asp Glu Ile
2930                 2935                 2940

Asn Leu Gln Pro Thr Val Thr Val Asn Met Ser Lys Cys Gln Val
2945                 2950                 2955

Thr Val Val Gly Glu Ala Lys Asn Met Thr Thr Gly Val Val Pro
2960                 2965                 2970

Leu Thr Val Thr Lys Glu Ala Cys Asn Gly Gln Asp Arg Ser Val
2975                 2980                 2985

Leu Asn Ile Gly Met Glu Glu Gly Glu Tyr Pro Gly Pro Ala Val
2990                 2995                 3000

Ser Thr Val Thr Val Gly Glu Ala Val Gln Ser Lys Asp Val Arg
3005                 3010                 3015

Pro Tyr Val Leu Val Ile Gly Ser Asn Lys Ala Thr Ser Asn Arg
3020                 3025                 3030

Ala Lys Thr Ala Lys Asn Val Lys Leu Tyr Lys Gly Gly Asp Ala
3035                 3040                 3045

Val Glu Val Arg Asp Leu Ile Lys Lys Gly Glu Met Leu Val Val
3050                 3055                 3060

Ala Leu Ala Asp Val Glu Gln Asp Leu Leu Glu Tyr Val Asp Tyr
3065                 3070                 3075

Lys Gly Thr Phe Leu Thr Arg Glu Thr Leu Glu Ala Leu Ser Leu
3080                 3085                 3090

Gly Lys Pro Lys Ala Lys Asn Ile Thr Lys Ala Asp Ala His Arg
3095                 3100                 3105

Leu Leu Asn Pro Glu Lys Glu Gln Ile Gly Leu Pro Asp Trp Phe
3110                 3115                 3120

Thr Ala Thr Glu Pro Ile Phe Leu Glu Ala Met Ile Lys Gln Glu
3125                 3130                 3135

Lys Tyr His Ile Thr Gly Asp Val Ala Thr Val Lys Asp Lys Ala
3140                 3145                 3150

Lys Gln Leu Gly Ala Thr Asp Ser Thr Arg Ile Val Lys Glu Val
3155                 3160                 3165

Gly Ala Arg Val Tyr Thr Met Lys Leu Asn Ser Trp Ala Leu Gln
3170                 3175                 3180

Ala Glu Arg Gly Asp Ala Asn Leu Lys Pro Leu Phe Glu Glu Leu
3185                 3190                 3195

Leu Leu Gln Cys Pro Pro Gly Arg Thr Val Lys Gly Gly Thr Met
3200                 3205                 3210

Val Ser Ala Tyr Gln Leu Ala Gln Gly Asn Trp Thr Pro Thr Ser
3215                 3220                 3225

Cys Lys Val Tyr Met Gly Thr Ile Thr Ala Lys Arg Val Lys Ile
3230                 3235                 3240

His Pro Tyr Glu Ala Tyr Ile Lys Leu Lys Glu Leu Ile Glu Glu
3245                 3250                 3255

Tyr Asn Met Lys Arg Val Thr Gly Asp Thr Gly Leu Lys Arg His
3260                 3265                 3270

Asn Glu Trp Ile Leu Lys Arg Ile Lys His His Gly Asn Leu Arg
3275                 3280                 3285

Thr Lys Lys Ile Leu Asn Pro Gly Lys Val Ala Glu Gln Leu Ser
3290                 3295                 3300
```

-continued

Arg Glu Gly His Lys His Asn Val Tyr Asn Lys Ile Ile Gly Ser
3305                3310                3315

Thr Met Ala Ser Val Gly Ile Lys Leu Glu Lys Leu Pro Val Val
3320                3325                3330

Arg Ala Gln Thr Asp Thr Thr Phe Phe His Gln Ala Ile Arg Asp
3335                3340                3345

Lys Ile Asp Lys Glu Glu Asn Pro Gln Thr Pro Asp Leu His Lys
3350                3355                3360

Glu Leu Lys Glu Val Phe Asn Ala Leu Lys Ile Pro Glu Leu Ala
3365                3370                3375

Ala Thr Tyr Asp Ala Val Glu Trp Glu Glu Leu Glu Thr Gly Ile
3380                3385                3390

Asn Arg Lys Gly Ala Ala Gly Phe Phe Glu Arg Lys Asn Ile Gly
3395                3400                3405

Glu Ile Leu Asp Thr Glu Lys Asn Lys Val Glu Asp Ile Ile Arg
3410                3415                3420

Asp Leu Lys Ser Gly Arg Pro Ile Lys Tyr Tyr Glu Thr Ala Ile
3425                3430                3435

Pro Lys Asn Glu Lys Arg Asp Val Asn Asp Asp Trp Glu Ser Gly
3440                3445                3450

Asp Phe Val Asp Glu Lys Lys Pro Arg Val Ile Gln Tyr Pro Glu
3455                3460                3465

Ala Lys Val Arg Leu Ala Ile Thr Lys Val Met Tyr Lys Trp Val
3470                3475                3480

Lys Gln Lys Pro Val Val Ile Pro Gly Tyr Glu Gly Lys Thr Pro
3485                3490                3495

Leu Phe Glu Ile Phe Asp Lys Val Lys Lys Glu Trp Gly Ser Phe
3500                3505                3510

Asp Asn Pro Val Ala Val Ser Phe Asp Thr Lys Ala Trp Asp Thr
3515                3520                3525

Gln Val Thr Ser Lys Ser Leu Glu Leu Ile Arg Asp Ile Gln Lys
3530                3535                3540

Tyr Tyr Phe Lys Lys Glu Trp His Lys Phe Ile Glu Thr Ile Thr
3545                3550                3555

Glu His Met Val Glu Val Pro Val Val Thr Ala Asp Gly Glu Val
3560                3565                3570

Tyr Ile Ser Glu Gly Gln Arg Gly Ser Gly Gln Pro Asp Thr Ser
3575                3580                3585

Ala Gly Asn Ser Met Leu Asn Val Leu Thr Met Val Tyr Ala Phe
3590                3595                3600

Cys Arg Ala Thr Gly Val Pro Tyr Lys Ser Phe Lys Arg Val Ala
3605                3610                3615

Lys Ile His Val Cys Gly Asp Asp Gly Phe Leu Ile Thr Glu Lys
3620                3625                3630

Ser Leu Gly Glu Lys Phe Ala Ser Lys Gly Ile Gln Ile Leu His
3635                3640                3645

Glu Ala Gly Lys Pro Gln Lys Ile Thr Glu Gly Asp Arg Met Lys
3650                3655                3660

Val Ala Tyr Lys Phe Glu Asp Ile Glu Phe Cys Ser His Thr Pro
3665                3670                3675

Val Pro Val Arg Trp Ser Asp Asn Thr Thr Ser Tyr Met Pro Gly
3680                3685                3690

Arg Asn Thr Ala Thr Ile Leu Ala Lys Met Ala Thr Arg Leu Asp

```
                    3695                3700                3705

Ser Ser Gly Glu Arg Gly Thr Thr Ala Tyr Glu Lys Ala Val Ala
    3710                3715                3720

Phe Ser Phe Leu Leu Met Tyr Ser Trp Asn Pro Leu Val Arg Arg
    3725                3730                3735

Ile Cys Leu Leu Thr Leu Ser Ser Glu Leu Gly Thr Lys Pro Ser
    3740                3745                3750

Lys Arg Thr Thr Tyr Tyr Tyr Glu Gly Asp Pro Ile Ser Ala Tyr
    3755                3760                3765

Arg Glu Val Ile Gly His Asn Leu Leu Asp Leu Lys Arg Thr Gly
    3770                3775                3780

Leu Glu Lys Leu Ala Leu Leu Asn Leu Ser Met Ser Thr Leu Gly
    3785                3790                3795

Ile Trp Thr Lys His Ile Ser Lys Arg Leu Leu Gln Asp Cys Val
    3800                3805                3810

Asp Val Gly Ser Lys Asp Gly Asn Trp Leu Val Asn Ala Asp Arg
    3815                3820                3825

Pro Glu Ser Arg Lys Thr Gly Lys Val Tyr Leu Gln Ser Gly Gly
    3830                3835                3840

His Thr Val Arg Gly Arg His Tyr Glu Asp Leu Ile Leu Pro Arg
    3845                3850                3855

Met Val Lys Pro Thr Phe Gln Gly Val Asp Arg Tyr Lys Leu Gly
    3860                3865                3870

Pro Ile Val Asn Val Ile Phe Arg Arg Leu Arg Val Met Met Met
    3875                3880                3885

Ala Leu Val Gly Arg Gly Met
    3890                3895

<210> SEQ ID NO 13
<211> LENGTH: 13
<212> TYPE: PRT
<213> ORGANISM: BVDV

<400> SEQUENCE: 13

Ser Leu His Gly Ile Trp Pro Glu Lys Ile Cys Thr Gly
1               5                   10

<210> SEQ ID NO 14
<211> LENGTH: 20
<212> TYPE: PRT
<213> ORGANISM: BVDV

<400> SEQUENCE: 14

Leu Gln Arg His Glu Trp Asn Lys His Gly Trp Cys Asn Trp Phe His
1               5                   10                  15

Ile Glu Pro Trp
            20

<210> SEQ ID NO 15
<211> LENGTH: 20
<212> TYPE: PRT
<213> ORGANISM: BVDV

<400> SEQUENCE: 15

Leu Gln Arg His Glu Trp Asn Lys His Gly Trp Cys Asn Trp Tyr Asn
1               5                   10                  15

Ile Glu Pro Trp
            20
```

```
<210> SEQ ID NO 16
<211> LENGTH: 13
<212> TYPE: PRT
<213> ORGANISM: BVDV

<400> SEQUENCE: 16

Ser Leu His Gly Ile Trp Pro Glu Lys Ile Cys Lys Gly
1               5                   10

<210> SEQ ID NO 17
<211> LENGTH: 20
<212> TYPE: PRT
<213> ORGANISM: BVDV

<400> SEQUENCE: 17

Leu Gln Arg His Glu Trp Asn Lys His Gly Trp Cys Asn Trp Tyr Asn
1               5                   10                  15

Ile Asp Pro Trp
            20

<210> SEQ ID NO 18
<211> LENGTH: 11
<212> TYPE: PRT
<213> ORGANISM: BVDV

<400> SEQUENCE: 18

Ser Leu His Gly Ile Trp Pro Glu Lys Ile Cys
1               5                   10

<210> SEQ ID NO 19
<211> LENGTH: 12
<212> TYPE: PRT
<213> ORGANISM: BVDV

<400> SEQUENCE: 19

Arg His Glu Trp Asn Lys His Gly Trp Cys Asn Trp
1               5                   10

<210> SEQ ID NO 20
<211> LENGTH: 3
<212> TYPE: PRT
<213> ORGANISM: BVDV

<400> SEQUENCE: 20

Met Glu Leu
1

<210> SEQ ID NO 21
<211> LENGTH: 6
<212> TYPE: PRT
<213> ORGANISM: BVDV

<400> SEQUENCE: 21

Ser Asn Glu Gly Ser Lys
1               5

<210> SEQ ID NO 22
<211> LENGTH: 6
<212> TYPE: PRT
<213> ORGANISM: BVDV

<400> SEQUENCE: 22

Ser Asp Glu Gly Ser Lys
```

-continued

```
<210> SEQ ID NO 23
<211> LENGTH: 5
<212> TYPE: PRT
<213> ORGANISM: BVDV

<400> SEQUENCE: 23

Met Glu Leu Phe Ser
1               5

<210> SEQ ID NO 24
<211> LENGTH: 7
<212> TYPE: PRT
<213> ORGANISM: BVDV

<400> SEQUENCE: 24

Met Glu Leu Phe Ser Asn Glu
1               5

<210> SEQ ID NO 25
<211> LENGTH: 8
<212> TYPE: PRT
<213> ORGANISM: BVDV

<400> SEQUENCE: 25

Met Glu Leu Phe Ser Asn Glu Leu
1               5

<210> SEQ ID NO 26
<211> LENGTH: 9
<212> TYPE: PRT
<213> ORGANISM: BVDV

<400> SEQUENCE: 26

Met Glu Leu Phe Ser Asn Glu Leu Leu
1               5

<210> SEQ ID NO 27
<211> LENGTH: 10
<212> TYPE: PRT
<213> ORGANISM: BVDV

<400> SEQUENCE: 27

Met Glu Leu Phe Ser Asn Glu Leu Leu Tyr
1               5                   10

<210> SEQ ID NO 28
<211> LENGTH: 11
<212> TYPE: PRT
<213> ORGANISM: BVDV

<400> SEQUENCE: 28

Met Glu Leu Phe Ser Asn Glu Leu Leu Tyr Lys
1               5                   10

<210> SEQ ID NO 29
<211> LENGTH: 12
<212> TYPE: PRT
<213> ORGANISM: BVDV

<400> SEQUENCE: 29

Met Glu Leu Phe Ser Asn Glu Leu Leu Tyr Lys Thr
1               5                   10
```

<210> SEQ ID NO 30
<211> LENGTH: 4
<212> TYPE: PRT
<213> ORGANISM: BVDV

<400> SEQUENCE: 30

Met Glu Leu Phe
1

<210> SEQ ID NO 31
<211> LENGTH: 6
<212> TYPE: PRT
<213> ORGANISM: BVDV

<400> SEQUENCE: 31

Met Glu Leu Phe Ser Asn
1               5

<210> SEQ ID NO 32
<211> LENGTH: 4
<212> TYPE: PRT
<213> ORGANISM: BVDV

<400> SEQUENCE: 32

Met Glu Leu Ile
1

<210> SEQ ID NO 33
<211> LENGTH: 5
<212> TYPE: PRT
<213> ORGANISM: BVDV

<400> SEQUENCE: 33

Met Glu Leu Ile Ser
1               5

<210> SEQ ID NO 34
<211> LENGTH: 6
<212> TYPE: PRT
<213> ORGANISM: BVDV

<400> SEQUENCE: 34

Met Glu Leu Ile Ser Asn
1               5

<210> SEQ ID NO 35
<211> LENGTH: 7
<212> TYPE: PRT
<213> ORGANISM: BVDV

<400> SEQUENCE: 35

Met Glu Leu Ile Ser Asn Glu
1               5

<210> SEQ ID NO 36
<211> LENGTH: 8
<212> TYPE: PRT
<213> ORGANISM: BVDV

<400> SEQUENCE: 36

Met Glu Leu Ile Ser Asn Glu Leu
1               5

<210> SEQ ID NO 37

<211> LENGTH: 9
<212> TYPE: PRT
<213> ORGANISM: BVDV

<400> SEQUENCE: 37

Met Glu Leu Ile Ser Asn Glu Leu Leu
1               5

<210> SEQ ID NO 38
<211> LENGTH: 10
<212> TYPE: PRT
<213> ORGANISM: BVDV

<400> SEQUENCE: 38

Met Glu Leu Ile Ser Asn Glu Leu Leu Tyr
1               5                   10

<210> SEQ ID NO 39
<211> LENGTH: 11
<212> TYPE: PRT
<213> ORGANISM: BVDV

<400> SEQUENCE: 39

Met Glu Leu Ile Ser Asn Glu Leu Leu Tyr Lys
1               5                   10

<210> SEQ ID NO 40
<211> LENGTH: 12
<212> TYPE: PRT
<213> ORGANISM: BVDV

<400> SEQUENCE: 40

Met Glu Leu Ile Ser Asn Glu Leu Leu Tyr Lys Thr
1               5                   10

<210> SEQ ID NO 41
<211> LENGTH: 5
<212> TYPE: PRT
<213> ORGANISM: BVDV

<400> SEQUENCE: 41

Met Glu Leu Ile Thr
1               5

<210> SEQ ID NO 42
<211> LENGTH: 6
<212> TYPE: PRT
<213> ORGANISM: BVDV

<400> SEQUENCE: 42

Met Glu Leu Ile Thr Asn
1               5

<210> SEQ ID NO 43
<211> LENGTH: 7
<212> TYPE: PRT
<213> ORGANISM: BVDV

<400> SEQUENCE: 43

Met Glu Leu Ile Thr Asn Glu
1               5

<210> SEQ ID NO 44
<211> LENGTH: 8
<212> TYPE: PRT

```
<213> ORGANISM: BVDV

<400> SEQUENCE: 44

Met Glu Leu Ile Thr Asn Glu Leu
1               5

<210> SEQ ID NO 45
<211> LENGTH: 9
<212> TYPE: PRT
<213> ORGANISM: BVDV

<400> SEQUENCE: 45

Met Glu Leu Ile Thr Asn Glu Leu Leu
1               5

<210> SEQ ID NO 46
<211> LENGTH: 10
<212> TYPE: PRT
<213> ORGANISM: BVDV

<400> SEQUENCE: 46

Met Glu Leu Ile Thr Asn Glu Leu Leu Tyr
1               5                   10

<210> SEQ ID NO 47
<211> LENGTH: 11
<212> TYPE: PRT
<213> ORGANISM: BVDV

<400> SEQUENCE: 47

Met Glu Leu Ile Thr Asn Glu Leu Leu Tyr Lys
1               5                   10

<210> SEQ ID NO 48
<211> LENGTH: 12
<212> TYPE: PRT
<213> ORGANISM: BVDV

<400> SEQUENCE: 48

Met Glu Leu Ile Thr Asn Glu Leu Leu Tyr Lys Thr
1               5                   10

<210> SEQ ID NO 49
<211> LENGTH: 5
<212> TYPE: PRT
<213> ORGANISM: BVDV

<400> SEQUENCE: 49

Glu Leu Phe Ser Asn
1               5
```